US012276656B2

(12) United States Patent
Peng et al.

(10) Patent No.: US 12,276,656 B2
(45) Date of Patent: *Apr. 15, 2025

(54) COMPOSITIONS AND METHODS FOR IDENTIFICATION OF ANTIGEN SPECIFIC T CELLS

(71) Applicant: ADOC SSF, LLC, South San Francisco, CA (US)

(72) Inventors: Songming Peng, San Mateo, CA (US); Boi Bryant Quach, San Mateo, CA (US); Duo An, San Mateo, CA (US); Xiaoyan Robert Bao, Foster City, CA (US); Alex Franzusoff, El Granada, CA (US); Barbara Sennino, San Francisco, CA (US); Olivier Dalmas, San Carlos, CA (US); Stefanie Mandl-Cashman, San Francisco, CA (US)

(73) Assignee: ADOC SSF, LLC, South San Francisco, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/050,715

(22) Filed: Oct. 28, 2022

(65) Prior Publication Data

US 2023/0194504 A1 Jun. 22, 2023

Related U.S. Application Data

(62) Division of application No. 16/788,745, filed on Feb. 12, 2020, now Pat. No. 11,513,113.

(60) Provisional application No. 62/876,380, filed on Jul. 19, 2019, provisional application No. 62/867,165, filed on Jun. 26, 2019, provisional application No. 62/826,823, filed on Mar. 29, 2019, provisional application No. 62/804,649, filed on Feb. 12, 2019.

(51) Int. Cl.

| | |
|---|---|
| ***G01N 33/50*** | (2006.01) |
| ***A61K 39/00*** | (2006.01) |
| ***A61P 35/00*** | (2006.01) |
| ***C12N 5/0783*** | (2010.01) |
| ***C12N 15/10*** | (2006.01) |
| ***C12N 15/85*** | (2006.01) |
| ***C12N 15/90*** | (2006.01) |
| ***C12Q 1/686*** | (2018.01) |

(52) U.S. Cl.

CPC ........ *G01N 33/505* (2013.01); *A61K 39/4611* (2023.05); *A61K 39/4632* (2023.05); *A61K 39/464401* (2023.05); *A61K 39/46449* (2023.05); *A61P 35/00* (2018.01); *C12N 5/0636* (2013.01); *C12N 5/0637* (2013.01); *C12N 5/0638* (2013.01); *C12N 15/1093* (2013.01); *C12N 15/85* (2013.01); *C12N 15/907* (2013.01); *C12Q 1/686* (2013.01); *A61K 2239/38* (2023.05); *A61K 2239/50* (2023.05); *A61K 2239/57* (2023.05); *C12N 2510/00* (2013.01)

(58) Field of Classification Search

CPC .. G01N 33/505; A61K 35/17; A61K 39/4632; A61P 35/00; C12N 5/0637; C12N 15/1093; C12N 15/907; C12N 2510/00; C12Q 1/686

See application file for complete search history.

(56) References Cited

U.S. PATENT DOCUMENTS

| | | | | |
|---|---|---|---|---|
| 7,709,224 | B2 | 5/2010 | Fang et al. | |
| 8,895,020 | B2 | 11/2014 | Hansen et al. | |
| 8,992,937 | B2 | 3/2015 | Hansen et al. | |
| 9,540,657 | B2 | 1/2017 | Yu et al. | |
| 2008/0219947 | A1 | 9/2008 | Linette et al. | |
| 2011/0236411 | A1 | 9/2011 | Scholler | |
| 2014/0272976 | A1 | 9/2014 | Lee et al. | |
| 2017/0003288 | A1 | 1/2017 | Heath et al. | |
| 2017/0067021 | A1* | 3/2017 | Moriarty | A61K 39/4632 |
| 2017/0153241 | A1 | 6/2017 | Pugia | |
| 2017/0176435 | A1 | 6/2017 | Seidell, III et al. | |
| 2018/0030533 | A1 | 2/2018 | Xie et al. | |
| 2018/0267036 | A1 | 9/2018 | Fan et al. | |
| 2018/0289741 | A1 | 10/2018 | Nicholson et al. | |

FOREIGN PATENT DOCUMENTS

| | | | |
|---|---|---|---|
| WO | WO 2014/153470 | A2 | 9/2014 |
| WO | WO 2016/069282 | A1 | 5/2016 |
| WO | WO 2016/071343 | A1 | 5/2016 |
| WO | WO 2017/023803 | A1 | 2/2017 |
| WO | WO 2017/062451 | A1 | 4/2017 |
| WO | WO 2017/156484 | A1 | 9/2017 |
| WO | WO 2018/073393 | A2 | 4/2018 |
| WO | WO 2018/119447 | A2 | 6/2018 |
| WO | WO 2018/165475 | A1 | 9/2018 |
| WO | WO 2019/084552 | A1 | 5/2019 |
| WO | WO 2019/195310 | A1 | 10/2019 |

OTHER PUBLICATIONS

Liu et al., "Systematic comparison of 2A peptides for cloning multi-genes in a polycistronic vector," Scientific Reports, 7, 9 pages (2017), DOI:10.1038/s41598-017-02460-2.

(Continued)

*Primary Examiner* — Sahana S Kaup

(74) *Attorney, Agent, or Firm* — Baker Botts L.L.P.

(57) ABSTRACT

Disclosed herein are antigenic peptide-MHC complexes, termed comPACT polypeptides and comPACT polynucleotides, and methods of producing such complexes. Also discloses herein are methods of producing libraries of comPACT polynucleotides and polypeptides, and their exemplary use in capturing cancer neoepitope-reactive T cells with high accuracy. Dual particle detection approaches for detection of neoantigen specific T cells with improved sensitivity and specificity are provided. Signal to noise ratio analysis of isolated T cells for detection of neoantigen-specific T cells with improved T cells is also provided.

16 Claims, 74 Drawing Sheets

Specification includes a Sequence Listing.

(56) References Cited

OTHER PUBLICATIONS

Gakamsky et al., "Photophysical Analysis of Class I Major Histocompatibility Complex Protein Assembly Using a Xanthene-Derivatized β2-Microglobulin," Biophysical Journal, 76:1552-1560 (1999).
U.S. Appl. No. 16/788,745 (U.S. Pat. No. 11,513,113), filed Feb. 12, 2020 (Nov. 29, 2022).
U.S. Appl. No. 16/552,714 (2019/0376091 A1), filed Aug. 27, 2019 (Dec. 12, 2019).
U.S. Appl. No. 16/552,786 (U.S. Pat. No. 10,550,406), filed Aug. 27, 2019 (Feb. 4, 2020).
U.S. Appl. No. 16/679,025, filed Nov. 8, 2019.
U.S. Appl. No. 16/782,450, filed Feb. 5, 2020.
U.S. Appl. No. 16/782,815, filed Feb. 5, 2020.
U.S. Appl. No. 16/788,745, Oct. 26, 2022 Issue Fee Payment.
U.S. Appl. No. 16/788,745, Jul. 27, 2022 Notice of Allowance.
U.S. Appl. No. 16/788,745, Jun. 1, 2022 Request for Continued Examination.
U.S. Appl. No. 16/788,745, Jun. 1, 2022 Response After Final Office Action.
U.S. Appl. No. 16/788,745, Feb. 1, 2022 Final Office Action.
U.S. Appl. No. 16/788,745, Jan. 3, 2022 Response to Non-Final Office Action.
U.S. Appl. No. 16/788,745, Aug. 5, 2021 Non-Final Office Action.
U.S. Appl. No. 16/788,745, Mar. 19, 2021 Request for Continued Examination.
U.S. Appl. No. 16/788,745, Mar. 19, 2021 Response After Final Office Action.
U.S. Appl. No. 16/788,745, Dec. 22, 2020 Final Office Action.
U.S. Appl. No. 16/788,745, Sep. 8, 2020 Response to Non-Final Office Action.
U.S. Appl. No. 16/788,745, Jun. 12, 2020 Non-Final Office Action.
U.S. Appl. No. 16/788,745, May 15, 2020 Response to Restriction Requirement.
U.S. Appl. No. 16/788,745, Apr. 30, 2020 Restriction Requirement.
U.S. Appl. No. 16/552,714, Feb. 5, 2020 Issue Fee Payment.
U.S. Appl. No. 16/552,714, Jan. 31, 2020 Notice of Allowance.
U.S. Appl. No. 16/552,714, Nov. 27, 2019 Response to Non-Final Office Action.
U.S. Appl. No. 16/552,714, Nov. 21, 2019 Applicant Initiated Interview Summary.
U.S. Appl. No. 16/552,714, Oct. 23, 2019 Non-Final Office Action.
U.S. Appl. No. 16/552,786, Dec. 20, 2019 Issue Fee Payment.
U.S. Appl. No. 16/552,786, Dec. 18, 2019 Notice of Allowance.
U.S. Appl. No. 16/552,786, Nov. 27, 2019 Response to Non-Final Office Action.
U.S. Appl. No. 16/552,786, Nov. 21, 2019 Applicant Initiated Interview Summary.
U.S. Appl. No. 16/552,786, Oct. 23, 2019, Non-Final Office Action.
Barsov et al., "Transduction of SIV-Specific TCR Genes into Rhesus Macaque CD8+ T Cells Conveys the Ability to Suppress SIV Replication," PLoS ONE, 6(8):e23703 (2011).
Bethune et al., "Preparation of Peptide-MHC and T-Cell Receptor Dextramers by Biotinylated Dextran Doping," BioTechniques 62:123-130 (2017).
Cebrian et al., "Neuronal MHC-I Expression and its Implications in Synaptic Function, Axonal Regeneration and Parkinson's and Other Brain Diseases," Frontiers in Neuroanatomy 8(114):1-9 (2014).
Chung et al., "Functional three-domain single-chain T-cell receptors," Proc. Natl. Acad. Sci., 91:12654-12658 (1994).
Foley et al., "HCV T Cell Receptor Chain Modifications to Enhance Expression, Pairing, and Antigen Recognition in T Cells for Adoptive Transfer," Molecular Therapy—Onco-lytics, 5:105-115 (2017).
International Search Report and Written Opinion dated Apr. 27, 2020 in International Application No. PCT/US2020/017887.
International Search Report mailed Jul. 29, 2019 in International Application No. PCT/US19/25415.
Kitz, "Generation and analysis of T cell receptor transgenic rats to model CNS autoim-munity," PhD Dissertation 2013. Georg-August University School of Science (GAUSS) Gottingen, Germany. (125 pages).
Knipping et al., "Genome-wide Specificity of Highly Efficient TALENs and CRISPR/Cas9 for T Cell Receptor Modification," Molecular Therapy—Methods and Clin-ical Development, 4:213-224 (2017).
Li et al., "The Implication and Significance of Beta 2 Microglobulin: A Conservative Multifunctional Regulator," Chinese Medical Journal 129(4):448-455 (2016).
Ohta et al., "Primordial Linkage of 02-Microglobulin to the MHC," J Immunol. 186:3563-3571 (2011).
Okamoto et al., "A Promising Vector for TCR Gene Therapy: Differential Effect of siR-NA, 2A Peptide, and Disulfide Bond on the Introduced TCR Expression," Molecular Therapy—Nucleic Acids, 1:e63 (2012).
Schober et al., "Orthotopic replacement of T-cell receptor α- and β-chains with preserva-tion of near-physiological T-cell function," Nature Biomedical Engineering, (2019).

* cited by examiner

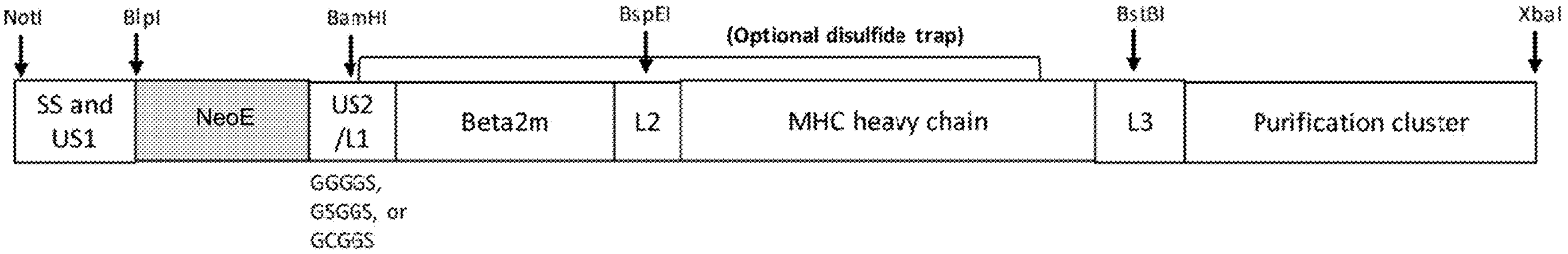
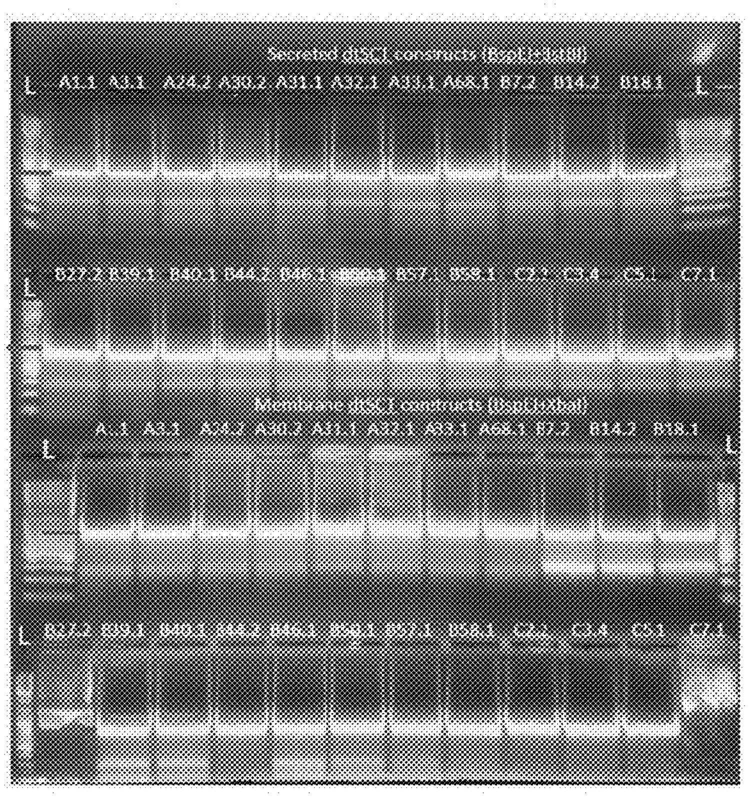
Rapid cloning of off-the-shelf MHC comPACT allele templates by PCR and insertion
| | | |
|---|---|---|
| HLA-A*01:01 | HLA-B*07:02 | HLA-C*02:02 |
| HLA-A*02:01 | HLA-B*14:02 | HLA-C*03:04 |
| HLA-A*03:01 | HLA-B*18:01 | HLA-C*05:01 |
| HLA-A*24:02 | HLA-B*27:02 | HLA-C*07:01 |
| HLA-A*30:02 | HLA-B*39:01 | |
| HLA-A*31:01 | HLA-B*40:01 | |
| HLA-A*32:01 | HLA-B*44:02 | |
| HLA-A*33:01 | HLA-B*46:01 | |
| HLA-A*68:01 | HLA-B*50:01 | |
| | HLA-B*57:01 | |
| | HLA-B*58:01 | |
FIG. 2

| Construct | Yield (from NiNTA+SEC) |
|---|---|
| 10 (neo12) | 18.6 mg |
| 15 (neo12) | 11.4 mg |
| 64 (CMV) | 17.9 mg |
| 65 (EBV) | 1.9 mg |
| 66 (Flu) | 2.3 mg |
| 67 (HBV) | 21.9 mg |
| 80 (Mart_ELA) | 16.1 mg |
| 83 (NY_QV) | 8.7 mg |

1. Untreated comPACT
2. BirA treated comPACT (biotinylated)
3. BirA treated and then TEV treated comPACT (biotinylated, $His_6$ tag cleaved)

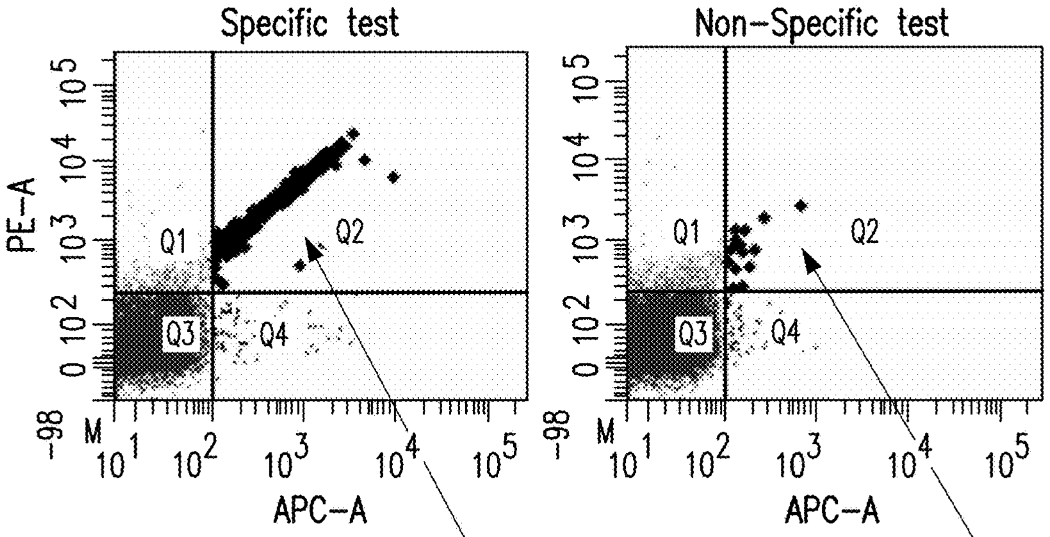

| | S/N |
|---|---|
| Signal Test 1 | 29 |
| Signal Test 2 | 60 |
| Signal Test 3 | 246 |
| Signal Test 4 | 234 |
| Signal Test 5 | 161 |
| Signal Test 6 | 129 |
| Signal Test 7 | 309 |
| Signal Test 8 | 275 |
| Signal Test 9 | 86 |
| Signal Test 10 | 251 |
| Signal Test 11 | 1 |
| Signal Test 12 | 124 |
| Signal Test 13 | 193 |
| Signal Test 14 | 93 |
| Signal Test 15 | 134 |
| Signal Test 16 | 253 |
| Signal Test 17 | 119 |
| Signal Test 18 | 138 |
| Signal Test 19 | 101 |
| Signal Test 20 | 141 |
| Signal Test 21 | 173 |
| Signal Test 22 | 140 |
| Average | 162 |

| | S/N |
|---|---|
| Noise Test 1 | 1.7 |
| Noise Test 2 | 1.1 |
| Noise Test 3 | 6.6 |
| Noise Test 4 | 1.5 |
| Noise Test 5 | 1.5 |
| Noise Test 6 | 1.1 |
| Noise Test 7 | 1.4 |
| Noise Test 8 | 1.7 |
| Noise Test 9 | 1.5 |
| Noise Test 10 | 1.6 |
| Noise Test 11 | 1.1 |
| Noise Test 12 | 1.4 |
| Noise Test 13 | 1.6 |
| Noise Test 14 | 1.0 |
| Signal Test 15 | 1.4 |
| Noise Test 16 | 1.6 |
| Noise Test 17 | 1.1 |
| Noise Test 18 | 1.7 |
| Noise Test 19 | 1.7 |
| Noise Test 20 | 1.2 |
| Noise Test 21 | 1.4 |
| Noise Test 22 | 1.4 |
| Average | 1.7 |

FIG. 31

| PACTID | EXPID | well.position | TRA | TRB | Sample. Name | Gene | peptideTumor | HLA | TCR ID | TCR (S/N1>10) |
|---|---|---|---|---|---|---|---|---|---|---|
| PACT032 | 846 | Plate01-F08 | CAVRDLYSSASKIIF | CASSYKGPEAFF | PACT032_T_194481_04_S_2_HLA-A02:01 | NEDD4 | ITFHDMESV | HLA-A02:01 | PACT032-TCR75 | 1 |

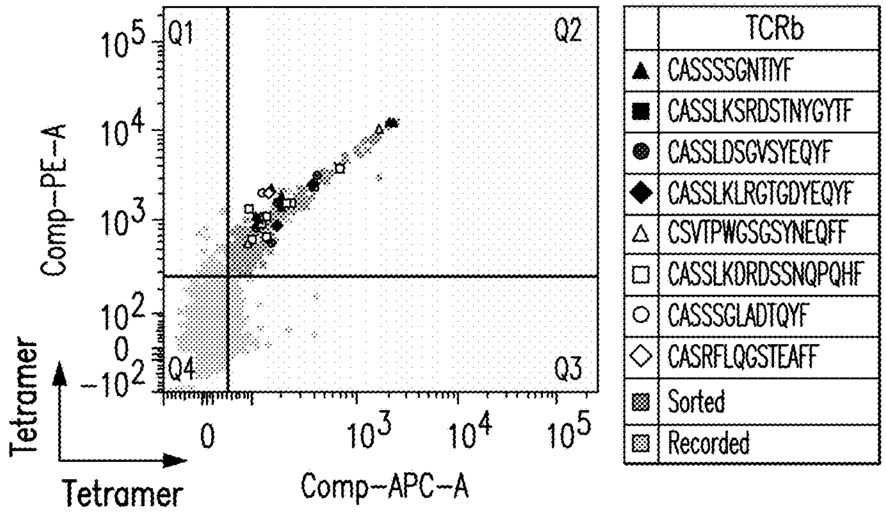

FIG. 34A

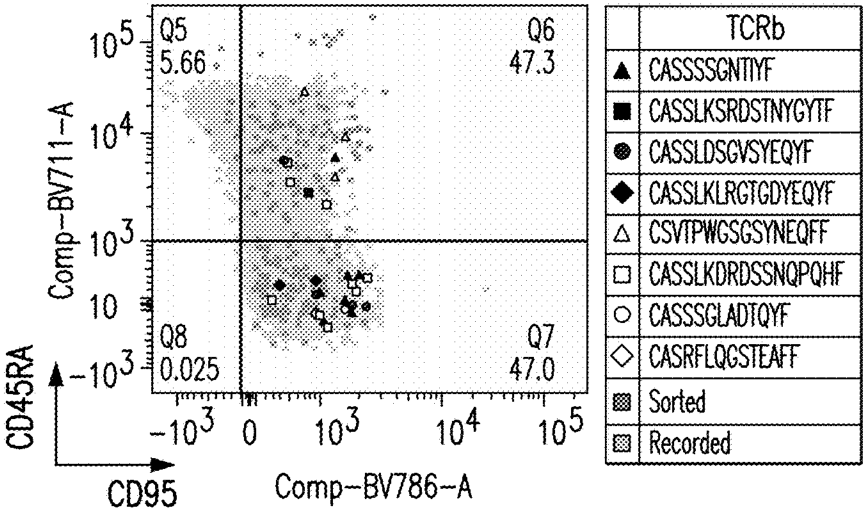

FIG. 34B

| PACTID | TRA | TRB | Gene | peptideTumor | HLA | TCR ID | TCR (S/N1>10) | TCR (S/N2>10) | TCR (S/N2<10) | Avg S/N1 | Avg S/N2 |
|---|---|---|---|---|---|---|---|---|---|---|---|
| PACT077 | CAVPQTSGAGSYQLTF | CASSSSGNTIYF | CDKL2 | IYNIIVTTL | HLA-A24:02 | PACT077-TCR135/138 | 7 | | 0 | 43.4 | 45.3 |
| PACT077 | CAVRTNYGGSQGNLIF | CASSLKSRDSTNYGYTF | SLC38A1 | EYIPGTTFL | HLA-A24:02 | PACT077-TCR136 | 1 | | 0 | 11.6 | 11.6 |
| PACT077 | CAVRLTGGNKLTF | CASSLDSGVSYEQYF | SLC38A1 | EYIPGTTFL | HLA-A24:02 | PACT077-TCR137/145 | 4 | | 0 | 29.3 | 29.3 |
| PACT077 | CALANQAGTALIF | CASSLKLRGTGDYEQYF | SLC38A1 | EYIPGTTFL | HLA-A24:02 | PACT077-TCR139 | 2 | | 0 | 45.1 | 45.1 |
| PACT077 | CAYRNFGNEKLTF | CSVTPWGSGSYNEQFF | PARK2 | KTSVALHLI | HLA-A24:01 | PACT077-TCR140/144 | 2 | | 0 | 19.0 | 19.0 |
| PACT077 | CAVRGRDSNYQLIW | CASSLKDRDSSNQPQHF | SLC38A1 | EYIPGTTFL | HLA-A24:02 | PACT077-TCR142 | 7 | | 0 | 25.2 | 25.2 |
| PACT077 | CAVNSNYQLIW | CASSSGLADTQYF | MADD | HLSLELLGVD | HLA-A24:01 | PACT077-TCR143 | | 1 | 0 | 1.4 | 21.1 |
| PACT077 | CAVWPNNNDMRF | CASRFLQGSTEAFF | SLC38A1 | DEYIPGTTF | HLA-B18:01 | PACT077-TCR164 | | 1 | 0 | 1.9 | 32.5 |

FIG. 34C

★ TCR clones detected in both PBMC and TILs

CDKL2: serine/threonine protein kinase. SLC38A1: Glutamine transporter. MADD:TNF-α receptor for apoptosis. PARK2: ubiquitin ligase.

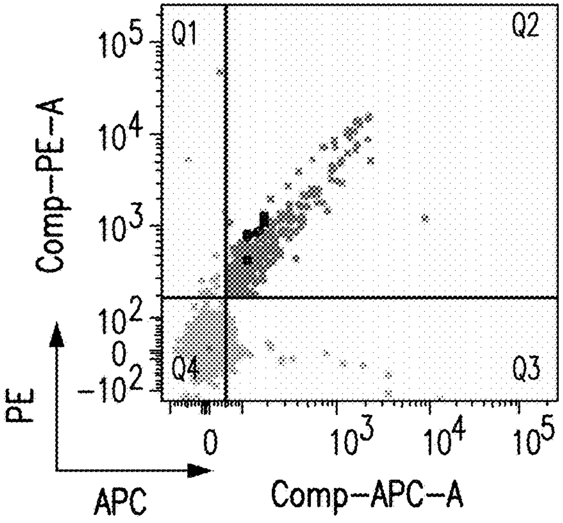

FIG. 37A

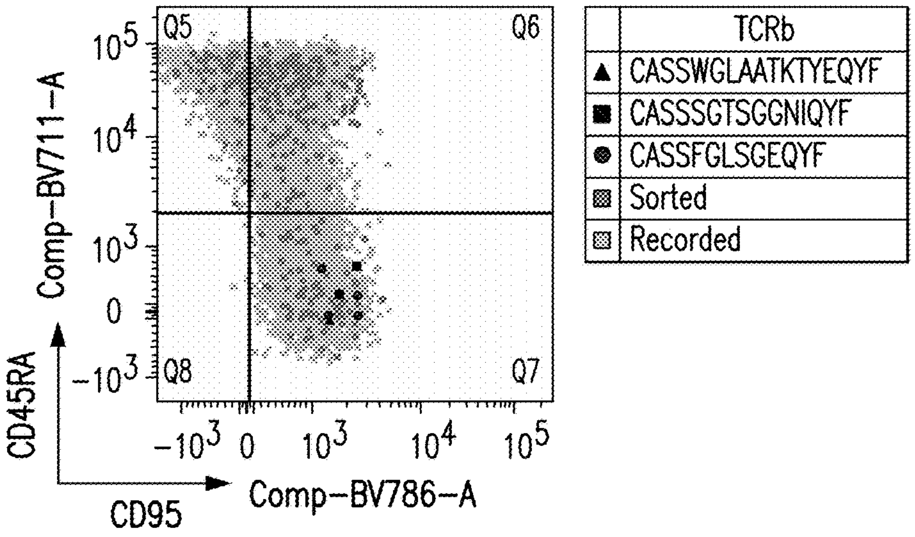

FIG. 37B

| Well ID | PE S/N | APC S/N | PE/APC Ratio | top1.NeoAg | top2.NeoAg | tra.CDR3 | trb.CDR3 | Gene | peptideTumor | HLA | TCR ID |
|---|---|---|---|---|---|---|---|---|---|---|---|
| Plate01-G06 | 50.25 | 3477.40 | 69.20 | LQEQVALKY | LTRPFNFVY | CAPRGDAGNMLTF | CASSLSDGPQPQHF | PPFIBP2 | LQEQVALKY | HLA-A01:01 | |
| Plate01-H06 | 48.16 | 1.60 | 30.10 | LQEQVALKY | LQEQVALKY | CLVGDNNNDMRF | CASSLEAGSTYEQYF | PPFIBP2 | LQEQVALKY | HLA-A01:01 | |
| Plate02-A06 | 37.06 | 28.47 | 1.30 | RCSPEQLKKAW | RCSPEQLKKAW | CAVRDSMEYGNKLVF | CASSSGTSGGNIQYF | PLEKHG3 | RCSPEQLKKAW | HLA-B57:01 | PACT049-TCR166 |
| Plate03-B04 | 35.87 | 14.07 | 2.55 | RCSPEQLKKAW | RCSPEQLKKAW | CAVRDSMEYGNKLVF | CASSSGTSGGNIQYF | PLEKHG3 | RCSPEQLKKAW | HLA-B57:01 | PACT049-TCR166 |
| Plate02-F08 | 66.18 | 42.22 | 1.57 | RCSPEQLKKAW | RCSPEQLKKAW | CAVRDSDNYGQNFVF | CASSWGLAATKTYEQYF | PLEKHG3 | RCSPEQLKKAW | HLA-B57:01 | PACT049-TCR165 |
| Plate02-A04 | 42.22 | 14.36 | 2.94 | RCSPEQLKKAW | RCSPEQLKKAW | CASLGAGGTSYGKLTF | CASSFGLSGEQYF | PLEKHG3 | RCSPEQLKKAW | HLA-B57:01 | PACT049-TCR167 |
| Plate01-B03 | 90.62 | 56.00 | 1.62 | RCSPEQLKKAW | RCSPEQLKKAW | CASLGAGGTSYGKLTF | CASSFGLSGEQYF | PLEKHG3 | RCSPEQLKKAW | HLA-B57:01 | PACT049-TCR167 |
| Plate02-H08 | 26.75 | 13.52 | 1.98 | RCSPEQLKKAW | RCSPEQLKKAW | CASLGAGGTSYGKLTF | CASSFGLSGEQYF | PLEKHG3 | RCSPEQLKKAW | HLA-B57:01 | PACT049-TCR167 |
| Plate03-E11 | 13.14 | 11.80 | 1.11 | RCSPEQLKKAW | RCSPEQLKKAW | CASLGAGGTSYGKLTF | CASSFGLSGEQYF | PLEKHG3 | RCSPEQLKKAW | HLA-B57:01 | PACT049-TCR167 |

FIG. 37C

| PACT ID | HLA- type | | | | | | | | | Cancer | Number of Targets | TCRs found in TILs |
|---|---|---|---|---|---|---|---|---|---|---|---|---|
| | A02:01 | A24:02 | B57:01 | A03:01 | C02:02 | B18:01 | A01:01 | C05:01 | A11:01 | | | |
| PACT037 | 0 | 0 | 0 | 0 | 2 | 0 | 0 | 0 | 0 | bladder cancer | 1 | 0 |
| PACT036 | 0 | 0 | 0 | 2 | 0 | 0 | 0 | 0 | 0 | Bladder | 1 | 0 |
| PACT035 | 7 | 0 | 0 | 0 | 0 | 0 | 0 | 0 | 0 | colorectal cancer | 1 | 0 |
| PACT049 | 0 | 0 | 3 | 0 | 0 | 0 | 0 | 0 | 0 | colorectal cancer | 1 | 0 |
| PACT052 | 0 | 0 | 1 | 0 | 0 | 0 | 0 | 0 | 0 | colorectal cancer | 1 | 0 |
| PACT053 | 0 | 0 | 0 | 1 | 0 | 0 | 0 | 0 | 0 | colorectal cancer | 1 | 0 |
| PACT032 | 1 | 0 | 0 | 0 | 0 | 0 | 0 | 0 | 0 | melanoma | 1 | 0 |
| PACT077 | 2 | 5 | 0 | 0 | 0 | 1 | 0 | 0 | 0 | melanoma | 5 | 4 |
| PACT078 | 0 | 0 | 0 | 0 | 0 | 0 | 1 | 0 | 0 | melanoma | 1 | 1 |
| PACT133 | 0 | 0 | 0 | 2 | 0 | 0 | 0 | 0 | 0 | melanoma | 1 | 0 |
| PACT131 | 0 | 0 | 0 | 0 | 0 | 0 | 0 | 1 | 3 | endometrial | 3 | 0 |
| PACT056 | 0 | 0 | 0 | 0 | 0 | 0 | 0 | 0 | 0 | colorectal cancer | 0 | 0 |
| PACT095 | 0 | 0 | 0 | 0 | 0 | 0 | 0 | 0 | 0 | colorectal cancer | 0 | 0 |

FIG. 38B

PACT157 pMMR Colorectal Cancer

| Gene | MAP3K7 | DYNC2H1 | PRLHR |
|---|---|---|---|
| HLA | A02:01 | A02:01 | C06:02 |
| neoE | TLY(D)HQLQPL | LLFGDLLS(R)VA | SVKLH(R)NRW |

PACT132 pMMR Colorectal Cancer

| Gene | CCT7 | ZNF200 |
|---|---|---|
| HLA | A68:02 | C12:03 |
| neoE | ETIKNPR**L(S)**TV | KQSFILRV**L(P)** |

PACT31 Endometrial Cancer

| Gene | TANC1 | KIF21B | PIK3CA | HIGD2A |
|---|---|---|---|---|
| HLA | C05:01 | A11:01 | A11:01 | B35:01 |
| neoE | STDSPS(C)STL | ARSVSSIM(V)R | RA(D)IDKIYVR | LATAAAI(L)TYG |

NeoTCR–T cell: Tumor cell ratio = 1:1 PACT476 (melanoma)–TCR219, in collaboration with PACT

COMPOSITIONS AND METHODS FOR IDENTIFICATION OF ANTIGEN SPECIFIC T CELLS

CROSS REFERENCE TO RELATED APPLICATIONS

This application is a divisional application of U.S. patent application Ser. No. 16/788,745, filed on Feb. 12, 2020, which claims priority to U.S. Provisional Application No. 62/804,649, filed on Feb. 12, 2019, U.S. Provisional Application No. 62/826,823, filed on Mar. 29, 2019, U.S. Provisional Application No. 62/876,380, filed on Jul. 19, 2019, and U.S. Provisional Application No. 62/867,165, filed on Jun. 26, 2019, the contents of each of which are incorporated by reference in their entirety, and to each of which priority is claimed.

SEQUENCE LISTING

A Sequence Listing conforming to the rules of WIPO Standard ST.26 is hereby incorporated by reference. Said Sequence Listing has been filed as an electronic document via EFS-Web in ASCII format encoded as XML. The electronic document, created on Feb. 27, 2023, is entitled "087520.0281_ST26.xml", and is 441,275 bytes in size. The Sequence Listing, electronically filed herewith, does not extend beyond the scope of the specification, and thus does not contain new matter.

BACKGROUND

T cells are the primary mediators of adaptive immunity. Directed by the specificity of each T cell's unique T cell receptor (TCR), T cells regulate autoimmunity, help activate B cells and innate effectors, and directly kill infected and cancerous cells in a precisely targeted manner. Each TCR recognizes a ligand presented by a major histocompatibility complex (MHC) molecule on target cells. Identification of relevant peptide-MHC complex ligands plays a role in understanding immune responses to tumors and pathogens. MHC complex ligands are also valuable for understanding responses to self and dietary antigens. This understanding enables clinically beneficial immunotherapies (e.g. TCR gene transfer and vaccines) that initiate, amplify, or attenuate immune responses to target antigens.

Mutated 'neoepitopes' are important targets of endogenous and engineered immune responses to cancer. Neoepitope-reactive tumor-infiltrating leukocytes (TILs) are present in the endogenous repertoire and regress tumors upon adoptive transfer. Likewise, tumor mutational burden predicts the clinical effectiveness of CTLA-4 or PD-1 blockade, suggesting these checkpoint inhibition strategies affect tumor regression by unleashing neoepitope-reactive T cells. Because neoepitopes result from somatic mutations in tumor cells, they are not generally presented by thymic epithelial cells to induce central tolerance. Thus, T cell responses directed at these neoepitopes are tumor-specific, likely highly-affinity, and patient-specific (i.e. private). From a clinical standpoint, this presents an opportunity and a challenge: neoepitopes are excellent targets for immunotherapy, but TCR isolation methods should be sufficiently high-throughput to enable therapeutic application on a clinically-useful scale.

There is an unmet need for rapid and robust TCR ligand discovery technologies for both basic and translational research. Peptide-MHC multimers enable sorting of T cells according to the antigenic specificity of their TCRs, an important step in isolating tumor-specific TCRs for gene therapy. A typical current peptide-MHC production protocol begins with solid-phase synthesis of the peptide ligand(s) of interest. In parallel, the universal $\beta_2$-microglobulin and relevant MHC class I molecules are heterologously expressed in *E. coli*, yielding misfolded inclusion bodies. Each peptide is added to a refolding reaction containing $\beta_2$-microglobulin and the relevant MHC class I molecule. Finally, the portion of ternary complex that refolds correctly can be purified and formulated for use in Peptide-MHC multimer production. To facilitate parallel production of a particular MHC molecule with many different peptide ligands, Schumacher and colleagues devised a photocleavable peptide that binds a particular MHC molecule as a conditional ligand. A single refolding reaction is performed to generate that MHC molecule bound to its conditional ligand. Upon exposure to UV light, the conditional ligand is cleaved and exchanged for a desired peptide present in excess. Many such exchange reactions can be performed in parallel, enabling the construction of a pMHC library for that particular MHC allele. Even so, this state-of-the-art technology has challenging limitations. First, the production, purification, and refolding of MHC molecules expressed in *E. coli* inclusion bodies is laborious and produces low yields of properly folded peptide-MHC complex. Second, the turnaround time (weeks) for commercial peptide synthesis is at odds with timescales optimal in the context of personalized on-demand TCR gene therapies directed at patient-specific neoepitopes. Third, many predicted ligands cannot be used to screen T cells through this approach because the biophysical properties (e.g. hydrophobicity) of the peptide precludes its synthesis or exchange. Fourth, exchange efficiency is generally poor (<50% exchange efficiency for a majority of predicted HLA-binding peptides). The resulting mixture of properly folded exchanged MHC and misfolded unliganded MHC results in multimer staining with low signal to noise, an issue that is exacerbated when screening T cells with a multiplexed pool of peptide-MHC reagents. Fifth, the design and validation of conditional ligands for each new MHC allele is a laborious and non-robust undertaking. As the MHC locus is the most multi-allelic locus in the human genome, this is a major hindrance to implementing neoepitope-targeted gene therapies across patients of varying MHC haplotypes. Together, these limitations underscore the need for novel technologies in this field. Disclosed herein are various compositions and processes for producing peptide-MHC multimers that address these limitations.

SUMMARY

The present disclosure provides compositions and methods for identifying neoepitopes, identifying and isolating T cell receptors, engineering of primary cells to express specific T cell receptors, expanding engineered T cells and for treatment of disorders using cell therapy. In various embodiments, the present invention provides improved cell therapy methods and compositions for identifying neoepitopes, identifying and isolating T cell receptors, engineering of primary cells to express specific T cell receptors, expanding engineered T cells and for treatment of proliferative diseases, disorders, and conditions.

In one aspect, provided herein is a method for identifying antigen specificity of a T cell, comprising providing two or more distinct particle sets, each distinct particle set comprising a unique antigen peptide and at least one defined barcode operably associated with the identity of the antigen peptide, and each set comprises a first particle comprising a first identifying label and a second particle comprising a second identifying label distinct from the first identifying label; providing a sample known or suspected to comprise one or more T cells; contacting the sample with the two or more particle sets, wherein the contacting comprises providing conditions sufficient for a single T cell to bind to the unique antigen of at least one particle set; isolating one or more T cells that are bound to the particle set(s) by their associated first and second identifying label; performing an assay to identify one or more barcodes bound to the particle set that is bound to the isolated T cell; determining a ratio of the barcodes bound to the isolated T cell wherein the ratio is calculated by identifying a first copy number of a predominant barcode and a second copy number of a distinct barcode and dividing the first copy number by the second copy number; and identifying the antigen specificity of the T cell based on the ratio.

In one aspect, provided herein is a method for identifying antigen specificity of a T cell, comprising: obtaining or having obtained at least one antigen-specific T cell bound to two or more distinct particle sets, each distinct particle set comprising a unique antigen peptide and at least one defined barcode operably associated with the identity of the antigen peptide, wherein each set comprises a first particle comprising a first identifying label and a second particle comprising a second identifying label distinct from the first identifying label; performing or having performed at least one assay to identify one or more barcodes detectably bound to the particle set that is bound to the T cell; and determining or having determined a ratio of the barcodes bound to the T cell that identifies the antigen specificity of the T cell, wherein the ratio is calculated by identifying a first copy number of a predominant barcode and a second copy number of a distinct barcode and dividing the first copy number by the second copy number.

In one aspect, provided herein is a method for identifying antigen specificity of a T cell, comprising: obtaining or having obtained a dataset comprising data associated with one or more barcodes detectably bound to the particle set that is bound, directly or indirectly, to the T cell, wherein the one or more barcodes are each operably associated with a unique antigen peptide; and determining or having determined a ratio of the barcodes bound to the T cell that identifies the antigen specificity of the T cell, wherein the ratio is calculated by identifying a first copy number of a predominant barcode and a second copy number of a distinct barcode and dividing the first copy number by the second copy number.

In some embodiments, the dataset comprises the one or more barcodes and the one or more barcode copy numbers.

In some embodiments, the unique antigen peptide is the same for each distinct particle set.

In some embodiments, the first particle comprises a first barcode and the second particle comprises a second barcode distinct from the first barcode, wherein the first and second barcodes are associated with the identity of the antigen.

In some embodiments, the ratio of the barcodes corresponds to the antigen specificity of the isolated T cell.

In some embodiments, the isolated T cell is identified as an antigen-specific T cell if the ratio of the barcodes is above a threshold.

In some embodiments, the threshold is at least or greater than 2.

In some embodiments, the threshold is at least or greater than 5.

In some embodiments, the threshold is at least or greater than 10.

In some embodiments, the threshold is between 2 and 5.

In some embodiments, the threshold is between 5 and 10.

In some embodiments, the threshold is at least or greater than 2, 3, 4, 5, 6, 7, 8, 9, 10, 2-5, 3-6, 4-7, 5-8, 5-10, 7-10, or greater than 10.

In some embodiments, the assay is a nucleotide-based assay.

In some embodiments, the nucleotide-based assay is a PCR assay, an RT-PCR assay, a sequencing assay, or a hybridization assay.

In some embodiments, the assay determines the sequence(s) of the one or more barcodes.

In some embodiments, the assay determines the sequence(s) and copy number(s) of the one or more barcodes.

In some embodiments, the method further comprises obtaining the T cell receptor (TCR) CDR sequences.

In some embodiments, the method further comprises obtaining the TCR alpha and beta chain sequences.

In some embodiments, the antigen specificity of the T cell comprises each of (a) the sequence of the antigen peptide and (b) the TCR sequences of the bound T cell.

In some embodiments, the first identifying label of each first particle is the same in each set.

In some embodiments, the second identifying label of each second particle is the same in each set.

In some embodiments, the first identifying label of each first particle is the same in each set, and wherein the second identifying label of each second particle is the same in each set.

In some embodiments, the first and second identifying labels are fluorophores.

In some embodiments, the first fluorophore is allophycocyanin (APC).

In some embodiments, the second fluorophore is phycoerythrin (PE).

In some embodiments, the particle set comprises a third particle comprising a third barcode distinct from the first and second barcode, wherein the first, second, and third barcodes are associated with the identity of the antigen.

In some embodiments, the unique antigen peptide is selected from the group consisting of: a tumor antigen peptide, a neoantigen peptide, a tumor neoantigen peptide, a viral antigen peptide, a bacterial antigen peptide, a phosphoantigen peptide, and a microbial antigen peptide.

In some embodiments, the unique antigen peptide is a neoantigen peptide.

In some embodiments, wherein the neoantigen is derived from tumor sequencing data from a subject used to identify one or more somatic mutations present in the data relative to wild-type.

In some embodiments, an in silico predictive algorithm is used to determine the neoantigen.

In some embodiments, the predictive algorithm further comprises an MHC binding algorithm to predict binding between the neoantigen and an MHC peptide.

In some embodiments, the sample is selected from a blood sample, a bone marrow sample, a tissue sample, a tumor sample, or a peripheral blood mononuclear cell (PBMC) sample.

In some embodiments, the sample is a PBMC sample.

In some embodiments, the sample is a tumor sample.

In some embodiments, the sample is a bone marrow sample.

In some embodiments, the T cell is a human T cell.

In some embodiments, the T cell is a CD8+ T cell.

In some embodiments, the CD8+ T cell is a human CD8+ T cell.

In some embodiments, the method comprises a library of distinct particle sets.

In some embodiments, the library comprises 2 to 500 distinct particle sets.

In some embodiments the library comprises at least 60 distinct particle sets.

In some embodiments, each particle comprises an MHC peptide.

In some embodiments, the MHC peptide is a mammalian MEW peptide.

In some embodiments, the MHC peptide is a human MHC peptide.

In some embodiments, the MHC peptide is a class I HLA peptide.

In some embodiments, the HLA peptide comprises an HLA-A, HLA-B, or HLA-C peptide.

In some embodiments, the HLA peptide comprises HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, or HLA-C*17:01.

In some embodiments, the HLA peptide comprises a Y84A or a Y84C mutation.

In some embodiments, each particle comprises an HLA I peptide and a β2M peptide.

In some embodiments, the β2M peptide is a mammalian β2M peptide.

In some embodiments, the β2M peptide is a human β2M peptide.

In some embodiments, the β2M peptide comprises a mutation to allow or increase binding to thiol dyes.

In some embodiments, the mutation is S88C.

In some embodiments, each particle comprises a polypeptide comprising, in an amino to carboxyl terminus orientation, (i) the antigen peptide, (ii) a β2M peptide, and (iii) an MHC peptide.

In some embodiments, the polypeptide further comprises a first universal target peptide before the antigen peptide, and a second universal target peptide that is distinct from the first universal target peptide between the antigen peptide and the β2M peptide.

In some embodiments, each particle comprises a polypeptide comprising, in an amino to carboxyl terminus orientation, (i) a first universal target peptide, (ii) the antigen peptide, (iii) a second universal target peptide that is distinct from the first universal target peptide, (iv) a β2M peptide, and (v) an MHC peptide.

In some embodiments, the antigen peptide is 7-15 amino acids, 7-10, 8-9, 7, 8, 9, 10, 11, 12, 13, 14, or 15 amino acids in length.

In some embodiments, the polypeptide comprising the unique antigen peptide is biotinylated.

In some embodiments, each particle in a distinct particle set comprises a streptavidin core and at least one copy of the unique antigen peptide.

In some embodiments, the particle comprises one, two, three, or four copies of the unique antigen peptide.

In one aspect, provided herein is a library comprising two or more distinct particle sets each comprising a unique antigen peptide and a defined barcode operably associated with the identity of the antigen peptide, wherein each set comprises a first particle comprising a first identifying label and a second particle comprising a second identifying label distinct from the first identifying label.

In some embodiments, the identifying label is a fluorophore.

In some embodiments, the fluorophore is APC or PE.

In one aspect, provided herein is a particle comprising a tetrameric solid support bound to a unique barcode and three or fewer attached polypeptide molecules, the polypeptide molecules comprising in an amino to carboxyl terminus orientation, (i) an antigenic peptide, (ii) a β2M peptide, and (iii) an MHC peptide, wherein the barcode is operably associated with the identity of the antigen peptide.

In some embodiments, the polypeptide further comprises a first universal target peptide before the antigen peptide, and a second universal target peptide that is distinct from the first universal target peptide between the antigen peptide and the β2M peptide.

In some embodiments, the solid support is a streptavidin core.

In some embodiments, the polypeptide molecules are biotinylated.

In some embodiments, the polypeptide molecules are bound to the streptavidin core via a biotin-streptavidin interaction.

In some embodiments, the particle further comprises an identifying label.

In some embodiments, the identifying label is a fluorophore.

In some embodiments, the fluorophore is APC or PE.

In one aspect, provided herein is a library comprising the particles, wherein the library comprises two or more distinct particles, wherein each distinct particle comprises a unique antigen peptide.

In one aspect, provided herein is a method of monitoring an immune repertoire in a subject, comprising: providing two or more distinct particle sets, each distinct particle set comprising a unique antigen peptide and at least one defined barcode operably associated with the identity of the antigen peptide, and each set comprises a first particle comprising a first identifying label and a second particle comprising a second identifying label distinct from the first identifying label; providing a sample known or suspected to comprise one or more T cells, wherein the sample is obtained from a subject over time; contacting the sample with the two or more particle sets, wherein the contacting comprises providing conditions sufficient for a single T cell to bind to the unique antigen of at least one particle set; isolating one or more T cells associated with the first and second identifying label; performing an assay to identify one or more barcodes bound to the isolated T cell; determining a ratio of the barcodes bound to the isolated T cell wherein the ratio is calculated by identifying a first copy number of a predominant barcode and a second copy number of a distinct barcode from step (e) and dividing the first copy number by the second copy number; identifying the antigen specificity of the T cell based on the ratio; and monitoring changes in the antigen specific T cells identified by the method in the subject.

In some embodiments, the first and second identifying labels are fluorophores.

In some embodiments, the fluorophore is APC or PE.

In one aspect, provided herein is a method of monitoring an immune repertoire in a subject, comprising obtaining or having obtained a dataset comprising data associated with one or more barcodes detectably bound, directly or indirectly, to the T cell, wherein the one or more barcodes are each operably associated with a unique antigen peptide; determining or having determined a ratio of the barcodes bound to the T cell that identifies the antigen specificity of the T cell, wherein the ratio is calculated by identifying a first copy number of a predominant barcode and a second copy number of a distinct barcode from step (a) and dividing the first copy number by the second copy number; identifying a sequence of the unique antigen peptide bound to an antigen specific T cell; and monitoring changes in the antigen specific T cells identified by the method in the subject.

In some embodiments, the dataset comprises the one or more barcodes and the one or more barcode copy numbers.

In some embodiments, the unique antigen peptide is the same for each distinct particle set.

In some embodiments, monitoring the changes in the T cells comprises administering to the subject a soluble, labeled antigen-specific TCR.

In some embodiments, the subject is administered an immunotherapy based upon the changes in the identified antigen-specific T cells.

In some embodiments, the immunotherapy is a checkpoint inhibitor.

In some embodiments, the checkpoint inhibitor is an anti-PD-1 antibody, an anti-PD-L1 antibody, or an anti-CTLA-4 antibody. In some embodiments the anti-PD-1 antibody is selected from the group comprising pembrolizumab, nivolumab, and cemiplimab. In some embodiments the anti-PD-L1 antibody is selected from the group comprising atezolizumab, avelumab, and durvalumab. In some embodiments, the anti-CTLA4 antibody is ipilimumab. In some embodiments the checkpoint inhibitor is an anti-TIGIT antibody. In some embodiments, the anti-TIGIT antibody is selected from the group comprising AB154 (Arcus), tiragolumab (Genentech), BMS-986297 (BMS), MK-7684 (Merck), and etigilimab (OncoMed).

In one aspect, provided herein is a method of identifying an antigen, comprising providing two or more distinct particle sets, each distinct particle set comprising a unique antigen peptide and at least one defined barcode operably associated with the identity of the antigen peptide, and each set comprises a first particle comprising a first identifying label and a second particle comprising a second identifying label distinct from the first identifying label; providing a sample known or suspected to comprise one or more T cells; contacting the sample with the two or more particle sets, wherein the contacting comprises providing conditions sufficient for a single T cell to bind to the unique antigen of at least one particle set; isolating one or more T cells associated with the first and second identifying labels; performing an assay to identify one or more barcodes bound to the isolated T cell; determining a ratio of the barcodes bound to the isolated T cell wherein the ratio is calculated by identifying a first copy number of a predominant barcode and a second copy number of a distinct barcode from step (e) and dividing the first copy number by the second copy number; and identifying a sequence of the unique antigen peptide bound to an antigen specific T cell.

In some embodiments, the first and second identifying labels are fluorophores.

In some embodiments, the fluorophore is APC or PE.

In one aspect, provided herein is a method of identifying an antigen, comprising obtaining or having obtained a dataset comprising data associated with one or more barcodes detectably bound, directly or indirectly, to the T cell, wherein the one or more barcodes are each operably associated with a unique antigen peptide; determining or having determined a ratio of the barcodes bound to the T cell, wherein the ratio is calculated by identifying a first copy number of a predominant barcode and a second copy number of a distinct barcode from step (a) and dividing the first copy number by the second copy number; and identifying a sequence of the unique antigen peptide bound to an antigen specific T cell.

In some embodiments, step (a) comprises obtaining a T cell-based sample and assaying it to obtain the dataset.

In some embodiments, the dataset comprises the one or more barcodes and the one or more barcode copy numbers.

In some embodiments, the unique antigen peptide is the same for each distinct particle set.

In one aspect, provided herein is a method of identifying an HLA and peptide complex, comprising providing two or more distinct particle sets, each distinct particle set comprising a unique antigen peptide and at least one defined barcode operably associated with the identity of the antigen peptide, and each set comprises a first particle comprising a first identifying label and a second particle comprising a second identifying label distinct from the first identifying label; providing a sample known or suspected to comprise one or more T cells; contacting the sample with the two or more particle sets, wherein the contacting comprises providing conditions sufficient for a single T cell to bind to the unique antigen of at least one particle set; isolating one or more T cells associated with the first and second identifying labels; performing an assay to identify one or more barcodes bound to the isolated T cell; determining a ratio of the barcodes bound to the isolated T cell wherein the ratio is calculated by identifying a first copy number of a predominant barcode and a second copy number of a distinct barcode from step (e) and dividing the first copy number by the second copy number; and identifying the HLA and peptide complex bound to an antigen specific T cell.

In some embodiments, the first and second identifying labels are fluorophores.

In some embodiments, the fluorophore is APC or PE.

In one aspect, provided herein is a method of identifying an HLA and peptide complex, comprising obtaining or having obtained a dataset comprising data associated with one or more barcodes detectably bound, directly or indirectly, to the T cell, wherein the one or more barcodes are each operably associated with a unique antigen peptide; determining or having determined a ratio of the barcodes bound to the T cell, wherein the ratio is calculated by identifying a first copy number of a predominant barcode and a second copy number of a distinct barcode from step (a) and dividing the first copy number by the second copy number; and identifying the HLA and peptide complex bound to an antigen specific T cell.

In some embodiments, step (a) comprises obtaining a T cell-based sample and assaying it to obtain the dataset.

In some embodiments, the dataset comprises the one or more barcodes and the one or more barcode copy numbers.

In some embodiments, the unique antigen peptide is the same for each distinct particle set.

In one aspect, provided herein is a method of identifying a subject for treatment with an immunotherapy, comprising providing two or more distinct particle sets, each distinct particle set comprising a unique antigen peptide and at least one defined barcode operably associated with the identity of the antigen peptide, and each set comprises a first particle comprising a first identifying label and a second particle comprising a second identifying label distinct from the first identifying label; providing a sample known or suspected to comprise one or more T cells; contacting the sample with the two or more particle sets, wherein the contacting comprises providing conditions sufficient for a single T cell to bind to the unique antigen of at least one particle set; isolating one or more T cells associated with the first and second identifying labels; performing an assay to identify one or more barcodes bound to the isolated T cell; determining a ratio of the barcodes bound to the isolated T cell wherein the ratio is calculated by identifying a first copy number of a predominant barcode and a second copy number of a distinct barcode from step (e) and dividing the first copy number by the second copy number.

In some embodiments, the first and second identifying labels are fluorophores.

In some embodiments, the fluorophore is APC or PE.

In one aspect, provided herein is a method of identifying a subject for treatment with an immunotherapy, comprising obtaining or having obtained a dataset comprising data associated with one or more barcodes detectably bound, directly or indirectly, to the T cell, wherein the one or more barcodes are each operably associated with a unique antigen peptide; and determining or having determined a ratio of the barcodes bound to the T cell, wherein the ratio is calculated by identifying a first copy number of a predominant barcode and a second copy number of a distinct barcode from step (a) and dividing the first copy number by the second copy number.

In some embodiments, step (a) comprises obtaining a T cell-based sample and assaying it to obtain the dataset.

In some embodiments, the dataset comprises the one or more barcodes and the one or more barcode copy numbers.

In some embodiments, the unique antigen peptide is the same for each distinct particle set.

In some embodiments, the immunotherapy comprises a T cell vaccine, a dendritic cell vaccine, a nucleic acid vaccine, a peptide vaccine, a viral vaccine, a soluble TCR, a TCR-drug conjugate, an antibody, or an antibody-drug conjugate.

In some embodiments, the antibody comprises a monoclonal antibody.

In one aspect, provided herein is a method of identifying a unique TCR sequence, comprising providing two or more distinct particle sets, each distinct particle set comprising a unique antigen peptide and at least one defined barcode operably associated with the identity of the antigen peptide, and each set comprises a first particle comprising a first identifying label and a second particle comprising a second identifying label distinct from the first identifying label; providing a sample known or suspected to comprise one or more T cells; contacting the sample with the two or more particle sets, wherein the contacting comprises providing conditions sufficient for a single T cell to bind to the unique antigen of at least one particle set; isolating one or more T cells associated with the first and second identifying labels; performing an assay to identify one or more barcodes bound to the isolated T cell; determining a ratio of the barcodes bound to the isolated T cell wherein the ratio is calculated by identifying a first copy number of a predominant barcode and a second copy number of a distinct barcode from step (e) and dividing the first copy number by the second copy number; and identifying the unique TCR sequence.

In some embodiments, the first and second identifying labels are fluorophores.

In some embodiments, the fluorophore is APC or PE.

In one aspect, provided herein is a method of identifying a unique TCR sequence, comprising obtaining or having obtained a dataset comprising data associated with one or more barcodes detectably bound, directly or indirectly, to the T cell, wherein the one or more barcodes are each operably associated with a unique antigen peptide; determining or having determined a ratio of the barcodes bound to the T cell, wherein the ratio is calculated by identifying a first copy number of a predominant barcode and a second copy number of a distinct barcode from step (a) and dividing the first copy number by the second copy number; and identifying the unique TCR sequence.

In some embodiments, step (a) comprises obtaining a T cell-based sample and assaying it to obtain the dataset.

In some embodiments, the dataset comprises the one or more barcode sequences and the one or more barcode copy numbers.

In some embodiments, the unique antigen peptide is the same for each distinct particle set.

In some embodiments, the method further comprises manufacturing a soluble TCR polypeptide comprising the identified unique TCR sequence.

In some embodiments, the soluble TCR polypeptide is linked to a label or a drug.

In some embodiments, the method is repeated to identify at least two unique TCR sequences.

In some embodiments, the method further comprises manufacturing a library comprising the at least two unique TCR sequences.

In one aspect, provided herein is a method of treating cancer in a subject, comprising obtaining or having obtained a dataset comprising data associated with one or more barcodes detectably bound, directly or indirectly, to a T cell, wherein the one or more barcodes are each operably associated with a unique antigen peptide; determining or having determined a ratio of the barcodes bound to the T cell that identifies the antigen specificity of the T cell, wherein the ratio is calculated by identifying a first copy number of a predominant barcode and a second copy number of a distinct barcode from step (a) and dividing the first copy number by the second copy number; identifying at least one or both of the T cell's TCR sequences and creating an engineered T cell comprising at least one or both of the TCR sequences; and administering the engineered T cell to the subject.

In some embodiments, the method further comprises administering an immunotherapy.

In some embodiments, the immunotherapy is a checkpoint inhibitor.

In some embodiments, the checkpoint inhibitor is an anti-PD-1 antibody, an anti-PD-L1 antibody, or an anti-CTLA-4 antibody.

In some embodiments, the T cell is autologous.

In some embodiments, the engineered T cell is autologous.

In some embodiments, the unique antigen peptide is presented by HLA class I on the cell surface of the subject's cancer.

In certain embodiments, the presently disclosed subject matter provides methods for processing T cells. In certain embodiments, the methods comprise: (a) contacting a sample with a plurality of distinct particle sets; (b) isolating one or more T cells bound to a particle; (c) identifying the barcode of the particle bound to the isolated T cell; and (d) determining a ratio of each barcode. In certain embodiments, each particle comprises a unique antigen peptide, an operably associated barcode, and at least one identifying label. In certain embodiments, the sample comprises T cells. In certain embodiments, contacting comprises providing conditions suitable for a single T cell to bind to a unique antigen peptide of at least one particle set.

In certain embodiments, the ratio is calculated by identifying a copy number of a first barcode and a copy number of a second barcode and dividing the copy number of the first barcode by the copy number of the second barcode. In certain embodiments, the unique antigen peptide is the same for each distinct particle set. In certain embodiments, each distinct particle set comprises at least one or more barcodes, wherein each barcode is associated with the identity of the antigen peptide. In certain embodiments, the ratio of each barcode corresponds to the antigen specificity of the isolated T cell.

In certain embodiments, the isolated T cell is identified as an antigen-specific T cell if the ratio of the first barcode is above a threshold. In certain embodiments, the threshold is at least or greater than 2, 3, 4, 5, 6, 7, 8, 9, 10, 2-5, 3-6, 4-7, 5-8, 5-10, 7-10, or greater than 10.

In certain embodiments, the identifying the barcode comprises a nucleotide-based assay. In certain embodiments, nucleotide-based assay is a PCR, an RT-PCR, a sequencing, or a hybridization assay. In certain embodiments, the nucleotide-based assay determines a sequence of each barcode. In certain embodiments, the nucleotide-based assay determines a copy number of each barcode. In certain embodiments, the nucleotide-based assay determines (a) a sequence of each barcode and/or (b) a copy number of each barcode.

In certain embodiments, the methods further comprise obtaining a T cell receptor (TCR) CDR sequence. In certain embodiments, the methods further comprise obtaining a TCR gene sequence. In certain embodiments, the TCR gene sequence is a TCR alpha or a TCR beta chain sequence.

In certain embodiments, the methods comprise identifying the antigen specificity of a T cell. In certain embodiments, the antigen specificity of the T cell comprises the sequence of the antigen peptide and the TCR sequences of the bound T cell.

In certain embodiments, the at least one identifying label is the same in each distinct particle set. In certain embodiments, the methods comprise at least two different identifying labels. In certain embodiments, the at least one identifying label is a fluorophore. In certain embodiments, the fluorophore is selected from the group comprising allophycocyanin (APC) and phycoerythrin (PE). In certain embodiments, the at least two different identifying labels are fluorophores, wherein the fluorophores are selected from the group comprising allophycocyanin (APC) and phycoerythrin (PE).

In certain embodiments, the antigen peptide is selected from the group consisting of a tumor antigen, a neoantigen, a tumor neoantigen, a viral antigen, a bacterial antigen, a phospho-antigen, and a microbial antigen. In certain embodiments, the neoantigen is identified from tumor sequencing data from a subject. In certain embodiments, an in silico predictive algorithm is used to determine the neoantigen. In certain embodiments, the predictive algorithm further comprises an MHC binding algorithm to predict binding between the neoantigen and an MHC peptide.

In certain embodiments, the sample is selected from a blood sample, a bone marrow sample, a tissue sample, a tumor sample, or a peripheral blood mononuclear cell (PBMC) sample. In certain embodiments, wherein the T cell is a human T cell. In certain embodiments, the T cell is a $CD8^+$ T cell.

In certain embodiments, the methods comprise a library of distinct particle sets. In certain embodiments, the library comprises 2 to 500 distinct particle sets. In certain embodiments, each particle comprises an MHC peptide. In certain embodiments, the MHC peptide is a human MHC peptide. In certain embodiments, the MHC peptide is a class I HLA peptide. In certain embodiments, the HLA peptide comprises an HLA-A, HLA-B, or HLA-C peptide. In certain embodiments, the HLA peptide comprises HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, or HLA-C*17:01.

In certain embodiments, each particle comprises an HLA peptide and a β2M peptide. In certain embodiments, the β2M peptide is a human β2M peptide. In certain embodiments, the β2M peptide comprises a mutation. In certain embodiments, the mutation is S88C.

In certain embodiments, each particle comprises a polypeptide comprising, in an amino to carboxyl terminus orientation, (i) the antigen peptide, (ii) a β2M peptide, and (iii) an MHC peptide. In certain embodiments, the antigen peptide is 7-15 amino acids, 7-10, 8-9, 7, 8, 9, 10, 11, 12, 13, 14, or 15 amino acids in length. In certain embodiments, the polypeptide is biotinylated. In certain embodiments, the particles are selected from the group consisting of magnetic beads, agarose beads, styrene polymer particles, and dextran polymer particles. In certain embodiments, wherein the particles are streptavidin coated.

In certain embodiments, the presently disclosed subject matter provides methods for monitoring an immune repertoire in a subject. In certain embodiments, the methods comprise monitoring changes in the antigen-specific T cells in the subject. In certain embodiments, the methods comprise administering an immunotherapy to the subject. In certain embodiments, the immunotherapy is an adoptive cell transfer or a checkpoint inhibitor. In certain embodiments, any of the methods disclosed herein are used for monitoring an immune repertoire in a subject.

In certain embodiments, the presently disclosed subject matter provides methods for identifying at least one TCR sequence. In certain embodiments, the at least one TCR sequence is a TCR alpha sequence, a TCR beta sequence, or a combination thereof. In certain embodiments, the methods further comprise manufacturing a soluble TCR polypeptide. In certain embodiments, any of the methods disclosed herein are used for identifying at least one TCR sequence.

In certain embodiments, the presently disclosed subject matter provides libraries of particles. In certain embodiments, the library comprises at least two particle sets. In certain embodiments, each particle set comprises an antigen peptide, a barcode operably associated with the identity of the antigen peptide, and at least one identifying label. In certain embodiments, the at least one identifying label is the same in each particle set. In certain embodiments, at least two different identifying labels in each distinct particle set. In certain embodiments, the at least one identifying label is a fluorophore. In certain embodiments, the fluorophore is selected from the group comprising allophycocyanin (APC) and phycoerythrin (PE). In certain embodiments, the at least two different identifying labels are fluorophores, wherein the fluorophores are selected from the group comprising allophycocyanin (APC) and phycoerythrin (PE).

In certain embodiments, the presently disclosed subject matter further provides particles. In certain embodiments, a particle comprises at least one polypeptide, a barcode, and an identifying label. In certain embodiments, the polypeptide comprises an antigen peptide, a β2M peptide, and an MHC peptide. In certain embodiments, the barcode is operably associated with the identity of the antigen peptide. In certain embodiments, the particle is selected from the group consisting of magnetic beads, agarose beads, styrene polymer particles, and dextran polymer particles. In certain embodiments, the identifying label is a fluorophore. In certain embodiments, the particle is streptavidin coated. In certain embodiments, the polypeptide is labeled.

In certain embodiments, the presently disclosed subject matter further discloses methods of treating cancer in a subject. In certain embodiments, the methods comprise: (a) preparing a plurality of particles each comprising a plurality of labeled polypeptides; (b) contacting the plurality of particles with a plurality of T cells from the subject under conditions suitable for antigen-specific binding of a T cell to the particle; (c) isolating the T cells bound to the particle and identifying the TCR gene sequence of the isolated T cell; (d) preparing a polynucleotide comprising homology arms and at least one TCR gene sequence; (e) recombining the polynucleotide into an endogenous locus of the T cell of the subject; (f) culturing the modified T cell to produce a population of T cells; and (g) administering a therapeutically effective number of the modified T cells to the subject to thereby treat the cancer. In certain embodiments, the polypeptides comprise an antigen peptide, a β2M sequence, an HLA sequence and a detectable label. In certain embodiments, the TCR gene sequence is patient specific. In certain embodiments, the TCR gene sequence is positioned between the homology arms.

In certain embodiments, the presently disclosed subject matter further discloses methods of modifying a cell. In certain embodiments, the methods comprise: (a) introducing into the cell a homologous recombination (HR) template nucleic acid sequence; and (b) recombining the HR template nucleic acid into an endogenous locus of the cell. In certain embodiments, the HR template nucleic acid comprises: (a) first and second homology arms homologous to first and second endogenous sequences of the cell; (b) a T cell receptor (TCR) gene sequence obtained by any of the methods disclosed herein; and (c) a first 2A-coding sequence positioned upstream of the TCR gene sequence and a second 2A-coding sequence positioned downstream of the TCR gene sequence, wherein the first and second 2A-coding sequences code for the same amino acid sequence that are codon-diverged relative to each other. In certain embodiments, the first and second endogenous sequences are homologous to the first and second homology arms of the HR template nucleic acid. In certain embodiments, the TCR gene sequence is positioned between the first and second HR arms. In certain embodiments, the 2A-coding sequence is a P2A-coding sequence. In certain embodiments, the HR template further comprises a sequence coding for a flexible linker. In certain embodiments, the sequence coding for the flexible linker is positioned immediately upstream of the 2A-coding sequences. In certain embodiments, the flexible linker has a Gly Ser Gly amino acid sequence. In certain embodiments, the HR template further comprises a sequence coding for a protease cleavage sequence. In certain embodiments, the protease cleavage sequence is a Furin sequence. In certain embodiments, the protease cleavage sequence is a TEV sequence. In certain embodiments, the protease cleavage sequence is upstream of the second 2A-coding sequence.

In certain embodiments, the presently disclosed subject matter further discloses compositions comprising modified cells. In certain embodiments, the modified cell comprises an exogenous nucleic acid sequence integrated into an endogenous locus. In certain embodiments, the exogenous nucleic acid sequence comprises: (a) a TCR gene sequence; and (b) a first 2A-coding sequence positioned upstream of the TCR gene sequence and a second 2A-coding sequence positioned downstream of the TCR gene sequence. In certain embodiments, the TCR gene sequence is identified by any of the methods disclosed herein. In certain embodiments, the first and second 2A-coding sequences code for the same amino acid sequence that are codon-diverged relative to each other. In certain embodiments, the 2A-coding sequence is a P2A-coding sequence. In certain embodiments, the exogenous nucleic acid sequence further comprises a sequence coding for a flexible linker. In certain embodiments, the sequence coding for the flexible linker is positioned immediately upstream of the 2A-coding sequences. In certain embodiments, the flexible linker has a Gly Ser Gly amino acid sequence. In certain embodiments, the exogenous nucleic acid further comprises a sequence coding for a protease cleavage sequence. In certain embodiments, the protease cleavage sequence is a Furin sequence. In certain embodiments, the protease cleavage sequence is a TEV sequence. In certain embodiments, the protease cleavage sequence is upstream of the second 2A-coding sequence.

BRIEF SUMMARY OF DRAWINGS

These and other features, aspects, and advantages of disclosed compositions and methods will become better understood with regard to the following description, and accompanying drawings, where:

FIG. 1 shows the design of an exemplary comPACT mini-gene. SS refers to the optional signal sequence; US1 refers to the first universal target site; NeoE refers to Neoepitope, the antigenic peptide sequence site; US2 refers to the second universal target site; L1 refers to the optional first linker sequence; Beta2m refers to the β-2-microglobulin domain sequence; L2 refers to the optional second linker sequence; MEW heavy chain refers to the MEW heavy chain allele; L3 refers to the optional third linker sequence; and purification cluster refers to the optional purification cluster with a biotinylation sequence, a protease cleavage site, and an affinity tag sequence. While FIG. 1 shows a His6 (SEQ ID NO: 34) (6-His tag (SEQ ID NO: 34)) as the affinity tag, any other appropriate affinity tag could be used including but not limited to histidine tags of different lengths (poly-His tags), HAT tags, FLAG tags (or FLAG epitopes), epitopes that are specific to any antibody used for purification, galactose-binding protein tags, fluorescent tags, GST tags, HA tags, HaloTags, MBP tags, Myc tags, poly-Asp tag, poly-Phe tag, protein C, Streptavidin/Biotin tags, Strep-tags, protein G, or any other protein purification tag that is capable of purifying a comPACT polypeptide.

Furthermore, while FIG. 1 shows that a nickel resin (see, “Ni” in figure) was used to purify the His6 tagged (SEQ ID NO: 34) comPACT polypeptide, other His6 (SEQ ID NO: 34) affinity resins have been used. Specifically, Zinc resin has been used to successfully purify a His6 tagged (SEQ ID NO: 34) comPACT polypeptide from a solution. Cobalt and Calcium resins are two other exemplary His6 (SEQ ID NO: 34) affinity resins that could be used.

FIG. 2 shows a diagram of an exemplary modular off-the-shelf platform for rapidly assembling libraries of antigenic peptide ligands complexed with a chosen MEW allele. FIG. 2 discloses SEQ ID NOS 9, 11 and 13, respectively, in order of appearance.

FIG. 3 discloses SEQ ID NOS 270-274, respectively, in order of appearance.

FIG. 4 discloses SEQ ID NOS 275-276, 271-274 and 277, respectively, in order of appearance.

FIG. 5 discloses SEQ ID NOS 278-279, 271-274 and 277, respectively, in order of appearance.

FIG. 11 discloses SEQ ID NOS 11 and 13, respectively, in order of appearance.

FIG. 14 discloses “(His6)” as SEQ ID NO: 34.

FIG. 15 discloses “His6” as SEQ ID NO: 34. FIG. 15 also discloses SEQ ID NOS 280, 280-281 and 281, respectively, in order of appearance.

FIG. 31 provides an example of the specificity of the impact neoantigen isolation process (i.e., the imPACT Isolation Technology).

FIG. 33A discloses SEQ ID NOS 282-284, respectively, in order of appearance.

FIG. 34A provides a FACS plot for dual stained T cells using the imPACT analysis of a PBMC sample using the single barcode method. FIG. 34A discloses SEQ ID NOS 285-292, respectively, in order of appearance. FIG. 34B provides a FACS plot for CD45RA and CD95 stained T cells after the dual tetramer staining. FIG. 34B discloses SEQ ID NOS 285-292, respectively, in order of appearance. FIG. 34C provides a table summarizing the TRA (SEQ ID NOS 293-300, respectively, in order of appearance), TRB (SEQ ID NOS 285-292, respectively, in order of appearance), gene, and neoantigen peptide (SEQ ID NOS 204, 203, 203, 203, 205, 203 and 206-207, respectively, in order of appearance) sequences of the isolated T cells after the imPACT analysis.

FIG. 35A discloses SEQ ID NOS 207, 301, 206 and 302, respectively, in order of appearance.

FIG. 37A provides a FACS plot for dual stained T cells using the imPACT analysis of a PBMC sample using the dual barcode method. FIG. 37B provides a FACS plot for CD45RA and CD95 stained T cells after the dual tetramer staining. FIG. 37B discloses SEQ ID NOS 303-305, respectively, in order of appearance. FIG. 37C provides a table summarizing the TRA, TRB, gene, and neoantigen peptide sequences of the isolated T cells after the imPACT analysis. FIG. 37C discloses the "top1.NeoAg" sequences as SEQ ID NOS 306, 306, 208, 208, 208, 208, 208, 208 and 208, the "top2.NeoAg" sequences as SEQ ID NOS 307, 306, 208, 208, 208, 208, 208, 208 and 208, the "tra.CDR3" sequences as SEQ ID NOS 308-310, 310-312, 312, 312 and 312, the "trb.CDR3" sequences as SEQ ID NOS 313-314, 304, 304, 303, 305, 305, 305 and 305 and the "peptide Tumor" sequences as SEQ ID NOS 306, 306, 208, 208, 208, 208, 208, 208 and 208, all respectively, in order of appearance.

FIG. 38B provides a table summarizing the HAL types, cancer, number of targets, and number of TCRs found in the TILs.

FIG. 42A discloses SEQ ID NOS 315-317, respectively, in order of appearance. FIG. 42B discloses SEQ ID NOS 318-319, respectively, in order of appearance. FIG. 42C discloses SEQ ID NOS 320-323, respectively, in order of appearance.

FIG. 45 discloses "KTYFKPFHPK" as SEQ ID NO: 256 and "YFKPFHPKF" as SEQ ID NO: 227.

FIG. 63 discloses SEQ ID NO: 324.

FIG. 67A illustrates the target TCRα locus (endogenous TRAC, top panel) and its CRISPR Cas9 target site (horizontal stripe, cleavage site designated by arrow), and the circular plasmid homologous recombination (HR) template (bottom panel) with the polynucleotide encoding the neoTCR, which is located between left and right homology arms ("LHA" and "RHA" respectively) prior to integration. RNP: CRISPR/Cas9 complex. FIG. 67B illustrates the integrated neoTCR in the TCRα locus (top panel), the transcribed and spliced neoTCR mRNA (middle panel), and translation and processing of the expressed neoTCR (bottom panel).

DETAILED DESCRIPTION

Definitions

Figure 1:
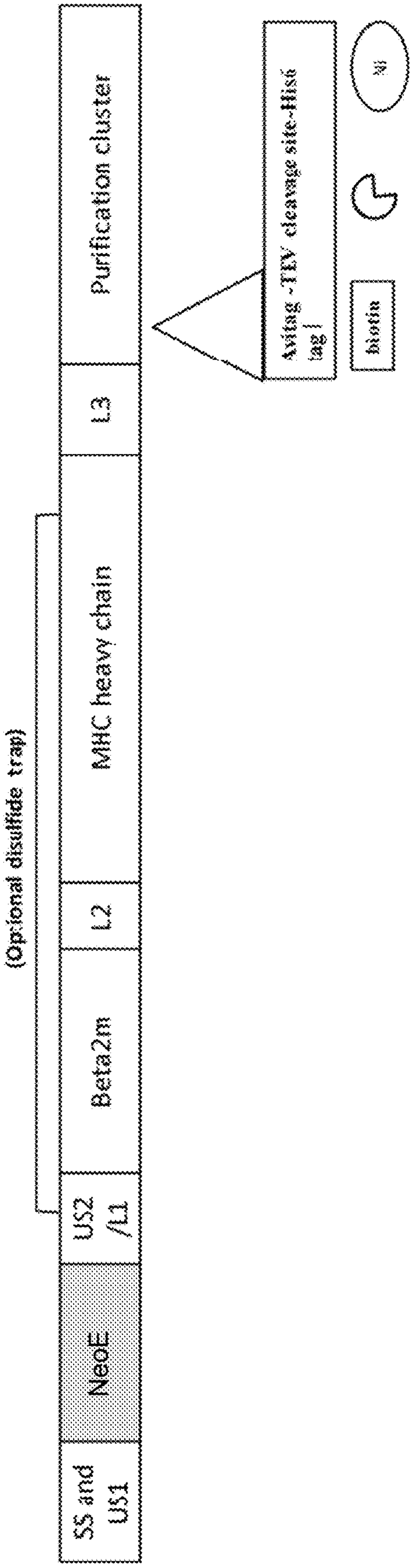

Terms used in the claims and specification are defined as set forth below unless otherwise specified.

As used herein, the term "antigen-specific T cells" refers to cells that are distinguished from one another by their T cell receptors (TCRs), which give them their antigen specificity.

Embodiments of the compositions and methods disclosed herein include a recombinant antigen-MHC complex that is capable of pairing with cognate T cells. As used herein, "antigen-MHC," "antigen-MHC complex," "recombinant antigen-MHC complex," "peptide MHC," and "p/MHC," are used interchangeably to refer to a major histocompatibility complex with a peptide in the antigen binding groove.

As used herein, "antigen" includes any antigen including patient-specific antigens.

"Antigen peptide" and "Antigenic Peptide" and "Neoepitope" and "NeoE" are used interchangeably and means the peptide that was derived from an antigen that was identified on a cell of interest (for example, if it a tumor cell the antigen that was expressed by the tumor cell), that is incorporated into a comPACT polypeptide using molecular biology techniques described herein. Furthermore, as expressly specified in the Examples, the terms "neoantigen sequence" and "neoantigen insert" can have the same meaning as "Antigen peptide" and "Antigenic Peptide" and "Neoepitope" and "NeoE". The terms also refer to a peptide or peptide fragment capable of binding an MHC molecule.

"Antigen-MHC Complex" and "Antigen-MHC" and "Recombinant Antigen-MHC Complex" and "Peptide MHC" and p/MHC" and "neoantigen-MHC Complex" are all used interchangeably and mean the ternary complex consisting of an HLA/MHC heavy chain, a (32M chain, and an antigen peptide.

"Anti-CTLA4 antibody" antibody that attaches to CTLA-4 and stops it from working. This can boost the body's immune response against cancer cells. include ipilimumab. Include AB154 (Arcus), tiragolumab (Genentech/Roche), BMS-986297 (BMS), MK-7684 (Merck), and etigilimab (OncoMed). In addition to anti-CTLA4 antibodies, CTLA4 inhibitors (both large and small molecules) can be used in combination with any neoTCR product.

"Anti-PD-1 antibody" and "an antibody that binds to PD-1" and "anti-PD-1 therapy" means an antibody that binds and is capable of binding PD-1 with sufficient affinity such that the antibody is useful as a diagnostic and/or therapeutic agent in targeting PD-1. In certain embodiments, antibodies that bind or are capable of binding PD-1 can block the interaction of PD-1 and PD-L1 and boost the immune response against cancer cells. Anti-PD-1 antibodies include but are not limited to pembrolizumab, nivolumab, and cemiplimab. In addition to anti-PD1 antibodies, PD1 inhibitors (both large and small molecule) can be used in combination with any neoTCR product.

"Anti-PD-L1 antibody" and "an antibody that binds to PD-L1" and "anti-PD-L1 therapy" means an antibody that binds and is capable of binding PD-L1 with sufficient affinity such that the antibody is useful as a diagnostic and/or therapeutic agent in targeting PD-L1. In certain embodiments, antibodies that bind or are capable of binding PD-L1 can block the interaction of PD-1 and PD-L1 and boost the immune response against cancer cells. Anti-PD-L1 antibodies include but are not limited to atezolizumab, avelumab, durvalumab. In addition to anti-PD-L1 antibodies, PD-L1 inhibitors (both large and small molecule) can be used in combination with any neoTCR product.

"Attachment Moiety" means any chemical or biologic moiety that can be used to attach to polynucleotides or polypeptides to a chemical or biologic substrate. As used herein, attachment moieties are used to attach polynucleotides or polypeptides to particles.

"Checkpoint inhibitor" means a type of drug that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include PD-1/PD-L1 and CTLA-4/B7-1/B7-2. Some immune checkpoint inhibitors are used to treat cancer.

"Barcode" and "Barcode Sequence" and "Nucleotide Barcode" and "Barcoded Polynucleotide" and "neoID" and "neoID Barcode" can be used interchangeably and refer to a nucleotide sequence that is used to tag and identify a specific peptide.

"Barcoded Particle" means a particle with a barcode attached to it.

"Beta-2-microglobulin", "β-2-microglobulin", "β2M" are used interchangeably and have the same meaning.

"comPACT" and "comPACT construct" are used interchangeably and mean either a polynucleotide or a polypeptide, based upon the context of how the term is used, comprising a neoantigen and an MCH complex. A comPACT can further comprise signal sequences, universal target sites, linkers, and purification clusters. FIG. 1 shows a non-limiting representation of a comPACT.

"comPACT Library" and "comPACT-neoID Library" are used interchangeably and mean one or more comPACT.

"comPACT mini-gene" or "comPACT polynucleotide" or "comPACT gene" or "comPACT polynucleotide molecule" are used interchangeably and means the nucleic acid sequence encoding the comPACT protein.

"comPACT protein" or "comPACT polypeptide" or "comPACT polypeptide molecule" means MHC molecules expressed as a single polypeptide fusion of a universal target sequence, an antigen peptide, a second universal target sequence, a β2-microglobulin, and an MHC class I heavy chain comprising the α1, α2, and α3 domains that form an MHC display moiety. The comPACT polypeptides described herein can further optionally comprise linker sequences between any or all of the individual components of the comPACT polypeptide. An example of the placement of optional linker sequences within a comPACT polypeptide is presented in the comPACT mini-gene of FIG. 1.

"Effective Amount" means an amount effective, at dosages and for periods of time necessary, to achieve the desired therapeutic or prophylactic result.

"Epitope" or "Epitope Tag" mean an affinity tag wherein a peptide sequence is genetically engineered into a polypeptide and wherein an antibody can bind to the peptide sequence. Epitope tags include but are not limited to V5-tags, Myc-tags, HA-tags Spot-tags, NE-tags, and all other epitopes that can be used as an affinity tag. Epitope tags can be formed both from contiguous amino acid stretches (linear epitope) or comprise non-contiguous amino acids (conformational epitope), e.g., coming in spatial proximity due to the folding of the antigen. "Linker" means any amino acid sequence (or the nucleic acid sequence encoding such amino acid sequence) that is used to link components in a fusion protein. As applied to comPACT proteins (fusion proteins), the linkers can be used to link, for example, the NeoE to the β2M or the β2M to the MHC heavy chain or the MHC heavy chain to the purification cluster.

"Host Cell" and "Producer Cell" both mean cells into which exogenous nucleic acid has been introduced, including the progeny of such cells. Host cells include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the individual or subject is a human.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"MHC Complex" means a complex that comprises a β2-microglobulin and MHC heavy chain. The MHC complex can be a polypeptide or a polynucleotide encoding such a polypeptide, An MHC Complex is included in all comPACT proteins and the polynucleotides encoding such β2-microglobulin and MHC heavy chain is included in all comPACT mini-genes. FIG. 1 and FIG. 2 show two examples of the inclusion of the MHC Complex in comPACT mini-genes FIG. 11, for example, shows a western blot of a comPACT protein which comprise an MHC Class I Heavy Chain Complex.

"MHC Display Moiety" means the MHC Class I Heavy Chain comprising the α1, α2, and α3 domains.

"MHC" means the major histocompatibility complex which is a set of genes that code for cell surface proteins essential for the acquired immune system of recognize foreign molecules. The main function of MHC molecules is to bind to foreign antigens (including antigens presented on endogenous cells that cause harm to the organism, e.g., a human) and display them on the cell surface for recognition by the appropriate T cell. The three subgroups of the MHC family are Class I, Class II, and Class III.

"MHC Class I" means the subgroup of the MHC family that comprises a Beta microglobulin subunit.

"Neoantigen" refers to an antigen that has at least one alteration that makes the neoantigen or presentation of the neoantigen distinct from its corresponding wild-type antigen, e.g., mutations in the polypeptide sequence, differences is post-translation modifications or differences in expression level. "Neoantigen" and "Tumor Neoantigen" mean a specific antigen on a cell that can be used as an identifying target for killing. As applied to cancer and tumors, a neoantigen is an antigen that is specific to the tumor or cancer. As applied to pathogens and pathogen-infected cells, a neoantigen is an antigen that is specific to the pathogen or pathogen-infected cell. "Tumor neoantigens" refers to neoantigens that are derived from a tumor or a cancer, e.g., from the tumor of a patient.

"neoTCR Product" and "neoTCR T Cell therapy" and "neoTCR T Cell treatment" and "neoTCR T Cell" are used interchangeably and all refer to the genetically engineered T cell expressing a TCR that recognizes the neoepitope that was identified and designed using comPACT polypeptides and polynucleotides and the imPACT Isolation Technology.

"Neo12" and "Neo12 protein" means an exemplary neoepitope.

"NTAmer" means a complex comprising comPACT polypeptides.

"Off-the-shelf" means, with regard to the design of a comPACT polynucleotide and the comPACT polypeptide made therefrom, the comPACT minigene comprising a Beta-2-microglobulin, an MHC heavy chain allele, and a place within such construct to insert a neoepitope. In certain embodiments, the order of the construct from 5' to 3' is 1) the neoepitope, 2) the Beta-2-microglobulin, and 3) the MHC heavy chain allele. In certain embodiments, signal sequences, universal target sites (e.g., restriction enzyme sites), flexible linkers, and a purification cluster is also incorporated into the construct. In certain embodiments, the structure of said construct with additional elements is the construct disclosed in FIG. 2.

"Operably associated" means, with regard to construction of particles, that each particle constructed using a given comPACT (with a specific neoantigen expressed therein) is associated with one or more barcodes unique to that particle. In this way, downstream sequencing determination of which barcodes are bound to a specific cell can be used to determine which comPACT (and in turn which neoantigen) was responsible for that binding.

"Particle", "Particle set", "Particle Pair, and "Distinct Particle Set" all mean, with regard to the term "Particle", refers to the core of the comPACT which comprises substrates capable of being specifically sorted or isolated and to which components of the comPACT (and additional polypeptide, polynucleotide, and chemical matter) can be attached. In certain embodiments, a "particle set" refers to a plurality of particles.

The terms "pharmaceutical composition" or "pharmaceutical formulation" refer to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is non-toxic to a subject. A pharmaceutically acceptable carrier includes, but is not limited to, a buffer, excipient, stabilizer, or preservative.

As used herein, a "polynucleotide" or a "nucleic acid" are used interchangeably and include any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Polynucleotide refers to any DNA (including but not limited to cDNA, ssDNA, and dsDNA) and any RNA (including but not limited to ssRNA, dsRNA, and mRNA) and further includes synthetic forms of DNA and RNA and mixed polymers comprising two or more of these molecules. One of skill in the art can understand which form is being referred to, e.g., based on the context in which the polynucleotide is being used. The polynucleotide may be linear or circular. In addition, the term polynucleotide includes both, sense and antisense strands, as well as single-stranded and double-stranded forms. The polynucleotide can contain naturally occurring or non-naturally occurring nucleotides. Examples of non-naturally occurring nucleotides include modified nucleotide bases with derivatized sugars or phosphate backbone linkages or chemically modified residues. Polynucleotides encompass DNA and RNA molecules that are suitable as a vector for direct expression of a polypeptide of the invention in vitro and/or in vivo.

"Proliferative disorder" means excess cell proliferation of one or more subset of cells in a multicellular organism resulting in harm (i.e. discomfort or decreased life expectancy) to the multicellular organism. Cell proliferative disorders can occur in different types of animals and humans. As used herein, proliferative disorders include neoplastic disorders.

"Protein" and "Polypeptide" are used interchangeably herein.

"Purification Cluster" means the optional portion of the comPACT that includes a genetically encoded element that allows for purification of the comPACT.

"Signal Sequence" means a short peptide present at the N-terminus of a newly synthesized protein that is destined towards the secretory pathway. A signal sequence may be included in a comPACT design and production.

As used herein, "treatment" (and grammatical variations thereof such as "treat" or "treating") refers to clinical intervention in an attempt to alter the natural course of disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

"Universal Target Site", "Universal Target Sequence", and "Universal Sequence" can be used interchangeably and mean a polynucleotide sequence that can be cleaved by a restriction enzyme or a primer binding site that can be used for binding of a primer and amplification of a desired sequence.

"Vector", "Expression Vector" and "Expression Construct" can be used interchangeably and mean the discrete elements that are used to introduce heterologous DNA into cells for either expression or replication thereof. As used herein, a vector can be engineered and used for in vivo or in vitro expression of a polypeptide gene product encoded by a coding sequence inserted into the vector.

"Young" or "Younger" as it relates to T cells means memory stem cells ($T_{MSC}$) and central memory cells ($T_{CM}$). These cells have T cell proliferation upon specific activation and are competent for multiple cell divisions. They also have the ability to engraft after re-infusion, to rapidly differentiate into effector T cells upon exposure to their cognate antigen and target and kill tumor cells, as well as to persist for ongoing cancer surveillance and control.

As used herein, the terms "barcoded T cell," "paired T cell," "T-cell bound nanoparticle," and "T cell paired antigen MHC complex" refer to the complex of a T cell having a T cell receptor that binds to an antigen peptide presented by an MHC molecule on a barcoded NP-antigen-MHC complex (i.e., the particle-comPACT complex)

As used herein, "antibody" or "antibodies" is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv, and scFab); single domain antibodies (dAbs); and multispecific antibodies formed from antibody fragments.

The term "in vivo" refers to processes that occur in a living organism, including a cell.

The term "mammal" as used herein includes both humans and non-humans and includes but is not limited to humans, non-human primates, canines, felines, murines, bovines, equines, and porcines.

The term "percent sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent sequence identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

It must be noted that, as used in the specification and the appended claims, the singular forms "a," "an" and "the" include plural referents unless the context clearly dictates otherwise.

Other Interpretational Conventions

Ranges recited herein are understood to be shorthand for all of the values within the range, inclusive of the recited endpoints. For example, a range of 1 to 50 is understood to include any number or fraction thereof, combination of numbers or fractions thereof, or sub-range from the group (including fractions of any of the numbers from the group) consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Introduction

T-cell mediated immunity can be characterized by the activation of antigen-specific cytotoxic T cells that are able to induce death in cells that display antigen in a major histocompatibility complex (MEW) on their surface. These cells displaying an MEW complex loaded with antigen include virus-infected cells, cells with intracellular bacteria, cells that have internalized or phagocytosed extracellular sources of protein, and cancer cells displaying tumor antigens.

A natural class I MHC heavy chain comprises about 350 amino acids; a natural β2-microglobulin comprises about 100 amino acids, and a class I antigen peptide typically has a length of from about 7 to about 15 amino acids. Class I heavy chains are encoded by genes of the major histocompatibility complex, designated HLA-A, -B and -C in humans, and H-2K, D, and L in mice. The class I heavy chains and β2-microglobulin are separately encoded on different chromosomes. Antigen peptides are normally processed by cells from protein sources such as for example, viruses, bacteria, or cancer cells. Diverse variants have been identified for the polypeptides encoded by the HLA-A, -B and -C MEW genes in humans, as well as the murine H-2K, D, and L MHC genes.

Embodiments of the method disclosed herein are directed to a method of manufacturing a single molecule in which a selected neoantigen is linked to an MEW complex comprising a β2-microglobulin (β2M) and an MHC heavy chain. Different MEW heavy chains can be linked to the β2M molecule to form a varying number of MEW templates. The methods disclosed herein of inserting a neoantigen into an MEW template via restriction digest or PCR-based assembly by utilizing universal target sequences flanking the neoepitope insertion site (also referred to as the neoantigen insertion site) results in the ability to construct a library of different neoantigen-MHC complexes in a high-throughput method that can be personalized for a given patient. These complexes are termed "comPACT proteins" and can then be, e.g., linked to a particle, barcoded particle, or surface for use in isolation and identification of patient-specific T cell populations targeted to patient-specific neoantigens. Methods of linking antigen-MHC complexes and use of such complexes are disclosed in PCT/US2018/21611, filed Mar. 8, 2018, herein incorporated by reference in its entirety.

Nucleotide and Peptide Compositions

MHC Complex

Briefly, as used herein, comPACT polypeptide refers to MHC molecules expressed as a single fusion polypeptide of a universal target sequence, an antigen peptide, a second universal target sequence, a β2-microglobulin, and an MEW class I heavy chain comprising the α1, α2, and α3 domains that forms an MEW display moiety. The comPACT polypeptides described herein can further optionally comprise linker sequences between any or all of the individual components of the comPACT polypeptide. An example of the placement of optional linker sequences within a comPACT polypeptide is presented in the comPACT mini-gene of FIG. 1. An MHC display moiety can include a recombinant MEW molecule. Design and manufacture of individual comPACT polypeptides and libraries of comPACT polypeptide molecules are described in International Application PCT/US2019/025415, filed Apr. 2, 2019, hereby incorporated by reference in its entirety. In certain embodiments, comPACT polypeptides can comprise disulfide traps, as described in US Publication No. 2009/0117153 and US Publication No. 2008/0219947; each of which is herein incorporated by reference. The antigen-MHC complex formed by a comPACT protein results in the display of the antigens such that they are capable of recognition by a cognate TCR molecule. In some embodiments, the MHC complex can be an MHC Class I (MHC I) complex that pairs with CD8-positive (CD8+) T "killer" cells. In some embodiments, the MEW complex can be an MHC Class II (MEW II) complex that pairs with CD4-positive (CD4+) T cells.

In some embodiments, the MHC class I heavy chain sequence of a comPACT can include single amino acid substitutions, additions, and/or deletions, such as a substitution of Tyr-84 with a non-aromatic amino acid other than proline. In these embodiments, the amino acid substitution can be any amino acid encoded by the standard genetic code such leucine, isoleucine, valine, serine, threonine, alanine, histidine, glutamine, asparagine, lysine, aspartic acid, glutamic acid, cysteine, arginine, serine or glycine, or can be a modified or unusual amino acid. In one embodiment, the MEW class I heavy chain sequence of a comPACT comprises a Tyrosine-84 to alanine substitution. In another embodiment, the MHC class I heavy chain sequence of a comPACT comprises a Tyrosine-84 to cysteine substitution.

The β2-microglobulin ((β2M) may include a recombinant β2M molecule. In some embodiments, the β2M sequence can include single amino acid substitutions, additions, and/or deletions as described above. In one embodiment, this substitution comprises a Serine-88 to cysteine substitution. In one embodiment, the substitution can be a substitution of any naturally occurring non-cysteine amino acid of the β2M to a cysteine wherein the substitution does not negatively affect the function of the β2M within the comPACT polypeptide and the substitution allows for conjugation of thiol-reactive moieties. Such substitutions can be accomplished, for example, by cysteine screening of the protein using mutagenesis techniques known to one of skill in the art. Such thiol-reactive moieties can be used to use detect the β2M or the entire comPACT polypeptide. In certain embodiments, the thiol-reactive moiety is a thiol-reactive-dye (fluorophore) conjugate which allowed the comPACT to be used to measure kinetic parameters of TCR-comPACT binding (see, e.g., Example 8). In certain embodiments, the thiol-reactive moiety is a dye (fluorophore) comprises a sulfhydryl-reactive crosslinker reactive group, including but not limited to maleimides, iodoacetamide or derivatives thereof, haloacetyls, pyridyl disulfides, and all other thiol-reactive conjugation partners (see, e.g., Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

Universal Sequences

An antigenic peptide is generally flanked by universal sequences or portions thereof. These sequences allow for rapid, high throughput methods for replacing or inserting the antigenic peptide encoding nucleotide in the polynucleotide MHC template. Universal sequences may comprise restriction sites for restriction digest based cloning. Exemplary restriction sites include, but are not limited to, NcoI, BamHI, BlpI, BspEI, BstBI, XbaI, HindIII, EcoRI, ApaI, NotI, any restriction site that is not present in the β2M, the MHC heavy chain, the NeoE, the signal sequence (if present) the purification cluster (if present), or the fusion of any component thereof (including optional linker sequences), and any combination thereof. Alternatively, the universal sequence may be a primer binding site. Universal primer sequences known in the art may be used in the compositions and methods disclosed herein, or the sequences may be different than the previously described universal primer sequences and can be designed to promote specific binding/amplification and eliminate non-specific binding/amplification. Universal sequences may be between 4-50, between 4-15, between 15-40, between 15-35, between 15-30, between 20-40, between 25-40, or between 30-40 nucleotides in length. Universal sequences may be at least 4, at least 10, at least 15, at least 20, at least 25, at least 30, at least 35, at least 40, at least 45, or at least 50 nucleotides in length. In some embodiments, the universal target sequence is 4-8 nucleotides in length. In other embodiments, the universal target sequence is between 9-25 nucleotides in length. In other embodiments, the universal target sequence is between 25-35 nucleotides in length. In other embodiments, the universal target sequence is at least about 15 nucleotides in length. In certain aspects, one or more universal target sequences are not present in the genetic material being manipulated, e.g., to reduce or eliminate off-target effects and/or to increase specificity.

Linkers

In various embodiments, a comPACT can comprise a first flexible linker interposed between the antigenic peptide segment and the β2-microglobulin segment. Such linkers can extend from and connect the carboxyl-terminal of the antigenic peptide segment to the amino-terminal of the β2-microglobulin segment. In a non-limiting example, when a comPACT is expressed the linked peptide ligand can fold into the binding groove resulting in a functional comPACT protein. In various embodiments, the linker is at least about 10 amino acids and up to about 15 amino acids. In various embodiments, the linker is between 4 and 32 amino acids.

In various embodiments, a comPACT can comprise a second flexible linker interposed between the β2-microglobulin segment and the MHC heavy chain segment. Such linkers can extend from and connect the carboxyl-terminal of the β2-microglobulin segment to the amino-terminal of the MHC heavy chain segment. In a non-limiting example, when a comPACT is expressed the β2-microglobulin and the MHC heavy chain can fold into the binding groove resulting in a molecule that can function in promoting T cell expansion. In various embodiments, this linker can comprise at least about 15 amino acids, up to about 20 amino acids. In various embodiments, the linker is at least about 10 amino acids and up to about 15 amino acids. In various embodiments, the linker is between 4 and 32 amino acids.

In various embodiments, a comPACT can comprise a third flexible linker interposed between the MHC heavy chain segment and the purification cluster. Such linkers can extend from and connect the carboxyl-terminal of the MHC heavy chain segment and the amino terminus of the purification cluster. In various embodiments, the linker is at least about 10 amino acids and up to about 15 amino acids. In various embodiments, the linker is between 4 and 32 amino acids. In various embodiments, the linker is only 2 or 3 amino acids.

In certain embodiments, the same linker can be used for the first and second linker, and optionally the third linker if present. In certain embodiments, the same linker is used for the first, second, and third linker. In certain embodiments, all three linkers are the (G4S)4 linker (SEQ ID NO: 19). In certain embodiments, all three linkers are a (G3S)n linker (SEQ ID NO: 201). In certain embodiments, all three linkers are a (GSGGS)n linker (SEQ ID NO: 11). In certain embodiments, all three linkers are a (GCGGS)n linker (SEQ ID NO: 13).

In certain embodiments, different sequences are used for each of the first and second linkers, and optionally the third linker if present.

In certain embodiments, two of the first, second, and optionally third linkers are the same and one is different.

Any appropriate flexible linker sequence known in the art may be used. Appropriate linker sequences include, but are not limited to, glycine-serine sequences comprising repeating units of a GGGGS ($G_4S$) (SEQ ID NO: 9), GGGS ($G_3S$) (SEQ ID NO: 201), GSGGS (SEQ ID NO: 11), or GCGGS (SEQ ID NO: 13) sequence motifs. In certain embodiments, a cleavable linker could be used for any of the first, second, and third linkers. In certain embodiments, a cleavable linker is used only for the first, second, or third linker. In certain embodiments, a cleavable linker is only used for the first linker. In certain embodiments, a cleavable linker is only used for the second linker. In certain embodiments, a cleavable linker is only used for the third linker.

In certain embodiments, the linkers (first, second, and/or third) could be selected from a group comprising rigid or less flexible linkers.

Signal Sequences

In various embodiments, the comPACT polynucleotide and polypeptide comprise a signal sequence and signal peptide. In one embodiment, the signal sequence is the signal sequence from Human Growth Hormone (hGH). Additional signal sequences may also be used, including but not limited to the signal sequence from β2M, or any other eukaryotic or prokaryotic signal sequence known in the art. Any signal sequence that directs the comPACT protein to the secretory pathway (for secretion of the comPACT from the cell) could be used.

In certain embodiments, the signal sequence comprises the amino acid sequence of SEQ ID NO: 2. In certain embodiments, the signal sequence comprises the nucleic acid sequence of SEQ ID NO: 1.

The signal sequence may be between 70 and 80 nucleotides in length. The signal sequence may be between 40-90, 40-60, 45-70, 50-80, 60-90, 55-70, 60-80, or 70-80 nucleotides in length. The signal peptide may be between 10-30, 10-20, 15-30, or 20-30 amino acids in length.

Promoters

A comPACT polynucleotide composition may further comprise a promoter for transcription of the encoded polynucleotide into an mRNA transcript that can be translated by the host cell. Promoters may be prokaryotic, viral, or eukaryotic (for example but not limited to mammalian) in origin. Any appropriate promoter for gene transcription in a cell may be used. In certain embodiments, a eukaryotic promoter may be used. In certain embodiments, the type of eukaryotic promoter is a constitutive promoter, an inducible promoter, or a specific promoter. In certain embodiments, the eukaryotic promoter is a EF1α, cytomegalovirus (CMV), CAG, PGK, RE, U6, or UAS promoter. In certain embodiments, a prokaryotic promoter may be used. In certain embodiments, the type of prokaryotic promoter is a constitutive promoter, a constitutive promoter that requires the presence of a specific polymerase (e.g., a T7 or Sp6 RNA polymerase), a promoter that is constitutive in the absence of an repressor and inducible in the presence of an inducer (for example, and non-limiting, the lac promoter which is constitutive in the absence of a lac repressor but which can be induced by IPTG or lactose), an inducible promoter, a repressible promoter, or a regulated promoter. In certain embodiments, the prokaryotic promoter is a T7, Sp6, lac, araBad, trp, or Ptac promoter. In certain embodiments, a viral promoter may be used. In certain embodiments, the type of viral promoter is an AAV promoter or an SV40 promoter.

In some embodiments, the comPACT polynucleotide comprises an SV40 or any viral promoter. In certain embodiments, a strong viral promoter may be beneficial depending on the cell line and reagents.

In some embodiments, the comPACT polynucleotide comprises a CMV promoter.

Affinity Tags

A comPACT polynucleotide composition may further comprise at least one sequence that encodes for an affinity tag or epitope tag. In some embodiments, the comPACT polynucleotide comprises at least two affinity tags or epitope tag sequences. Any appropriate affinity tag or epitope tag may be used in the comPACT polynucleotide or polypeptide. Such epitope tags include, but are not limited to, AviTag (or any avidin/streptavidin tag), strep-tag, polyhistidine (His6)-tag (SEQ ID NO: 34), FLAG-tag, HA-tag, and Myc-tag. The sequences in the polynucleotide comPACT gene are translated into peptides in the comPACT polypeptide. These epitope tags may be used for affinity chromatography purification or quantification of the expressed comPACT polypeptide. For instance, the His6 tag (SEQ ID NO: 34) may be used to purify the comPACT protein via HA-tag binding affinity chromatography. In certain embodiments, a metal ion resin can be used to purify an HA-tagged protein. In certain embodiments, a Ni2+(nickel) resin, Co2+(cobalt) resin, Cu2+(copper) resin, Ca2+(calcium) resin, Zn2+(zinc) resin, or any combination thereof can be used to purify an HA-tagged protein. In certain embodiments, a Ni2+ resin is used to purify an HA-tagged comPACT protein. In certain embodiments, a mixture of a Ni2+ and a Zn2+ resin is used to purify an HA-tagged comPACT protein. In certain embodiments, the resin is an immobilized-metal affinity chromatography resin (IMAC). In certain embodiments, the metal ion is coupled to the resin matrix with a chelating ligand. In certain embodiments, the metal ion is coupled to the resin matrix with nitrilotriacetic acid (NTA) or iminodiacetic acid (IDA).

In addition, the AviTag encodes a known biotinylation site that is recognized by the BirA enzyme. Inclusion of this peptide sequence in a protein allows for biotinylation of the sequence via enzymatic modification by BirA. Thus, a comPACT polypeptide comprising an AviTag (or any avidin/streptavidin tag) sequence and a His6 tag (SEQ ID NO: 34) may be biotinylated, purified via metal affinity chromatography (e.g., Ni-NTA affinity chromatography or any other metal affinity resin described herein) via the His6 tag (SEQ ID NO: 34), and the purity or quantity of the purified protein assessed via biotin visualization with streptavidin or other avidin reagents. In some embodiments, the comPACT polynucleotide comprises an AviTag (or any avidin/streptavidin tag) sequence. In some embodiments, the comPACT polypeptide comprises an AviTag (or any avidin/streptavidin) epitope. In some embodiments, the comPACT polynucleotide comprises a His6 sequence (SEQ ID NO: 34). In some embodiments, the comPACT polypeptide comprises a His6 epitope (SEQ ID NO: 34). In some embodiments, the comPACT polynucleotide comprises an AviTag (or any avidin/streptavidin) sequence and a His6 sequence (SEQ ID NO: 34). In some embodiments, the comPACT polypeptide comprises an AviTag (or any avidin/streptavidin) epitope and a His6 epitope (SEQ ID NO: 34).

Protease Cleavage Sites

A comPACT polynucleotide composition may further comprise a sequence that encodes for a protease cleavage site in the purification cluster. This cleavage site may be encoded between the first and second affinity tag sequences and allows for cleavage of the second affinity tag from the comPACT protein once the comPACT has been expressed and undergone a round of purification. Any appropriate protease cleavage site known in the art may be used, including, but not limited, cleavage sites that are recognized by TEV, thrombin, Factor Xa, enteropeptidases, and rhinovirus 3C protease, among others. In one embodiment, the protease cleavage site nucleotide sequence encodes for a TEV cleavage site. In another embodiment, the comPACT polypeptide comprises a TEV protease cleavage site.

PolyA Tail

A comPACT polynucleotide composition may further comprise a polyadenylation (polyA) tail. Eukaryotic (including mammalian) or prokaryotic polyA sequence motifs may be used. This sequence may be included when the comPACT polynucleotide is assembled via PCR for direct transfection into a host cell (e.g., not in the context of an expression construct or vector). Any appropriate polyA tail and sequence motif may be used in the comPACT polynucleotide, including, but not limited to the polyA tails of SV40, hGH, bGG, and rbGlob sequences. Such sequences include the sequence motif AAUAA. In one embodiment, the comPACT polynucleotide comprises a BHG polyA tail sequence.

Antigenic Sequences

Antigenic sequences (i.e., the sequence of the neoantigen that the neoepitope portion of the comPACT polypeptide is designed to bind) may be between 20-60, between 20-30, between 25-35, between 20-45, between 30-45, between 40-60, or between 45-60 nucleotides in length. The antigenic peptide may be or be derived from an exogenous antigen, an endogenous antigen (including heterologous, autologous, and homologous antigens), or an autoantigen. The antigenic peptide may be or be derived from an antigen that originates as an exogenous antigen and then later becomes an endogenous antigen (for example, an intracellular virus). The antigenic peptide may be or be derived from a tumor antigen, a neoantigen, a tumor neoantigen, a viral antigen, bacterial antigen, phosphoantigen, or a microbial antigen. In one embodiment, the antigenic peptide is a neoantigen. The antigenic peptides may be selected from patient data and may comprise one or more somatic mutations.

In order to make an inclusive comPACT library with multiple neoepitopes and in turn multiple comPACT polypeptides, antigenic sequences need to be predicted and identified. The prediction of the antigenic peptide may include a predictive algorithm and which may be designed to predict the binding of the antigenic peptide or neoantigen and an MHC allele. Prediction of the antigenic peptide is further discussed below.

In some embodiments, the nucleotide sequence encoding an antigenic peptide is between 20-60, between 20-30, between 25-35, between 20-45, between 30-45, between 40-60, or between 45-60 nucleotides in length. In other embodiments, the nucleotide sequence encoding an antigenic peptide is between 20-30 nucleotides in length. In some embodiments, the antigenic peptide is 7-15 amino acids, 7-10, 8-9, 7, 8, 9, 10, 11, 12, 13, 14, or 15 amino acids in length.

Biotinylation

The comPACT proteins described herein may further be biotinylated via any appropriate method. One such method utilizes the BirA Biotin-protein ligase and is commercially available. A specific amino acid sequence, known as the AviTag sequence (GLNDIFEAQKIEWHE (SEQ ID NO: 30)), is encoded in the protein of interest. BirA ligase, d-biotin and ATP are added to a reaction mixture containing the protein of interest. BirA covalently ligates the biotin to the lysine in the AviTag sequence, thereby biotinylating the protein of interest. The newly biotinylated protein can then be purified and used in downstream applications. Other methods known in the art to biotinylate proteins may also be utilized. For clarity, any applicable avidin/streptavidin sequence may be used in the comPACT protein preparation.

Expression Constructs and Vectors

The comPACT polynucleotide molecules can be inserted into expression constructs or expression vectors, e.g., for plasmid (to increase the number of expression constructs or expression vectors encoding the comPACT polynucleotide for protein production) and protein production. The expression construct or expression vector can be a eukaryotic, prokaryotic, or viral expression vector. Any suitable expression construct or expression vector known in the art may be used, including bacterial expression plasmids, such as *Escherichia coli* or *Bacillus subtilis* plasmids; eukaryotic expression vectors, such as mammalian expression vectors or yeast expression vectors; or viral vectors, such as adenovirus expression vectors, lentiviral expression vectors, vaccinia expression vectors, or baculovirus expression vectors. Mammalian expression constructs or expression vectors can be used (e.g., transfected) in cultured mammalian cell lines such as Chinese hamster ovary (CHO), J558, NSO, SP2-O, HEK293, HECK293T, Expi293, HeLa, or any derivative or modification of CHO, HEK293, Expi293, or HeLa cell lines, and any other suitable mammalian cell line. Mammalian expression constructs or expression vectors can be used in primary mammalian cell lines such as immune cells or tumor cells either directly acquired from an organism (e.g., a human) or collected (e.g. from a human), frozen, and then thawed as needed. In addition to the mammalian expression vectors and expression constructs, when appropriate, eukaryotic expression vectors and expression constructs can be used (e.g., transfected) in insect cell lines such as Sf9 or Sf12 (or any derivative or modification thereof) or yeast cell lines such as *Pichia pastoris* (or any derivative or modification thereof). Additionally, the expression construct or expression vector may comprise a nucleotide barcode. The nucleotide barcode can be unique for each expression construct or vector. In some embodiments, the nucleotide sequences encoding for the signal sequence, beta-2-microglobulin, and MHC allele can be ligated into an expression construct or expression vector with a non-coding or dummy antigen insert. This non-coding antigen insert can then be removed by an appropriate cloning technique, such as restriction digest, and a desired antigen sequence (as used in this instance for clarity, antigen sequence refers to the neoantigen sequence) inserted via ligation or any other appropriate cloning technique.

In some aspects, provided herein are a comPACT library comprises two or more comPACT polypeptides. Such libraries are created by encoding two or more comPACT polypeptides in expression constructs or expression vectors. In certain embodiments, each expression construct or expression vector comprises a single comPACT polynucleotide. In certain embodiments, the number of expression constructs or expression vectors (each expression construct or expression vector can be the same expression construct or expression vector) is the same number as the number of distinct comPACT polynucleotides. In certain embodiments, the comPACT polynucleotides are inserted into the expression constructs or expression vectors using the same or different universal target site. In other aspects, provided herein are MHC libraries that comprise two or more MHCs. Such libraries are created by encoding two or more MHC polypeptides in expression constructs or expression vectors. In other aspects, provided herein are HLA libraries that comprise two or more HLAs. Such libraries are created by encoding two or more HLA polypeptides in expression constructs or expression vectors.

Host Cells

In another aspect, provided herein are host cells comprising the polynucleotide molecule or the expression construct as described herein. The host cell can be any suitable host cell know in the art, including, but not limited to bacterial cells such as *Escherichia coli* or *Bacillus subtilis*, or eukaryotic host cells such as Chinese hamster ovary (CHO), J558, NSO, SP2-O, HEK293, HEK293T, Expi293, HeLa, insect cell lines such as Sf9 or Sf12, yeast cells such as *Pichia pastoris*, other suitable eukaryotic or prokaryotic cell line that would be scientifically reasonable based on the construct and vector selection, or any derivative or modification of any such cell line. The host cells may also stably express the biotinylation enzyme BirA. The host cell can be a primary cell or an immortalized cell line.

In some embodiments, the polynucleotide is integrated into the cell genome. In some embodiments, the polynucleotide is extrachromosomal. In some embodiments, the host cell is a mammalian cell. In some embodiments, the cell is a human cell. In some embodiments, the cell is selected from the group consisting of a stem cell, a tumor cell, an immortalized cell, and a fetal cell. In some embodiments, the host cell is a prokaryotic cell. In some embodiments, the cell is an *Escherichia coli* cell. In some embodiments, the cell expresses a BirA protein or fragment thereof.

In certain embodiments, any of the expression constructs or expression vectors described herein can be inserted into a host cell (e.g., inserted through transfection, transformation, or a similar process based on the host cell type) for polypeptide production. In certain embodiments, the expression constructs or expression vectors encoding the libraries of comPACT polypeptides, MHCs, or HLAs as described above can be inserted into a host cell (e.g., inserted through transfection, transformation, or a similar process based on the host cell type) for polypeptide production and purification. In certain embodiments, the expression constructs or expression vectors encoding the libraries of comPACT polypeptides as described below can be inserted into a host cell (e.g., inserted through transfection, transformation, or a similar process based on the host cell type) for polypeptide production and purification.

Libraries

In certain embodiments, libraries comprise two or more distinct comPACT polynucleotide molecules. In certain embodiments, libraries comprise two or more distinct polypeptide molecules. In certain embodiments, libraries comprise two or more distinct comPACT polypeptides molecules attached to particles.

In certain embodiments, any one of the 1) comPACT polynucleotide library, 2) comPACT polypeptide library, or 3) comPACT polypeptides that are attached to particle libraries, contain more than two respective molecules in such respective library. In certain embodiments, any one of the 1) comPACT polynucleotide library, 2) comPACT polypeptide library, or 3) comPACT polypeptides that are attached to particles libraries, have no upper limit to the number of respective molecules in such respective library and in turn contain as many respective comPACT polypeptides, comPACT polypeptides attached to particles, or comPACT polynucleotides. In certain embodiments, the upper limit is determined by the number of tumor neoantigens detected. In certain embodiments, the upper limit is determined by the number of potential neoepitopes identified based on the detected tumor neoantigens. In certain embodiments, the upper limit is determined by an algorithm.

A library may comprise 2 to 1000 comPACT polypeptides, comPACT polypeptides attached to particles, or comPACT polynucleotides. In some embodiments, a library comprises between 2-900, 2-800, 2-700, 2-600, 2-500, 2-480, 2-400, 2-300, 2-200, 2-100, 2-50, 2-66, 2-48, 2-30, 2-20, 2-19, 10-1000, 10-900, 10-800, 10-700, 10-600, 10-500, 10-480, 10-400, 10-300, 10-200, 10-100, 10-50, 10-66, 10-48, 10-30, 10-20, 20-1000, 20-900, 20-800, 20-700, 20-600, 20-500, 20-480, 20-400, 20-300, 20-200, 20-100, 20-50, 20-50, 20-66, 20-48, 20-30, 30-1000, 30-900, 30-800, 30-700, 30-600, 30-500, 30-480, 30-400, 30-300, 30-200, 30-100, 30-50, 30-50, 30-66, 30-48, 30-40, 40-1000, 40-900, 40-800, 40-700, 40-600, 40-500, 40-480, 40-400, 40-300, 40-200, 40-100, 40-60, 40-50, 40-66, 40-48, 50-1000, 50-900, 50-800, 50-700, 50-600, 50-500, 50-480, 50-400, 50-300, 50-200, 50-100, 50-60, 50-66, 60-1000, 60-900, 60-800, 60-700, 60-600, 60-500, 60-480, 60-400, 60-300, 60-200, 60-100, 70-1000, 70-900, 70-800, 70-700, 70-600, 70-500, 70-480, 70-400, 70-300, 70-200, 70-100, 70-80, 70-90, 80-1000, 80-900, 80-800, 80-700, 80-600, 80-500, 80-480, 80-400, 80-300, 80-200, 80-100 comPACT polypeptides, comPACT polypeptides attached to particles, or comPACT polynucleotides. In some embodiments, the library comprises between 2-19, 48-480, between 48-66, between 66-480, between 220-240, between 40-60, between 48-66, between 50-70, or between 60-80 comPACT polypeptides, comPACT polypeptides attached to particles, or comPACT polynucleotides. In some embodiments, the library comprises at least 2, 5, 10, 15, 20, 25, 30, 35, 40, 45, 48, 50, 55, 60, 65, 66, 70, 75, 80, 85, 90, 100, 110, 120, 130, 140, 150, 160, 170, 180, 190, 200, 225, 250, 275, 300, 325, 350, 375, 400, 425, 450, 475, 500, 525, 550, 600, 562, 650, 675, 700, 725, 750, 775, 800, 825, 850, 875, 900, 925, 950, 975, or 1000 comPACT polypeptides, comPACT polypeptides attached to particles, or comPACT polynucleotides. In some embodiments, the library comprises 2, 10, 15, 20, 24, 48, 66, 100, 200, 300, 400, 500, 600, 700, 800, 900, or 1000 comPACT polypeptides, comPACT polypeptides attached to particles, or comPACT polynucleotides. In some embodiments, the two or more comPACT polypeptides, comPACT polypeptides attached to particles, or comPACT polynucleotides in a library have a distinct neoepitope sequence and distinct MHC sequence.

In certain embodiments, the library comprises two or more comPACT polynucleotides wherein each comPACT polynucleotide in the library comprises a neoepitope sequence and an MHC heavy chain sequence that correspond to the neoantigen detected from a patient sample.

In some embodiments, the library comprises greater than or equal to two distinct polynucleotide molecules, wherein each distinct polynucleotide molecule comprises (i) the first universal sequence, (ii) the nucleotide sequence encoding a antigenic peptide, wherein the nucleotide sequence is not the same for each of the greater than or equal to two polynucleotide molecules (iii) the second universal target sequence, (iv) the β2M sequence, and (v) the MHC allele sequence. In some embodiments, the MHC allele sequence is not the same for each of the greater than or equal to two polynucleotide molecules.

In one embodiment, the library comprises at least two or more of the HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, and HLA-C*17:01 alleles. In one embodiment, the library comprises at least HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, and HLA-C*17:01 alleles.

In certain embodiments, the HLA library comprises HLA-A*01:01, HLA-A*02:01, HLA-A*03:01, HLA-A*11:01, HLA-A*23:01, HLA-A*24:02, HLA-A*25:01, HLA-A*26:01, HLA-A*29:02, HLA-A*30:01, HLA-A*30:02, HLA-A*31:01, HLA-A*32:01, HLA-A*33:01, HLA-A*33:03, HLA-A*68:01, HLA-A*68:02, HLA-B*07:02, HLA-B*08:01, HLA-B*13:02, HLA-B*14:02, HLA-B*15:01, HLA-B*15:03, HLA-B*15:07, HLA-B*18:01, HLA-B*27:02, HLA-B*27:05, HLA-B*35:01, HLA-B*35:03, HLA-B*37:01, HLA-B*38:01, HLA-B*39:01, HLA-B*40:01, HLA-B*40:02, HLA-B*41:02, HLA-B*42:01, HLA-B*44:02, HLA-B*44:03, HLA-B*44:05, HLA-B*46:01, HLA-B*49:01, HLA-B*50:01, HLA-B*51:01, HLA-B*52:01, HLA-B*53:01, HLA-B*55:01, HLA-B*57:01, HLA-B*58:01, HLA-C*01:02, HLA-C*02:02, HLA-C*03:03, HLA-C*03:04, HLA-C*04:01, HLA-C*05:01, HLA-C*06:02, HLA-C*07:01, HLA-C*07:02, HLA-C*07:04, HLA-C*08:01, HLA-C*08:02, HLA-C*12:02, HLA-C*12:03, HLA-C*14:02, HLA-C*15:02, HLA-C*16:01, HLA-C*17:01. In certain embodiments, the HLA library consists of HLA-A*01:01, HLA-A*02:01, HLA-A*03:01, HLA-A*11:01, HLA-A*23:01, HLA-A*24:02, HLA-A*25:01, HLA-A*26:01, HLA-A*29:02, HLA-A*30:01, HLA-A*30:02, HLA-A*31:01, HLA-A*32:01, HLA-A*33:01, HLA-A*33:03, HLA-A*68:01, HLA-A*68:02, HLA-B*07:02, HLA-B*08:01, HLA-B*13:02, HLA-B*14:02, HLA-B*15:01, HLA-B*15:03, HLA-B*15:07, HLA-B*18:01, HLA-B*27:02, HLA-B*27:05, HLA-B*35:01, HLA-B*35:03, HLA-B*37:01, HLA-B*38:01, HLA-B*39:01, HLA-B*40:01, HLA-B*40:02, HLA-B*41:02, HLA-B*42:01, HLA-B*44:02, HLA-B*44:03, HLA-B*44:05, HLA-B*46:01, HLA-B*49:01, HLA-B*50:01, HLA-B*51:01, HLA-B*52:01, HLA-B*53:01, HLA-B*55:01, HLA-B*57:01, HLA-B*58:01, HLA-C*01:02, HLA-C*02:02, HLA-C*03:03, HLA-C*03:04, HLA-C*04:01, HLA-C*05:01, HLA-C*06:02, HLA-C*07:01, HLA-C*07:02, HLA-C*07:04, HLA-C*08:01, HLA-C*08:02, HLA-C*12:02, HLA-C*12:03, HLA-C*14:02, HLA-C*15:02, HLA-C*16:01, HLA-C*17:01. In certain embodiments, the HLA library comprises at least 50%, 60%, 70%, 80%, or 90% or more of the following HLA alleles: HLA-A*01:01, HLA-A*02:01, HLA-A*03:01, HLA-A*11:01, HLA-A*23:01, HLA-A*24:02, HLA-A*25:01, HLA-A*26:01, HLA-A*29:02, HLA-A*30:01, HLA-A*30:02, HLA-A*31:01, HLA-A*32:01, HLA-A*33:01, HLA-A*33:03, HLA-A*68:01, HLA-A*68:02, HLA-B*07:02, HLA-B*08:01, HLA-B*13:02, HLA-B*14:02, HLA-B*15:01, HLA-B*15:03, HLA-B*15:07, HLA-B*18:01, HLA-B*27:02, HLA-B*27:05, HLA-B*35:01, HLA-B*35:03, HLA-B*37:01, HLA-B*38:01, HLA-B*39:01, HLA-B*40:01, HLA-B*40:02, HLA-B*41:02, HLA-B*42:01, HLA-B*44:02, HLA-B*44:03, HLA-B*44:05, HLA-B*46:01, HLA-B*49:01, HLA-B*50:01, HLA-B*51:01, HLA-B*52:01, HLA-B*53:01, HLA-B*55:01, HLA-B*57:01, HLA-B*58:01, HLA-C*01:02, HLA-C*02:02, HLA-C*03:03, HLA-C*03:04, HLA-C*04:01, HLA-C*05:01, HLA-C*06:02, HLA-C*07:01, HLA-C*07:02, HLA-C*07:04, HLA-C*08:01, HLA-C*08:02, HLA-C*12:02, HLA-C*12:03, HLA-C*14:02, HLA-C*15:02, HLA-C*16:01, HLA-C*17:01.

In some embodiments, the library comprises greater than or equal to two distinct polypeptide molecules, wherein the antigenic peptide is not the same for each of the greater than or equal to two polypeptide molecules, and wherein each distinct polypeptide is attached to a particle. In some embodiments, the library further comprises a unique defined barcode sequence operably associated with the identity of each distinct polypeptide.

Embodiments include barcoded polynucleotides comprising a defined barcode sequence. The barcoded polynucleotides can be a polynucleotide that provides a unique antigen-specific sequence for identification after T cell isolation. Therefore, each unique comPACT is attached to a particle with a unique defined barcode sequence. This allows an operative association between a given antigen and a given barcode that is unique to the pair.

The barcoded polynucleotides can be ssDNA or dsDNA. The polynucleotides comprising the barcodes can be modified at their 5' end to comprise an attachment moiety for attachment to a particle. For example, the polynucleotides comprising the barcode sequences are conjugated to a biotin molecule for binding to a streptavidin-core attached to a particle, such as dextran. However, any suitable attachment moiety may be used for attachment of polynucleotides to a particle. As described herein and as understood by a person skilled in the art, suitable attachment moiety pairs are known in the art. Non-limiting examples of attachment moieties include thiol, maleimide, adamantane, cyclodextrin, amine, carboxy, azide, and alkyne.

Particles

As used herein, "nanoparticles" or alternatively referred to as "particles" refer to substrates capable of being specifically sorted or isolated, and to which other entities can be attached. In certain embodiments, the "entities" attached to the particles are the comPACT and the barcode. In certain embodiments, in addition to the comPACT and the barcode, additional entities (e.g., fluorophores or other imaging agents) can be attached to the particle. In certain embodiments, in addition to the comPACT and the barcode, additional proteins can be attached to the particle. For example, additional proteins may be attached to the particle to facilitate T cell binding or to increase stability of the comPACT. In certain embodiments, comPACT proteins, barcodes, imaging agents and additional proteins may be attached to the particle. In certain embodiments, multiple comPACT proteins are attached to a particle.

In some embodiments, the particle is magnetic, e.g., for isolation using a magnet. In some embodiments, the magnetic particle comprises magnetic iron oxide. Examples of magnetic particles include, but are not limited, to Dynabeads (Thermo Fisher). In some embodiments, the particle is a polystyrene particle, e.g., for isolation by gravity. In other embodiments, the particle can be a surface, a bead, or a polymer. Examples of beads include, but are not limited to, agarose beads and sepharose beads. In particular embodiments, the particle can be fluorescent or attached to a fluorophore directly or indirectly.

According to certain embodiments, the particle is modified with an attachment moiety for attaching additional molecules. Modification of the particle includes an attachment moiety that can pair with (e.g., covalently bind to) a corresponding cognate (e.g., complementary) attachment moiety attached to polynucleotides. Any suitable pair of attachment moieties may be used to modify the particle and the polynucleotide detection tag for attachment. Non-limiting examples of attachment moiety pairs include a streptavidin/biotin system, a thiol group (e.g., cysteine) and a cysteine reactive moiety (e.g., maleimide, adamantane, and cyclodextrin), an amino group and a carboxy group, and an azido group and alkynl group. In some embodiments, the attachment moiety can comprise a cleavage moiety. In other embodiments, the attachment moiety bound to complementary cognate attachment moiety can be reversible, such as a reducible thiol group. In an exemplary embodiment, the modified particle is a streptavidin coated magnetic nanoparticle, such as 1 μm particle (e.g., Dynabeads MyOne Streptavidin T1 beads from ThermoFisher Scientific), and the polynucleotides can be biotinylated for attachment to the modified particle.

The particle can be a dextran, such as a biotinylated dextran or streptavidin coated dextran. Modified dextrans are described in further detail in Bethune et al., *BioTechniques* 62:123-130 March 2017 and US Publication No. 2015/0329617, herein incorporated by reference in its entirety. Biotinylated comPACTs can be attached to streptavidin coated dextran.

The comPACT proteins can also be assembled into tetramers, comprising 1, 2, 3, or 4 biotinylated comPACT proteins bound to a streptavidin core. The tetramer can also comprise a fluorophore, such as phycoerythrin (PE) or allophycocyanin (APC) bound to the streptavidin core. MHC class I and II tetramers are well known in the art. MHC class I tetramers are described in further detail in Burrow S R et al, *J Immunol* Dec. 1, 2000, 165 (11) 6229-6234 and MHC class II tetramers are described in further detail in Nepom G T, *J Immunol* Mar. 15, 2012, 188 (6) 2477-2482, both of which are herein incorporated by reference in their entirety.

comPACT proteins can also be assembled into multimers. In some embodiments, the comPACT protein multimers can be a dimer, trimer, tetramer, pentamer, hexamer, or higher order multimer. In some embodiments, a multimer can comprise at least two or more comPACT proteins. In some embodiments, a multimer can comprise at least 2, 3, 4, 5, 6, 7, 8, 9, or 10 comPACT proteins.

Particle Sets and Libraries

Also considered are distinct particle sets, each distinct particle set comprising a unique antigen peptide (as used herein referring to the comPACT) and at least one defined barcode operably associated with the identity of the antigen peptide. A particle set comprises at least two particles, each individual particle comprising a unique antigen peptide and at least one defined barcode operably associated with the identity of the antigen peptide. In some embodiments, the distinct particle set comprises at least two particles. In some embodiments, the distinct particle set comprises at least three particles. In some embodiments, the distinct particle set comprises at least four particles. In some embodiments, the unique antigen peptide (as used herein referring to the comPACT) comprises a comPACT polynucleotide molecule, or polypeptide molecule.

Also considered are libraries of distinct particle sets. The library of distinct particle sets may comprise 2 to 1000 particle sets. In some embodiments, the library comprises between 2-900, 2-800, 2-700, 2-600, 2-500, 2-480, 2-400, 2-300, 2-200, 2-100, 2-50, 2-66, 2-48, 2-30, 2-20, 2-19, 10-1000, 10-900, 10-800, 10-700, 10-600, 10-500, 10-480, 10-400, 10-300, 10-200, 10-100, 10-50, 10-66, 10-48, 10-30, 10-20, 20-1000, 20-900, 20-800, 20-700, 20-600, 20-500, 20-480, 20-400, 20-300, 20-200, 20-100, 20-50, 20-50, 20-66, 20-48, 20-30, 30-1000, 30-900, 30-800, 30-700, 30-600, 30-500, 30-480, 30-400, 30-300, 30-200, 30-100, 30-50, 30-50, 30-66, 30-48, 30-40, 40-1000, 40-900, 40-800, 40-700, 40-600, 40-500, 40-480, 40-400, 40-300, 40-200, 40-100, 40-60, 40-50, 40-66, 40-48, 50-1000, 50-900, 50-800, 50-700, 50-600, 50-500, 50-480, 50-400, 50-300, 50-200, 50-100, 50-60, 50-66, 60-1000, 60-900, 60-800, 60-700, 60-600, 60-500, 60-480, 60-400, 60-300, 60-200, 60-100, 70-1000, 70-900, 70-800, 70-700, 70-600, 70-500, 70-480, 70-400, 70-300, 70-200, 70-100, 70-80, 70-90, 80-1000, 80-900, 80-800, 80-700, 80-600, 80-500, 80-480, 80-400, 80-300, 80-200, 80-100, 100-150, 150-200, 200-250, 250-300, 300-350, 350-400, 400-450, or 450-500 particle sets. In some embodiments, the library comprises between 2-19, 48-480, between 48-66, between 66-480, between 220-240, between 40-60, between 48-66, between 50-70, or between 60-80 particle sets. In some embodiments, the library comprises at least 2, 5, 10, 15, 20, 25, 30, 35, 40, 45, 48, 50, 55, 60, 65, 66, 70, 75, 80, 85, 90, 100, 110, 120, 130, 140, 150, 160, 170, 180, 190, 200, 225, 250, 275, 300, 325, 350, 375, 400, 425, 450, 475, 500, 525, 550, 600, 562, 650, 675, 700, 725, 750, 775, 800, 825, 850, 875, 900, 925, 950, 975, or 1000 particle sets. In some embodiments, the library comprises 2, 10, 15, 20, 24, 48, 66, 100, 200, 300, 400, 500, 600, 700, 800, 900, or 1000 particle sets.

In certain embodiments, a library of particle sets of the present disclosure can comprise one, two, three, four, five or more particle sets. In certain embodiments, each particle set can comprise one, two, three, four, five or more or more types of particles. In certain embodiments, a particle set can comprise a single type of particle. In certain embodiments, a particle set can comprise multiple types of particles. For example, but not by way of limitation, a particle set can comprise particles bound to the same barcode or particles bound to the different barcodes, or a combination thereof. In certain embodiments, a particle set can comprise particles bound to a comPACT polypeptide. In certain embodiments, a particle set can comprise particles bound to the same comPACT polypeptide, to different compact polypeptides, or a combination thereof.

Dextramers and Tetramers

The comPACT polypeptides can be attached to a dextran, such as a biotinylated dextran or streptavidin coated dextran. Modified dextrans are described in further detail in Bethune et al., BioTechniques 62:123-130 March 2017 and US Publication No. 2015/0329617, herein incorporated by reference in its entirety. Biotinylated comPACT polypeptides can be attached to streptavidin coated dextran. In certain embodiments, the dextran is coated with streptavidin. In certain embodiments, the streptavidin is covalently conjugated to dextran. In certain embodiments, the streptavidin is non-covalently conjugated to a biotin-dextran.

The comPACTs can also be assembled into tetramers, comprising 1, 2, 3, or 4 biotinylated comPACT proteins bound to a streptavidin core. The tetramer can also comprise a fluorophore, such as phycoerythrin (PE) or allophycocyanin (APC) bound to the streptavidin core. In certain embodiments, the fluorophore is selected from a group comprising PerCP, Cy3, Cy5, and Alexa488. In certain embodiments, the fluorophore is quantum dots (a non-limiting example being Qdot800). In certain embodiments, any fluorophore with a high extinction coefficient could be used. MHC class I and II tetramers are well known in the art. MHC class I tetramers are described in further detail in Burrow S R et al, *J Immunol* Dec. 1, 2000, 165 (11) 6229-6234 and MHC class II tetramers are described in further detail in Nepom G T, *J Immunol* Mar. 15, 2012, 188 (6) 2477-2482, both of which are herein incorporated by reference in their entirety.

Methods of Producing Compact Polypeptides

Antigen Prediction

To manufacture a comPACT, one of the initial steps can include identification of the patient's tumor-specific antigens (e.g., neoantigens). The compositions produced by this method can then be utilized in a T-cell mediated immunity process, e.g., for patient-specific cancer immunotherapy. For identification of a patient's putative neoantigens (tumor or pathogen), in silico predictive algorithmic programs can be utilized that analyze the tumor, viral, or bacterial sequencing data including whole genome, whole exome, or transcriptome sequencing data, to identify one or more mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, (see, Fritsch et al., 2014, *Cancer Immunol Res.,* 2:522-529, the entire contents of which are herein incorporated by reference). HLAs commonly found in the human population can also be included in neoantigen prediction algorithms, such as HLA-A*02, 24, 01; HLA-B*35, 44, 51; DRB1*11, 13, 07 in Caucasians, HLA-A*02, 03, 30; HLA-B*35, 15, 44; DRB1*13, 11, 03 in Afro-Brazilians, and HLA-A*24, 02, 26; HLA-B*40, 51, 52; DRB1*04, 15, 09 in Asians. Specific pairing of HLA alleles can also be used. Common alleles found in the human population are further described in Bardi et al. (Rev Bras Hematol Hemoter. 2012; 34(1): 25-30.)

Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

Restriction Digest Assembly

In general, preparation of a comPACT polynucleotide can be accomplished by procedures disclosed herein and by recognized recombinant DNA techniques, e.g., preparation of plasmid DNA, cleavage of DNA with restriction enzymes, ligation of DNA, transformation or transfection of a host, culturing of the host, and isolation and purification of the expressed fusion complex. Such procedures are generally known and disclosed in standard references such as in Sambrook et al., supra.

In some aspects, DNA encoding an MHC class I heavy chain can be obtained from a suitable cell line such as, for example, human lymphoblastoid cells. In various configurations, a gene or cDNA encoding a class I heavy chain can be amplified by the polymerase chain reaction (PCR) or other means known in the art. In some aspects, a PCR product can also include sequences encoding linkers, and/or one or more restriction enzyme sites for ligation of such sequences.

In some embodiments, a vector encoding a comPACT polynucleotide can be prepared by ligation of sequences encoding the MHC class I heavy chain and the β2-microglobulin to a sequence encoding an antigen peptide.

DNA encoding the antigen peptide can be obtained by isolating DNA from natural sources or by known synthetic methods, e.g., the phosphate triester method. See, e.g., Oligonucleotide Synthesis, IRL Press (M. Gait, ed., 1984). Synthetic oligonucleotides can also be prepared using commercially available automated oligonucleotide synthesizers. A DNA sequence encoding a universal target sequence as discussed herein can be interposed between a sequence encoding a signal sequence and a sequence encoding an antigenic peptide and a second universal target sequence can be interposed between the sequence encoding an antigen peptide segment and a sequence encoding a β2-microglobulin segment. In some embodiments, the segments can be joined using a ligase.

PCR Assembly

In some aspects, the comPACT may be assembled via polymerase chain reaction (PCR) amplification. Similar to the restriction digest method, DNA encoding the MHC heavy chain and the β2-microglobulin may be obtained from a suitable source. A second DNA fragment encoding a chosen signal sequence may also be obtained from a suitable source. Both fragments of DNA may have different universal target sequences, such that primers for one universal sequence do not anneal to the second universal sequence. Two sequences encoding for a chosen antigenic peptide may be synthesized; one forward primer with the antigenic sequence at the 5' end and the complement of the universal primer sequence on the MHC DNA fragment at the 3' end; and one reverse primer with the reverse complement of the chosen antigenic sequence at the 5' end and the reverse complement of the universal primer from the signal sequence fragment at the 3' end. A PCR reaction with all four DNA fragments and primer for the 5' end of the signal sequence fragment and 3' end of the MHC allele fragment will result in amplification of two DNA fragments, one with the signal sequence at the 3' end and the antigenic sequence at the 5' end, and one with the antigenic sequence at the 3' end and the MHC allele at the 3' end. A further PCR amplification cycle will allow the overlapping antigenic peptide sequences to anneal and result in a single full-length DNA fragment. In some embodiments, the signal peptide fragment further comprises a promoter sequence. In some embodiments, the MHC fragment further comprises a purification cluster and/or a polyA tail.

Transfection, Transduction, and Genetic Modification of Host Cells

A comPACT polynucleotide may be inserted into the host cell via an appropriate method known, including, but not limited to, transfection, transduction, electroporation, lipofection, sonoporation, mechanical disruption, or viral vectors. Exemplary transfection reagents include, but are not limited to, FectorPro, Expifectamine, Lipofectamine, polyethyleneimine (PEI), Fugene, or any other transfection reagent that provides optimal transfection rates based on cell type, transfection system, transfection type, transfection conditions, and construct to be transfected. In some examples, Expifectamine is used to transfect mammalian cells with the comPACT polynucleotide. In some examples, polyethyleneimine is used to transfect mammalian cells with the comPACT polynucleotide. In some examples, FectorPro is used to transfect mammalian cells with the comPACT polynucleotide.

A comPACT polynucleotide may be transiently or stably expressed in the host cell. In some embodiments, the comPACT polynucleotide is integrated into the host genome. In other embodiments, the comPACT polynucleotide remains extra-chromosomal. Any appropriate genetic editing technique known in the art may also be employed to modify the host cell with the comPACT polynucleotide, including CRISPR/Cas9, zinc-finger nucleases, or TALEN nucleases.

Expression

A number of strategies can be employed to express a comPACT polypeptide. For example, the comPACT polynucleotide can be incorporated into a suitable vector by known methods such as by use of restriction enzymes and ligases (see, e.g., Sambrook et al., supra). A vector can be selected based on factors relating to the cloning protocol. For example, the vector can be compatible with and have the proper replicon for the host that is being employed. Suitable host cells include eukaryotic and prokaryotic cells, and can be cells that can be easily transformed and exhibit rapid growth in culture medium. Examples of host cells include prokaryotes such as *E. coli* and *Bacillus subtilis*, and eukaryotes such as animal cells and yeasts, such as, for example, mammalian cells and human cells. Non-limiting examples of mammalian cells that can be used as hosts to express a comPACT include J558, NSO, SP2-O, 293T, Expi293, and CHO (and any derivatives or modifications of any of the J558, NSO, SP2-O, 293T, Expi293, and CHO cell lines). Other examples of possible hosts include insect cells such as Sf9, which can be grown using conventional culturing conditions. See Sambrook, et al., supra. In various embodiments, cells expressing a comPACT polypeptide can be identified using known methods. For example, expression of a comPACT polypeptide can be determined by an ELISA, FACS, or Western blot. In certain embodiments, expression of a comPACT polypeptide can be determined by an ELISA, FACS, or Western blot using an antibody probe directed against the MHC heavy chain portion of the comPACT, or an antibody against an affinity tag, such as His6 (SEQ ID NO: 34), or a streptavidin reagent if the comPACT has been biotinylated.

In some aspects, a comPACT is expressed in mammalian cells. The benefits of expressing protein in mammalian cells instead of in *E. coli* cells are multifold. Protein expressed in *E. coli* cells must be carefully purified away from lipopolysaccharide (LPS) Expression of proteins in mammalian cells results in no LPS contamination of the purified proteins. In addition, mammalian cells are more likely to properly fold mammalian proteins since mammalian cells produce proteins with correct post-translation modifications required for proper folding, including the proper formation of disulfide bonds. In addition, mammalian cells provide the correct chaperone proteins to assist with protein folding in the endoplasmic reticulum or Golgi apparatus. This results in increased purification of homogenously well-folded proteins, as compared to proteins expressed in *E. coli* cells.

In some aspects, a comPACT is expressed in prokaryotic cells. In certain embodiments, a prokaryotic cell that has been genetically modified to post-translationally modify the comPACT. In certain embodiments, the comPACT that was expressed in prokaryotic cells is substantially free of LPS or has no detectable LPS as measured using LPS-detection methods known in the art.

A comPACT can be substantially-free of LPS. A comPACT can be free of LPS, e.g., a comPACT can have no detectable LPS as measured using LPS-detection methods known in the art. A comPACT can be glycosylated. A comPACT can have one or more post-translational modifications. A comPACT can be modified via expression in a eukaryotic or in specific embodiments a mammalian cell, e.g., via one or more posttranslational modifications such as glycosylation. A comPACT can include one or more post-translational modifications. A comPACT can (1) be substantially free of LPS or free of LPS, and (2) be glycosylated.

Exemplary comPACT Workflow Process

Figure 23:
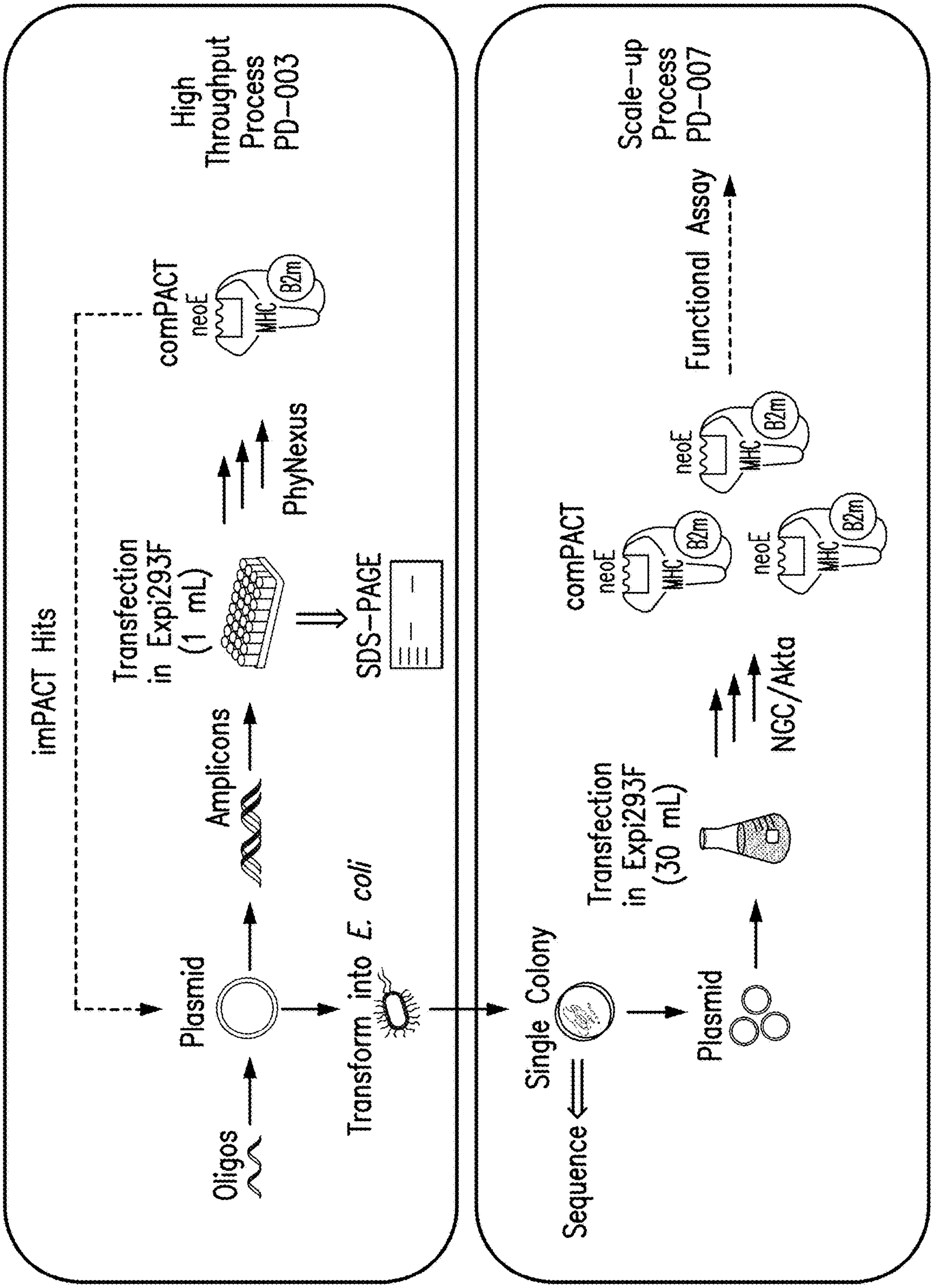
FIG. 23 provides an exemplary diagram of the workflow to manufacture comPACT polynucleotides and proteins.

FIG. 23 shows an exemplary schematic representation of the assembly and expression of a comPACT protein. Sense and antisense oligos that encode for the desired neoantigen peptide sequence are synthesized and annealed to form a double stranded oligo with overhangs at the 5' and 3' ends, which can then be ligated into a plasmid containing a β2M gene and an MHC allele. The full comPACT oligo can be amplified into a double stranded amplicon and transfected into cells for protein expression and optional biotinylation. The comPACT protein can be assessed via SDS-PAGE. comPACT polynucleotides can then be chosen for scaled up plasmid production in *E. coli*. Protein producer cells are transfected with the selected plasmids and the comPACTs are purified from the producer cells for use in functional assays.

Purification (Chromatography)

An expressed comPACT polypeptide can be isolated and purified by known methods. For example, a comPACT comprising a His6 affinity tag (SEQ ID NO: 34) may be purified via affinity chromatography on a metal affinity chromatography column (e.g., a Ni-NTA column or any other metal affinity resin column described herein such as Co2+, Ca2+, Zn2+, Cu2+ resins or any combinations thereof (including Ni2+)) by procedures that are generally known and disclosed. Additionally, a comPACT containing human HLA sequences can be purified by affinity chromatography on a monoclonal antibody-Sepharose column by procedures that are generally known and disclosed.

Methods for Isolating Antigen Specific T Cells

Figure 26:
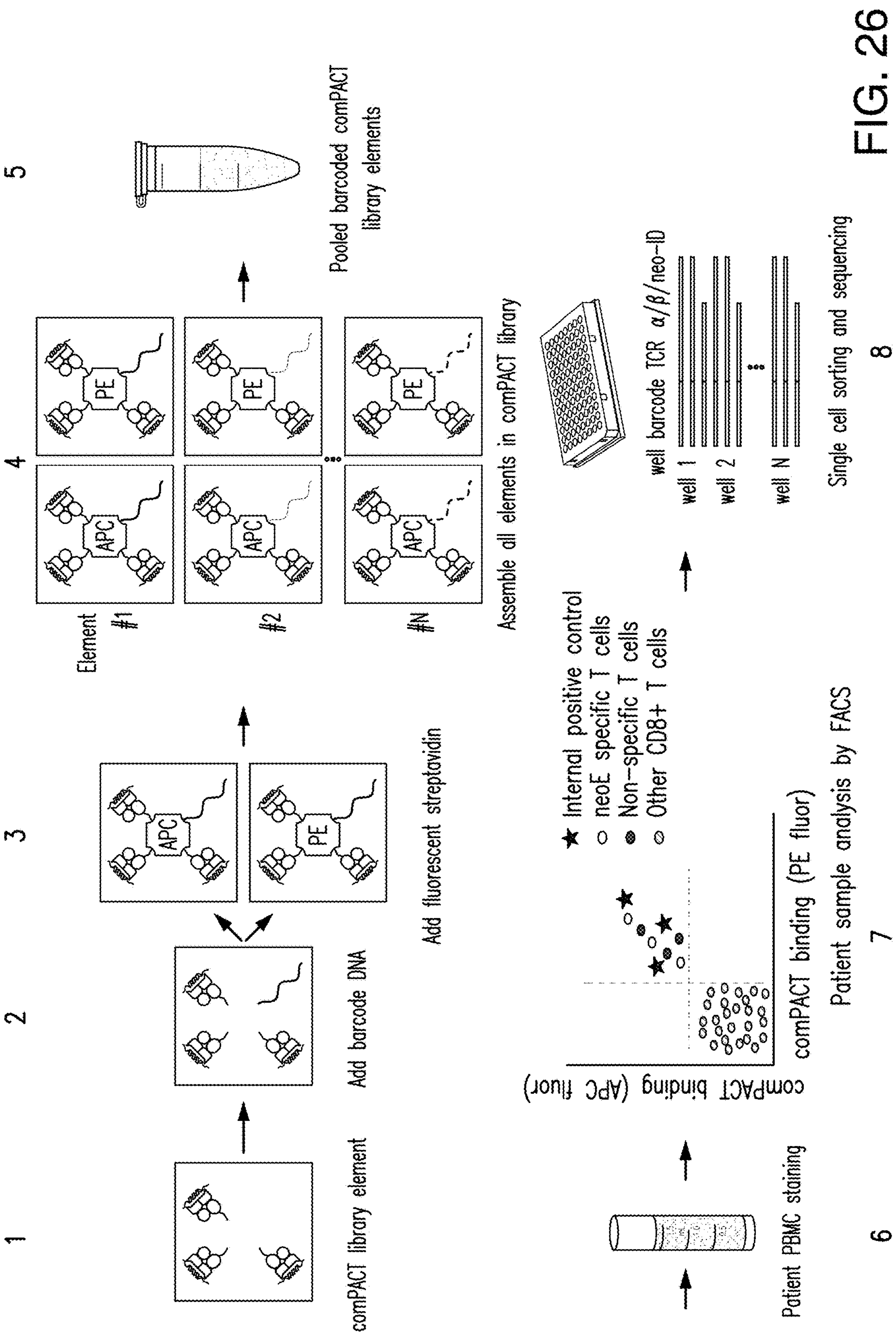
FIG. 26 provides a schematic of the imPACT signal-to-noise neoantigen T cell isolation process.

The comPACT library described herein has been used to isolate antigen specific T cells and can be used to isolate any cell that presents a neoantigen. A diagram of a T cell isolation process, according to an embodiment, is shown in FIG. 26. This process can also be referred to herein as the 'imPACT' or 'imPACT Isolation Technology' method.

The steps and components of the imPACT Isolation Technology method include but are not limited to Steps (1)-(5) diagramed in FIG. 26:

(1) Create a comPACT element library produced for patient-specific neoantigen T cell isolation (2) Add a unique DNA oligonucleotide, neoID, or barcode to the comPACT element library (3) Each individual comPACT polypeptide and its corresponding neoID barcode, DNA oligonucleotide, neoID, or barcode is bound to two separate fluorescent streptavidin proteins (in the example provided in FIG. 26 phycoerythrin (PE) and allophycocyanin (APC))

(4) This assembly process resulted in two paired barcoded fluorescent tetramers per comPACT polypeptide and barcode element (5) A library of tetramers assembled with all the comPACT polypeptides and neoID barcode, DNA oligonucleotide, neoID, or barcode targeting the predicted neoantigen candidates per patient is pooled together for the isolation of neoantigen-specific T cells from the subject's peripheral blood.

Use of a comPACT library to identify and characterize neoantigen specific T cells is also shown in FIG. 26 in panels 6-8. Incubation of the comPACT-neoID library with patient samples (6) is followed by fluorescent-activated cell sorting (FACS) (7). A fixed number of T cells engineered to express a tool neoTCR can be added to the patient sample as an internal positive control to calibrate each analysis. Dual fluorescently-labeled (PE and APC) tetramer-bound neoantigen-specific T cells, as well as the internal positive control cells, and potential non-specific T cells are sorted as single cells into individual wells in plates for subsequent RT-PCR analysis, including barcode and neo-TCR sequencing (8).

Barcode Signal to Noise (S/N) Analysis

Figure 27A:
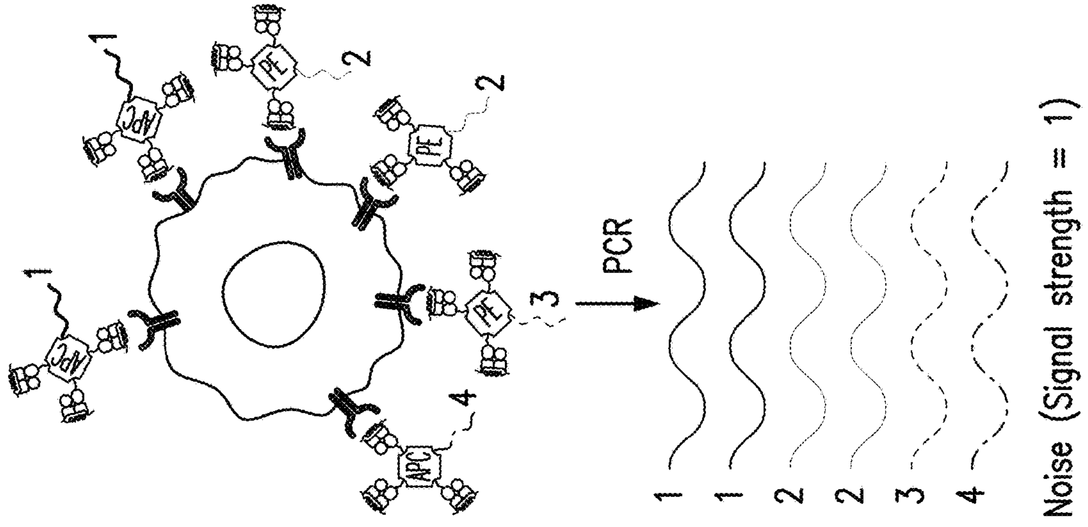
FIG. 27A provides an illustration of non-specific barcode signal strength to identify signal and noise.
Figure 27B:
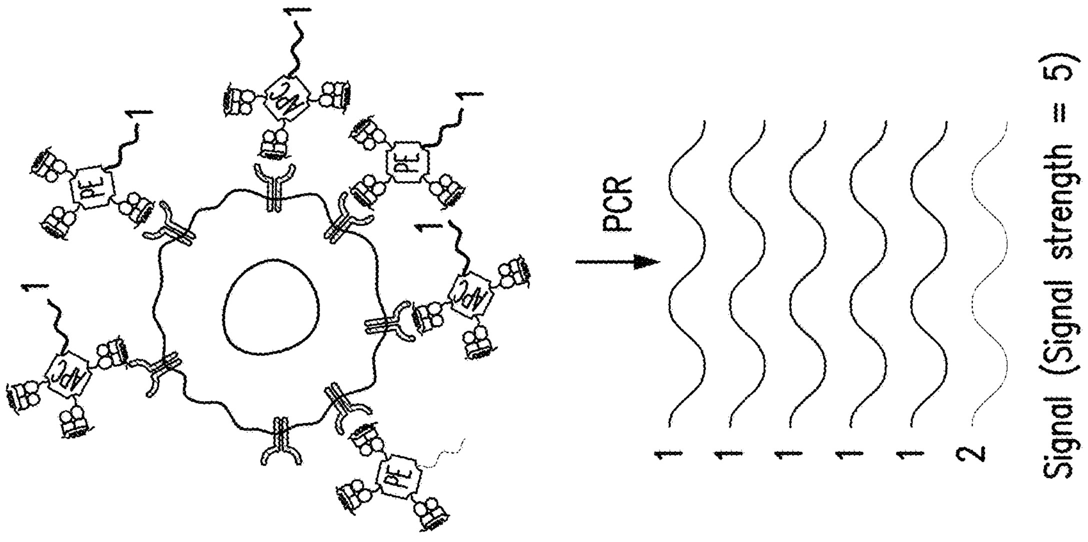
FIG. 27B provides an illustration of specific barcode signal strength to identify signal and noise.

True positive neoantigen-specific dual-labeled T cells can be resolved from false positive T cells identified by flow cytometry by sequence analysis of the neoID barcodes bound to the isolated T cell. The presence of multiple copies of the same neoID barcode yields a high ratio of specific neoID barcode species compared to non-specific bound barcodes. This results in a higher signal-to-noise barcode ratio (S/N). Non-specific T cells bind relatively equal numbers of different tetramer species resulting in lower ratio of distinct neoID barcodes. A schematic of non-specific vs specific T cell binding is shown in FIG. 27A (non-specific) and FIG. 27B (specific). The numbers indicate the different neoID barcodes. In FIG. 27A the ratio of unique DNA copy number for the most dominant neoID divided by the second most dominant neoID is 1, indicating a cell that is non-specifically bound by comPACT elements. In FIG. 27B the ratio of unique DNA copy number for the most dominant neoID divided by the second most dominant neoID is 5, indicating this T cell is bound by a dominant comPACT element and represents a true positive neoantigen-specific CD8 T cell. This can be further confirmed via functional characterization of T cells engineered with the neoTCR cloned from that individual cell.

S/N1 and S/N2 Analysis

In some embodiments, one TCR may recognize two different neoantigens. In such cases, even though the T cell is specific, the S/N ratio might be lower than 10. In such instances, two different S/N calculations may be used, S/N1 and S/N2. S/N1 is the highest signal divided by the second highest signal, while S/N2 is the highest signal from one mutation divided by the highest signal from a different mutation. In an S/N2 analysis, the highest signal from a different mutation may not be the second highest signal in the sample.

In an illustrative example, 8 different TCRs may be identified in one sample. 6 of them may have an S/N1 ratio more than 10, and can be confirmed to be specific neoantigen T cells. For the other 2 T cells, the S/N1 ratio may be lower than 10. However, the S/N2 may be higher than 10. Cloning the 2 TCRs shows that they can recognize two different neoantigens sharing the same mutation, explaining the reason for low S/N1 ratio. In some embodiments, S/N2 analysis may be useful for calling the non-specific from specific cells, when there are multiple neoantigens derived from the same mutation.

In some embodiments, a higher S/N ratio indicates a higher TCR binding specificity.

Threshold

In some embodiments, the isolated T cell is identified as said antigen specific T cell if the barcode signal-to-noise S/N1 or S/N2 ratio is above a threshold.

In some embodiments, the threshold is at least or greater than 2, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 550, 600, 650, 700, 750, 800, 850, 900, 950, or 1000. In some embodiments, the threshold is at least or greater than 2, 5, 10, or 20. In some embodiments, the ratio corresponds to the specificity of the isolated antigen specific T cell. In some embodiments, the S/N ratio is 10 or more.

Labels

As used herein, "identifying label" or "identifying labels" means a molecule or compound used to label a particle set. In some embodiments, the identifying label is a fluorophore. In some embodiments, the identifying label is a metal, a lanthanide, a quantum dot, a radioisotope, a nanoparticle, or a dye. Any appropriate fluorophore can be used, including but not limited to allophycocyanin (APC), phycoerythrin (PE), fluorescein (FITC), rhodamine, Texas red, DAPI, C2, Cy3, Cy5, Cy7, AlexaFluor fluorophores, BODIPY fluorophores, DyLight fluorophores, FluoProbes fluorophores, or any combination thereof.

Barcodes

As used herein, "barcode" or "barcodes" means a nucleotide sequence used to tag and identify a specific peptide, including but not limited to an antigen peptide. In certain embodiments, the barcode is selected from a group consisting of a 3-mer, 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, and a 20-mer. In certain embodiments the barcode is an 8-mer.

In some embodiments, the distinct particle pair comprises a unique antigen peptide and a defined barcode operably associated with the identity of the antigen peptide.

In some embodiments, the first particle comprises a first barcode and said second particle comprise a second barcode distinct from the second barcode, wherein the first and second barcodes are associated with the identity of the antigen.

In some embodiments, the particle pair comprises a third particle comprising a third barcode distinct from the first and second barcode, wherein the first, second, and third barcodes are associated with the identity of the antigen.

An exemplary barcode and barcode structure are provided in Table A below. Barcodes may also be termed "neoIDs."

TABLE A

| Name | Sequence |
|---|---|
| Barcode structure | Biotin-Universal primer 1-NNNNN-Barcode-NNNNNN-Universal primer 2 |
| Representative barcode sequence | /5Biosg/CTCGCCACGTCGGCTATCCTGAT CGGATGNNNNNNNTCAATCCGNNNNNNCTGGA CGTGAGCAAGCTACAGCGACCTC (SEQ ID NO: 202) |

In some embodiments, the barcode signal-to-noise ratio is based on at least one barcode. In such embodiments, each of the paired particles comprises the same antigen, a different label, and at least one barcode, wherein the at least one barcode is associated with the neoantigen. In some embodiments, the paired particles have at least 1, 2, 3, 4, 5, 6, 7, 8, 9, 10, or more than 10 barcode(s).

In some instances, aggregates of the particles with fluorophore labels can result in single fluorophore high mean fluorescent intensity of stained cells during isolation. This is not due to specific binding of the fluorescent particles, but rather non-specific binding of a comPACT particle aggregate, which results in a high neoantigen barcode SN, as there may be a large number of the same barcode bound to a T cell non-specifically. Use of a dual barcode system can be used to address this problem.

Figure 28:
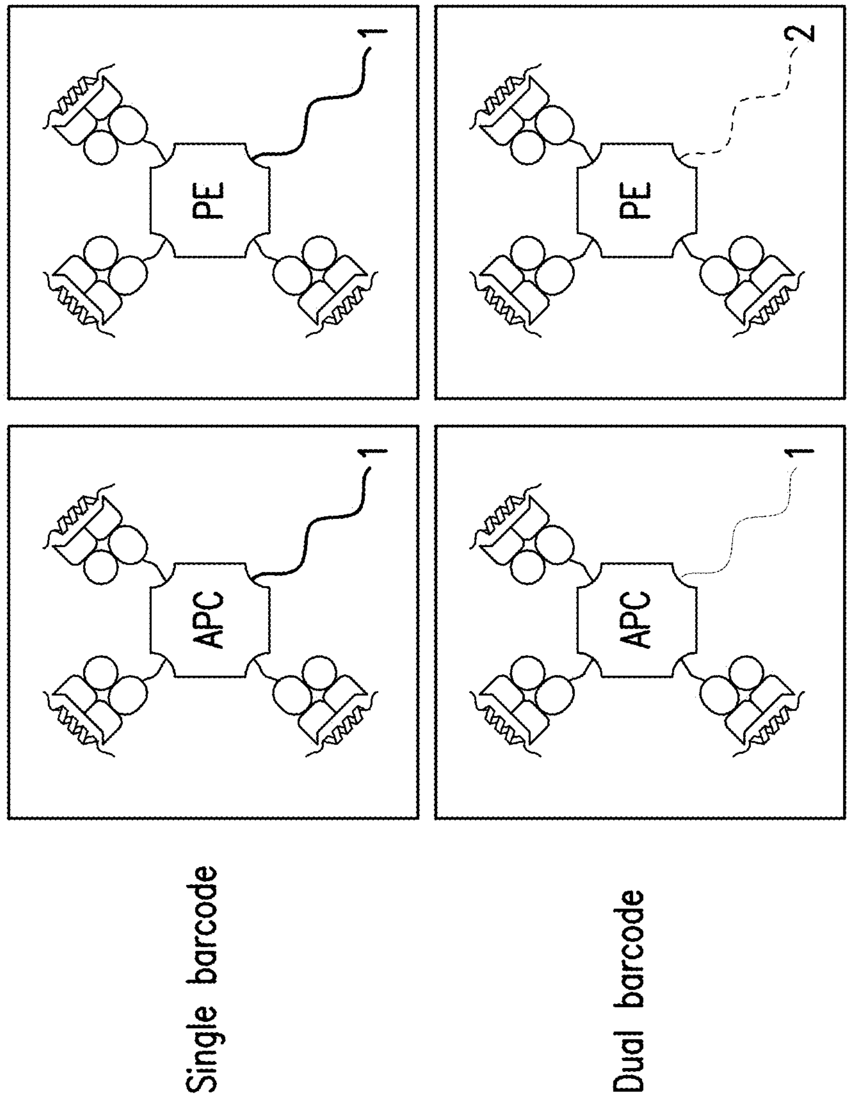
FIG. 28 provides an illustration of single versus dual barcoding.

In some embodiments, each particle pair of the comPACT library elements comprises at least two barcodes. Dual barcoding conjugates two different DNA barcodes per antigen to each comPACT tetramer, respectively. A diagram of the comparison of the single and dual barcoding for one antigen is shown in FIG. 28. In the top panels, the same neoantigen is associated with two different particles, two different fluorophores, and a single barcode, labeled "1". In the bottom panels, the same antigen is associated with two different particles, two different fluorophores, and two different barcodes, labeled "1" and "2". This results in increased identification of false positives with high signal to noise ratios caused by tetramer aggregation. The signal to noise ratios of each DNA barcode assigned to each fluorescent particle and the same antigen can be analyzed separately.

In some embodiments, each particle pair of the comPACT library elements comprises at least two barcodes. Dual barcoding conjugates two different DNA barcodes per antigen peptide to each comPACT tetramer, respectively. A diagram of the comparison of the single and dual barcoding for one antigen peptide is shown in FIG. 28. In the top panels, the same antigen peptide is associated with two different particles, two different fluorophores, and a single barcode, labeled "1". In the bottom panels, the same antigen peptide is associated with two different particles, two different fluorophores, and two different barcodes, labeled "1" and "2". This results in increased identification of false positives with high signal to noise ratios caused by tetramer aggregation. The signal to noise ratios of each DNA barcode assigned to each fluorescent particle and the same antigen peptide can be analyzed separately.

Cell Samples

The imPACT method (i.e., imPACT Isolation Technology) can be used to isolate immune cells, such as T cells and B cells, from any appropriate patient-derived sample that comprises immune cells including, but not limited to, blood, plasma, peripheral blood mononuclear cell (PBMC) samples, bone marrow, tumor infiltrating lymphocyte (TIL) samples, tissues, solid tumors, hematologic cancers, and liquid tumors, or any combination thereof. For example, both CD4+ and CD8+ T cells can be labeled and sorted from PBMCs or TILS using anti-CD4 and anti-CD8 fluorescent antibodies, with live populations of CD4+ and CD8+ single-positive cells sorted using fluorescence-activated cell sorting (FACS), to isolate only CD4+ or CD8+ cells. In some embodiments, T cells that are positive for both CD4 and CD8 can be isolated using an anti-CD3 fluorescent antibody followed by FACS. In addition, the imPACT method can also be used for antibody discovery for B cells. A person skilled in the art is able to determine the type of immune cells to isolate for the type or types of comPACT protein being used. In some embodiments, the sample is a blood sample. In some embodiments, the sample is a PBMC sample. In some embodiments, the sample is a solid tumor sample. In some embodiments, the sample is a hematologic tumor sample. In some embodiments, the sample is a bone marrow sample. In some embodiments, the sample is a tumor sample comprising tumor infiltrating lymphocytes. The T cells can be CD8+ T cells or CD4+ T cells. In some embodiments, the T cell is a CD8+ T cell. In some embodiments, the T cell is a CD4+ T cell. In some embodiments, the T cell is a human T cell. In some embodiments, the T cell is a human CD8+ T cell.

T Cell Isolation

In another aspect, provided herein are methods of isolating an antigen specific T cell, the method comprising the steps of (a) providing a polypeptide comprising, in an amino terminus to carboxyl terminus orientation, (i) a first universal target peptide, (ii) an antigenic peptide, (iii) a second universal target peptide that is distinct from the first universal target peptide, (iv) a β2M peptide, and (v) an MEW peptide, wherein the polypeptide is linked to one particle; (b) providing a sample known or suspected to comprise one or more T cells; (c) contacting the polypeptide with the sample, wherein the contacting comprises providing conditions sufficient for a single T cell to bind the polypeptide attached to the particle, and (d) isolating the single T cell associated with the particle.

Isolation and identification of patient-derived and antigen-specific T cells using a comPACT as described herein can include incubating the comPACT protein with patient-derived T cells or with a sample containing patient-derived T cells. In some embodiments, a library comprising at least two comPACTs can be incubated with patient-derived T cells. T cells can be prepared using standard methods that start from a tissue such as blood, a lymph node, or a tumor.

Incubation of the comPACT or comPACT library with the T cell suspension allows for a complete and thorough exposure of the particle-bound antigen peptide to the various T-cell receptors. This method may include rocking or rotation of the cells. In some embodiments, the comPACT is associated with a particle.

Following incubation of the comPACT or comPACT library (both of which bound to a particle) and the T cells, the bound comPACT-T cell complex is selectively separated or selectively collected. T cells will likely be bound to many identical copies of identical comPACT library elements (i.e., the individual comPACT polypeptides and the comPACT polypeptides associated with a particle) and can be separated based on these interactions. For example, if the comPACT or comPACT that is associated with a particle comprises a fluorophore, or is attached to a particle with a fluorophore, fluorescent associated cell sorting (FACS), including single-cell sorting, can be used to selectively isolate the T cells. If the comPACT or the particle which is associated with is attached to a magnetic particle, applying a magnet to the suspension can allow for separation of particles complexed with antigen-paired T cells and removal of unpaired T cells. Alternatively, if the particle which is associated with the comPACT is a polystyrene particle, the unpaired T cells may be separated by gravity (e.g., centrifugation). After removal of unpaired T cells, in some embodiments, the separated bound particles are washed at least once to remove any non-specifically associated T cells.

comPACT-bound T cells can be also separated by FACS into individual collection containers, such as a multi-well plate. The individual collection container can be single-cell reaction vessels. For example, components used for downstream processing and analysis can be added to each single-cell reaction vessel. The comPACT-bound T cells can be separated by FACS into a bulk collection container (e.g., every T cell isolated is collected in the same container).

comPACT-bound T cells can also be individually isolated in droplets using a droplet generating microfluidic device (i.e., a "droplet generator"). Droplet generating devices used to encapsulate single cells are known to those skilled in the art, e.g., as described in US Publication No. 2006/0079583, US Publication No. 2006/0079584, US Publication No. 2010/0021984, US Publication No. 2015/0376609, US Publication No. 2009/0235990, and US Publication No. 2004/0180346.

After isolation of comPACT-bound T cells into single-cell reaction vessels (e.g., isolated in individual well or droplets), the nucleic acid of the comPACT-bound T cell can be further processed for downstream analysis. Specifically, the expressed TCRα and TCRβ mRNA transcripts can be first converted to cDNA by reverse transcription and the cDNA amplified for next generation sequencing (NGS) methods known to those skilled in the art, including, but not limited to, sequencing by synthesis technologies (e.g., Illumina or any other NGS sequencing machine).

Methods for Identifying T Cell Antigen-Specificity

In certain embodiments, the presently disclosed subject matter provides for methods for identifying the antigen-specificity of a T cell. In certain embodiments, the T cell isolation methods described herein provide information concerning the antigen-specificity of the isolated T cell. For example, but not by way of limitation, information concerning the antigen-specificity can be obtained by nucleic acid analysis of the isolated T cell. In certain embodiments, nucleic acids of the isolated T cell can be analyzed to determine the sequence of the T cell receptor gene sequences (e.g., TCR alpha and TCR beta sequences). In certain embodiments, information concerning the antigen-specificity of isolated T cells can be used for downstream applications. Non-limiting examples of downstream applications include analysis of immune repertoire, manufacturing processes, and clinical follow-up of a patient undergoing immunotherapy. In certain embodiments, information concerning the antigen-specificity of an isolated T cell can be used to prepare reagents and composition for manufacturing cells useful in adoptive cell transfer therapies.

In non-limiting embodiments, a monitoring of the immune repertoire is performed. In certain embodiments, the monitoring of the immune repertoire is performed before, during, or after a treatment. In certain embodiments, the treatment is an immunotherapy. Non-limiting examples of immunotherapy comprise administration of vaccines, oncolytic viruses, antibodies, T cells expressing chimeric antigen receptor, T cells expressing recombinant T cell receptors, tumor-infiltrating lymphocytes Methods of Treatment In certain embodiments, the presently disclosed subject matter provides methods of treatment, including, but not limited to, the induction of and/or increasing of an immune response in a subject in need thereof. In certain embodiments of the present disclosure, the methods of treatment disclosed herein involve the isolation and/or administration of cells. For example, but not by way of limitation, the cells employed in the methods described herein can be, in certain embodiments, obtained from a subject. In certain embodiments, the cells are tumor cells, non-cancer cells, T cells, or any combination thereof. In certain embodiments, nucleic acids can be extracted from the cells as outlined herein. In certain embodiments, the nucleic acids of the cells can be sequenced as outlined herein. In certain embodiments, information, e.g., nucleic acid sequence information, obtained from the subject provides information concerning antigen-specific T cells. In certain embodiments, the information concerns the identity (e.g., amino acid sequence) of antigen peptides. In certain embodiments, the antigen peptide is a tumor neoantigen. In certain embodiments, the information concerns the identity of MHC sequences.

In certain embodiments, the methods described herein relate to the treatment of cancer. In certain embodiments, the cancer is a solid cancer. Non-limiting examples of tumors treatable by the methods described herein include, for example, carcinomas, lymphomas, sarcomas, blastomas, and leukemias. Non-limiting specific examples, include, for example, breast cancer, pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, brain cancers of all histopathologic types, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, cancers associated with viral infection (such as but not limited to human papilloma virus (HPV) associated tumors (e.g., cancer cervix, vagina, vulva, head and neck, anal, and penile carcinomas)).

In certain embodiments, a comPACT mini-gene comprising a candidate antigen-peptide is produced according to the methods disclosed herein. In certain embodiments, a comPACT polypeptide comprising the antigen peptide is produced. In certain embodiments, a particle comprising a comPACT polypeptide is produced according to the methods disclosed herein. In certain embodiments, at least one particle set comprising a comPACT polypeptide is produced according to the methods disclosed herein.

In certain embodiments of the methods of treatment disclosed herein, a T cell is isolated by virtue of being bound to a particle. In certain embodiments, the T cell isolated in this manner was obtained from the subject. In certain embodiments, the T cell is a $CD8^+$ T cell.

In certain embodiments, the isolated T cell is sorted and its genome analyzed. In certain embodiments, the TCR sequences of the isolated T cell are obtained. In certain embodiments, the TCR gene sequences, or portions thereof, are inserted into a homologous recombination template. In certain embodiments, the homologous recombination template comprises the features described in International Patent Application No. PCT/US2018/058230, the content of which is herein incorporated by reference in its entirety.

In certain embodiments, a T cell is modified by inserting the homologous recombination template comprising the TCR gene sequences, or portions thereof of the isolated T cell.

In certain embodiments, the modified T cell is adoptively transferred to the patient. Adoptive cell transfer (ACT) is an effective form of immunotherapy and involves the transfer of immune cells with antitumor activity into cancer patients. Lymphocytes used for adoptive transfer can be derived from the blood or the stroma of resected tumors, although other sources of such cells are known in the art. In certain embodiments, the lymphocytes employed in ACT can be administered in a single dose. Such administration can be by injection, e.g., intravenous injection. In certain embodiments, the lymphocytes can be administered in multiple doses. Dosing may be once, twice, three times, four times, five times, six times, or more than six times per year. Dosing may be once a month, once every two weeks, once a week, or once every other day. Administration of cytotoxic lymphocytes can continue as long as necessary. In certain embodiments, the methods described herein can be used to determine the immunorepertoire of a subject. In certain embodiments, the immunorepertoire is analyzed: before a treatment, during a treatment, and/or after a treatment. In certain embodiments, the treatment is a cancer treatment. In certain embodiments, the cancer treatment is an immunotherapy. In certain embodiments, the immunotherapy comprises administration of an antibody. In certain embodiments, the immunotherapy comprises an adoptive cell transfer of T cells. In certain embodiments, the T cells comprise a recombinant TCR or a chimeric antigen receptor. In certain embodiments, the immunorepertoire provides information to provide a targeted therapy.

Methods of Modifying a Cell

In certain embodiments, the presently disclosed subject matter provides methods for modifying a cell. For example, but not by way of limitation, modified cells can be obtained using the methods and compositions described herein.

In certain embodiments, the presently disclosed subject matter provides a method of modifying a cell by introducing and recombining a homologous recombination (HR) template nucleic acid sequence into an endogenous locus of a cell. In certain embodiments, the cell is modified with non-viral methods. In certain embodiments, the HR template nucleic acid sequence is circular. In certain embodiments, the HR template nucleic acid sequence is linear. In certain embodiments, the HR template nucleic acid sequence comprises a first and second homology arms. In certain embodiments, the homology arms can be of about 300 bases to about 2,000 bases. For example, each homology arm can be 1,000 bases. In certain embodiments, the homology arms can be homologous to first and second endogenous sequences of the cell. In certain embodiments, the endogenous locus is a TCR locus. For example, the first and second endogenous sequences are within a TCR alpha locus or a TCR beta locus. In certain embodiments, the HR template comprises a TCR gene sequence. In non-limiting embodiments, the TCR gene sequence is a patient specific TCR gene sequence. In non-limiting embodiments, the TCR gene sequence is identified and obtained using the methods described herein. For example, the methods for identifying antigen-specificity of a T cell can be used to obtain the sequences of the TCR gene from a patient and the TCR sequences can be incorporated in the HR template. In certain embodiments, the HR template comprises a TCR alpha gene sequence and a TCR beta gene sequence. Additional information on the HR template nucleic acids and methods of modifying a cell thereof can be found in International Patent Application no. PCT/US2018/058230, the content of which is herein incorporated by reference.

In certain embodiments, constructs containing genes of interest can be inserted into endogenous loci using non-viral gene editing methods. In certain embodiments, this can be accomplished with the use of homologous repair templates containing the coding sequence of the gene of interest flanked by left and right HR arms. In certain embodiments, in addition to the HR arms, the gene of interest is sandwiched between 2A peptides, a protease cleavage site that is upstream of the 2A peptide to remove the 2A tag from the upstream translated gene of interest, and signal sequences; wherein once integrated into the genome, the gene of interested expression gene cassette is transcribed as single messenger RNA. In certain embodiments, during translation of the gene of interest messenger RNA, the flanking regions are unlinked from the gene of interest by the self-cleaving 2A peptide and the protease cleavage site was cleaved for the removal of the 2A sequence upstream from the translated gene of interest. In certain embodiments, in addition to the 2A and protease cleavage site, a gly-ser-gly (GSG) linker can be inserted before each 2A peptide to further enhance the separation of the gene of interest from the other elements in the expression cassette. In certain embodiments, P2A peptides are used because they are superior to other 2A peptides because of their efficient cleavage. In certain embodiments, two (2) P2A peptides and codon divergence are used in order to express the gene of interest without introducing any exogenous epitopes from remaining amino acids on either end of the gene of interest from the P2A peptide.

In certain embodiments and as described in PCT/US/2018/058230, neoTCRs are integrated into the TCRα locus of T cells. In certain embodiments, a homologous repair template containing a neoTCR coding sequence flanked by left and right HR Arms are used. In certain embodiments, the endogenous TCRβ locus is disrupted leading to expression of only TCR sequences encoded by the neoTCR construct. In certain embodiments, the general strategy is applied using circular HR templates. In certain embodiments, the general strategy is applied using linear templates.

Figure 67A:
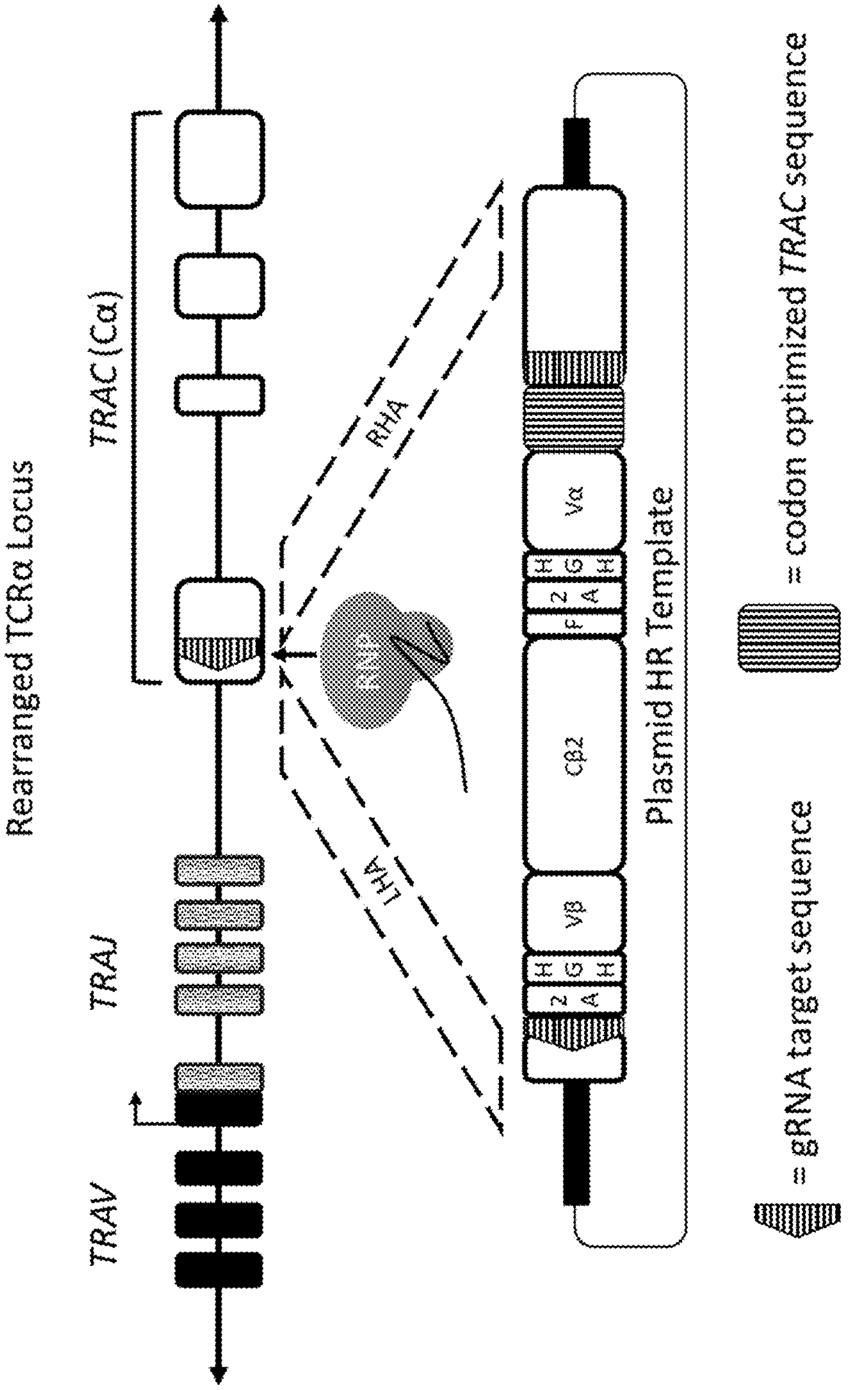
FIGS. 67A and 67B illustrate the neoantigen-specific TCR construct design used for integrating neoantigen-specific TCR constructs (neoTCRs) into the TCRα locus.
Figure 67B:
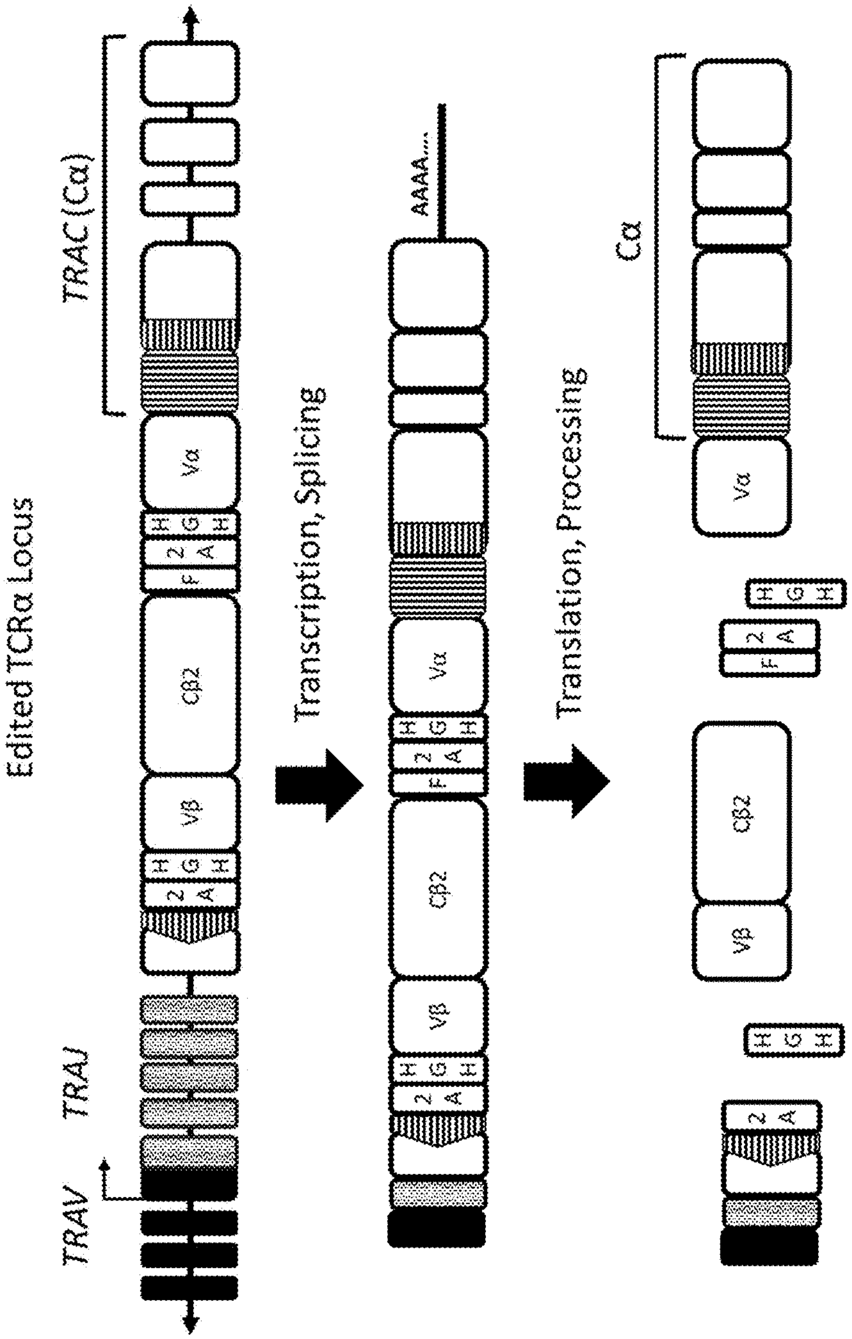

In certain embodiments, the target TCRα locus (Cα) is shown along with the plasmid HR template, and the resulting edited sequence and downstream mRNA/protein products are shown in FIGS. 67A and 67B. In certain embodiments, additional elements in the neoTCR cassette include: 2A=P2A ribosome skipping element; F=furin cleavage site upstream of 2A that removes the 2A tag from the upstream TCRβ protein; HGH=human growth hormone signal sequence. The HR template of the neoTCR expression gene cassette includes two flanking homology arms to direct insertion into the TCRα genomic locus targeted by the CRISPR Cas9 nuclease RNP with the TCRα guide RNA. In certain embodiments, the homology arms (LHA and RHA) flank the neoE-specific TCR sequences of the neoTCR expression gene cassette. In certain embodiments, the protease cleavage site is any appropriate protease cleavage site known to one of skill in the art could be used. In certain embodiments, any signal sequence known to one of skill in the art could be selected based on desired trafficking and use.

In certain embodiments, once integrated into the genome, the neoTCR expression gene cassette is transcribed as a single messenger RNA from the endogenous TCRα promoter, which still includes a portion of the endogenous TCRα polypeptide from that individual T cell. In certain embodiments, during ribosomal polypeptide translation of the single neoTCR messenger RNA, the neoTCR sequences are unlinked from the endogenous, CRISPR-disrupted TCRα polypeptide by self-cleavage at a P2A peptide. In certain embodiments, the encoded neoTCRα and neoTCRβ polypeptides are also unlinked from each other through cleavage by the endogenous cellular human furin protease and a second self-cleaving P2A sequence motifs included in the neoTCR expression gene cassette (FIG. 67B). In certain embodiments, the neoTCRα and neoTCRβ polypeptides are separately targeted by signal leader sequences (e.g., derived from the human growth hormone, HGH) to the endoplasmic reticulum for multimer assembly and trafficking of the neoTCR protein complexes to the T cell surface. In certain embodiments, the inclusion of the furin protease cleavage site facilitates removal of the 2A sequence from the upstream TCRβ chain to reduce potential interference with TCRβ function. In certain embodiments, inclusion of a gly-ser-gly linker before each 2A (not shown) further enhances the separation of the three polypeptides.

In certain embodiments, three repeated protein sequences are codon diverged within the HR template to promote genomic stability. In certain embodiments, the two P2A are codon diverged relative to each other, as well as the two HGH signal sequences relative to each other, within the TCR gene cassette to promote stability of the introduced neoTCR cassette sequences within the genome of the ex vivo engineered T cells. In certain embodiments, the re-introduced 5' end of TRAC exon 1 (FIGS. 67A and 67B, vertical stripe) reduces the likelihood of the entire cassette being lost over time through removal of intervening sequence of two direct repeats.

The presently disclosed subject matter further provides for compositions comprising cells modified by the methods disclosed herein.

EXEMPLARY EMBODIMENTS

A. In certain non-limiting embodiments, the presently disclosed subject matter provides for a method comprising: (a) contacting a sample with a plurality of distinct particle sets, wherein each particle comprises a unique antigen peptide, an operably associated barcode, and at least one identifying label, wherein the sample comprises T cells, and wherein contacting comprises providing conditions suitable for a single T cell to bind to a unique antigen peptide of at least one particle set; (b) isolating one or more T cells bound to a particle; (c) identifying the barcode of the particle bound to the isolated T cell; and (d) determining a ratio of each barcode.

A1. The foregoing method of A, wherein the ratio is calculated by identifying a copy number of a first barcode and a copy number of a second barcode and dividing the copy number of the first barcode by the copy number of the second barcode.

A2. The foregoing method of A or A1, wherein the unique antigen peptide is the same for each distinct particle set.

A3. The foregoing method of any one of A-A2, wherein each distinct particle set comprises at least one or more barcodes, wherein each barcode is associated with the identity of the antigen peptide.

A4. The foregoing method of any one of A-A3, wherein the ratio of each barcode corresponds to the antigen specificity of the isolated T cell.

A5. The foregoing method of any one of A-A4, wherein the isolated T cell is identified as an antigen-specific T cell if the ratio of the first barcode is above a threshold.

A6. The foregoing method of A5, wherein the threshold is at least or greater than 2, 3, 4, 5, 6, 7, 8, 9, 10, 2-5, 3-6, 4-7, 5-8, 5-10, 7-10, or greater than 10.

A7. The foregoing method of any one of A-A6, wherein the identifying the barcode comprises a nucleotide-based assay.

A8. The foregoing method of A7, wherein the nucleotide-based assay is a PCR, an RT-PCR, a sequencing, or a hybridization assay.

A9. The foregoing method of A7 or A8, wherein the nucleotide-based assay determines (a) a sequence of each barcode and/or (b) a copy number of each barcode.

A10. The foregoing method of any of A-A9, further comprising obtaining a T cell receptor (TCR) CDR sequence.

A11. The foregoing method of any of A-A10, further comprising obtaining a TCR gene sequence.

A12. The foregoing method of A11, wherein the TCR sequence is a TCR alpha or a TCR beta chain sequences.

A13. The foregoing method of any of A-A12 for identifying the antigen specificity of a T cell.

A14. The foregoing method of A13, wherein the antigen specificity of the T cell comprises the sequence of the antigen peptide and the TCR sequences of the bound T cell.

A15. The foregoing method of any of A-A14, wherein the at least one identifying label is the same in each distinct particle set.

A16. The foregoing method of any of A-A15, comprising at least two different identifying labels.

A17. The foregoing method of any of A-A16, wherein the at least one identifying label is a fluorophore.

A18. The foregoing method of A17, wherein the fluorophore is selected from the group comprising allophycocyanin (APC) and phycoerythrin (PE).

A19. The foregoing method of A18, wherein the at least two different identifying labels are fluorophores, wherein the fluorophores are selected from the group comprising allophycocyanin (APC) and phycoerythrin (PE).

A20. The foregoing method of any of A-A19, wherein the antigen peptide is selected from the group consisting of a tumor antigen, a neoantigen, a tumor neoantigen, a viral antigen, a bacterial antigen, a phospho-antigen, and a microbial antigen.

A21. The foregoing method of A20, wherein the neoantigen is identified from tumor sequencing data from a subject.

A22. The foregoing method of A21, wherein an in silico predictive algorithm is used to determine the neoantigen.

A23. The foregoing method of A22, wherein the predictive algorithm further comprises an MHC binding algorithm to predict binding between the neoantigen and an MHC peptide.

A24. The foregoing method of any of A-A23, wherein the sample is selected from a blood sample, a bone marrow sample, a tissue sample, a tumor sample, or a peripheral blood mononuclear cell (PBMC) sample.

A25. The foregoing method of any of A-A24, wherein the T cell is a human T cell.

A26. The foregoing method of A25, wherein the T cell is a CD8+ T cell.

A27. The foregoing method of any of claims A-A26, wherein the method comprises a library of distinct particle sets.

A28. The foregoing method of A27, wherein the library comprises 2 to 500 distinct particle sets.

A29. The foregoing method of any of A-A28, wherein each particle comprises an MHC peptide.

A30. The foregoing method of A29, wherein the MHC peptide is a human MHC peptide.

A31. The foregoing method of A29, wherein the MHC peptide is a class I HLA peptide.

A32. The foregoing method of A29, wherein the HLA peptide comprises an HLA-A, HLA-B, or HLA-C peptide.

A33. The foregoing method of A32, wherein the HLA peptide comprises HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, or HLA-C*17:01.

A34. The foregoing method of any of A-A33, wherein each particle comprises an HLA peptide and a β2M peptide.

A35. The foregoing method of A34, wherein the β2M peptide is a human β2M peptide.

A36. The foregoing method of A35, wherein the β2M peptide comprises a mutation.

A37. The foregoing method of A36, wherein the mutation is S88C.

A38. The foregoing method of any of A-A37, wherein each particle comprises a polypeptide comprising, in an amino to carboxyl terminus orientation, (i) the antigen peptide, (ii) a β2M peptide, and (iii) an MHC peptide.

A39. The foregoing method of any of A-A38, wherein the antigen peptide is 7-15 amino acids, 7-10, 8-9, 7, 8, 9, 10, 11, 12, 13, 14, or 15 amino acids in length.

A40. The foregoing method of A38 or A39, wherein the polypeptide is biotinylated.

A41. The foregoing method of any of A-A40, wherein the particles are selected from the group consisting of magnetic beads, agarose beads, styrene polymer particles, and dextran polymer particles.

A42. The foregoing method of any of A-A41, wherein the particles are streptavidin coated.

A43. The foregoing method of any of A-A42 for monitoring an immune repertoire in a subject.

A44. The foregoing method of A43, further comprising monitoring changes in the antigen-specific T cells in the subject.

A45. The foregoing method of A43 or A44, comprising administering an immunotherapy to the subject.

A46. The foregoing method of A45, wherein the immunotherapy is an adoptive cell transfer or a checkpoint inhibitor.

A47. The foregoing method of any of A-A46 for identifying at least one TCR sequence.

A48. The foregoing method of A47, wherein the at least one TCR sequence is a TCR alpha sequence, a TCR beta sequence, or a combination thereof.

A49. The foregoing method of A47 or A48, further comprising manufacturing a soluble TCR polypeptide.

B. In certain non-limiting embodiments, the presently disclosed subject matter provides for a library comprising at least two particle sets, each particle set comprising an antigen peptide, a barcode operably associated with the identity of the antigen peptide, and at least one identifying label.

B1. The foregoing library of B, wherein the at least one identifying label is the same in each particle set.

B2. The foregoing library of B or B1, comprising at least two different identifying labels in each distinct particle set.

B3. The foregoing library of any of B-B2, wherein the at least one identifying label is a fluorophore.

B4. The foregoing library of B3, wherein the fluorophore is selected from the group comprising allophycocyanin (APC) and phycoerythrin (PE).

B5. The foregoing library of B2, wherein the at least two different identifying labels are fluorophores, wherein the fluorophores are selected from the group comprising allophycocyanin (APC) and phycoerythrin (PE).

C. In certain non-limiting embodiments, the presently disclosed subject matter provides for a particle comprising at least one polypeptide, a barcode, and an identifying label, wherein the polypeptide comprises an antigen peptide, a β2M peptide, and an MHC peptide, and wherein the barcode is operably associated with the identity of the antigen peptide.

C1. The foregoing particle of C that is selected from the group consisting of magnetic beads, agarose beads, styrene polymer particles, and dextran polymer particles.

C2. The foregoing particle of C or C1, wherein the identifying label is a fluorophore.

C3. The foregoing particle of any of C-C2 that is streptavidin coated.

C4. The foregoing particle of any of C-C3, wherein the polypeptide is labeled.

D. In certain non-limiting embodiments, the presently disclosed subject matter provides for a method of treating cancer in a subject, comprising: (a) preparing a plurality of particles each comprising a plurality of labeled polypeptides, wherein said polypeptides comprise an antigen peptide, a β2M sequence, an HLA sequence and a detectable label; (b) contacting the plurality of particles with a plurality of T cells from the subject under conditions suitable for antigen-specific binding of a T cell to the particle; (c) isolating the T cells bound to the particle and identifying the TCR gene sequence of the isolated T cell; (d) preparing a polynucleotide comprising homology arms and at least one TCR gene sequence, wherein the TCR gene sequence is positioned between the homology arms; (e) recombining the polynucleotide into an endogenous locus of the T cell of the subject; (f) culturing the modified T cell of step to produce a population of T cells; and (g) administering a therapeutically effective number of the modified T cells to the subject to thereby treat the cancer.

E. In certain non-limiting embodiments, the presently disclosed subject matter provides for a method of modifying a cell, comprising: (a) introducing into the cell a homologous recombination (HR) template nucleic acid sequence, wherein the HR template nucleic acid sequence comprises (i) first and second homology arms homologous to first and second endogenous sequences of the cell, (ii) a T cell receptor (TCR) gene sequence obtained by a method according to any of A-A49, wherein the TCR gene sequence is positioned between the first and second HR arms, and (iii) a first 2A-coding sequence positioned upstream of the TCR gene sequence and a second 2A-coding sequence positioned downstream of the TCR gene sequence, wherein the first and second 2A-coding sequences code for the same amino acid sequence that are codon-diverged relative to each other; and (b) recombining the HR template nucleic acid into an endogenous locus of the cell comprising the first and second endogenous sequences homologous to the first and second homology arms of the HR template nucleic acid.

F. In certain non-limiting embodiments, the presently disclosed subject matter provides for a composition comprising a modified cell, wherein the modified cell comprises an exogenous nucleic acid sequence integrated into an endogenous locus, the exogenous nucleic acid sequence comprising: (a) a TCR gene sequence identified by a method according to any of A-A49, and (b) a first 2A-coding sequence positioned upstream of the TCR gene sequence and a second 2A-coding sequence positioned downstream of the TCR gene sequence, wherein the first and second 2A-coding sequences code for the same amino acid sequence that are codon-diverged relative to each other.

EXAMPLES

The following examples are merely illustrative of the presently disclosed subject matter and should not be considered as limitations in any way.

Example 1: Design and Cloning of Compact Mini-Genes Via Restriction Digest Cloning Structure of comPACT Mini-Genes for Restriction Digest:

The basic components of a comPACT mini-gene include a signal sequence that directs the secretion of the encoded protein, universal target sequences such as restriction sites or primer binding sites, an encoded antigenic peptide (or neoantigen, NeoE), a second universal target site, a $\beta_2$m, an extracellular domain of an MHC allele, and a purification cluster, e.g., enabling enzymatic modification (e.g. biotinylation) and purification of the comPACT via affinity tags. The cluster may also contain a protease cleavage site and linker sequences between the components as made and shown in the figures and examples. The mini-gene may also encode cysteine mutations that can act as a disulfide trap. Certain comPACT mini-genes as made and disclosed herein encoded cysteine mutations that act as a disulfide trap. Such min-genes were made to include a disulfide trap in order to increase the success rate of manufacturing the comPACT polypeptides by stabilizing the protein. A diagram of a comPACT mini-gene is shown in FIG. 1. Additional restriction sites upstream and downstream of the MHC heavy chain sequence can be used to insert other MHC alleles to construct different MHC templates and build a library of MHC templates (FIG. 2). DNA encoding the signal sequence, universal target sequences, $\beta_2$m, and extracellular domain of an MHC allele are the base MHC template.

Figure 3:
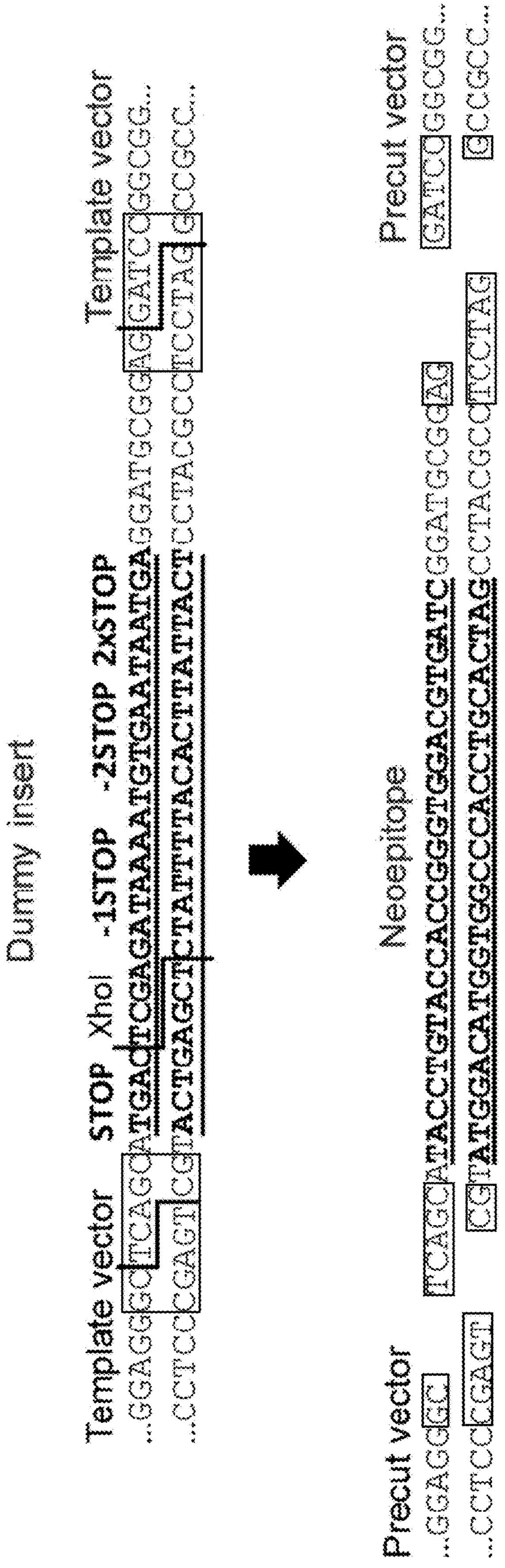
FIG. 3 is a diagram of an exemplary restriction digest cloning reaction to replace the dummy insert in the MEW template with a chosen neoepitope sequence. The dummy insert (underlined, bold; top set of sequences in the figure) contains four stop codons in different frames and a unique restriction site for destruction of uncut or re-ligated template. The restriction sites on either side of the insert are shown in boxes. The bottom set of sequences shows the NeoE insert after the dummy insert has been cut and ligated with the correct NeoE sequence.

For restriction digest cloning methods, each comPACT DNA construct is a base MHC template with a dummy antigenic sequence insert containing stop codons in three frames and a unique restriction site for destruction of uncut or re-ligated template (FIG. 3) and can be used as part of an off-the-shelf platform for rapidly assembling libraries of antigenic peptides complexed with that MHC allele. The MHC alleles may also be modified or mutated (e.g., Y84A or Y84C), for example, to improve folding or increase binding of the antigenic peptide with the MHC protein. In addition, β2m protein can also be mutated (e.g., S88C), for example, to allow it to bind thiol dyes.

In this example, a comPACT mini-gene is shown with the following structure: a NotI restriction site at the 5' end; the signal sequence from human growth hormone, hGH, shown in Table 1; a restriction site Blp1 upstream of the antigenic peptide region and a BamHI restriction site downstream of the antigenic peptide regions, shown in Table 2; an encoded linker sequence of predominantly glycine and serine residues (i.e. Gly-Ser linkers); the $\beta_2$m sequence; a second encoded Gly-Ser linker sequence with a BspI restriction site; an MHC heavy chain; a third encoded Gly-Ser linker sequence with a BstBI restriction site; and a encoded purification cluster with an AviTag (or any avidin/streptavidin) sequence, a TEV cleavage site, and a concatenated histidine tag.

TABLE 1

Signal Sequence

| SEQ ID NO. | Signal Protein | Sequence |
|---|---|---|
| 1 | Human Growth Hormone nucleotide sequence | ATGGCGACGGGTTCAAGAACTTCCCTACT TCTTGCATTTGGCCTGCTTTGTTTGCCGTG GTTACAGGAGGGCTCAGCA |
| 2 | Human Growth Hormone peptide sequence | MATGSRTSLLLAFGLLCLPWLQEGSA |

TABLE 2

Universal Target Sequences

| SEQ ID NO. | Restriction Site | Sequence |
|---|---|---|
| 3 | BlpI | CGTGGTTACAGGAGGGCTCAGCA |
| 4 | BamHI | GGATGCGGAGGATCCGGCG |
| 5 | BamHI | GGAAGCGGAGGATCCGGCG |
| 6 | BamHI | GGAAGCGGAGGATCCACCAGC |

Restriction Digest Cloning and Assembly of comPACT Mini Gene

Figure 4:
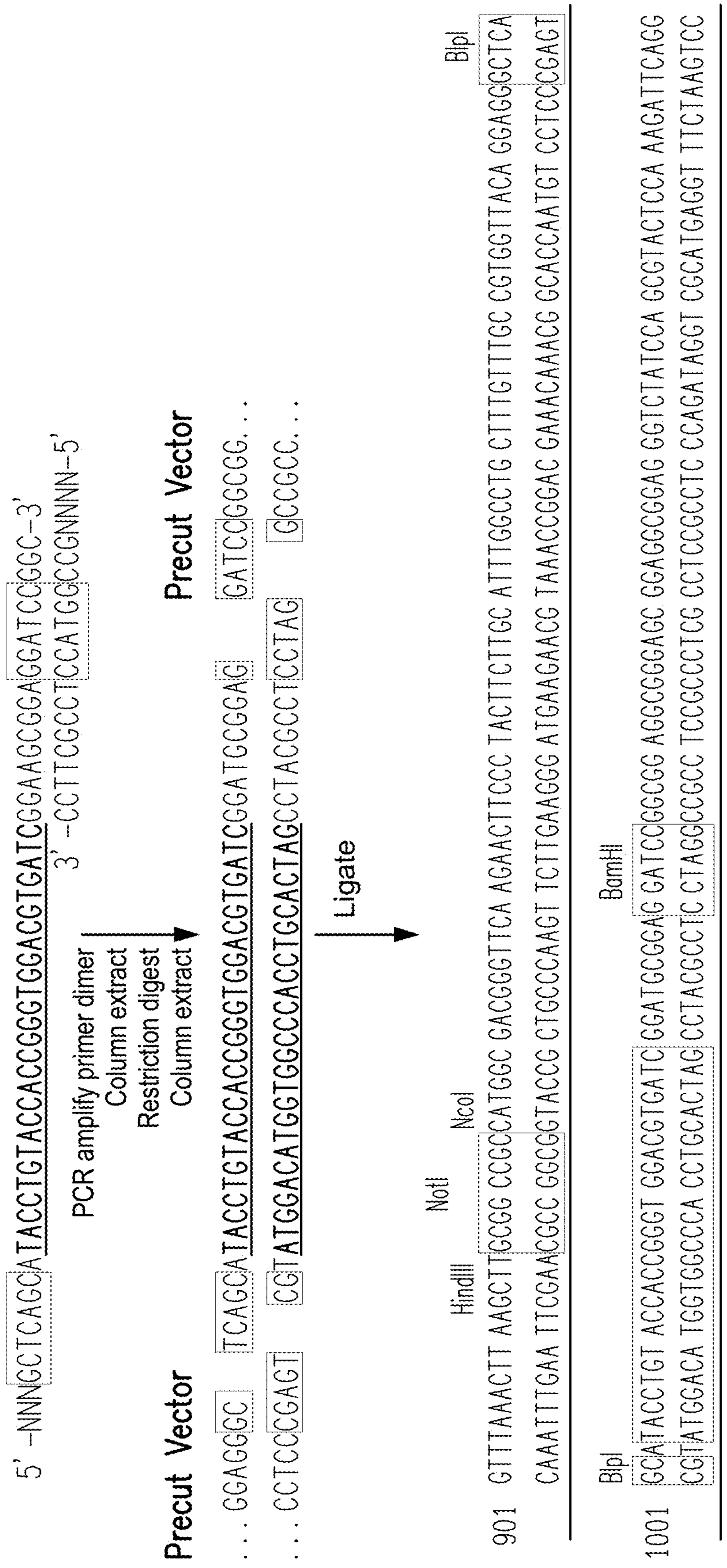
FIG. 4 is a diagram of an exemplary restriction digest cloning reaction to insert a chosen neoepitope sequence in the MHC template. The neoepitope sequence (underlined, bold) is synthesized as a primer flanked by two different restriction sites (boxed). A universal primer with the reverse complement sequence e of the 3' restriction site is used in a PCR reaction to form a double-stranded primer dimer of the neoepitope sequence. Restriction digest of both the neoepitope and the MCH template vector allows for a ligation reaction to insert the chosen neoepitope sequence into the MHC template sequence. Ligation reactions are transformed into *E. coli* and plasmids prepared from transformed *E. coli* are used in mammalian producer cell transfection reactions.

Three different methods of inserting an encoded neoantigen via restriction digest are described herein. In the first, shown as a diagram in FIG. 4, the antigenic peptide (NeoE)-encoding primer spans the first restriction site (BlpI in this example) at the 5' end and the second restriction site (BamHI in this example) at the 3' end. This primer amplifies off a universal reverse primer encoding the second restriction site, yielding a primer dimer of ~70 bp.

In the second method, the antigenic peptide-encoding primer spans the second restriction site as the 5' end and is the reverse complement of the antigen-encoding sequence. This primer primes in reverse orientation of the template DNA encoding the signal sequence. Paired with a forward primer spanning the first restriction site sequence, this reaction yields a 70 bp product, or an ~140 bp product if a forward primer spanning a restriction site farther upstream of the antigen site is used.

In both the first and second methods, the insert is typically cleaned up on a commercial column, digested with appropriate restriction enzymes, cleaned again on a commercial column, and then ligated with a pre-digested MHC template into a vector. Ligation reactions are transformed into *E. coli* and plasmids prepared from transformed *E. coli* are used in mammalian producer cell transfection reactions.

Example 2: Design and Cloning of Compact Mini-Genes Via Primer Annealing

Figure 5:
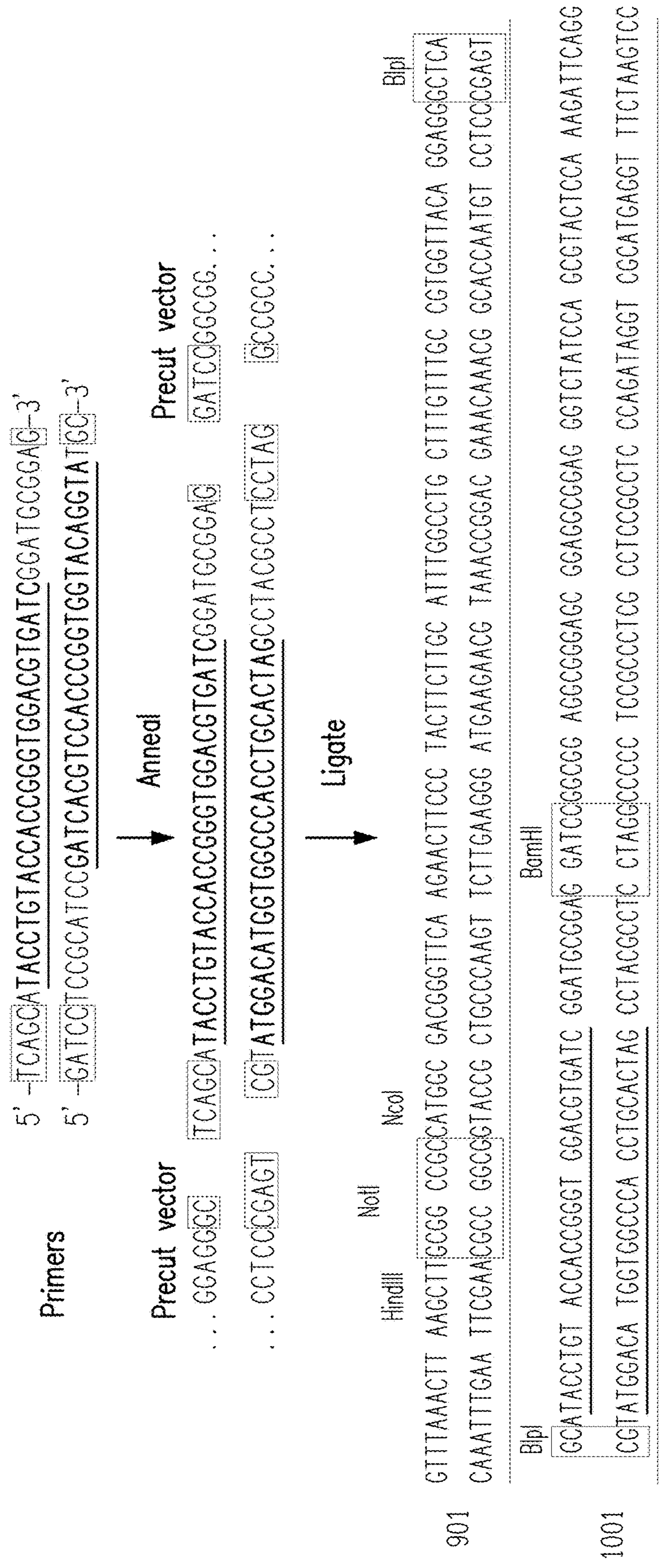
FIG. 5 is a diagram of an exemplary alternative form of a restriction digest cloning reaction to insert a chosen neoepitope sequence in the MEW template. Two complementary NeoE-encoding primers are synthesized with a portion of the 5' and 3' restriction sites. These primers are annealed and simulate the overhangs from restriction digestion. A precut vector (which critically retains 5' phosphates on its overhang ends) is then ligated with the annealed NeoE insert and the ligation product is transformed into *E. coli* for plasmid production.
Figure 22A:
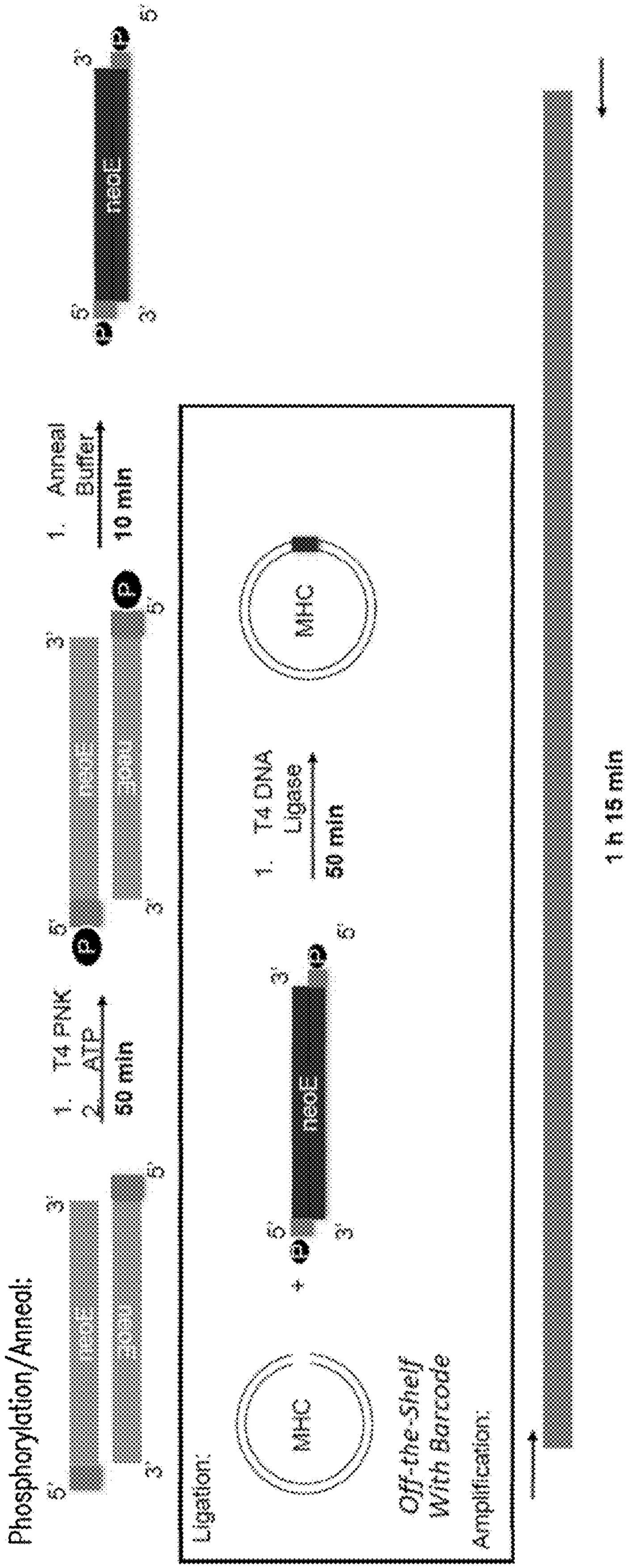
FIG. 22A shows an exemplary diagram of a cloning strategy to manufacture comPACT polynucleotides.

In a third variation on MHC template vector ligation, PCR and restriction digestion were bypassed by annealing two reverse complementary neoantigen-encoding primers. These primers were designed to have 5' and 3' ends that begin and terminate in complementary sequences that simulate the overhangs from restriction digestion (FIG. 5). The sense and antisense primers were incubated with T4 polynucleotide kinase and ATP to phosphorylate the 5' ends (FIG. 22A). When these primers annealed to each other, they formed a double stranded oligonucleotide sequence that had overhang nucleotides as if it had been digested with a restriction enzyme.

Figure 22B:
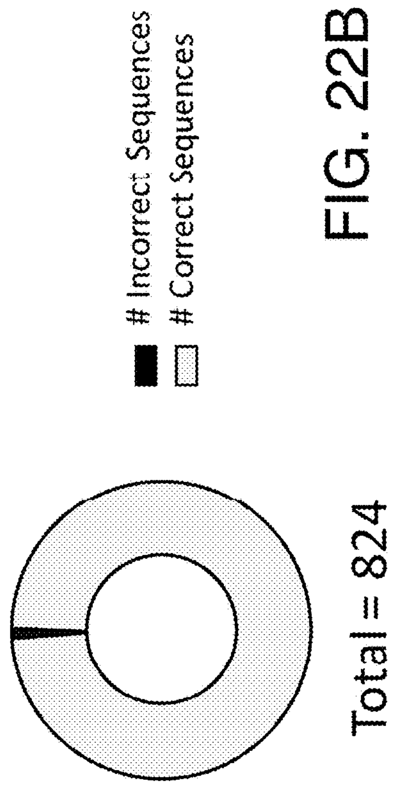
FIG. 22B provides sequence verification statistics obtained from 824 individual comPACT polynucleotides.

The phosphorylated neoantigen insert (alternatively referred to as the neoepitope) was ligated into a precut MHC template in a vector. The comPACT mini-gene had the same structure as that described in Example 1. The ligation product was then used for PCR amplification of a linear comPACT amplicon using bookend universal primers to amplify the complete comPACT mini-gene and sequenced. 824 comPACT mini-genes with unique neoantigen sequences (alternatively referred to as the neoepitope sequences) were made using this method, with greater than 99% of the generated comPACT mini-genes having the correct neoantigen sequence (alternatively referred to as the neoepitope sequences) (FIG. 22B). The neoantigen sequences (alternatively referred to as the neoepitope sequences) cloned into the comPACT polynucleotides and expressed as polypeptides were based on tumor neoantigens identified from patient samples (e.g., tumor samples or other patient samples that express tumor antigens). Based on the identified neoantigens, a series of predicted neoantigen sequences (alternatively referred to as the neoepitope sequences) were made for each identified neoantigen.

Next, *E. coli* were transformed with the ligation product plasmids and plated onto selective agar plates containing ampicillin. Individual colonies were picked and grown overnight for plasmid purification and sequenced for full gene verification. After sequencing verification, plasmid lots were archived and propagated into larger quantities.

Alternatively, T4 kinase is not used if the precut MEW template vector retains 5' phosphates on its overhang ends. The annealed antigen insert neoantigen sequences (alternatively referred to as the neoepitope insert) can then be ligated with the cut MEW vector and the ligation product transformed into *E. coli* for plasmid production.

Example 3: Design and Cloning of Compact Mini-Genes Via PCR Assembly

Figure 6:
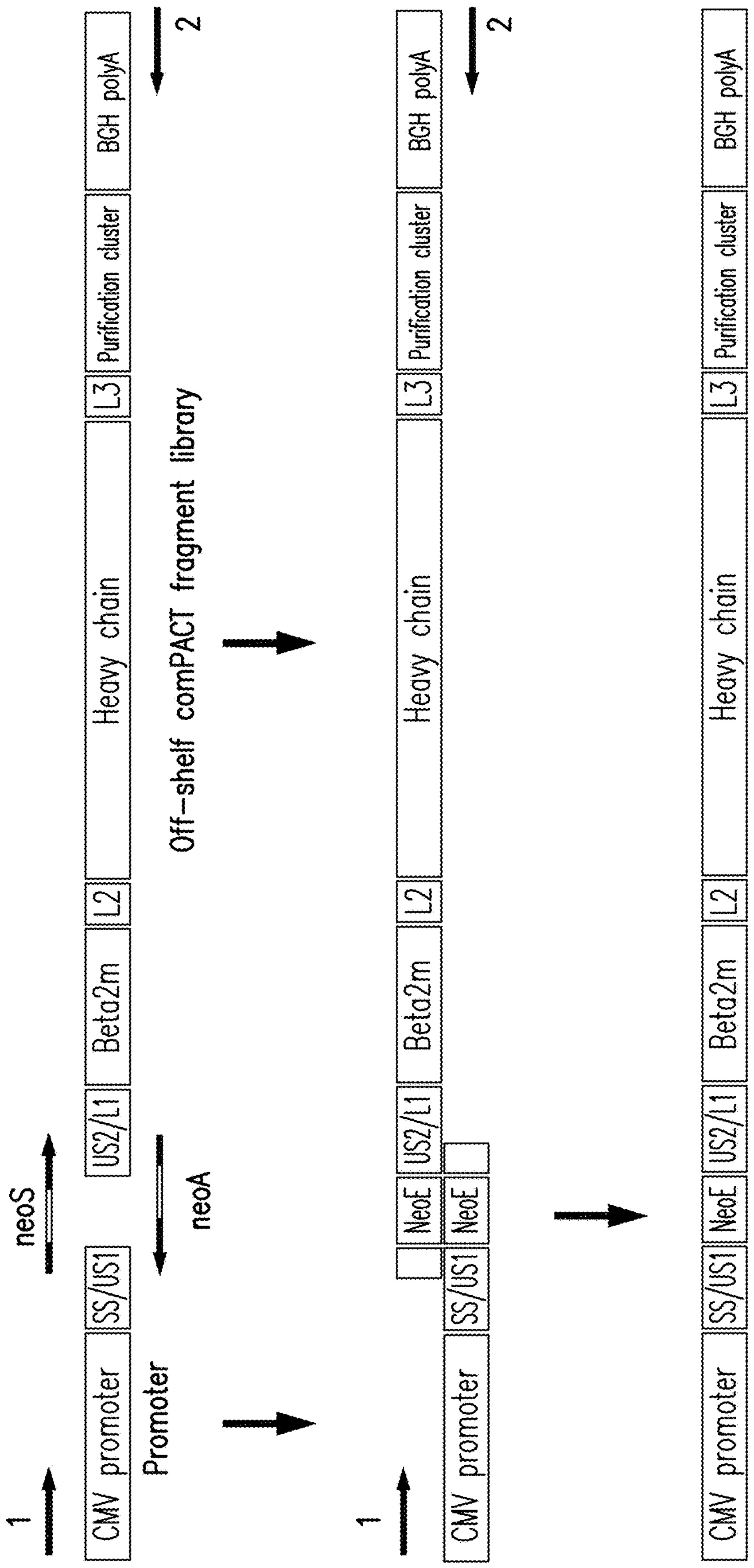
FIG. 6 is a diagram of an exemplary PCR-based method to insert a chosen neoepitope sequence in the MEW template. Two complementary NeoE-encoding primers are synthesized, the forward primer with a 3' sequence for the second universal site in the MHC template; and the reverse primer with a 3' sequence for the complementary sequence of the first universal site in the MEW template. These primers are mixed with a 5' fragment of the MEW template with the first universal sequence site, and a second fragment of the MHC template with the second universal site and remainder of the comPACT mini-gene. The first PCR amplification cycle produces two nucleotide fragments, one fragment encoding the first universal site region with downstream neoepitope and the other encoding the neoepitope followed by the remainder of the comPACT gene. These two fragments, overlapping at the unique neoepitope sequence are then assembled and the full assemble amplified and cleaned up for transfection.

Structure of comPACT Mini-Genes for PCR Assembly:

A fourth method of inserting an antigen, e.g., a neoantigen, (as used for this example for clarity, both referring to the NeoE insert in FIG. 6 and as described as neoepitopes in Example 2) may also be used. In this method, the antigen-encoding sequence (as used for this example for clarity, antigen-encoding sequence refers to the neoepitope sequences described in Example 2) is inserted into the MEW template which is flanked by an upstream promoter and a downstream polyadenylation signal via polymerase chain reaction to form a 2.5 kb mini-gene. A diagram of the PCR assembly reaction is shown in FIG. 6.

In this example, a comPACT mini-gene is shown with the following structure: a promoter at the 5' end; a signal sequence with a first universal target sequence; an encoded antigenic peptide; a second universal target sequence with an encoded linker sequence of predominantly glycine and serine residues (i.e. GlySer linkers); $\beta_2$M sequence; a second encoded Gly-Ser linker sequence; an MEW heavy chain allele; a third Gly-Ser linker sequence; a purification cluster; and a polyA sequence. The universal target sequences are not the same in this exemplary method, i.e., they are distinct from one another.

PCR Assembly of comPACT Mini-Genes:

In this method, two primers (<60 nt) with a chosen antigen sequence (as used for this example for clarity, antigen sequence refers to the neoantigen sequence) are synthesized. The first primer has the neoantigen sequence (as used for this example for clarity, neoantigen sequence refers to the neoepitope sequences described in Example 2) at the 5' end followed by a stretch of the second universal target sequence at the 3' end. The second primer has the reverse complement of the neoantigen sequence (as used for this example for clarity, neoantigen sequence refers to the neoepitope sequences described in Example 2) at the 5' end and the reverse complement of the first universal sequence at the 3' end. These primers are mixed with a DNA fragment encoding the promoter region, signal sequence and first universal target sequence, and another DNA fragment encoding the second universal target sequence, the $\beta_2$m sequence, MHC allele, purification cluster and a polyA sequence. Each antigenic peptide primer anneals to its complementary sequence and a PCR reaction is run that amplifies the neoantigen sequence (as used for this example for clarity, neoantigen sequence refers to the neoepitope sequences described in Example 2) onto either the promoter fragment or the MHC allele fragment. These two newly synthesized fragments now each have the neoantigen sequence (as used for this example for clarity, neoantigen sequence refers to the neoepitope sequences described in Example 2). Further PCR reactions, along with primers for the 5' end of the promoter sequence and 3' end of the polyA sequence, allow the neoantigen sequences (as used for this example for clarity, neoantigen sequence refers to the neoepitope sequences described in Example 2) to anneal to each other and prime the assembly of a full length linear comPACT amplicon.

The fully assembled linear comPACT polynucleotide is then cleaned up for direct transfection into mammalian producer cells, bypassing the steps using *E. coli* and plasmid production altogether.

Example 4: Expression and Purification of Compact Proteins from Plasmids

Expression of Protein

Neoantigen12 (neo12) was ligated into an HLA-A2 template sequence and inserted into an expression plasmid (pPACT0010) via restriction digest of the NotI and BamHI restriction sites and ligation as previously described in Example 1.

Figure 7:
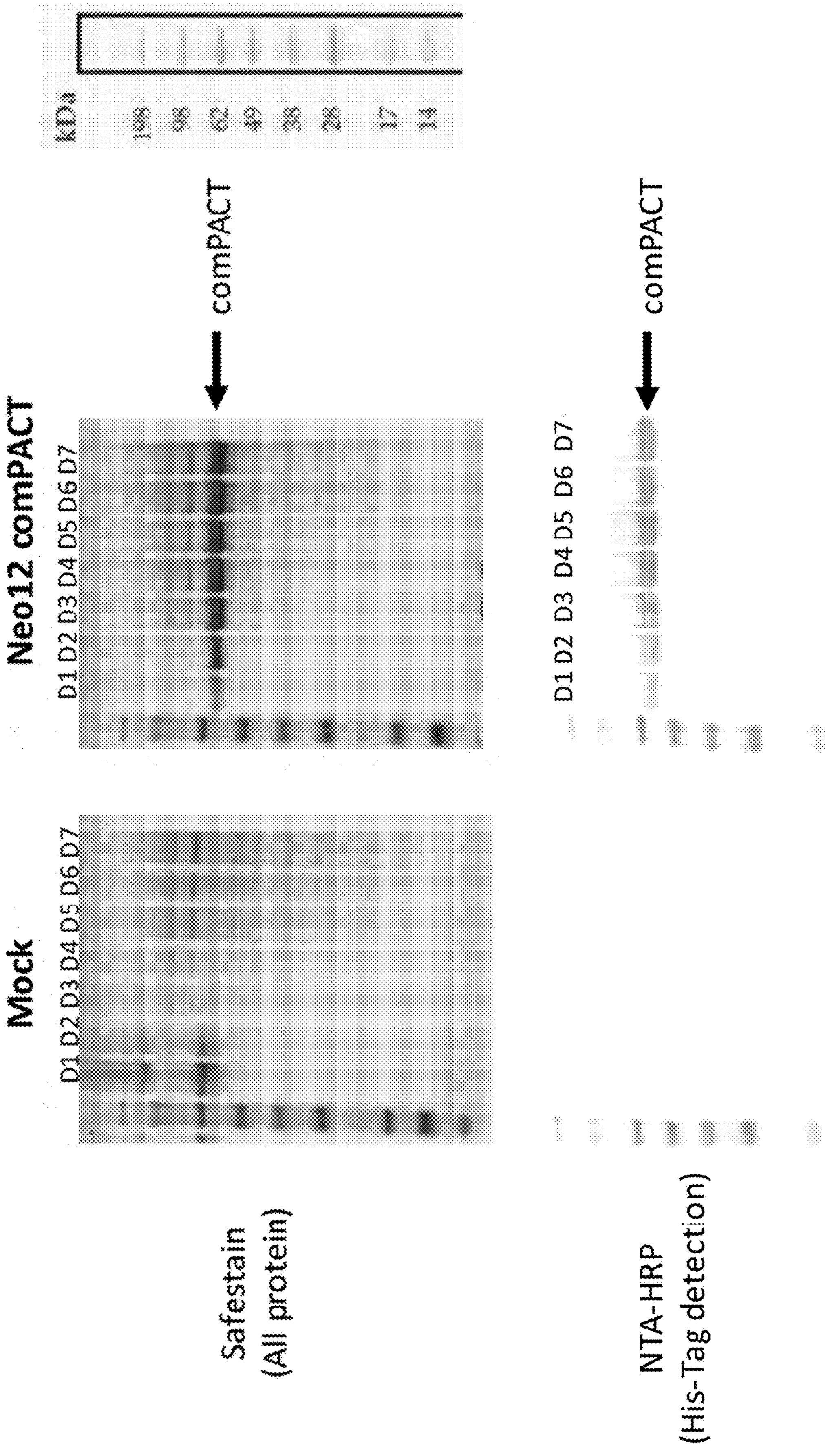
FIG. 7 shows the total protein expression in 30 mL of mammalian cells transfected with a comPACT gene (Neo12) over a seven day time course and a Western Blot using an NTA-HRP reagent that detects the His-tag.

Expi293 mammalian producer cells in a 30 mL shake flask volume were transfected with pPACT0010 incubated with Expifectamine transfection reagent on day −1. Enhancers included in the Expifectamine transfection kit were added on day 0. Samples were collected from the cell supernatant on days 1 to day 7 and assessed for secreted protein via SDS-PAGE and total protein staining using Safestain (ThermoFisher). Levels of secreted comPACT protein increased until day 3, at which point the protein secretion leveled off (FIG. 7). Secreted comPACT protein was initially identified by its apparent molecular weight (=53 kDa) and confirmed by a Western blot using NTA-HRP to detect the His6 affinity tag (SEQ ID NO: 34).

Purification of Protein

Figure 8:
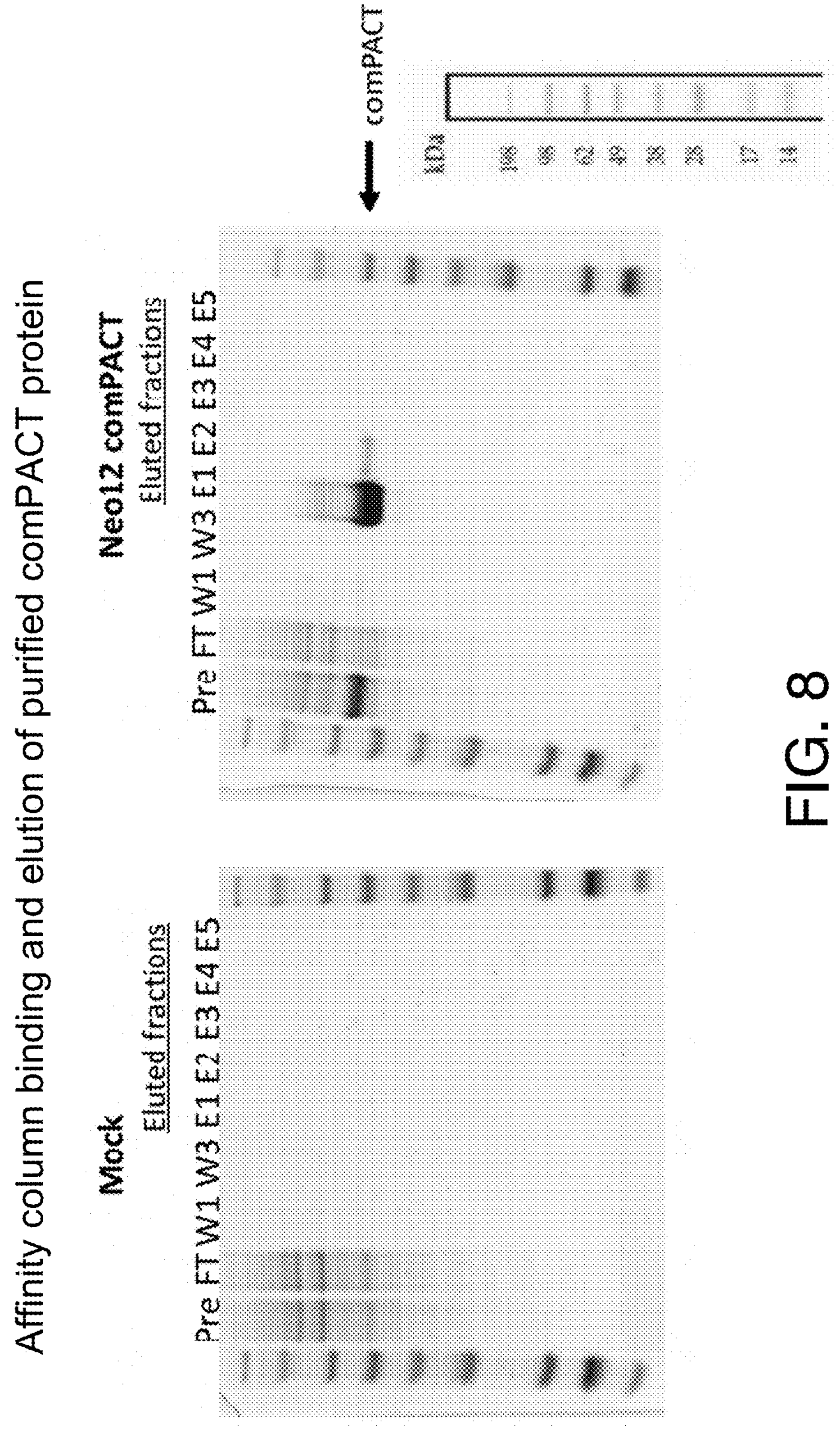
FIG. 8 shows gels of Ni-NTA affinity chromatography purification of the Neo12 comPACT protein. Pre stands for crude lysate, FT stands for Flow-through, W stands for Wash, and E stands for Eluted.

The Neo12 comPACT protein collected on day 7 was purified by Ni-NTA affinity chromatography via binding of the His6 affinity tag (SEQ ID NO: 34). Samples were assayed for total protein via SDS-PAGE and Safestain. The lack of comPACT protein in the flow-through (FT) fraction of the affinity column confirmed that the His6 tag (SEQ ID NO: 34) was not cleaved during expression and purification (FIG. 8). The purified yield was >400 mg per L of culture volume.

Figure 9:
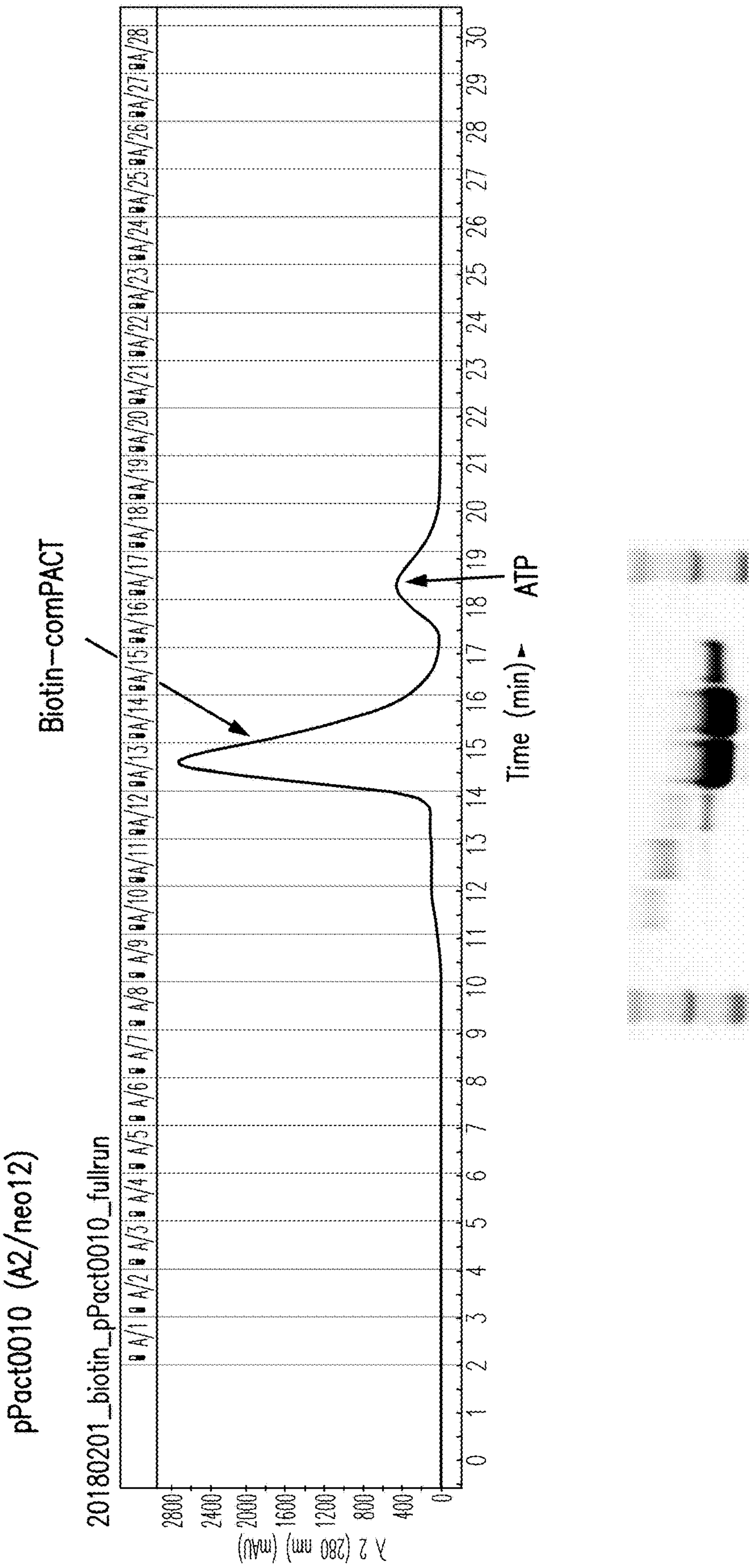
FIG. 9 shows the size exclusion chromatography spectra of the purified Neo12 protein. The major peak is the Neo12 protein, and the minor peak is ATP added during a biotinylation step.

The Neo12 comPACT protein was biotinylated (discussed below in Example 5) and further purified by size-exclusion chromatography. A single major peak was observed, suggesting the protein was properly-folded and monomeric, with little aggregation (FIG. 9). The second peak is ATP, which was added for the BirA-catalyzed biotinylation reaction.

While Ni-NTA chromatography was used in Example 4, any HA-affinity chromatography (including but not limited to the metal affinity chromatography described herein) could be used to purify the HA-tagged comPACT.

Optimization of Production Volume and Parallel Production

Figure 10:
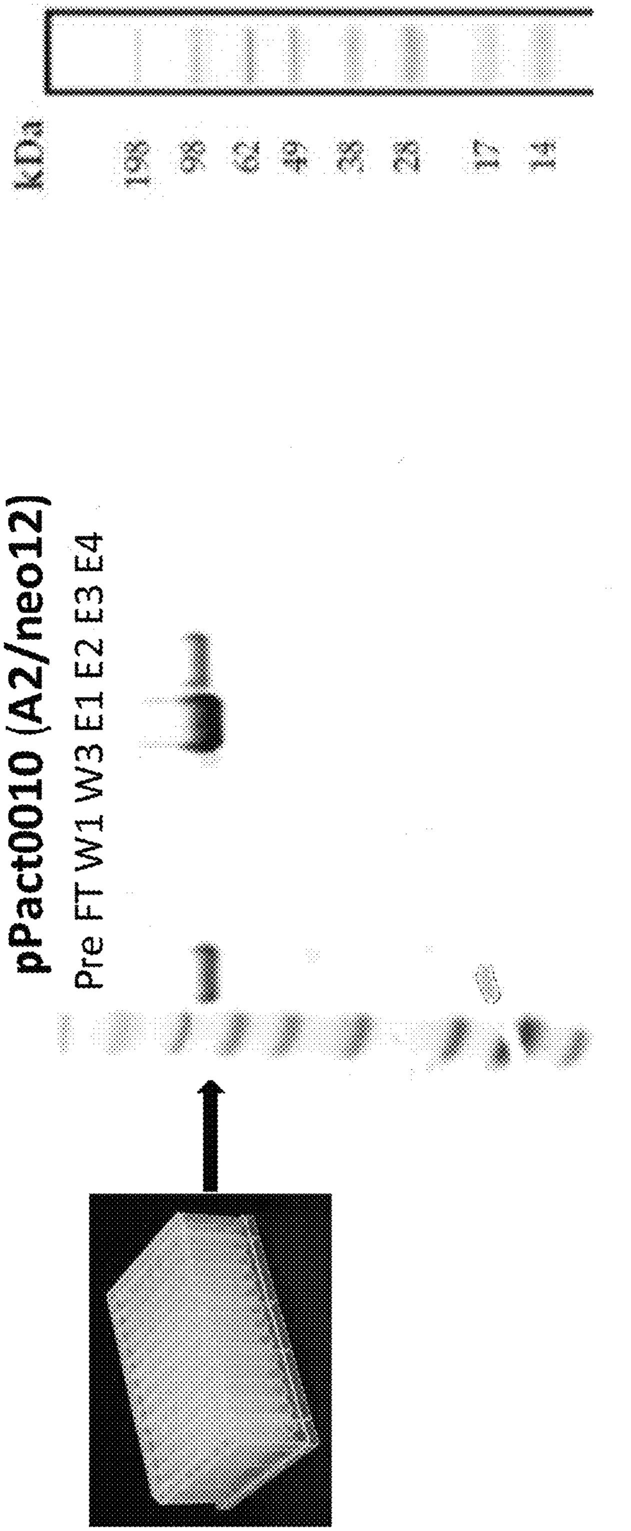
FIG. 10 shows a purification experiment similar to the one shown in FIG. 8, using a 0.7 cell culture volume.

The production of comPACTs was scaled down from a culture volume of 30 mL in a shake flask to 0.7 mL in a 96 deep-well shake block. Expi293 mammalian producer cells were transfected with plasmid DNA containing the pPACT0010 plasmid, and the secreted Neo12 comPACT protein was purified as previously described. 437 mg/L of purified Neo12 comPACT protein was collected from a 0.7 mL well volume as compared to the previously described yield of >400 mg/L from the 30 mL purification experiment (FIG. 10). The protein yield from the 0.7 mL experiment corresponds to >300 micrograms of protein, or ~1000-fold more than is needed for a typical flow cytometry experiment.

Figure 11:
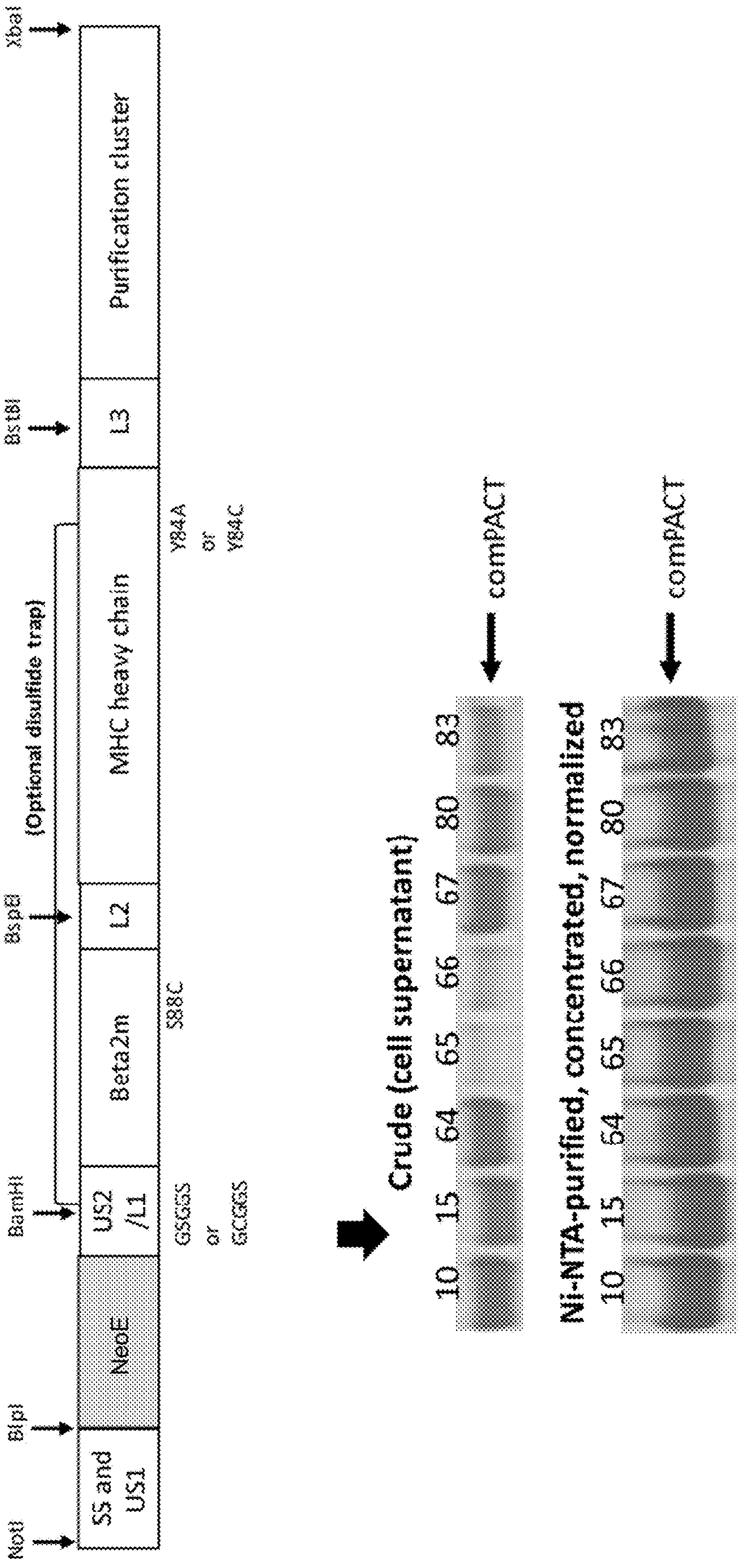
FIG. 11 shows crude and purified protein of eight different NeoE comPACT proteins, each with a different antigenic sequence.
Figure 12:
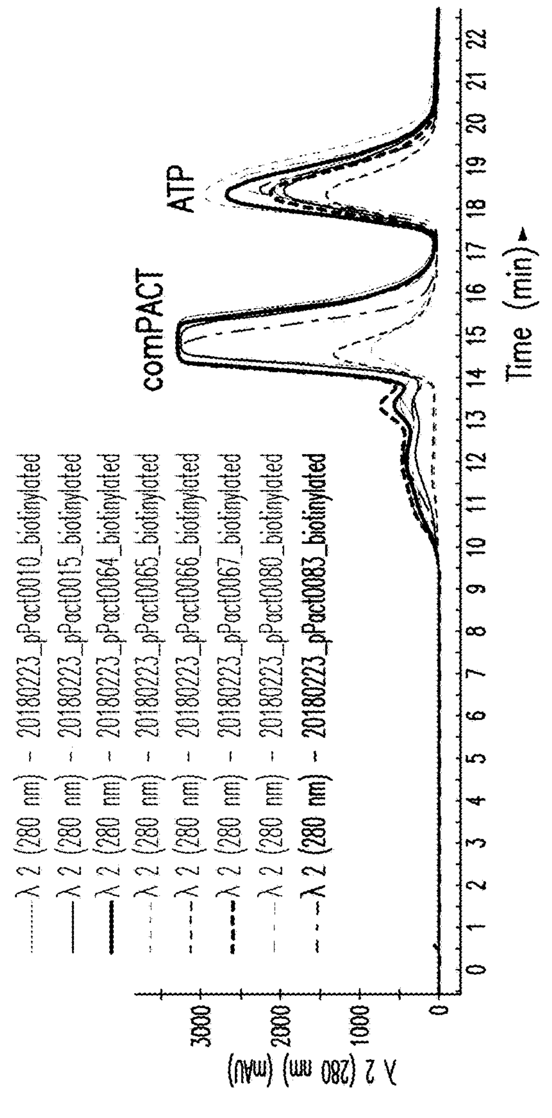
FIG. 12 shows the size exclusion chromatography spectra of the eight NeoE comPACT protein of FIG. 11.

Next, parallel expression of multiple comPACT constructs was assessed. Eight different comPACT constructs with different neoantigens (neoantigens 10, 15, 64, 65, 66, 67, 80, and 83) were expressed in 30 mL shaker flasks as a mid-throughput assay (FIG. 11). Each comPACT construct was transfected into cells as previously described where the comPACT protein was expressed and secreted into the cell supernatant. The expressed protein was purified as previously described, concentrated, and normalized. Samples of crude supernatant and concentrated proteins were assayed for total protein as previously described. The comPACT proteins were purified via size exclusion chromatography (FIG. 12). A single peak, containing 2-20 mg of protein, was seen for each protein, also suggesting that the comPACT proteins were properly-folded and monomeric.

Figure 13A:
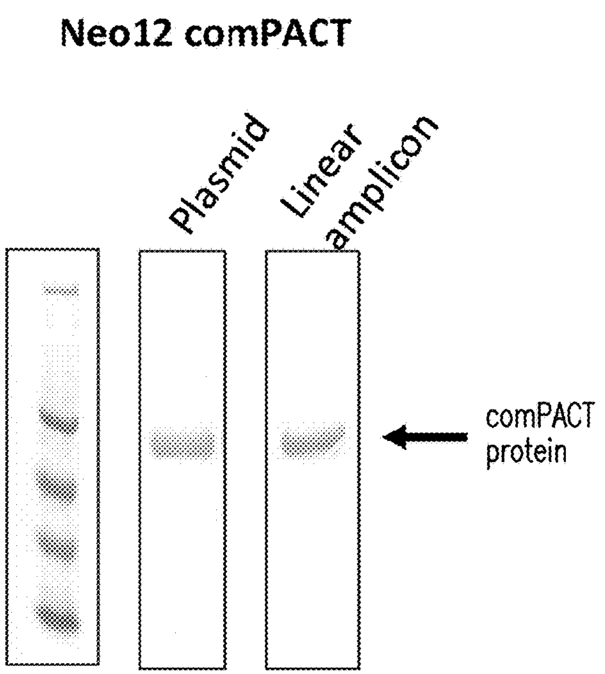
FIG. 13A shows a NeoE comPACT protein (specifically the Neo12 comPACT protein) produced using the PCR assembly method described in FIG. 6 (Linear amplicon) compared to a NeoE comPACT protein (specifically the Neo12 comPACT protein) produced from a plasmid (plasmid).
Figure 13B:
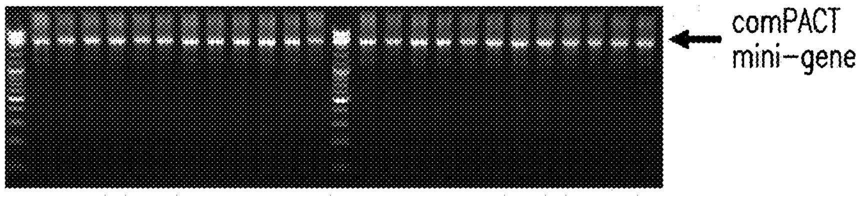
FIG. 13B shows a DNA gel of linear amplicons produced by the PCR assembly method. Each lane contains a comPACT mini-gene (specifically the Neo12 comPACT mini-gene) with a different neoepitope sequence.

Example 5: Expression and Purification of Compact Proteins From Linear Amplicons In the previous examples, comPACT proteins were expressed from plasmids transfected into mammalian producer cells. As an alternative approach, linear amplicons of the neo12 comPACT mini-gene (neoantigen 12 assembled into a mini-gene with the HLA-A2 template sequence) flanked by a promoter sequence and a polyA sequence were transfected into 0.7 mL of the producer cells in a 96-deep well plate. As a control, the pPACT0010 plasmid was also transfected into separate producer cells. Protein from both samples was expressed, purified and assayed for total protein as previously described. Similar levels of expressed proteins were produced by both the linear amplicon and the plasmid (FIG. 13A), suggesting that the protein encoded by a comPACT mini-gene can be produced without the need of a plasmid intermediate. Multiple different comPACT mini-genes with different neo-epitope sequences have been produced (FIG. 13B) for direct transfection of producer cells.

Additional comPACTs with different HLA alleles were made using the annealing and phosphorylation workflow described in Example 2. Linear amplicons were derived from the expression vector using bookend PCR and universal primers, and were transfected into Expi293F cells for comPACT protein production (data not shown).

Example 6: Biotinylation of Compact Proteins

In Vitro Biotinylation of comPACTs with Isolated BirA Enzyme

Figure 14:
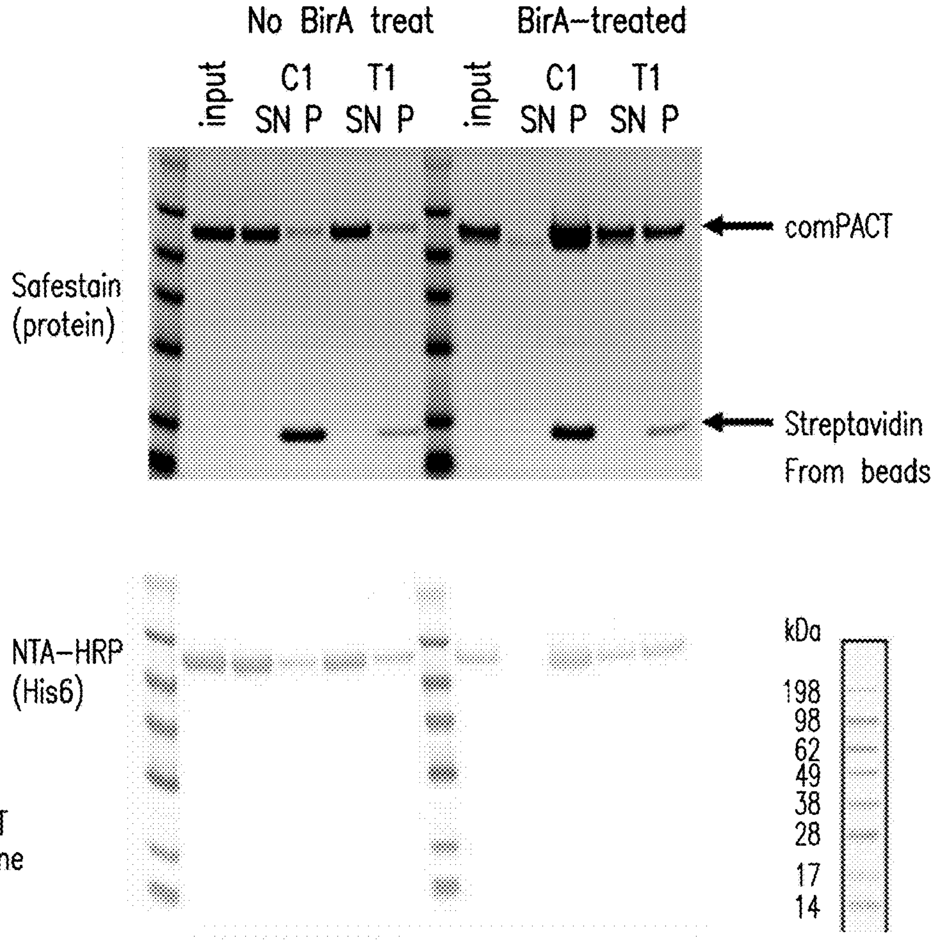
FIG. 14 shows a streptavidin bead pulldown assay to test for complete biotinylation of the comPACT protein.
Figure 15:
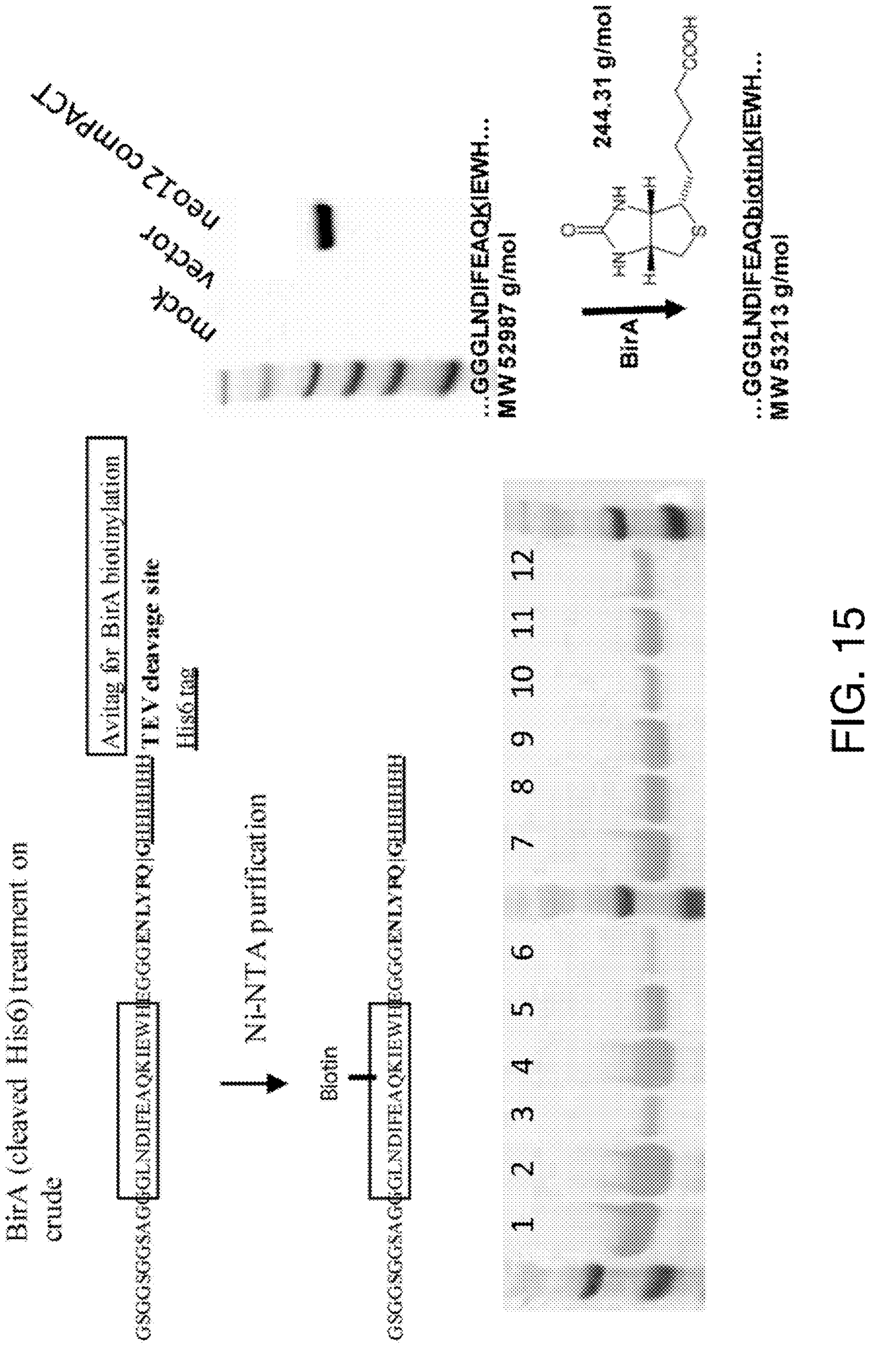
FIG. 15 shows biotinylation of different comPACT proteins in crude cell lysate, visualized via a Western Blot using streptavidin-HRP.

The comPACT purification cluster included a BirA recognition sequence (Avitag) for biotinylation. Purified comPACT proteins were unbiotinylated (No BirA treat) or biotinylated with commercial BirA protein according to the manufacturer's instructions (BirA-treated). Following overnight BirA enzymatic treatment, samples were bound to two different types of magnetic streptavidin beads (C1 and T1) and incubated to allow the biotinylated protein to bind to the streptavidin beads. The supernatant (SN) and beads ("pellet," P) were separated via SDS-PAGE. Samples were assayed for total protein with Safestain and the presence of comPACT protein via Western Blot with NTA-HRP (FIG. 14). In the untreated samples, the comPACT protein was mainly found in the SN fraction, confirming that it was unbiotinylated. In the biotinylated samples, the comPACT protein was found in the pellet samples of both C1 and T1 streptavidin beads, although the interaction between the biotinylated proteins and the C1 streptavidin beads was the most complete. Biotinylated comPACT protein was not detected via Western Blot in the C1 streptavidin bead-depleted supernatant, suggesting ~100% of comPACT protein was biotinylated.

comPACT proteins may also be biotinylated in the clarified supernatant, prior to purification. Multiple comPACT proteins were expressed in producer cells as previously described. The cell culture supernatant was collected and clarified via centrifugation. The clarified supernatant was treated with commercial BirA protein according to the manufacturer's instructions and then purified via Ni-NTA affinity chromatography and biotinylation was assessed via Western Blot (FIG. 15). All comPACT proteins tested were biotinylated using this method, indicating that biotinylation of comPACT proteins in clarified cell supernatants is effective. While Ni-NTA chromatography was used in Example 6, any HA-affinity chromatography (including but not limited to the metal affinity chromatography described herein) could be used to purify the HA-tagged comPACT.

Figure 16A:
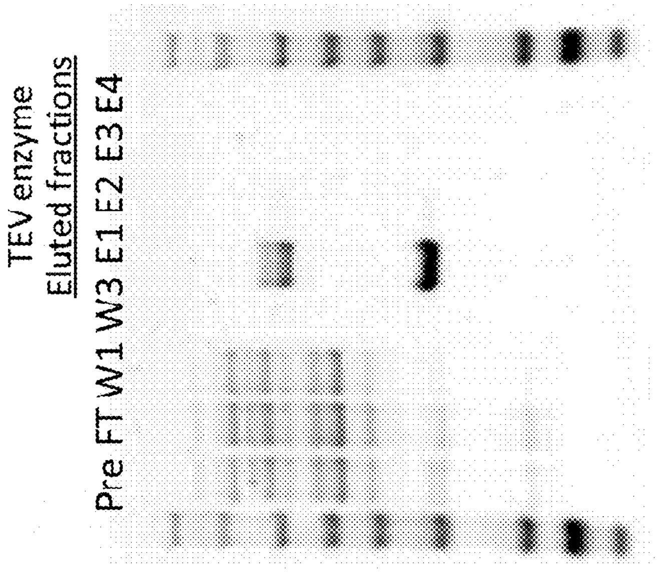
FIGS. 16A, 16B, and 16C show production and purification of BirA enzyme (FIGS. 16B and 16C) and TEV protease (FIG. 16A) in *E. coli.*
Figure 16B:
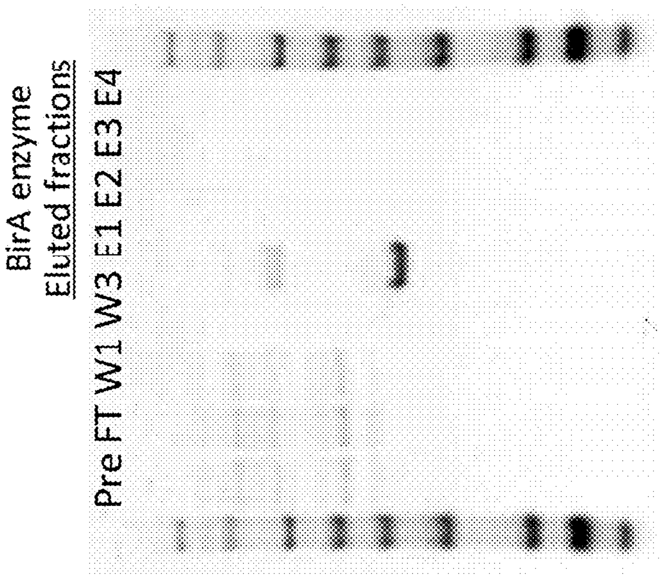
Figure 16C:
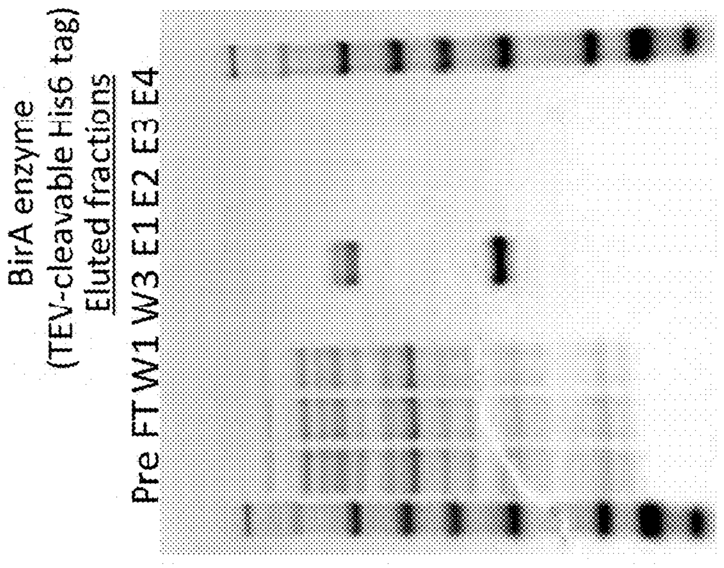

To produce enough BirA for high-throughput biotinylation of comPACT proteins, a BirA protein with a His6 tag (SEQ ID NO: 34) was expressed in *E. coli* cells. This His6 tagged (SEQ ID NO: 34) BirA was purified via Ni-NTA affinity chromatography (FIG. 16B) and can be used to biotinylated the comPACT proteins. A second version of BirA-His6 ("His6" disclosed as SEQ ID NO: 34) with a TEV-cleavable His6 tag (SEQ ID NO: 34) was also expressed and purified via Ni-NTA affinity chromatography (FIG. 16C). This BirA-TEV-His6 protein ("His6" disclosed as SEQ ID NO: 34) can be purified via Ni-NTA, the His6 tag (SEQ ID NO: 34) removed via TEV cleavage, and the tagless BirA then used to biotinylated comPACT proteins. After biotinylation of the comPACT proteins, the tagless BirA protein can then be purified away via Ni-NTA affinity chromatography. In addition, TEV protease was expressed heterologously in *E. coli* for use with the BirA-TEV-His6 ("His6" disclosed as SEQ ID NO: 34) (FIG. 16A) for use in biotinylated comPACT protein production. While Ni-NTA chromatography was used in Example 6, any HA-affinity chromatography (including but not limited to the metal affinity chromatography described herein) could be used to purify the HA-tagged compACT.

Figure 17:
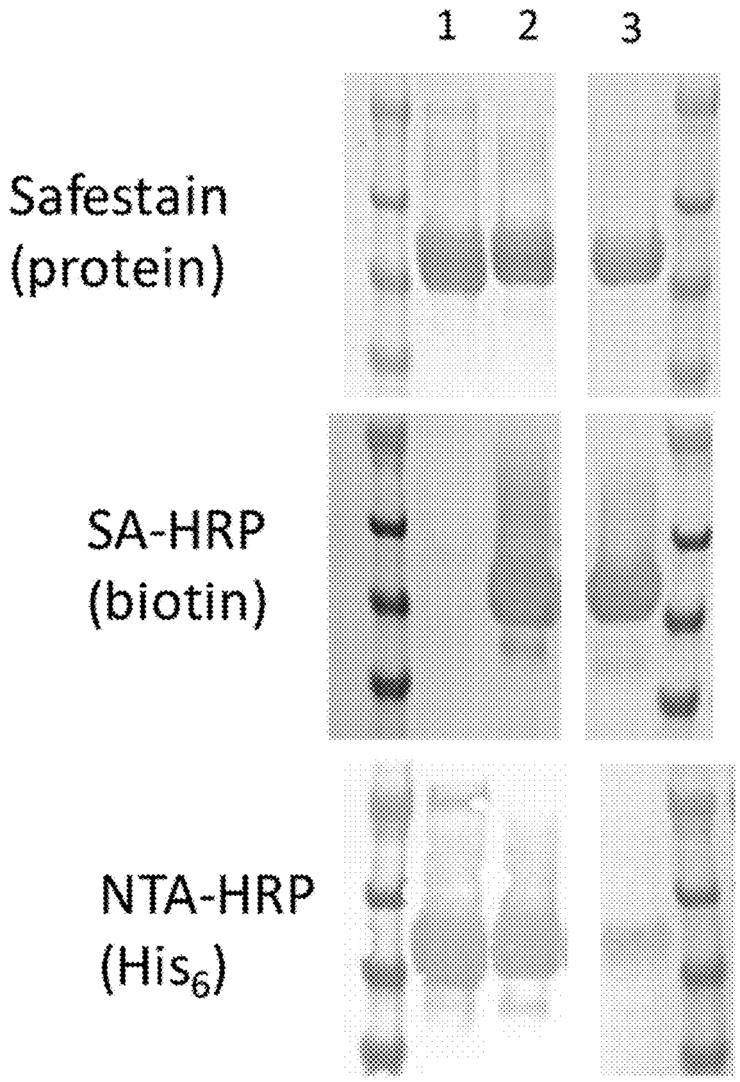
FIG. 17 shows biotinylation of a comPACT protein using BirA (lane 2) and cleavage of the His6 tag (SEQ ID NO: 34) using TEV protease (lane 3).

Cleavage of the His6 tag (SEQ ID NO: 34) on comPACT proteins after biotinylation was also assessed and the results shown in FIG. 17. comPACT proteins were treated or untreated with BirA to biotinylate them as previously described (lanes 1 and 2 of FIG. 17). A third sample of comPACT protein was treated with BirA and then with TEV to cleave the His6 tag (SEQ ID NO: 34) present on the protein (lane 3). Samples were separated via SDS-PAGE, and total protein was assessed via Safestain. All three samples had equal amounts of comPACT protein. Biotinylation of the comPACT proteins and cleavage of the His6 tag (SEQ ID NO: 34) was assessed via Western blot using an SA-HRP reagent for the biotin signal and an NTA-HRP reagent for the His6 tag (SEQ ID NO: 34). The unbiotinylated sample did not show biotin signal, but did have a His6 signal (SEQ ID NO: 34) and the biotinylated and uncleaved sample had both signals. The biotinylated and TEV cleaved sample only had the biotin signal, indicating that the His6 tag (SEQ ID NO: 34) was successfully cleaved off the comPACT protein.

Figure 18:
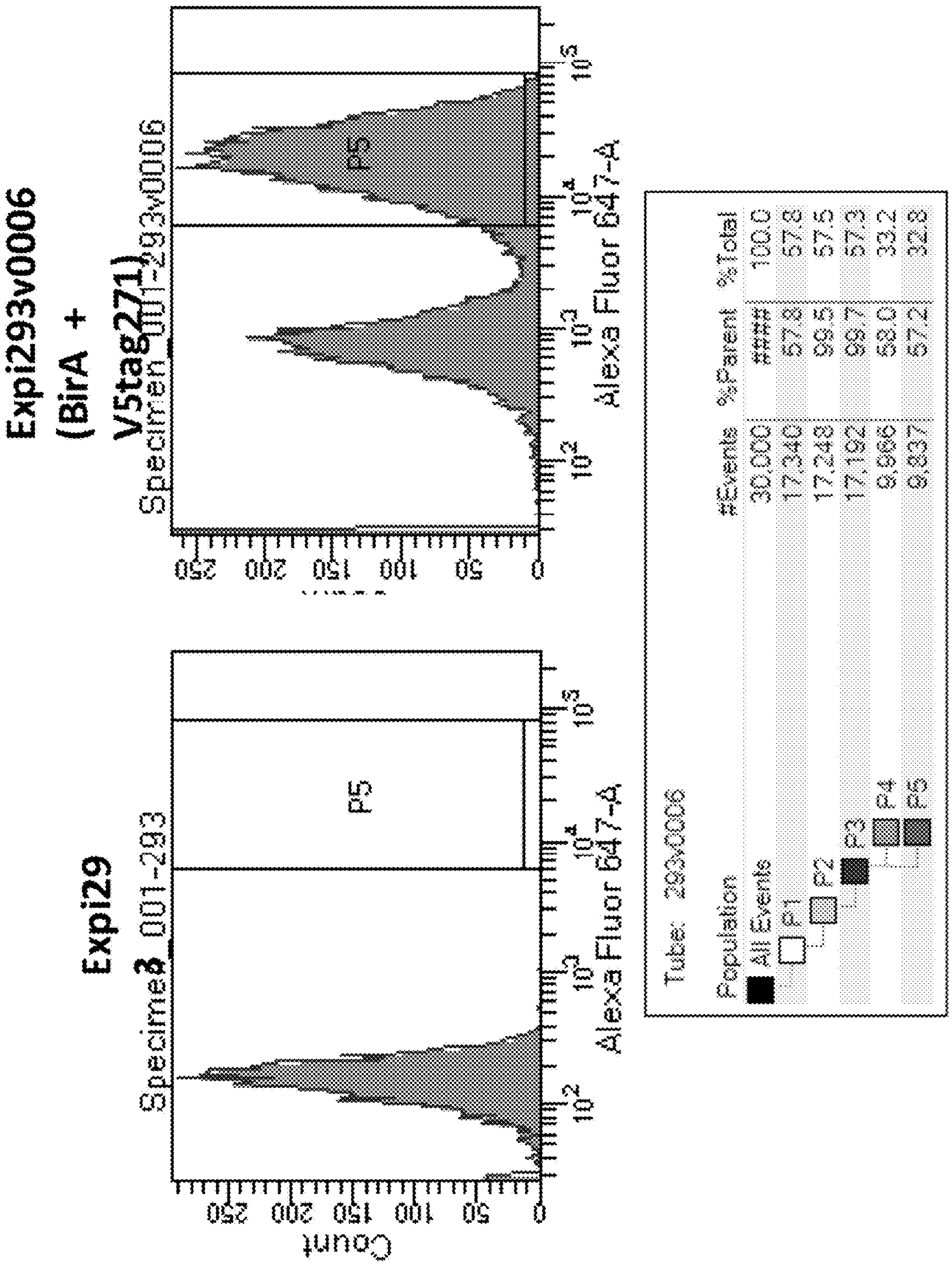
FIG. 18 shows cell sorting of cells transduced with BirA and V5 based on V5 expression.

A third approach for biotinylating the comPACTs in vitro is to express BirA in the Expi293 producer cells. Expi293 cells were generated that co-express BirA and a cell surface transduction marker tagged with V5. Transduced cells sorted for V5+ also express BirA (FIG. 18). These cells can be used to produce biotinylated comPACTs in vivo before comPACT protein purification.

Figure 19:
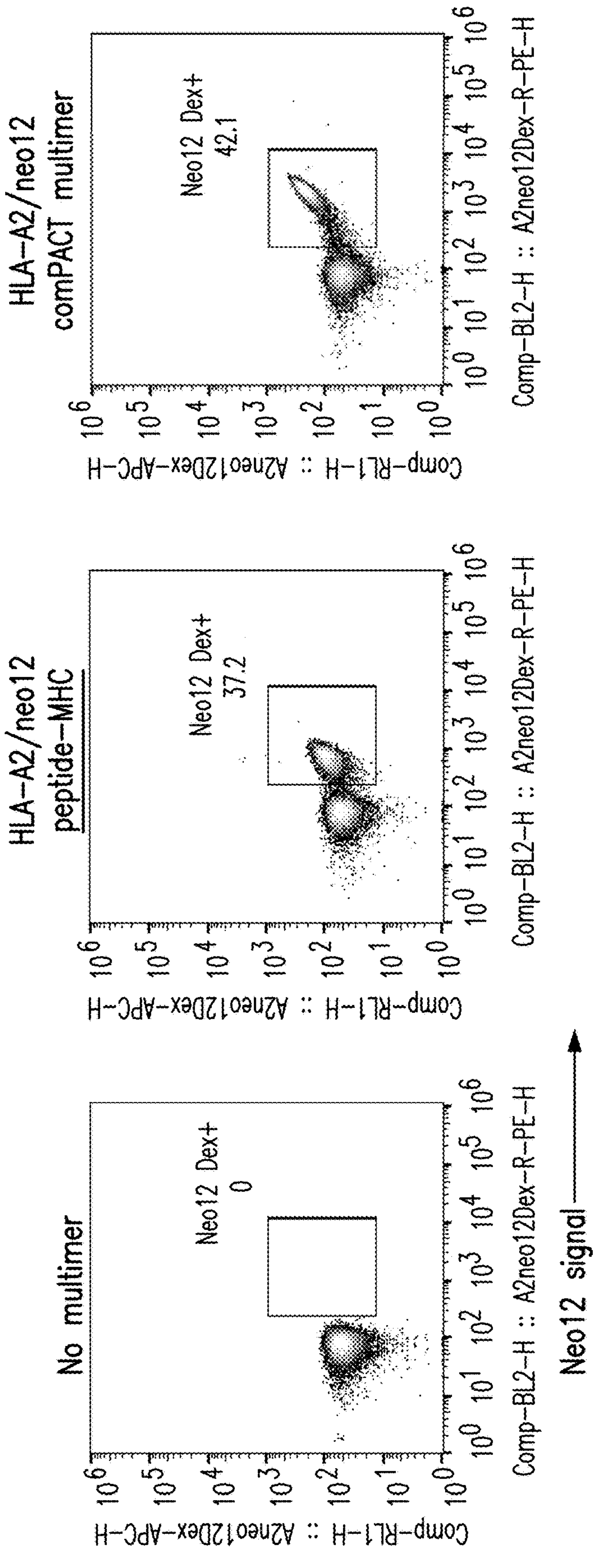
FIG. 19 shows antigen-specific capture of T cells using multimerized comPACT protein.

Example 7: Antigen-Specific T Cell Staining and Affinity Evaluation Using Compact Proteins To compare antigen-specific T cell staining using comPACT proteins and conventional peptide-MHCs, comPACT dextramers were prepared according to a published protocol (Bethune, M. T., et al. *BioTechniques* 62, 123-130, doi: 10.2144/000114525 (2017)). T cells were engineered to express an A2/neo12-specific TCR and stained with either HLA-A2/neo12 peptide-MHC dextramers or HLA-A2/neo12 peptide comPACT dextramers. Staining with the comPACT dextramers was at least as efficient as that for peptide-MHC dextramers (FIG. 19). This data suggests that comPACT dextramers can be used to sort antigen-specific T cells for TCR sequencing.

Example 8: Functional T Cell Assays

Figure 20:
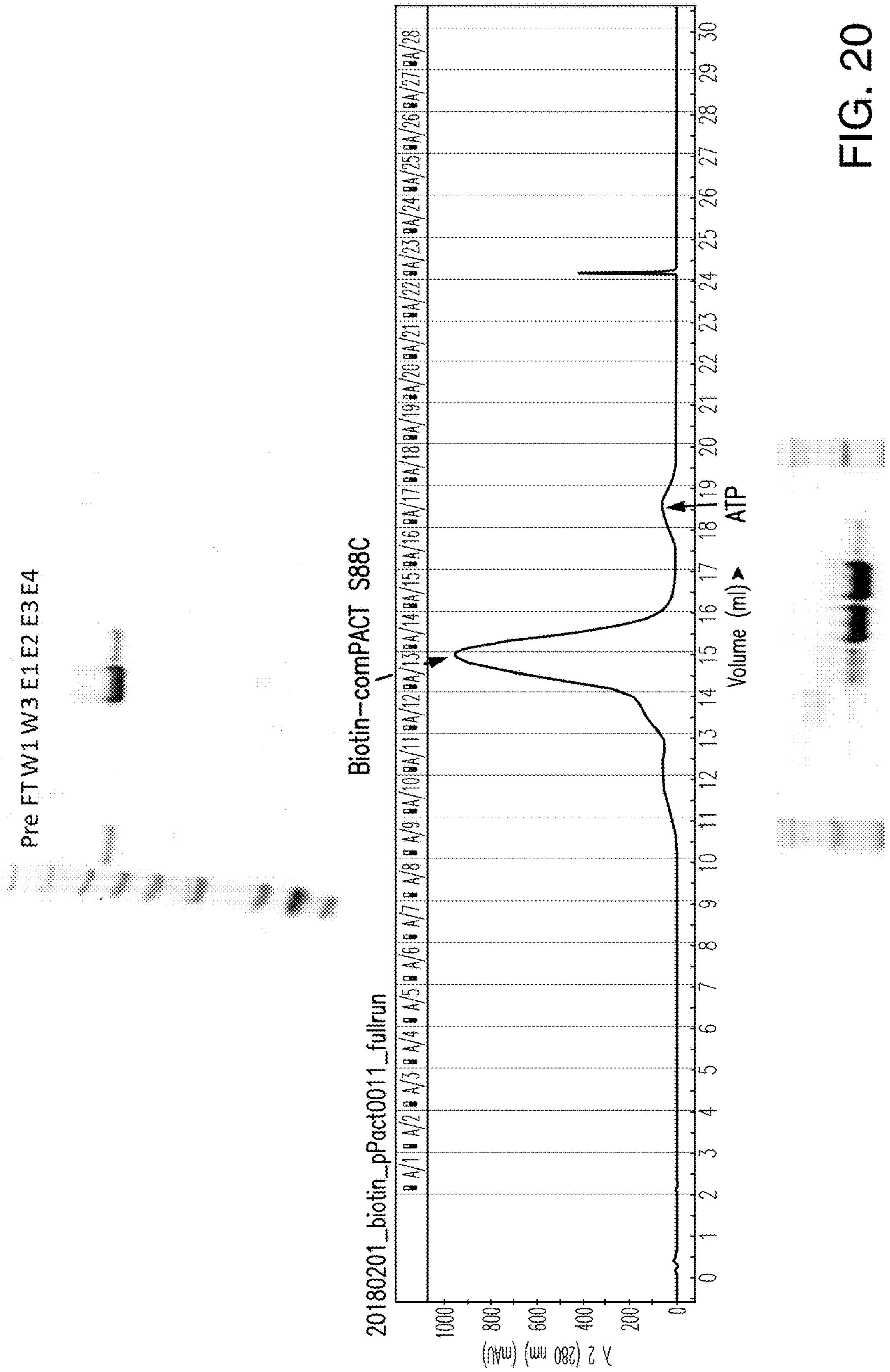
FIG. 20 shows comPACT NTAmer production using an S88C β2M comPACT protein.
Figure 21:
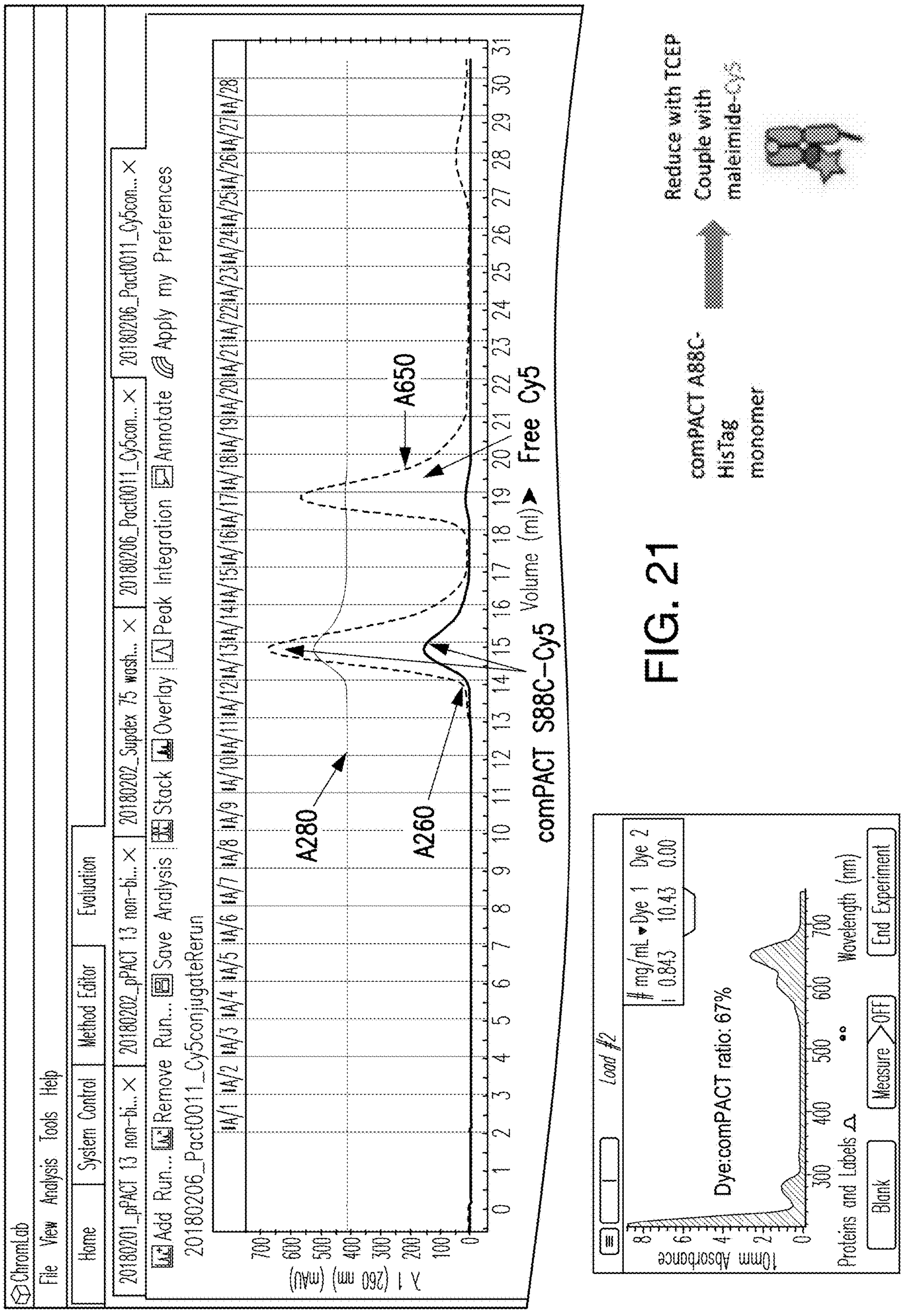
FIG. 21 shows coupling of Cy5 to S88C comPACT protein monomers.

Beyond antigen-specific capture of T cells, the modular design and ease-of-production of comPACTs facilitate their use in functional T cell assays. For example, incorporation of a mutated version (S88C) of β2m enables comPACTs to be labeled with a maleimide-dye conjugate, assembled as NTAmers, and used to measure kinetic parameters of TCR-comPACT binding. S88C mutant comPACT proteins were constructed and are expressed at ~150 mg/L. These mutant comPACTs exhibit similar purity and elution profiles as un-mutated comPACTs (FIG. 20). Other dyes, such as Cy5, can also be conjugated to S88C comPACTs (FIG. 21).

Example 9: Compact Library Production

Figure 24B:
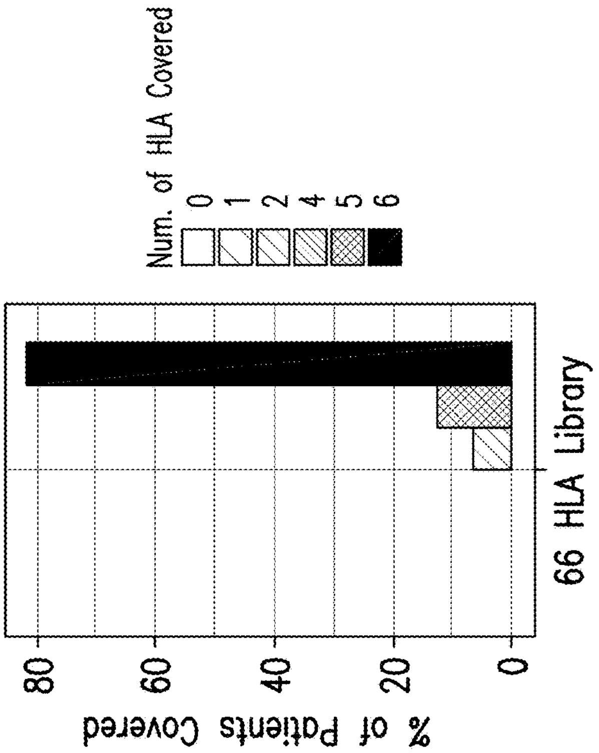
FIGS. 24A and 24B show the percent of patients covered by top HLA I alleles in the United States relative to comPACT HLA repertoire size.
Figure 24A:
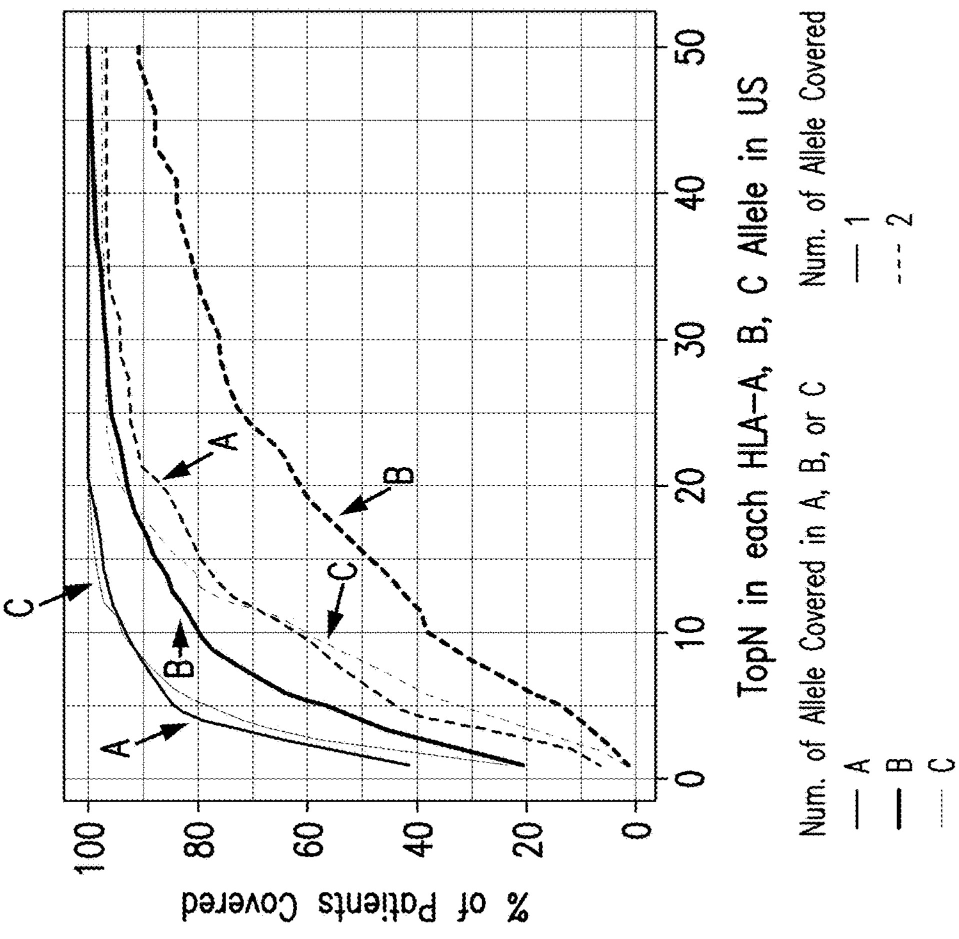

HLA allele diversity across the US human populations was analyzed from the Allele Frequency Net Database (www.allelefrequencies.net) by bioinformatics to identify the optimal number of alleles to include in the HLA repertoire to effect high coverage of subject HLA frequencies. 9736 alleles were analyzed. FIG. 24A shows the analysis of the percentage of patients in which one or both alleles from each of HLA A, B, and C loci are covered by a library of 66 HLA alleles. Solid lines indicate 1 allele is covered, while dashed lines indicate both alleles are covered. 66 alleles enable the coverage of at least 4 of 6 HLA alleles per patient in >95% of total population and 6/6 alleles in >80% of population (FIG. 24B). The most frequent HLA-I allele is HLA-A02:01 with ~50% US prevalence. HLA libraries first shown herein therefore allow the most potential for broad implementation of personalized neoTCR-T cell therapies for a global and diverse population.

Figure 25A:
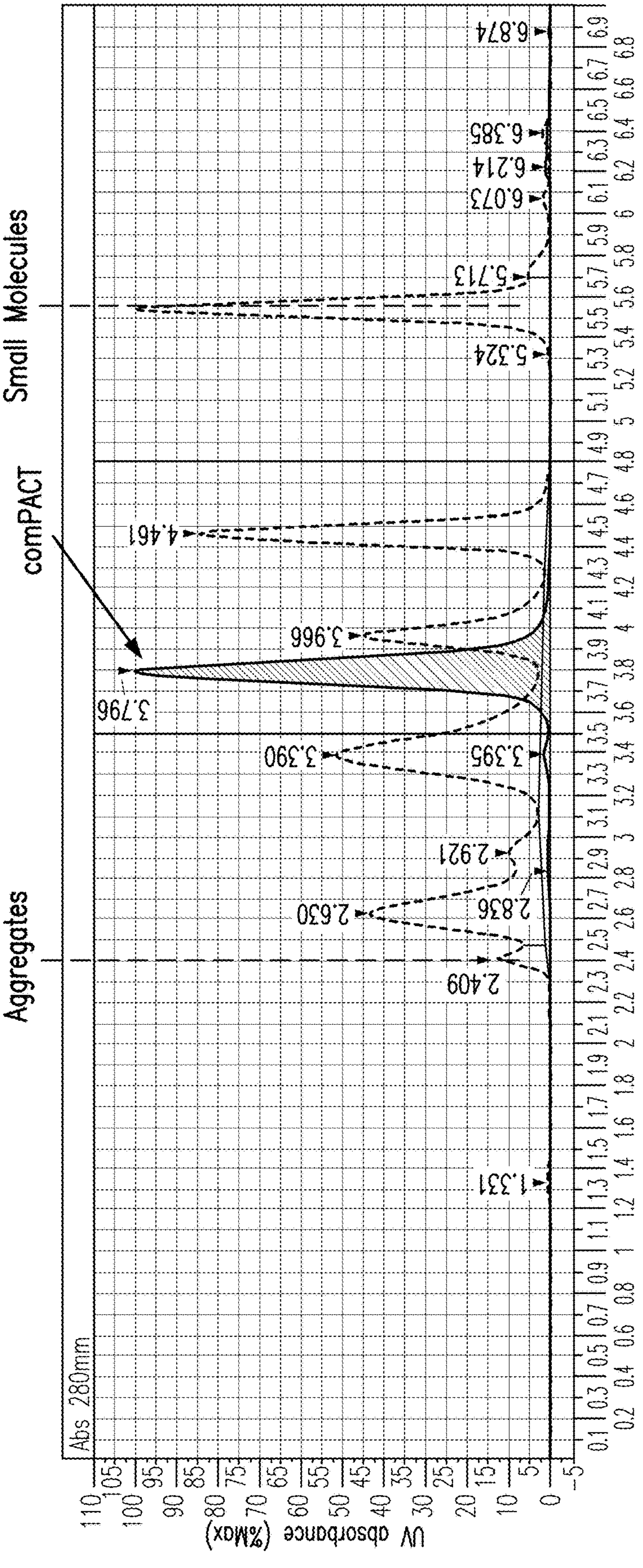
FIG. 25A shows comPACT protein monodispersity for a representative selection of comPACT proteins.
Figure 25B:
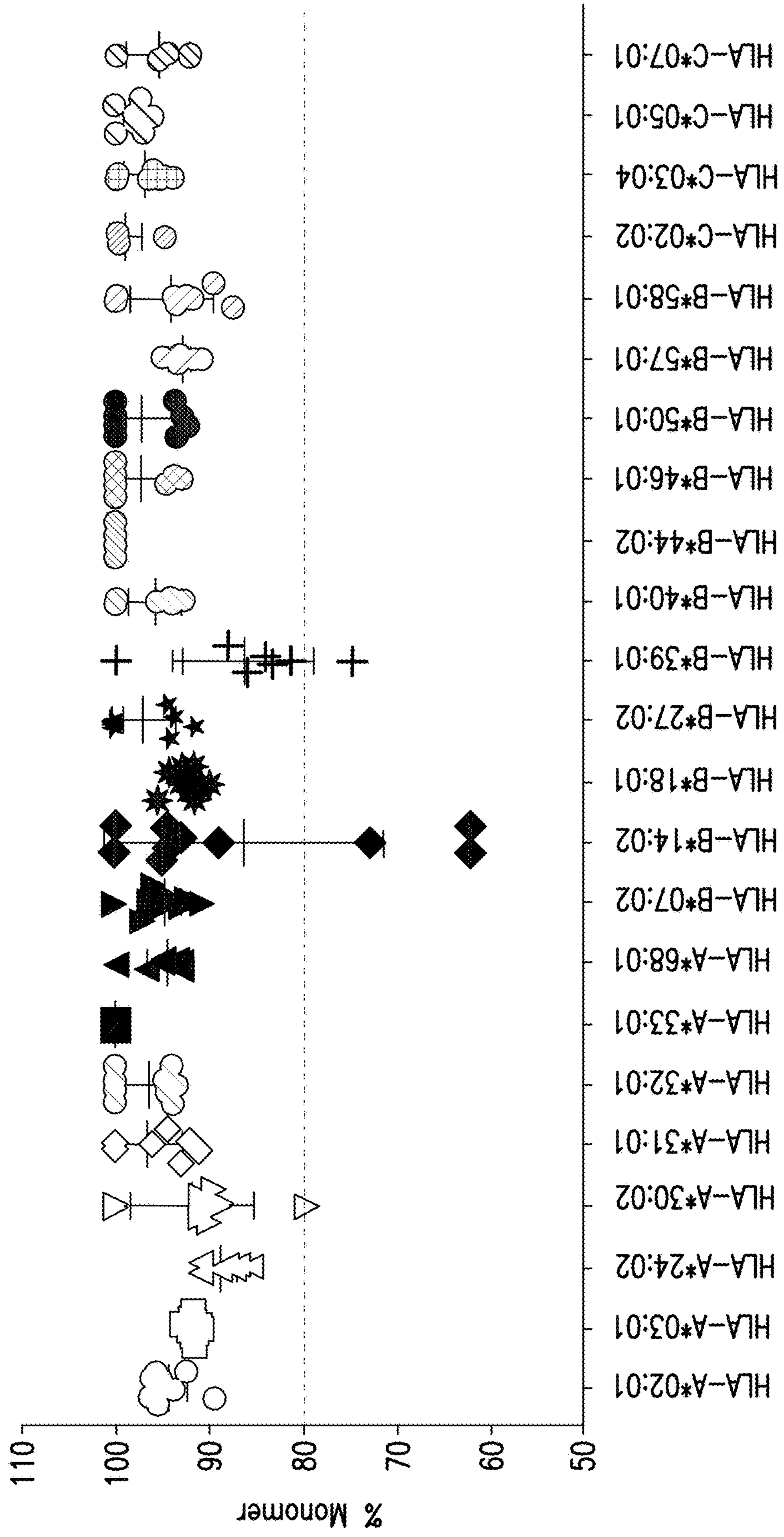
FIG. 25B shows comPACT protein yield for a representative selection of comPACT proteins.
Figure 25C:
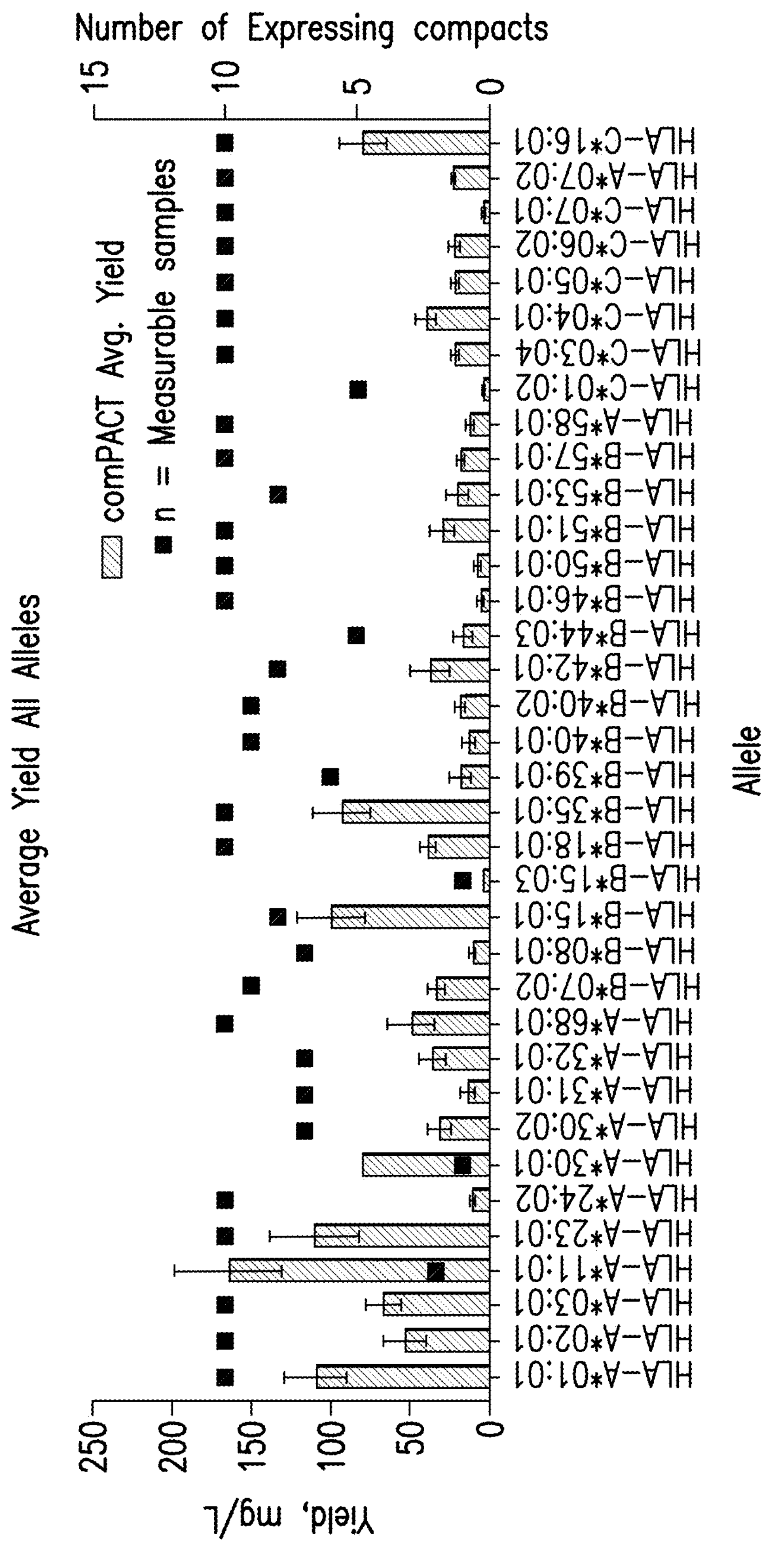
FIG. 25C shows comPACT protein expression for a representative selection of comPACT proteins.

Next, a library of comPACT proteins with different neoepitopes and selected HLA alleles was made. Neoepitope candidates were chosen from the Immune Epitope Database (www.iedb.org). Full sequences for each of the 66 HLA-I alleles in the repertoire were obtained from the IMGT database and modified to include the Y84C mutation. All clones were sequence verified and banked in the database and reagent inventory. Ten neoepitope peptides were chosen from the IEDB database and inserted into a panel of 36 HLA alleles. comPACT polypeptides of the selected neoepitopes and HLA alleles were expressed and purified via Size Exclusion Chromatography column (Agilent Sec Bio 300) connected to an Agilent Infinity II HPLC system (SEC-HPLC) according to the manufacturer's instructions. The results are shown in FIGS. 25A-C. The comPACT polypeptides were purified as monodisperse polypeptides, as assessed via SEC-HPLC by measuring the area under the curve of the monomer peak divided by the area under the whole chromatogram (FIGS. 25A and 25B). Most comPACT polypeptides were expressed at a high titer (FIG. 25C). At least one comPACT protein for each HLA allele described has been purified and characterized via HPLC, indicating that the comPACT platform is robust and amenable to many alleles.

Example 10: Impact T Cell Isolation Method

Materials and Methods comPACT Library Preparation

Paired PE and APC tetramer particles with three comPACT library elements and a barcode were prepared prior to the experiment. Biotinylated comPACT (1 μM, generated inhouse) and DNA barcode (1 μM, IDT) were mixed at a molar ratio of 3:1. PE-streptavidin (3.33 μM, Life Technologies) or APC-streptavidin (6.26 μM, Life Technologies) were added to react with the biotin at a ratio of 1:4. After incubation, additional biotin was introduced to occupy free streptavidin sites.

CD8 T Cell Staining

Cells were incubated with 40 nM fluorescent comPACT tetramers for neoantigen-specific T cell staining. Fc receptor blocking solution was added subsequently to minimize non-specific antibody staining. The samples were also incubated with an antibody cocktail containing FITC CD4, CD14, CD19, CD20, CD40, PerCp-Cy5.5 CD8, BV711 CD45RA, BV786 CD95, and BV510 IP26 (Biolegend) to identify the phenotype of the T cells.

Single Cell Sorting

Fluorescently labeled cells were sorted into single cells using FACSAria III (BD Biosciences). Cells were sorted first for T cell phenotype based on IP26 and CD3 staining, then sorted for double p-HLA binding based on APC and PE staining. comPACT positive cells were sorted into a 96-well plate containing lysis buffer of 10 mM Tris and RNAse inhibitor (Promega).

TCR Cloning

RT-PCR master mix containing the following reagent was prepared: nuclease-free water (Invitrogen), 5× buffer (Qiagen), 10 mM dNTP (Qiagen), alpha multi primer mix, beta multi primer mix, alpha antisense primer, beta antisense primer, DNA barcode sense primer, DNA barcode antisense primer (all primers ordered through IDT), Onestep RT-PCR enzyme (Qiagen), and KOD polymerase (Millipore). RT-PCR master mix was then added to each well to initiate the reverse transcription and polymerase chain amplification for TCR and DNA barcode sequences.

on the gating strategy described above for APC and PE dual labeled CD8 T cells. Barcodes and S/N ratios of each barcode associated with a given cell were determined.

Results

Sensitivity

Figure 29C:
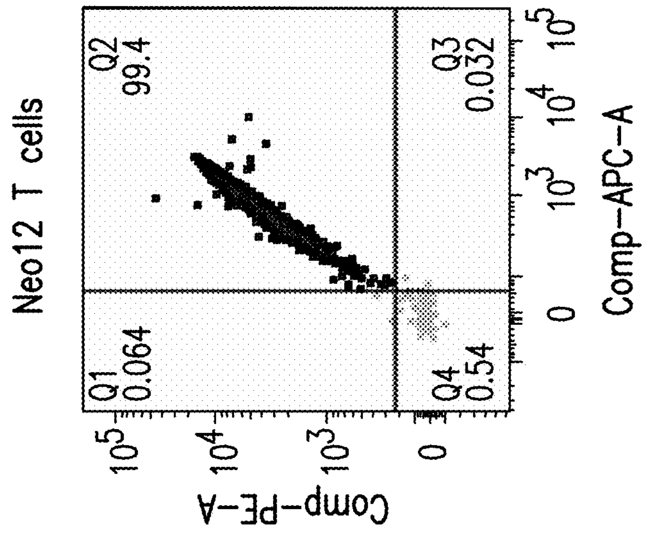
FIG. 29C provides data showing the imPACT tetramer staining of neo12 antigen specific T cells.
Figure 29B:
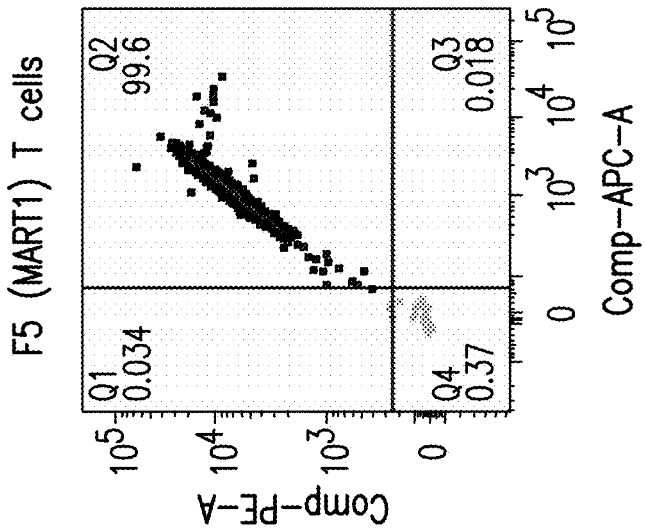
FIG. 29B provides data showing the imPACT tetramer staining of MARTS antigen specific T cells.
Figure 29A:
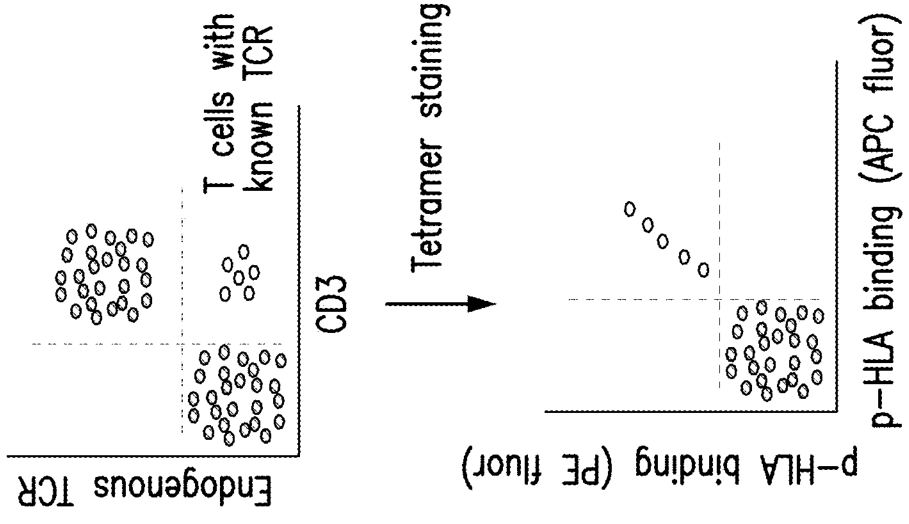
FIG. 29A provides a schematic of the dual tetramer staining process.

FIG. 29A provides a diagram of the endogenous TCR gating strategy for isolating PACT neoantigen CD8 T cells (upper panel) and tetramer positive dual labeled T cells (bottom panel). T cells expressing the neoantigens F5 (FIG. 29B) or neo12 (FIG. 29C) were labeled and gated according to the gating strategy. The corresponding tetramer staining yielded a greater than 99% precision for F5 and Neo12 comPACT neoantigen T cells. A replicate of this assay resulted in greater than 99% tetramer staining of both gene edited F5 and neo12 T cells (data not shown). Thus, the imPACT method has a high staining and sorting sensitivity of greater than 98% or 99%.

To test the sensitivity of the imPACT tetramer method, a cell-doping experiment was conducted. T cells expressing neoantigen neo12 were doped into a control PBMC sample at 1 to 300,000 ratio (1 neo12 T cell per 300,000 PBMCs). imPACT tetramer analysis was conducted using tetramers made from neo12 comPACTs and 32 irrelevant control comPACTs. Cells positive for the 33 comPACT tetramers were sorted from the CD8 T cell gating as described above. The cells were sequenced for the relevant TCR and neoID sequence. After sequencing, a signal-to-noise ratio (S/N) was used to determine the specificity of the tetramer binding. The S/N calculation for this example was the DNA copy number for the most dominant neoID divided by the second most dominant neoID. In this example, an S/N greater than 10 was considered to be specific binding of the comPACT to a T cell. The indexed flow result of IP26 staining for each cell indicates whether a given cell is gene edited or naïve.

Table 4 summarizes the cells sorted from this experiment. 1686,717 total cells were analyzed by the flow cytometry and 11 cells were sorted from the positive gate.

TABLE 4

| Number of cell number processed | Number of cell sorted | Number of neo12 cell in theory | Number of neo12 cell identified | Number of non-specific cells | Average S/N |
|---|---|---|---|---|---|
| 1686717 | 11 | 5.6 | 5 | — | 83.1 |
| | | — | — | 6 | 1.1 |

Sensitivity and S/N Assay

CD8 T cells expressing a TCR against a MART1 antigen (F5) or a neoantigen neo12 were incubated with fluorescent comPACT particles with the corresponding comPACT neoantigen element (MART1 or neo12). Cells were stained and sorted via FACS as described above (FIGS. 29A-C).

Figure 30:
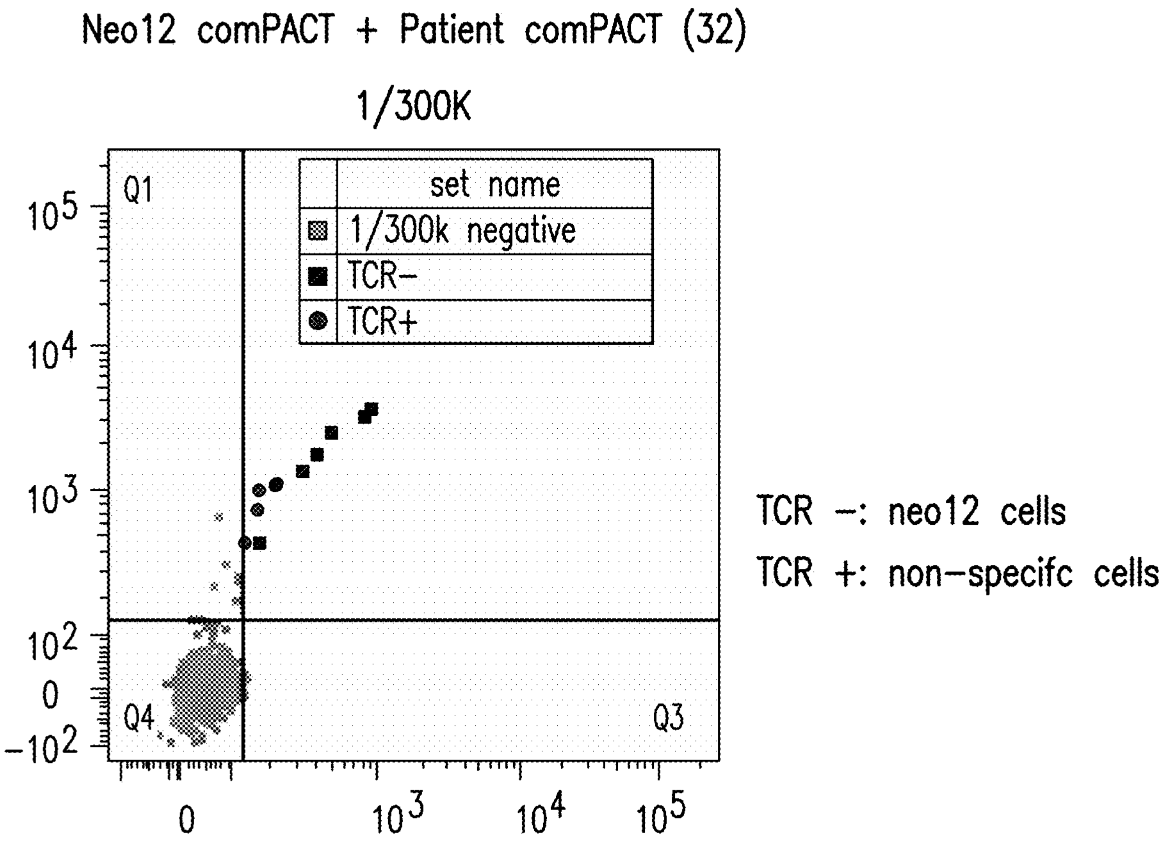
FIG. 30 provides an example of the sensitivity of isolated neoantigen T cells via neoID signal to noise ratio.

CD8 T cells expressing a TCR against neoantigen neo12 were doped into a control PBMC sample at a 1 to 300,000 ratio. The doped sample was incubated with a library of 33 tetramers, comprising the neo12 comPACT and 32 additional neoantigen comPACT elements. Single cells were sorted based on the gating strategy described above for APC and PE dual labeled CD8 T cells (FIG. 30).

Specificity and S/N Assay

CD8 T cells expressing a TCR against neoantigen neo12 were doped into a control PBMC sample at a 1 to 300,000 ratio or at a 1 to 30,000 ratio. PBMCs alone were used as negative control. The doped sample was incubated with a library comprising the neo12 comPACT and 28 irrelevant control comPACT elements. Single cells were sorted based 5 of the 11 positive cells have an S/N higher than 10 (average S/N=83.1), while the other 6 have S/N lower than 10 (average=1.1). Based on the ratio of neo12 doped cells (1:3000,000) and the number of cells processed (1,686,717) there should be approximately 5-6 neo12 cells in the sample analyzed. The sequencing result shows that 5 neo12 cells were isolated using the method. Thus, the imPACT tetramer method is sensitive enough to isolate antigen specific cells at a low frequency of 1/300,000. FIG. 30 shows the gated FACS cells for the 1:300,000 doped sample. TCR-indicates the neo12 positive T cells, while TCR+ indicates the non-specifically bound T cells. The average S/N ratio of the specific neo12 cells was 83, while the average S/N ratio of the non-specific cells was 1.1.

Specificity

Next, the imPACT isolation method was assessed for neoantigen specificity. The neo12 doping assay was repeated with a second library comprising the neo12 comPACT and 28 irrelevant control comPACTs added to a PBMC sample. PBMCs alone were used as negative control. The dual positive cells were isolated, the barcodes sequenced, and the S/N ratio of each barcode associated with a given cell was determined. FIG. 31 shows the PE and ACP FACS gating data for the neo12 antigen doped PBMC sample and the non-doped PBMC sample. Tables summarizing the barcode S/N sequencing results are shown below each test. In the Specific Test, the S/N average was 162, indicating 162 copies of the neo12 neoID barcode for each non-neo12 neoID barcode. This indicates a high specificity of the neo12 barcode for the sorted cells from the neo12 and PBMC samples. In contrast, the S/N average in the Non-Specific test was 1.7, indicating only 1.7 copies of the neo12 neoID barcode for each non-neo12 neoID barcode. This indicates a low specificity of the neo12 barcode for the sorted cells in the PMBCs only sample.

Figure 32A:
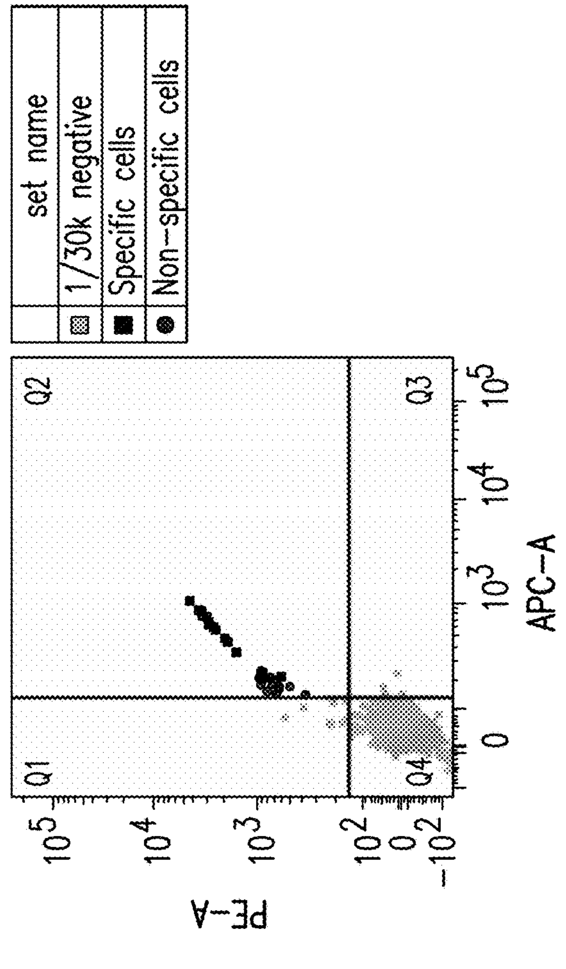
FIG. 32A provides a FACS plot of gene edited, specific T cells (full squares) that exhibit a NeoID signal to noise ratio greater than 10. Non-specific T cells (circles) exhibit S/N<10.
Figure 32B:
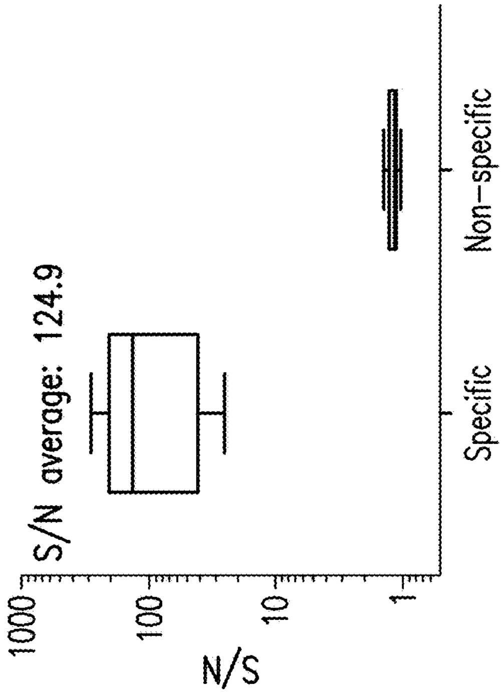
FIG. 32B shows quantification of the signal to noise ratio and average of the specific and non-specific T cells.

The assay was repeated with a comPACT library with 33 elements added to a PBMC sample at a ratio of 1 neo12 T cell to 30,000 PBMCs. FIG. 32A shows the gated dual positive cells, while FIG. 32B shows the barcode S/N average of the specific and non-specific T cells. The signal-to-noise ratio of 33 tetramer positive cells was determined. The S/N average of the T cells with specific binding was 124.9, while the non-specific S/N ratio was 1.2, confirming the high specificity of the imPACT method for isolating neoantigen specific T cells. Table 3 summarizes the information for the sorted cells, as well as if the isolated cell was genetically modified (gene edited).

TABLE 3

| Cell number | Gene edited | S/N |
|---|---|---|
| 1 | Yes | 285.2 |
| 2 | Yes | 231.5 |
| 3 | Yes | 227.0 |
| 4 | Yes | 217.8 |
| 5 | Yes | 215.9 |
| 6 | Yes | 215.4 |
| 7 | Yes | 180.8 |
| 8 | Yes | 171.4 |
| 9 | Yes | 166.4 |
| 10 | Yes | 145.4 |
| 11 | Yes | 135.8 |
| 12 | Yes | 100.9 |
| 13 | Yes | 42.8 |
| 14 | Yes | 42.6 |
| 15 | Yes | 42.3 |
| 16 | Yes | 41.1 |
| 17 | Yes | 38.6 |
| 18 | Yes | 35.1 |
| 19 | Yes | 31.0 |
| 20 | Yes | 29.1 |
| 21 | Yes | 25.7 |
| 22 | No | 1.4 |
| 23 | No | 1.4 |
| 24 | No | 1.4 |
| 25 | No | 1.2 |
| 26 | No | 1.2 |
| 27 | No | 1.2 |
| 28 | No | 1.1 |
| 29 | No | 1.1 |
| 30 | No | 1.1 |
| 31 | No | 1.1 |
| 32 | No | 1.0 |
| 33 | No | 1.0 |

Example 11: Isolation of Neoantigen T Cells from Patient Samples

Materials and Methods

Tetramer Preparation

Tetramers were prepared as previously discussed above.

CD8 Selection and Cell Staining

Cryopreserved patient PBMCs were thawed and CD8 T cells were selected using CD8+ T cell isolation kit (Miltenyi) according to manufacturer-recommended protocol. Isolated CD8 T cells were used for subsequent staining. Cells were incubated with 40 nM fluorescent comPACT tetramer libraries for neoE-specific T cell staining. Fc receptor blocking solution was added subsequently to minimize non-specific antibody staining. The samples were incubated with an antibody cocktail containing FITC CD4, CD14, CD19, CD20, CD40, PerCp-Cy5.5 CD8, BV711 CD45RA, BV786 CD95, and BV510 IP26 (Biolegend) to identify the phenotype of the T cells. Live/dead near-IR cell stain (Invitrogen) was used to differentiate between viable and non-viable cells. BV605 Annexin-V (Biolegend) was used to further differentiate between viable and apoptotic cells.

Single Cell Sorting and TCR Cloning

Fluorescently labeled cells were sorted into single cells using FACSAria III (BD Biosciences). Viable, CD8+, tetramer positive cells were sorted into a 96-well plate containing lysis buffer of 10 mM Tris and RNAse inhibitor (Promega). Cells were then frozen for subsequent TCR cloning. RT-PCR master mix containing the following reagent was prepared: nuclease-free water (Invitrogen), 5× buffer (Qiagen), 10 mM dNTP (Qiagen), alpha multi primer mix, beta multi primer mix, alpha antisense primer, beta antisense primer, DNA barcode sense primer, DNA barcode antisense primer (all primers ordered through IDT), Onestep RT-PCR enzyme (Qiagen), and KOD polymerase (Millipore). RT-PCR master mix was then added to each well to initiate the reverse transcription and polymerase chain amplification for TCR and DNA barcode sequences. An additional two rounds of PCR were performed to further amplify the TCR and DNA barcode sequence, as well as to append adaptor sequences for next-generation sequencing (NGS).

Next Generation Sequencing

Next-generation sequencing was done on a Miniseq (Illumina) using the recommended reagents. Library preparation was done according to Illumina's recommended protocol. Target species and PhiX were mixed at equal parts to provide diversity.

Results

Figure 33A:
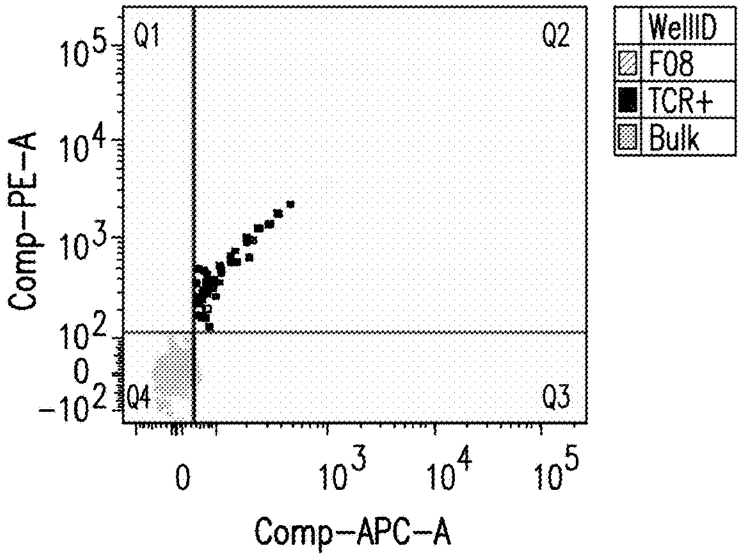
FIG. 33A provides an example of the imPACT analysis of a PBMC sample using the single barcode method and the validation for the imPACT isolated TCR.

First, a stage IIIA melanoma patient sample (PACT032) was analyzed using a 26-element comPACT library with an HLA A02:01 allele type. Of the $3.9\times10^6$ PBMCs in the sample, 231 were dual positive for APC and PE. The cells were analyzed for the neoID barcode and the signal-to-noise ratios of all the dual positive cells were determined. FIG. 33A shows the FACS dot plot of the dual positive T cells. After neoID sequencing, one T cell showed specificity to one mutation, with a signal-to-noise (S/N1) of greater than 10. This neoantigen TCR was cloned and screened against the predicted neoantigen. The remaining dual positive cells all had signal-to-noise ratios of 1, and were not specific for the neoantigen associated with the bound comPACTs. A secondary screen (FIG. 33B) confirmed specificity of the neoantigen TCR isolated via the impact analysis. Table 5 below provides a summary of the signal-to-noise ratio of the specific and non-specific T cell.

TABLE 5

| TCR clonotype | Count | S/N (UMI) |
|---|---|---|
| TCR+ | 230 | 1 |
| PACT32-TCR75 | 1 | 13 |

Example 12: S/N1 and S/N2 Analysis to Identify TCRS

Figure 34D:
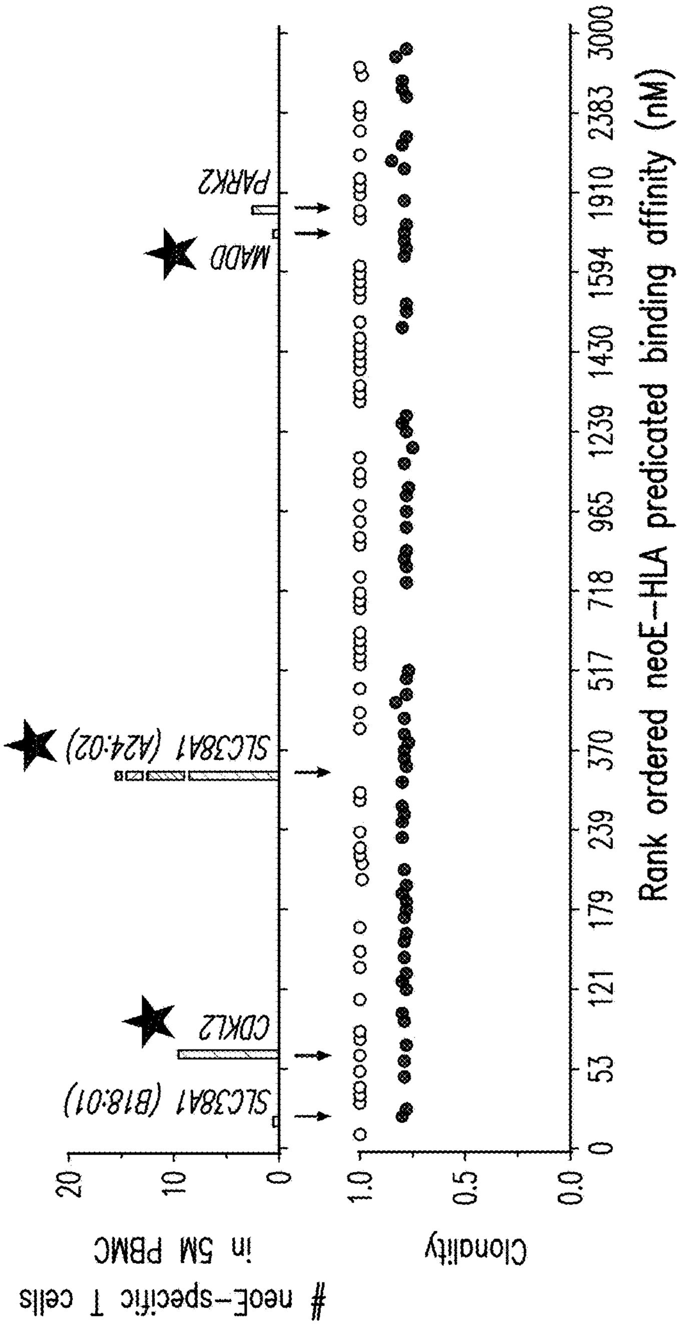
FIG. 34D provides a summary of the neoantigen specific T cells isolated.
Figure 34E:
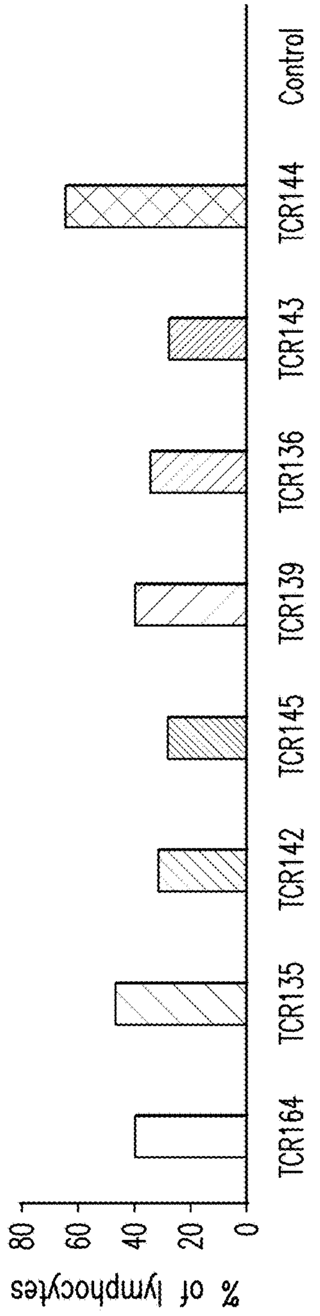
FIG. 34E provides a summary of the number of lymphocytes isolated for each TCR identified using the imPACT method.

Next, a stage III melanoma patient sample (PACT077) was analyzed using a 138-element comPACT library with HLA A02:01, A24:02, B18:01, and C07:01 types. Of the $5.1\times10^6$ PBMCs in the sample, 250 were dual positive for APC and PE. The cells were analyzed for the neoID barcode and the signal-to-noise ratios of all the dual positive cells were determined. FIG. 34A shows the FACS dot plot of the dual positive T cells. FIG. 34D shows the neoantigen-specific T cells identified in the peripheral blood. Stars indicate the same TCR clonotype is found in tumor-infiltrating lymphocytes (TILs) from tumor sequencing. After neoID sequencing, 25 T cells showed specificity to one mutation, with a signal-to-noise (S/N1) of greater than 10 (FIG. 34C). FIG. 34B shows that all candidate cells came from antigen experienced CD95+ cells. The neoantigen TCRs were cloned and screened against the predicted neoantigens. FIG. 34E shows the percentage of neoTCR gene-edited lymphocytes that can recognize the cognate antigens. The remaining dual positive cells all had signal-to-noise ratios of 1, and were not specific for the neoantigen associated with the bound comPACTs. Table 6 below provides a summary of the signal-to-noise ratio of T cells for selected neoantigens.

TABLE 6

| SEQ ID NO: | Neoantigen | Average S/N |
|---|---|---|
| 203 | EYIPGTTFL | 25 |
| 204 | IYNIIVTTL | 43 |
| 205 | KTSVALHLI | 19 |
| 206 | HLSLELLGVD | 21 |
| 207 | DEYIPGTTF | 32 |

Figure 35A:
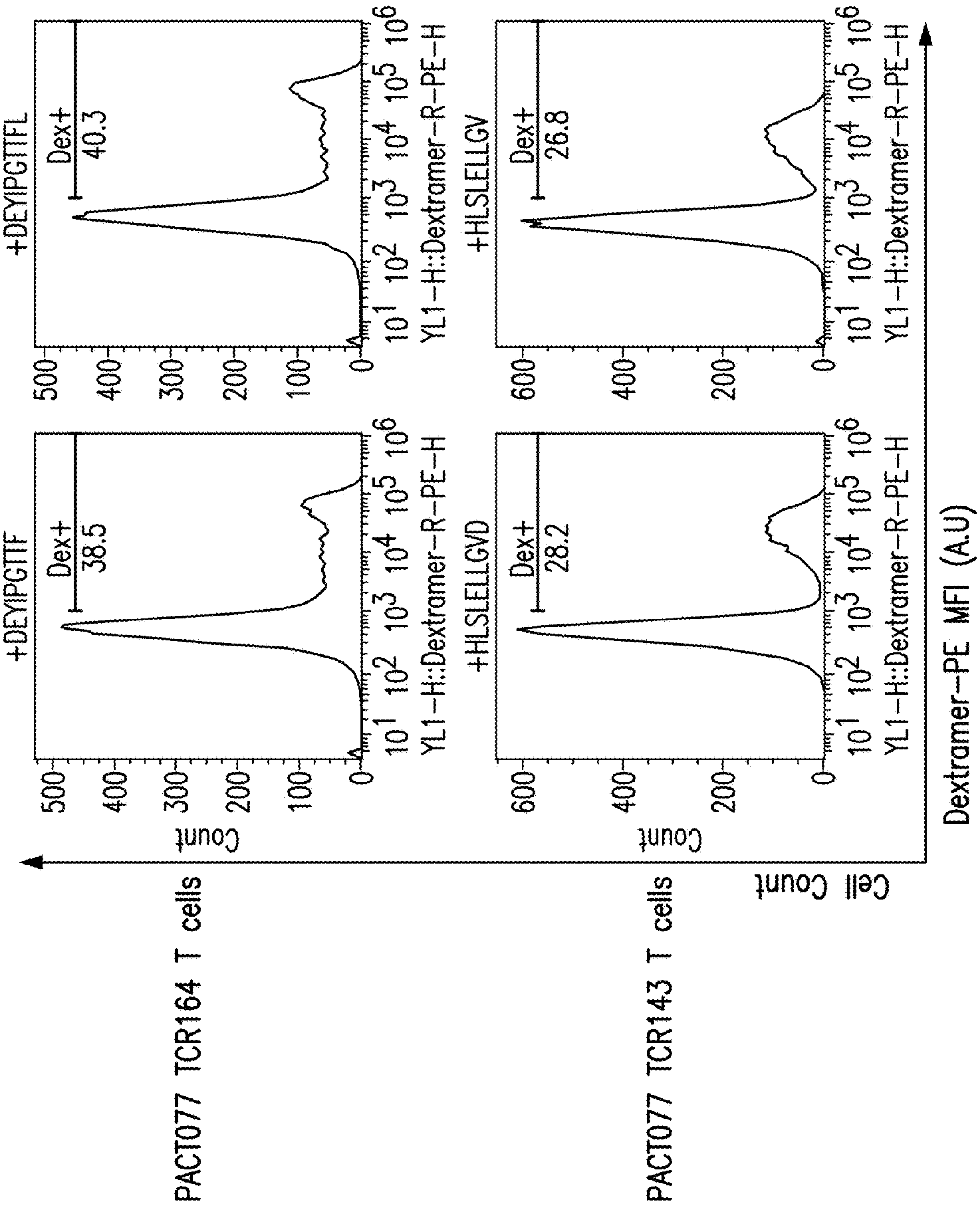
FIG. 35A provides an example of the validation screening of the imPACT analysis of the PBMC sample used in FIG. 34.

Interestingly, analysis of the TCRs from PACT077 identified 8 different TCRs. 6 of them had S/N1 ratios of more than 10, and were confirmed to be specific neoantigen T cells. For the other 2 T cells, the S/N1 ratios were lower than 10 but the S/N2 ratios were higher than 10 (FIG. 34C). Cloning of the two TCRs (TCR143 and TCR164) revealed that they can recognize two different neoantigens sharing the same mutation, further explaining the reason for low S/N1 (FIG. 35A). These results indicate that S/N2 ratios can be used to distinguish the non-specific cells from specific cells, when there are multiple neoantigens derived from the same mutation.

Figure 35B:
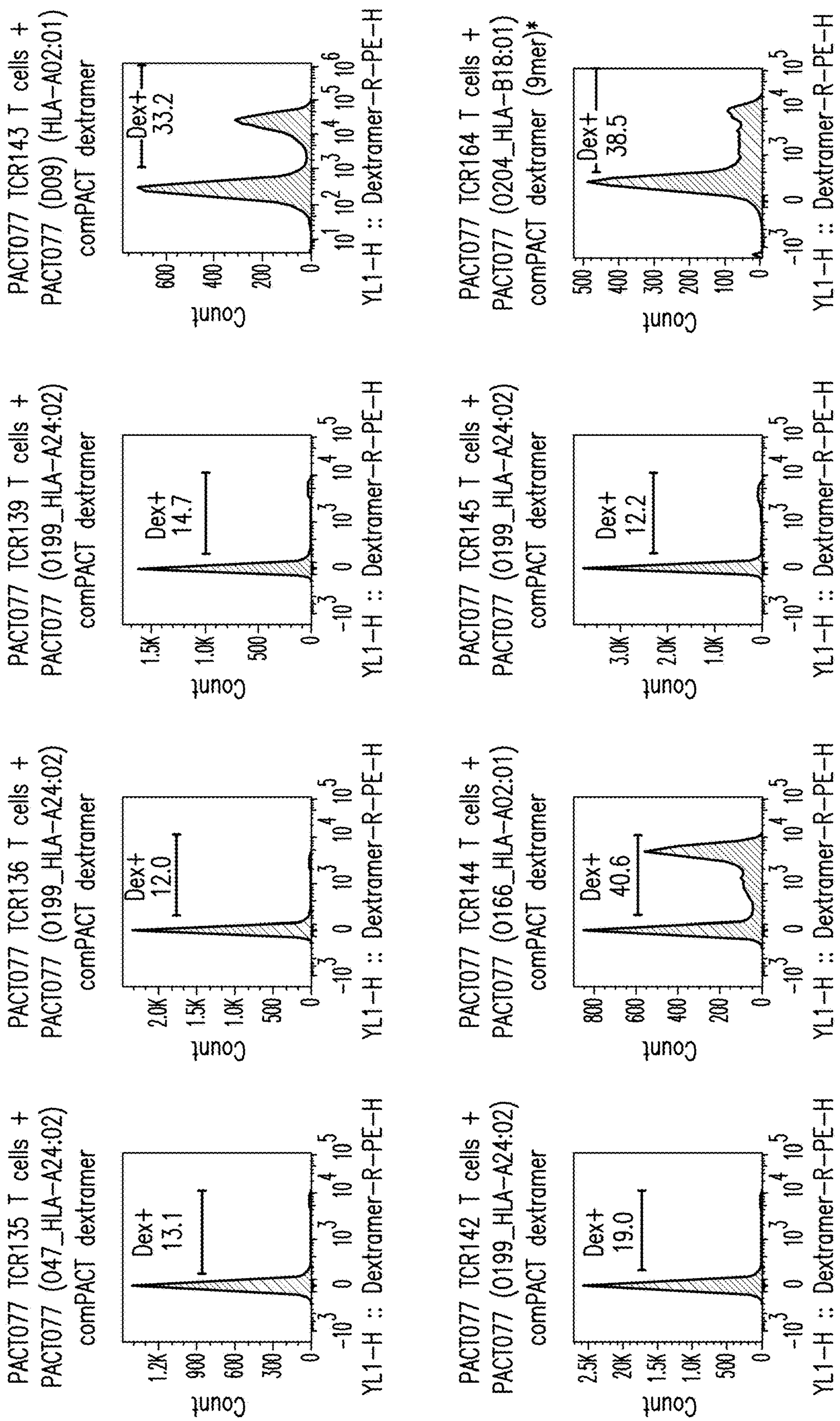
FIG. 35B provides an example of the validation screening of the imPACT analysis of the PBMC sample used in FIG. 34.

A secondary screen (FIG. 35B) confirmed specificity of the neoantigen TCRs TCR135, TCR136, TCR139, TCR142, TCR144, and TCR145 isolated via the imPACT analysis.

Figure 36:
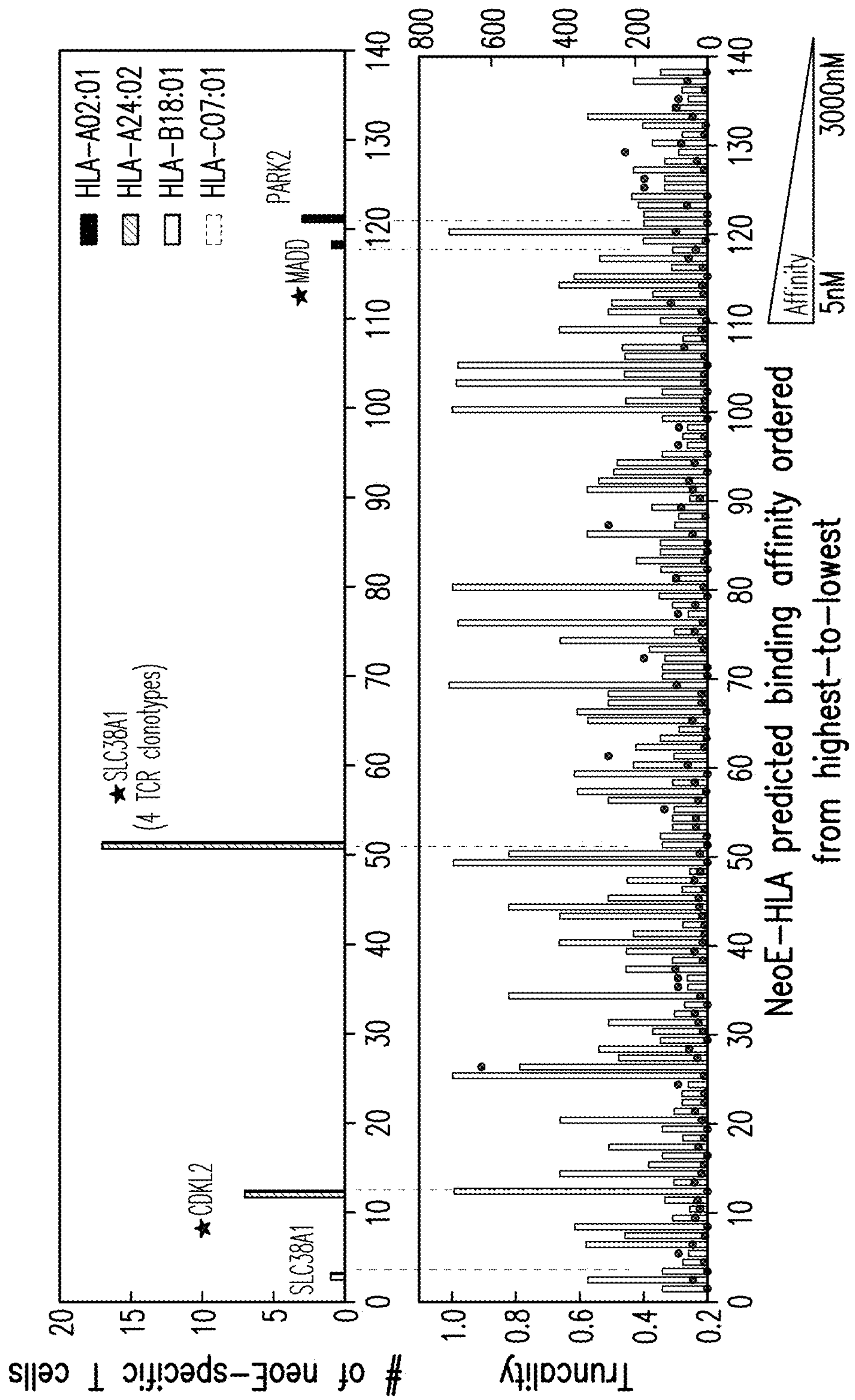
FIG. 36 provides an illustration of the mutation-targeted T Cells of the PBMC sample used in FIG. 34.

FIG. 36 shows that the TCRs isolated varied across mutations with various levels of clonality, truncality, and in situ neoantigen expression levels.

Example 13: Isolation of Neoantigen T Cells with Dual NeoID Barcode

Materials and Methods

Tetramer Preparation

Paired fluorescent tetramer particles were prepared as previously discussed above, with the exception that each particle pair had a different unique neoID barcode associated with the neoantigen (see FIG. 28 for a diagram of the dual barcoded paired particles).

CD8 Selection and Cell Staining

Cryopreserved patient PBMCs were thawed and CD8 T cells were selected using CD8+ T cell isolation kit (Miltenyi) according to manufacturer-recommended protocol. Isolated CD8 T cells were used for subsequent staining as previously described.

Single Cell Sorting and TCR Cloning

Fluorescently labeled cells were sorted into single cells using FACSAria III (BD Biosciences) as previously described.

Next Generation Sequencing

Next-generation sequencing was done on a Miniseq (Illumina) using the recommended reagents as previously described.

Results

Figure 33B:
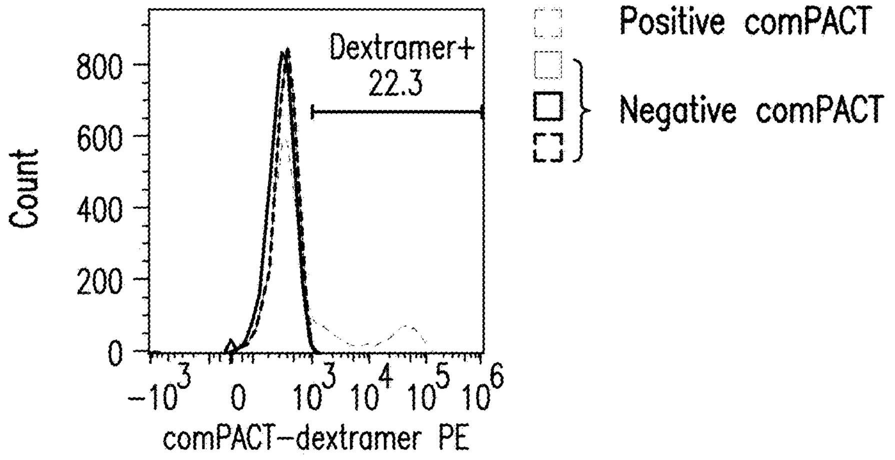
FIG. 33B provides an example of the imPACT analysis of a PBMC sample using the single barcode method and the validation for the imPACT isolated TCR.
Figure 37D:
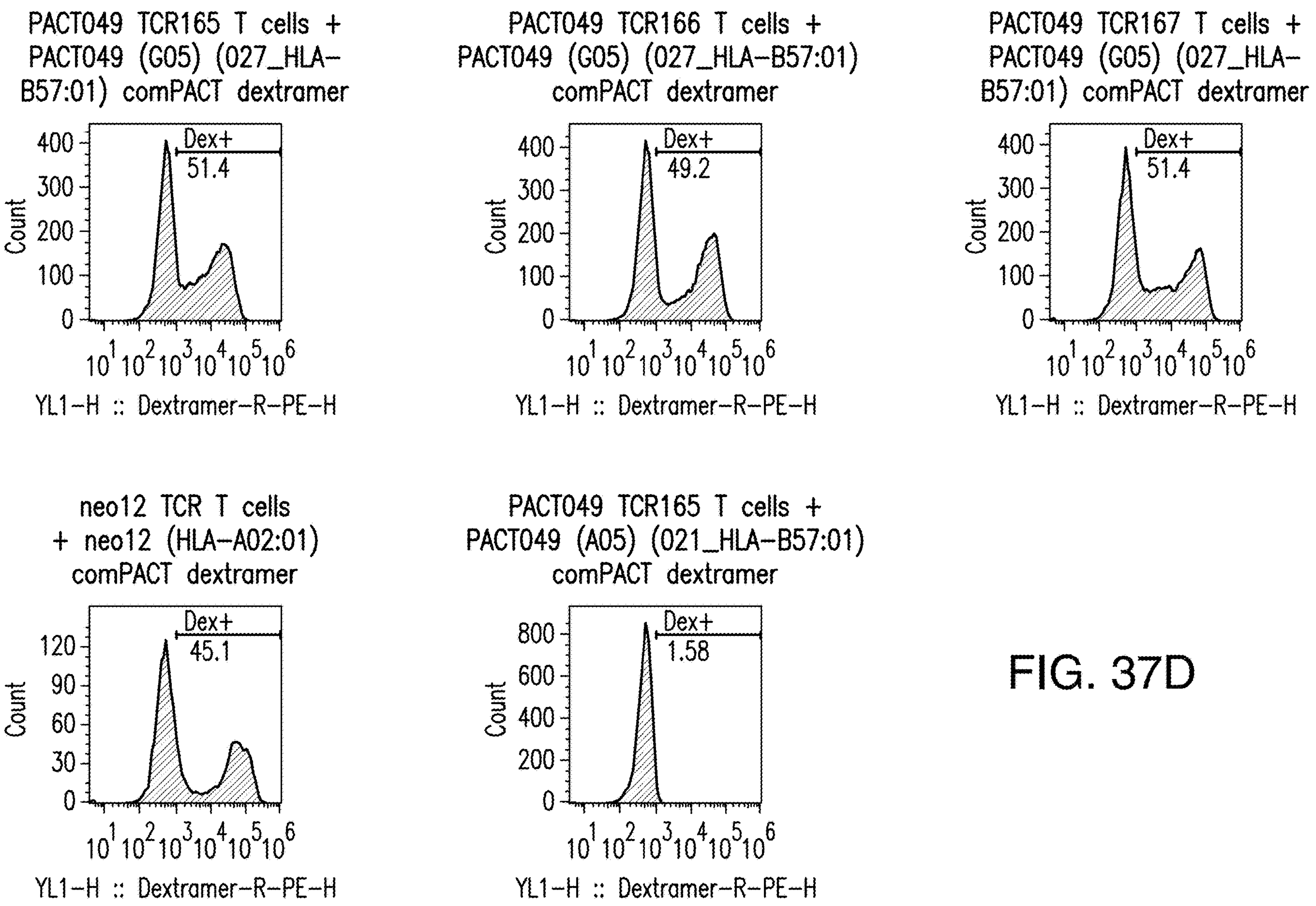
FIG. 37D provides an example of the validation screening of the imPACT analysis using comPACT dextramers.

PACT049 (Stage 4 CRC, naïve) PBMCs were screened using the imPACT process and dual barcodes. A six-element dual barcode comPACT library (HLA-B57:01, A01:01, and C06:02) was produced and used to interrogate for neoantigen TCRs. 352 single cells were sorted. After sequencing analysis, three neoantigen TCR candidates were identified against one HLA-B57:01 neoantigen, RCSPEQLKKAW (SEQ ID NO: 208) (FIG. 37A). These three candidates were sorted based on tetramer MFI (mean fluorescent intensity) and were all considered antigen experienced, CD95+(FIG. 33B). After cloning PACT049 neoantigen T cells, these TCRs were confirmed via dextramer staining with the relevant predicted neoantigen (FIG. 37C and FIG. 37D).

Example 14: Additional Isolation of Neoantigen T Cells from Patient Samples

Figure 38A:
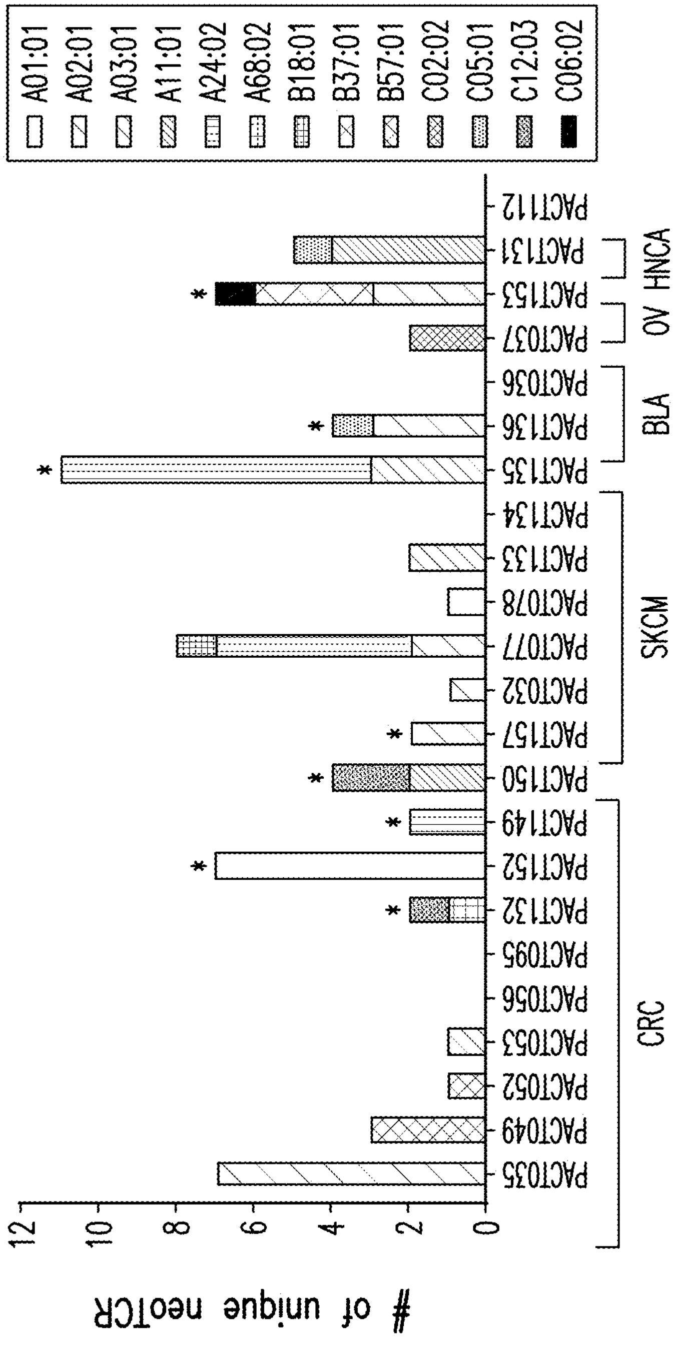
FIG. 38A provides a summary of neoantigen-specific TCRs isolated from patient samples.

Additional patient samples were incubated with comPACT libraries and isolated according to the imPACT method described above. Patient samples were analyzed using the imPACT signal to noise method and single or dual barcoding methods. A graph of the neoantigen numbers and HLA types identified from each sample and cancer type is provided in FIG. 38A and the HLA-type is tabulated in FIG. 38B. Thirty-two neoantigen-specific TCRs were identified across five cancer types and thirteen HLA-types from the periphery. Neoantigens were identified in colorectal cancer (11), melanoma (7), bladder cancer (3), endometrial adenocarcinoma (1), and head and neck cancer (1) samples. Two patient samples (PACT056 and 095) did not yield any neoantigen-specific TCRs. Four patient samples (PACT032, 052, 053 and 078) have one neoantigen-specific TCR. Multiple neoantigen-specific TCRs were isolated in each of the following seven samples: PACT035, 036, 037, 049, 077, 131, and 133. Multiple neoantigen-specific TCRs enables the selection of the best TCR for the patients. Two samples (PACT077 and 078) had peripheral TCRs that were also found in situ by deep sequencing of TILs. These results indicate that the neoantigen-specific TCR identification success rate is 100% from a patient undergoing drug treatment and greater than 80% from patient without treatment.

The results indicate that the imPACT technology is able to successfully isolate antigen-paired, neoantigen-specific TCRs from patient samples with high precisions and specificity. As the imPACT technology is targeting neoantigens and the antigen presentation pathway is universal, the imPACT platform technology can be applied to different cancer types, enabling the development of personalized neoTCR-T cell therapies for the eradication of solid tumors.

Example 15: Reproducibility of T Cell Isolation Method

Next, a comPACT element library was used to analyze a healthy donor's PBMCs. 15 paired fluorescent comPACTs (HLA A02:01) with neoantigens for cytomegalovirus (CMV), Epstein-Barr virus (EBV) and influenza were made as previously described. The comPACT libraries were incubated with PBMCs and the dual positive T cells were sorted and isolated. The neoID barcodes were sequenced and the TCRs cloned and sequenced as previously described. The experiment was done in triplicate.

Figure 39B:
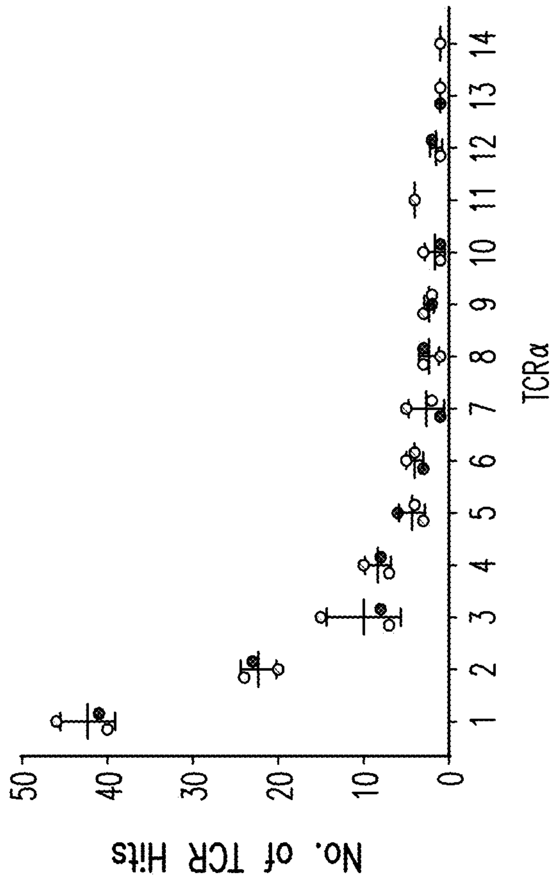
FIG. 39B shows the number of TCR hits.
Figure 39A:
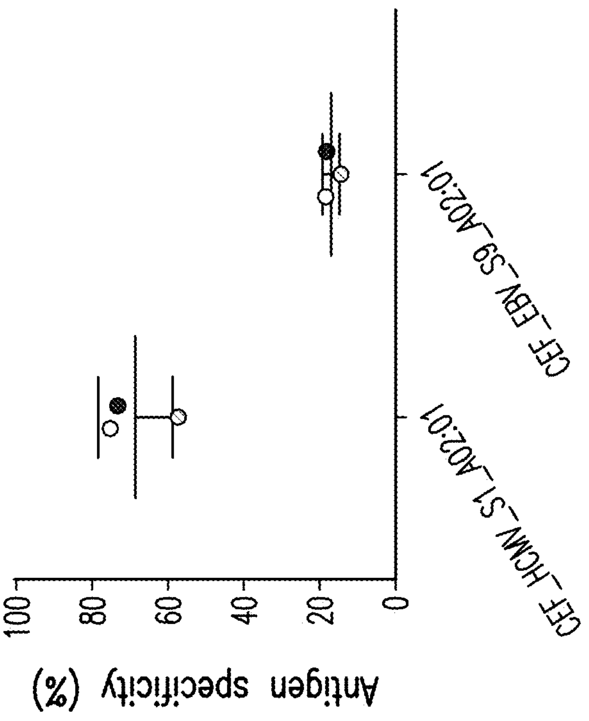
FIG. 39A shows the antigen specificity of HCMV and EBV T cells.

FIG. 39A shows the percent antigen specificity for the isolated T cells with neoantigens against CMV and EBV in each of the three replicates. FIG. 39B shows the number of TCR alpha chains isolated from each experiment. Table 7 provides a summary of the TCR alpha chains identified. 14 unique TCR alpha chains were identified and 10 out of the 14 are shared in all three experiments. This reproducibility experiment shows that the imPACT method can consistently isolate antigen-specific T cells from the same sample at similar levels in independent experiments, indicating that the method of isolating dual positive T cells by incubating the cells with paired comPACT tetramers with different fluorophores is highly reproducible in multiple settings.

TABLE 7

| | SEQ ID | | TCR count | | |
|---|---|---|---|---|---|
| TCR No. | NO: | TCRa | 1st | 2nd | 3rd |
| 1 | 209 | CAVRDVSARLMF | 40 | 46 | 41 |
| 2 | 210 | CARNTGNQFYF | 20 | 23 | 24 |
| 3 | 211 | CAVLMDSNYQLIW | 15 | 8 | 7 |
| 4 | 212 | CAVRDVNARLMF | 8 | 7 | 10 |
| 5 | 213 | CAVMLYTDKLIF | 6 | 4 | 3 |
| 6 | 214 | CAFNDYKLSF | 4 | 3 | 5 |
| 7 | 215 | CAVFFGNVLHC | 1 | 5 | 2 |
| 8 | 216 | CASSPVAGNNRKLIW | 3 | 1 | 3 |
| 9 | 217 | CILVNNNDMRF | 2 | 3 | 2 |
| 10 | 218 | CAVLRDSNYQLIW | 3 | 1 | 1 |
| 11 | 219 | CALVYDKIIF | 4 | 0 | 0 |
| 12 | 220 | CAFPYGSNRLAF | 0 | 1 | 2 |
| 13 | 221 | CAHNYGQNFVF | 1 | 1 | 0 |
| 14 | 222 | CAGPHAGGTSYGKLTF | 1 | 0 | 0 |

Figure 40A:
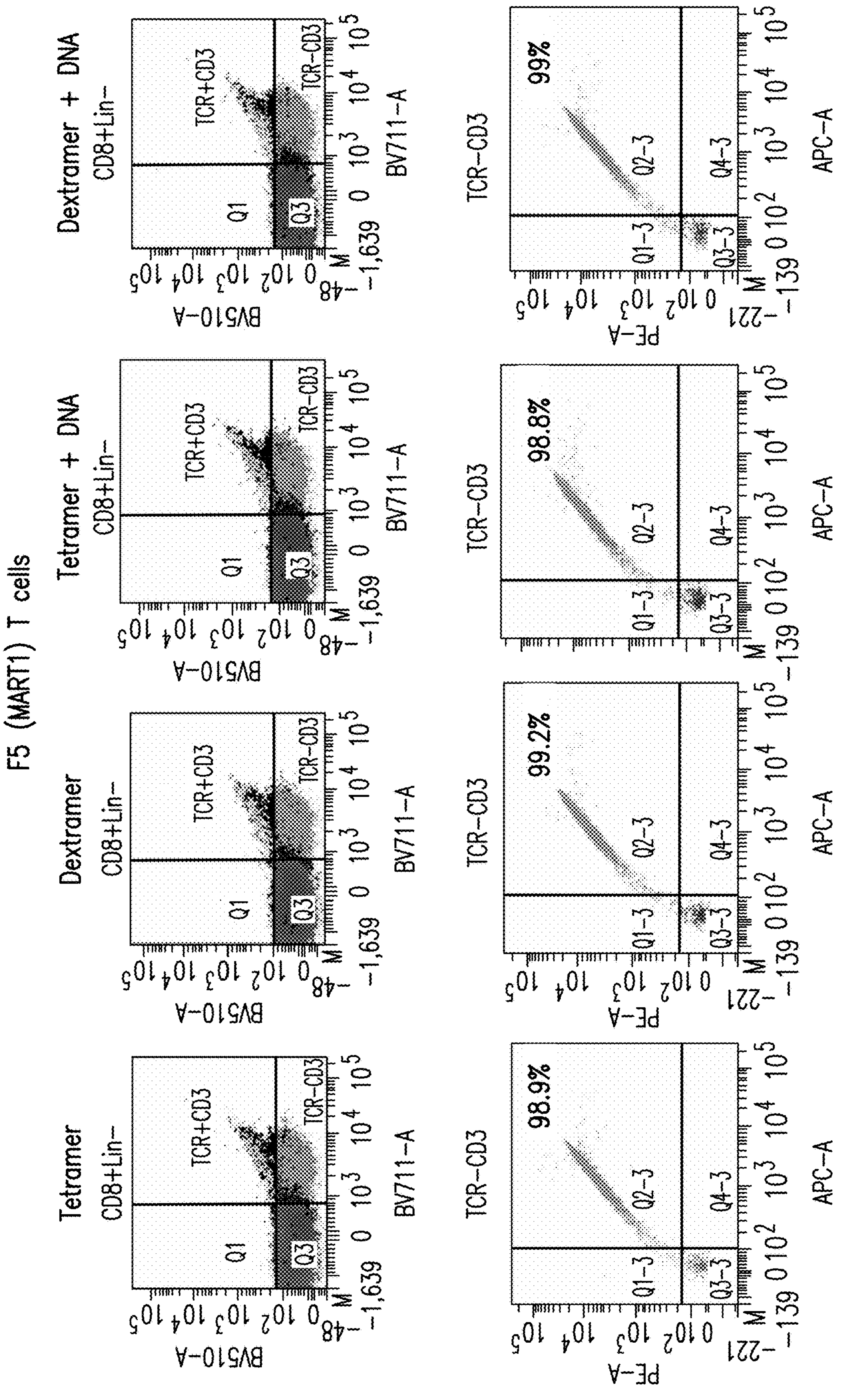
FIG. 40A shows a comparison of the tetramer, trimer, and dextramer isolation methods using F5 T cells.
Figure 40B:
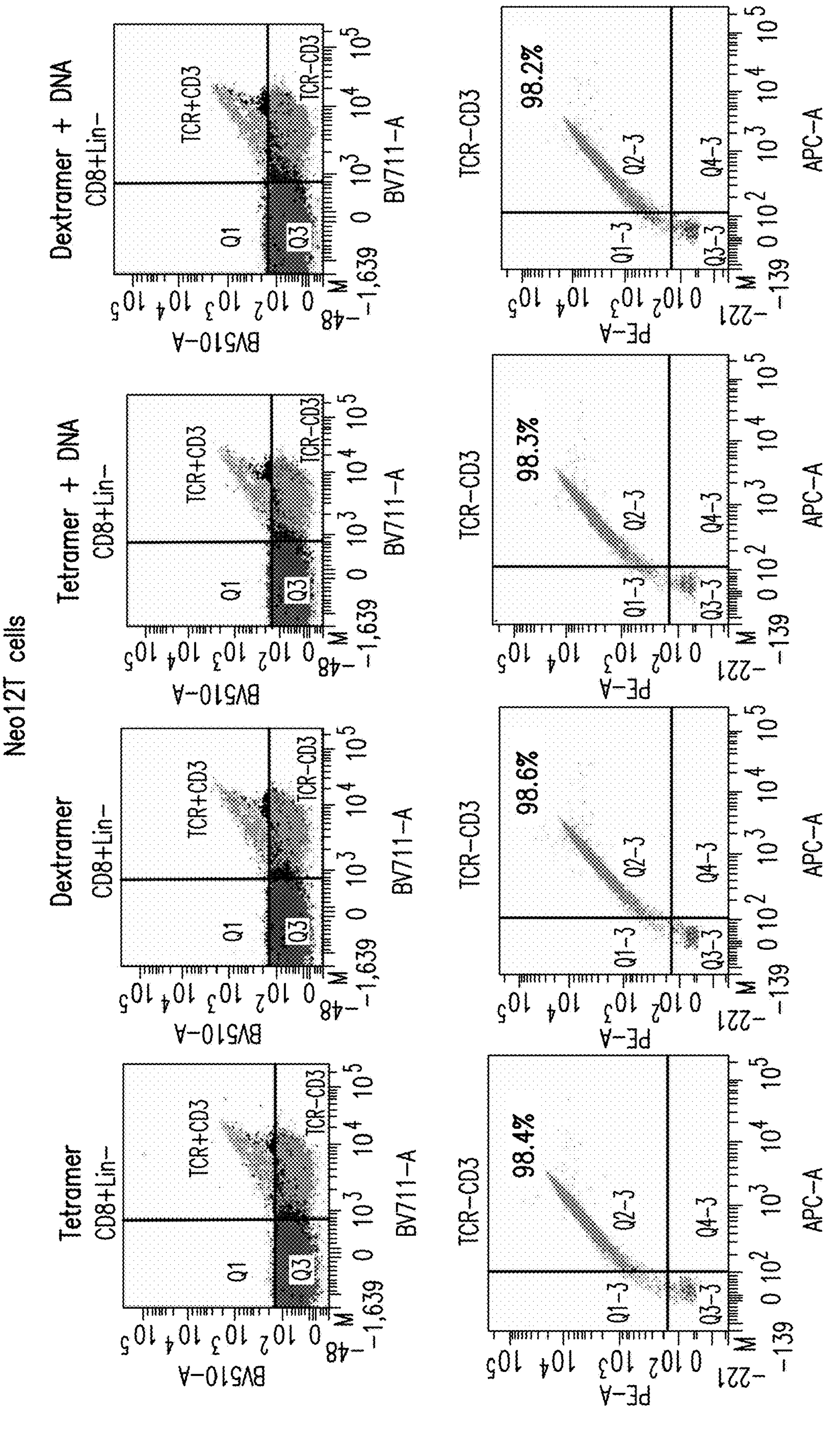
FIG. 40B shows a comparison of the tetramer, trimer, and dextramer isolation methods using neo12 T cells.

Example 16: T Cell Isolation Comparison with Compact Tetramers, Dextramers, and Trimers The isolation efficiency of tetramers, dextramers, and trimers of comPACT library elements in the dual staining method was assessed. Tetramers of a streptavidin core with four copies of each comPACT element (tetramer), trimers of a streptavidin core with three copies of each comPACT element and a nucleic acid barcode (trimer+DNA), and dextramers of a dextran polymer with multiple copies of a comPACT element with and without a nucleic acid barcode (dextramer and dextramer+DNA), were incubated with T cells genetically edited to overexpress F5 (MART1) or neo12 neoantigen. The T cells were isolated based on the gating strategy described in Example 10 above and the percentage of dual stained T cells isolated by each staining method quantified. As shown in FIG. 40A (F5 T cells) and FIG. 40B (neo12 antigen specific T cells) greater than 98% of the gene edited cells were stained with the corresponding comPACT elements. The data indicates that for tetramer, dextramer, trimer with DNA and dextramer with DNA similar staining efficiency for T cells with a common TCR (F5 Mart-1) and a neoantigen TCR (neo12) was achieved.

Example 17: Comparison of Signal to Noise Analysis

Figure 41B:
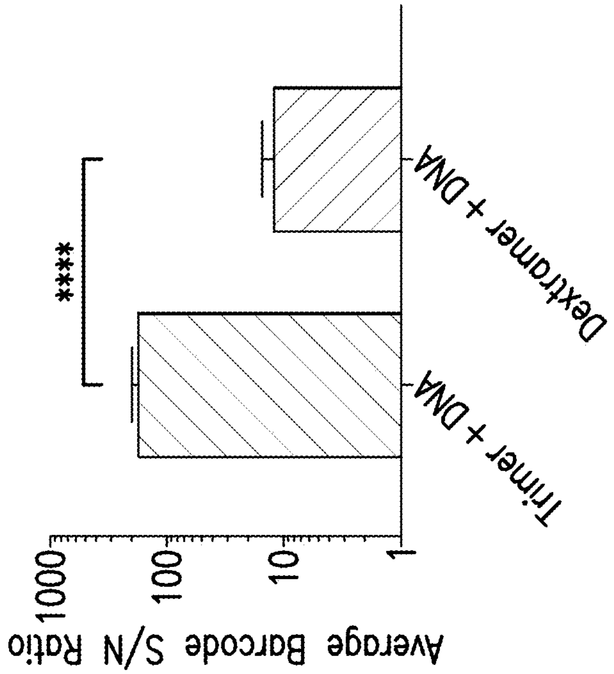
FIG. 41B shows the average barcode signal to noise ratio when using a trimer or a dextramer.
Figure 41A:
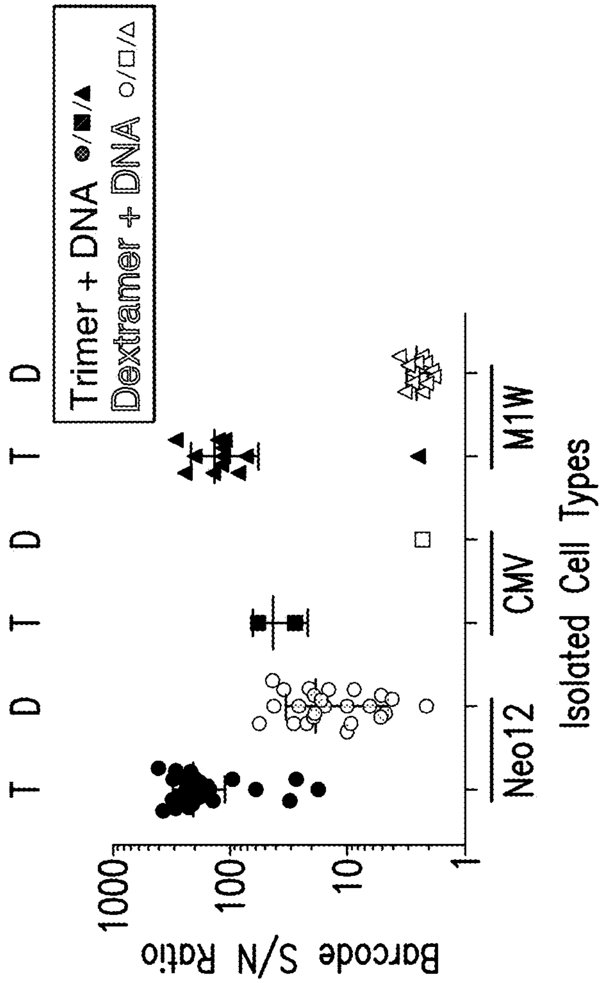
FIG. 41A shows a comparison of the trimer and dextramer isolation methods using PBMC samples and neo12 T cells, CMV T cells, and M1W T cells.

PACT Neo12 T cells, PACT M1W T cells, and viral donor PBMCs were incubated with trimer comPACT particles with a nucleic acid barcode (Trimer+DNA) and dextramers with multiple copies of a comPACT element with a nucleic acid barcode (Dextramer+DNA). The cells were sorted into single cells via FACS. The TCR alpha/beta and neoID barcodes for each sample were cloned and sequenced. All TCRs were confirmed to be correct for neo12, CMV, or M1W. S/N analysis was performed on each cell as previously described. The S/N ratios of each method (Trimer, T; or dextramer, D) for each sample are shown in FIG. 41A. The average of the S/N ratio of each method is provided in FIG. 41B. Notably, the analysis of the neoID barcode DNA signal-to-noise ratio indicates a higher signal-to-noise ratio for cell isolated with the Trimer+DNA particles as compared to the cells isolated with Dextramer+DNA. The data indicates that the Trimer+DNA particles have much better S/N ratio compared to Dextramer+DNA.

Example 18: Isolation and Characterization of Neoantigen T Cells from Patient Samples Following Cancer Immunotherapy Subjects with pMMR colorectal cancer (which are not generally considered responsive to anti-PD1 antibody therapy) or endometrial adenocarcinoma were treated with AB122 (anti-PD-1 antibody). Pre-treatment blood samples were incubated with comPACT libraries and isolated according to the imPACT method described above to identify the baseline repertoire of neoantigen-specific T cells. PBMC were then collected at different time points and analyzed by the imPACT signal to noise method to monitor the on-treatment evolution of mutation-targeted T cell repertoires. Changes in the neoantigen-specific T cell repertoire during AB122 treatment were monitored to enable correlation of immune phenotyping with clinical outcomes.

Results

Figure 42A:
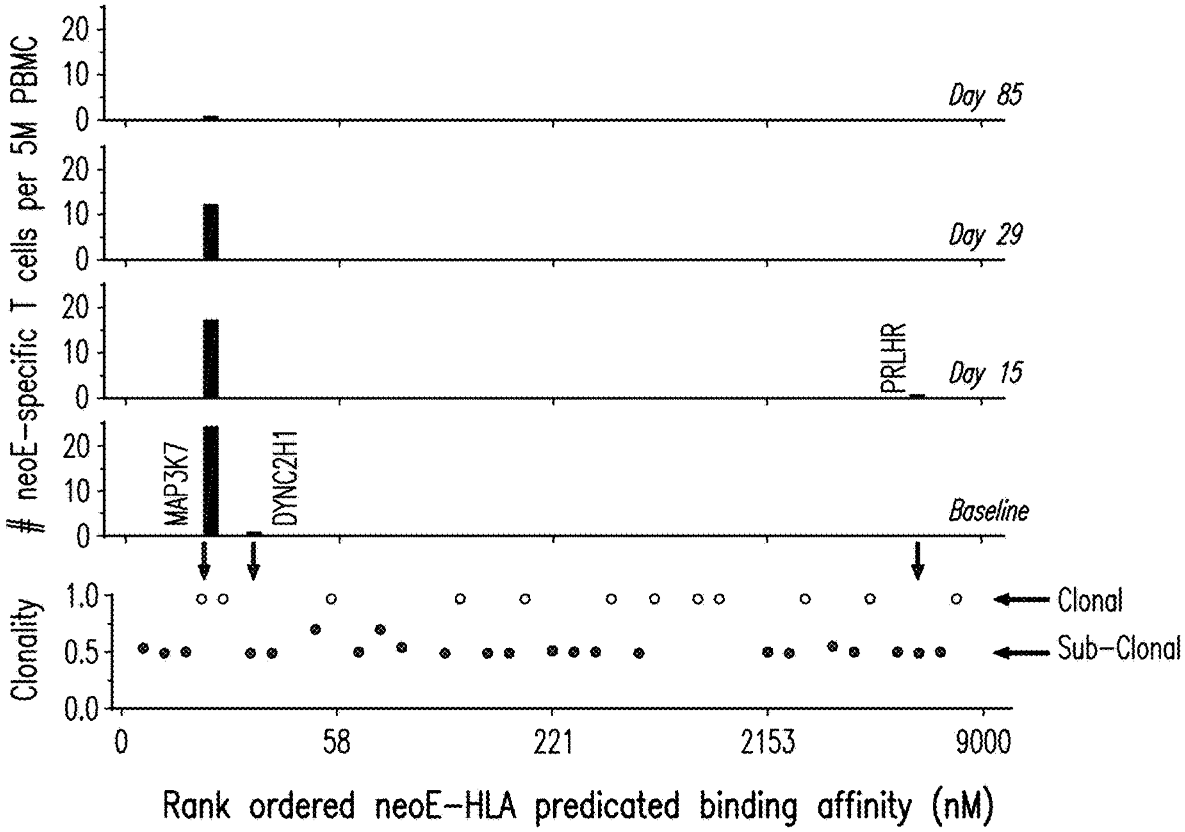
FIG. 42A shows changes in neoantigen-specific T cells in peripheral blood of patient PACT157 over time.
Figure 42B:
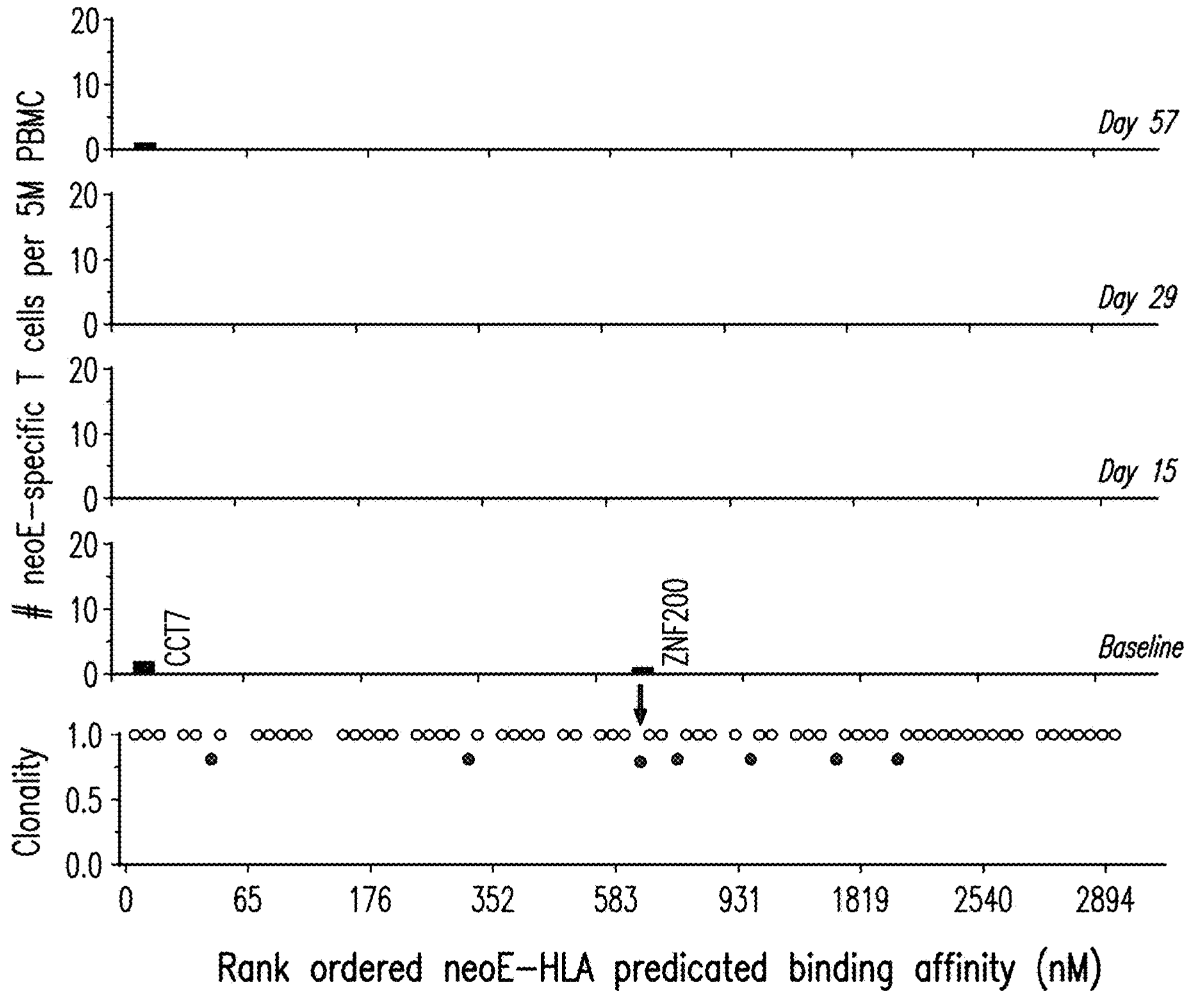
FIG. 42B shows changes in neoantigen-specific T cells in peripheral blood of patient PACT132 over time.
Figure 42C:
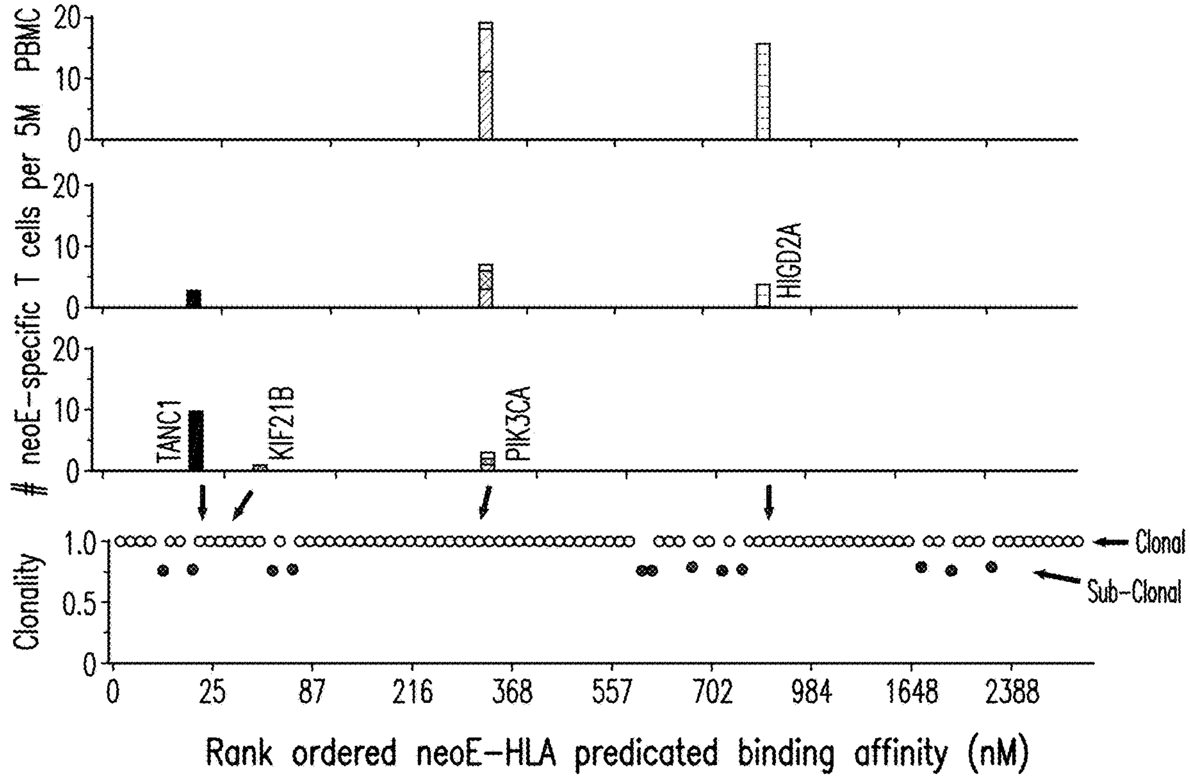
FIG. 42C shows changes in neoantigen-specific T cells in peripheral blood of patient PACT131 over time.

The top panels of FIGS. 42A-C show the longitudinal evolution of neoantigen-specific T cells in peripheral blood during treatment for patients with colorectal cancer, PACT157 (FIG. 42A) and PACT132 (FIG. 42B); or endometrial cancer, PACT131 (FIG. 42C).

The bottom panels of FIGS. 42A-C show the neoantigen clonality and predicted neoantigen-HLA binding affinity for each sample. The top dot indicates a clonal mutation, while the bottom dot indicates a sub-clonal mutation.

Gene, HLA type, and neoantigen sequences for each of the TCRs identified by the imPact method in each subject are also shown in FIGS. 42A-C.

Longitudinal monitoring of patients during therapy enables analysis of T cells targeting neoantigens and identify driver mutations that correlate with therapeutic benefit. In addition, monitoring changes of the neoantigens-specific T cell repertoire in response to immunotherapy can inform next steps of treatment.

Example 19: Phenotype and Functional Characterization of Neoantigen-Specific T Cells from PACT131

Figure 43:
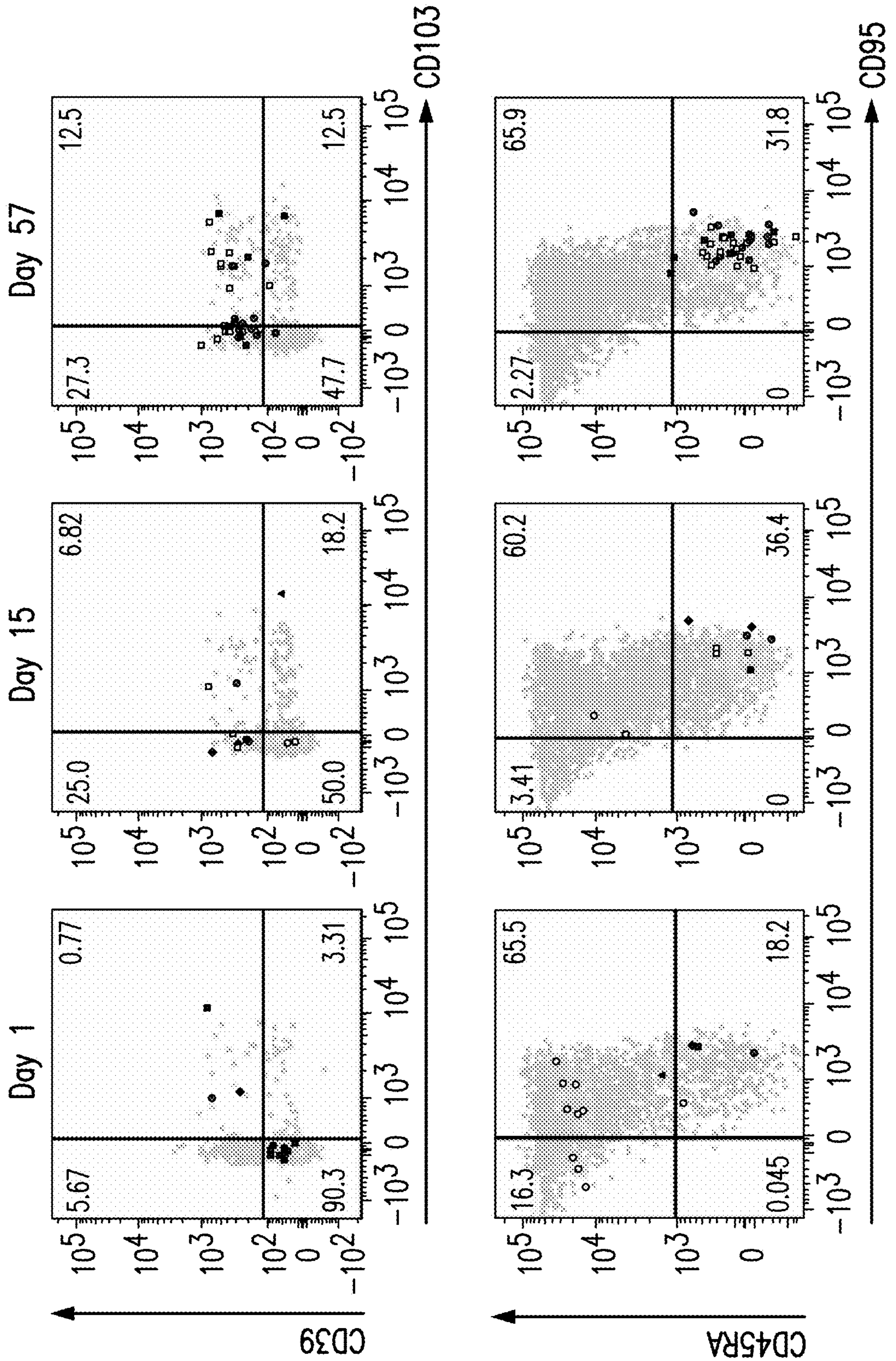
FIG. 43 shows the phenotypic characterization of neoantigen-specific T cells from one patient.

T cells isolated by the imPACT Isolation Technology method from patient sample PACT131 were characterized for cell surface markers CD45RA, CD95, CD39, and CD103 via flow cytometry. The flow cytometry results of T cells isolated from the patient on Day 1, 15, and 57 are shown in FIG. 43. The black dots indicate the neoantigen-specific T cells. CD45RA+CD95+ T cells are antigen-experienced, while CD39+CD103+ positivity suggests that T cells have trafficked through the tumor compartment.

Figure 44A:
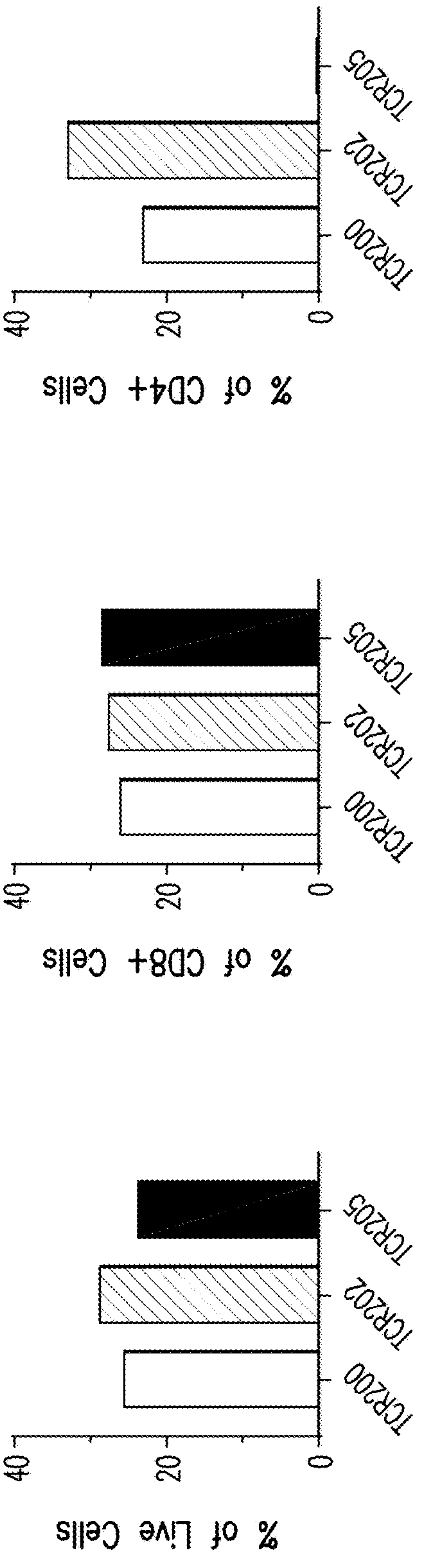
FIG. 44A shows the functional characterization of TCR clones isolated against a PIK3CA neoantigen target.
Figure 44B:
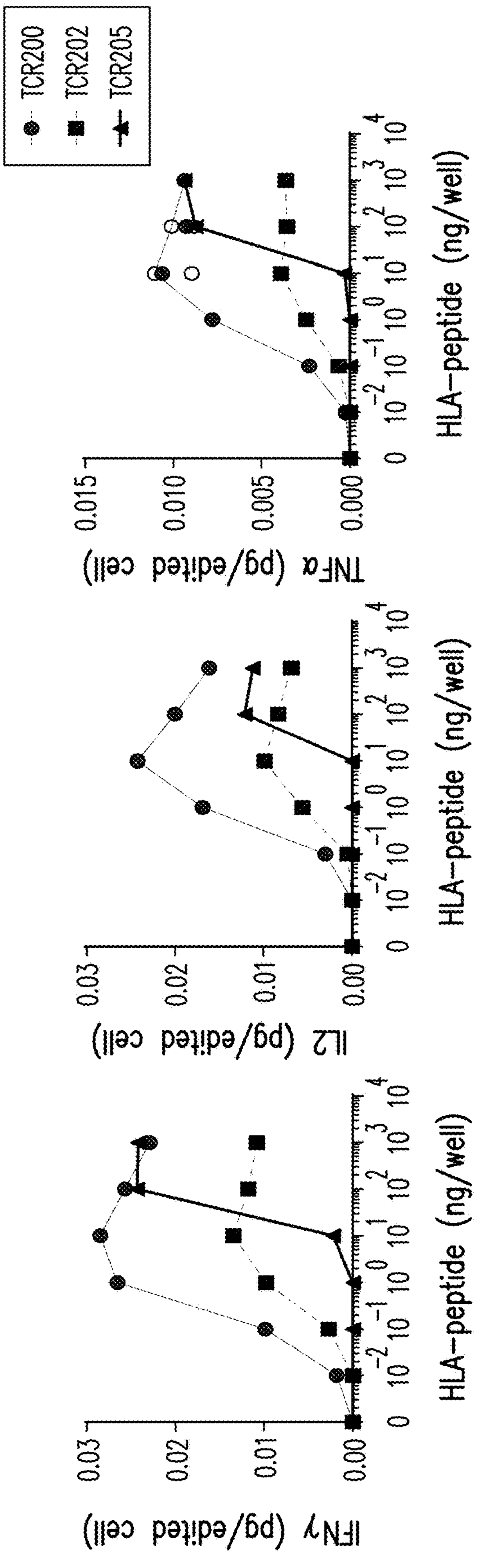
FIG. 44B shows the functional characterization of TCR clones isolated against a PIK3CA neoantigen target.

Next, three TCR clones (TCR200, TCR202, and TCR205) against the same PIK3CA neoantigen target captured from the patient sample were characterized. T cells were edited to express the selected TCRs. The percentage of live, CD8+, and CD4+ T cells is shown in FIG. 44A. Activation of the neoantigen-specific T cells was determined by incubating the edited T cells with increasing amounts of an HLA-cognate peptide and measuring secretion of IFNγ IL2, and TNFα. Cytokine release for each TCR clone is shown in FIG. 44B. All T cells were activated by the cognate neoantigen. No cytokine release was detectable against non-cognate neoantigens (data not shown).

Example 20: Validation of NeoTCRs Isolated from Melanoma Patient Samples Using the Impact Method

Materials and Methods comPACT Library Preparation

Whole exome sequencing of a tumor biopsy and the patient's normal PBMC, and RNA-Seq transcriptome sequencing of tumor biopsy were used identified somatic nonsynonymous mutations in patient PACT135. The patient has stage IV metastatic melanoma and was undergoing anti-PD1 antibody therapy with nivolumab. 2566 coding mutations were identified. 632 neoepitopes were predicted from the tumor mutational burden, and a library of 243 comPACTs (neoepitope-HLA complexes) was produced across HLA-A*03:01, A*24:02, and C*12:03, as described in Examples 10 and 11. HLA typing was predicted by OptiType program based on patient's normal PBMC whole exome sequencing. 3 of 6 HLAs were covered in the library.

T Cell Isolation

PBMC and TIL samples were collected from the subject PACT135 at various time points before or during anti-PD-1 antibody therapy. PBMC samples were collected on day 14, day 43 and day 84 after the start of therapy. TIL samples were collected on day −37 before the anti-PD1 treatment started and on day 82 after the therapy started. T cells were incubated with the comPACT library and neoantigen-specific T cells were isolated using the imPACT method as described in Examples 10 and 11.

14 TCRs specific for 5 neoantigen-HLAs were isolated; one neoTCR recognizing PUM1, one neoTCR recognizing TTP2, two neoTCRs recognizing IL8-HLA-A*24:01, and ten neoTCRs recognizing IL8-HLA-A*03:01. The neoTCR expressing T cells were expanded in medium containing IL2, IL7, IL15, or combinations thereof for 14 days. At the end of the expansion, the T cells preserved a "younger" T cell phenotypes, resulting in NeoTCR-P1 T cells that exhibit T memory stem cell and T central memory cell phenotypes.

NeoTCR Gene Editing

Healthy donor-derived CD4 and CD8 T cells were engineered to express each identified neoantigen-specific TCR using a CRISPR-based non-viral method as described in International Patent Application No. WO2019089610, published May 9, 2019, hereby incorporated by reference in its entirety.

neoTCR Expression

The expression of the neoTCRs in the gene edited CD4 and CD8 T cells was analyzed using a fluorophore-comPACT trimer dextran complex. Biotinylated comPACT proteins were bound to streptavidin dextramer and incubated with the neoTCR CD4 and CD8 T cells. Binding of a comPACT-dextramer to the respective neoTCR-expressing T cell was determined via the method described in more detail in Bethune, et al. (*BioTechniques* 62:123-130 March 2017) and Bethune, et al. (*eLife* 5: 2016), each herein incorporated by reference for all they teach. Dextramers were prepared by using fluorescently-labeled streptavidin (Life Technologies, Carlsbad, CA).

Matched Autologous Melanoma Cell Line Production

A matched autologous melanoma cell line was established from a biopsy of a patient (M489). As a negative control, a second cell line from a mismatched melanoma was established from a biopsy of a different patient (M202). NeoTCR-expressing T cells were assessed for functionality (expression of activation markers, cytokine secretion, antigen-specific target cell killing, and T cell proliferation) using the matched and mismatched autologous melanoma cell lines.

T Cell Activation

NeoTCR-expressing T cells were incubated with or without IFNγ and co-cultured with the M489 matched melanoma tumor cell line and neoantigen-matched comPACT-dextramers. As a negative control, neoTCR T cells incubated with or without IFNγ were also co-cultured with the M202 mismatched melanoma tumor cell line and neoantigen-matched comPACT-dextramers. Stimulation of T cells with anti-CD3 antibody OKT3 was used as positive control. Internalization of the neoTCRs after comPACT-dextramer binding was assessed via FACS.

Expression of activation markers 4-1BB and OX-40 were also determined in the CD4 and CD8 neoTCR T cells co-cultured with the matched and mismatched melanoma cell lines. Expression of the activation markers was determined via FACS. Anti-OX-40 antibody (clone Ber-ACT35, cat #350012) and anti-4-1BB antibody (clone 4B4-1, cat #309810) were purchased from Biolegend.

T Cell Cytotoxicity Assay

T cell-induced killing of the tumor cells over time was monitored via immunofluorescence using the IncuCyte imaging system (Essen BioSciences). Each of the 14 neoTCR-expressing T cells was co-cultured with the patient matched M489 tumor cells. NeoTCR T cells were also co-cultured with the M202 mismatched cell line as a negative control. M489 and M202 tumor cells were labeled using the NucLight Red Lentivirus (Essen BioSciences).

The M489 or M202 tumor cells were seeded in a 96-well plate at 25,000 cells/well and incubated overnight in the incubator. The following day the neoTCR T cells were added at the following concentration: 25,000 T cells/well (1:1 T cell:tumor cell ratio) or 100,000 T cells/well (5:1 T cell: tumor cell ratio). The co-culture preparations were then monitored by collecting time-lapse images at 2 hour intervals for 12 days using the IncuCyte imaging system with the 10× objective.

Cytokine Secretion Assay

Cytokine production was assessed in the supernatant of the co-cultured T cells and melanoma cell lines using the cytokine bead assay (CBA BEAD-BASED IMMUNOASSAY, BD BioSciences). CBA is a flow cytometry multiplexed bead-based immunoassays application that allows quantification of multiple proteins simultaneously by using antibody-coated beads to efficiently capture analytes. After 24 or 48 hours of co-culturing T cells and target cells, supernatants were collected and analyzed for IFNγ, IL-2, and TNFα secretion.

Results

Identification of neoTCRs in PACT135 Over Time

The imPACT analysis resulted in isolation of 14 TCRs specific for 5 neoantigen-HLAs one neoTCR recognizing PUM1, one neoTCR recognizing TTP2, two neoTCRs recognizing IL8-HLA-A24:02, and ten neoTCRs recognizing IL8-HLA-A03:01. The neoantigen peptide sequences, alpha and beta TCR CDR3 sequences, and HLA alleles isolated from patient PACT135 are shown in Table 8 below.

Figure 45:
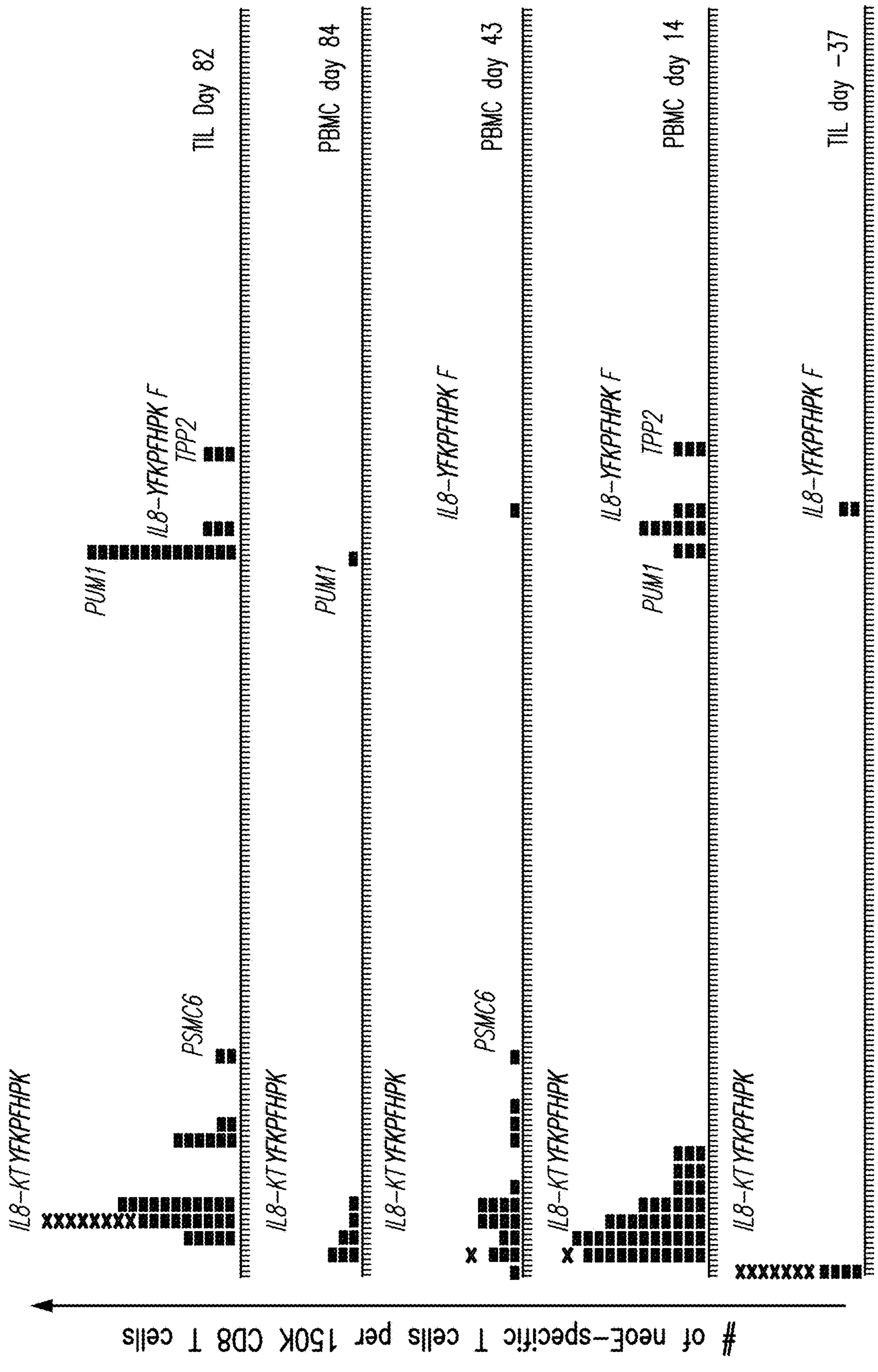
FIG. 45 provides a summary of the number of neoantigen-specific T cells per CD8 T cells in each T cell sample collected during the course of anti-PD-1 antibody treatment in patient PACT135.

FIG. 45 provides a summary of the number of neoantigen-specific T cells per CD8 T cells in each sample collected during the course of anti-PD-1 antibody treatment. Each box represents one T cell, each cross represented ten T cells. Each column of boxes or crosses represents a unique neoTCR clonotype.

TCR219, TCR220, TCR223, TCR224, TCR225, TCR228, TCR229, TCR232, TCR240, and TCR241 recognize the IL8-KTYFKPFHPK neoantigen (SEQ ID NO: 256).

TCR221 and TCR227 recognize the IL8-YFKPFHPKF neoantigen (SEQ ID NO: 227).

TCR218 recognizes the TPP2-CFSEVSAKF neoantigen (SEQ ID NO: 223).

TCR222 recognizes the PUM1-AMMDYFFQR neoantigen (SEQ ID NO: 226).

neoTCR Expression

Figure 46:
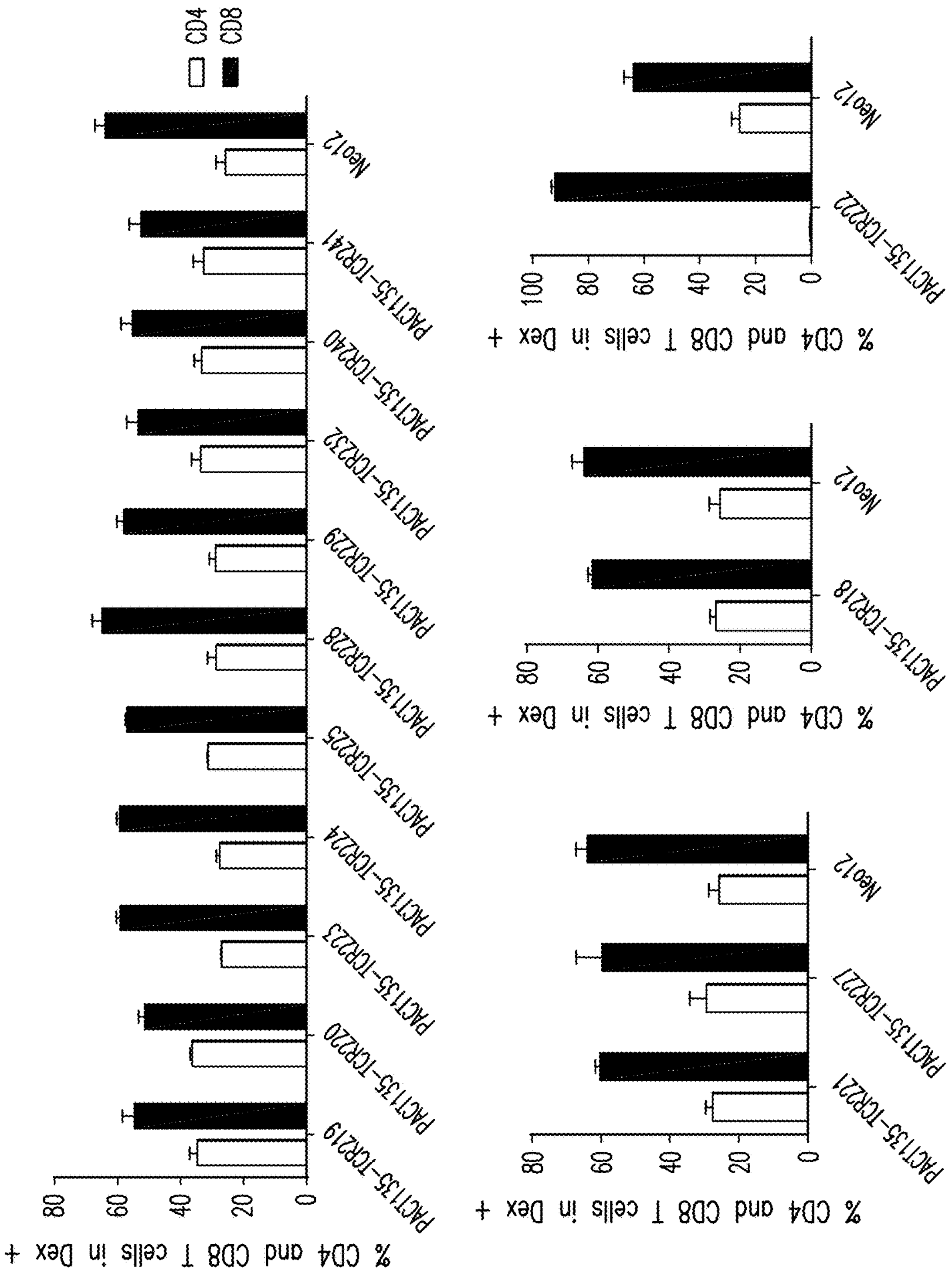
FIG. 46 shows strong T cell gene editing efficiency of the 14 neoTCRs in both CD4 and CD8 T cells.

FIG. 46 shows that the T cell gene editing efficiency was strong for the 14 neoTCRs in both CD4 and CD8 T cells. For 13 of the neoTCR T cells, the CD4 and CD8 T cells bound the cognate comPACT-dextramer complexes. However, only the CD8 T cells expressing the neoTCR against PUM1 (TCR222) bound to the cognate comPACT-dextramer, and no comPACT-dextramer binding was observed in the CD4 neoTCR T cells.

TABLE 8

| ID # | Gene | SEQ ID NO: | Neoantigen peptide | SEQ ID NO: | Alpha CDR3 | SEQ ID NO: | Beta CDR3 | HLA |
|---|---|---|---|---|---|---|---|---|
| TCR218 | TPP2 | 223 | CFSEVSAKF | 228 | CAESSPSGGYNKLIF | 242 | CASSAIRTYEQYF | A24:02 |
| TCR219 | IL8 | 224 | KTYF(S)KPFHPK | 229 | CAVNSGSARQLTF | 243 | CASSNNNEQFF | A03:01 |
| TCR220 | IL8 | 224 | KTYF(S)KPFHPK | 230 | CVVNGENDYKLSF | 244 | CASQRMYDNEQFF | A03:01 |
| TCR221 | IL8 | 225 | YF(S)KPFHPKF | 231 | CAMTYGNNRLAF | 245 | CASSMGQGADEQYF | A24:02 |
| TCR222 | PUM1 | 226 | AMMDYFFQR | 232 | CAVRRGSGAGSYQLTF | 246 | CASGPDTPLYGYTF | A03:01 |
| TCR223 | IL8 | 224 | KTYF(S)KPFHPK | 233 | CAVRDYNQGGKLIF | 247 | CASSEAWGYEQYF | A03:01 |
| TCR224 | IL8 | 224 | KTYF(S)KPFHPK | 234 | CAVNDPNDYKLSF | 248 | CASSHKWSTEAFF | A03:01 |
| TCR225 | IL8 | 224 | KTYF(S)KPFHPK | 235 | CAGYQGGSEKLVF | 249 | CASSQNNEQYF | A03:01 |
| TCR227 | IL8 | 227 | YFKPFHPKF | 236 | CAVGSNAGGTSYGKLTF | 250 | CASSSDRAPPLHF | A24:02 |
| TCR228 | IL8 | 224 | KTYF(S)KPFHPK | 237 | CVVNVPNDYKLSF | 251 | CASSLAYRVEQYF | A03:01 |
| TCR229 | IL8 | 224 | KTYF(S)KPFHPK | 238 | CVVNPSGGSYIPTF | 252 | CASSYEGGLAAFTGELFF | A03:01 |
| TCR232 | IL8 | 224 | KTYF(S)KPFHPK | 239 | CVVNLSNDYKLSF | 253 | CASSSSWNTEAFF | A03:01 |
| TCR240 | IL8 | 224 | KTYF(S)KPFHPK | 240 | CAVSGDDYKLSF | 254 | CASSSSTVVEQYF | A03:01 |
| TCR241 | IL8 | 224 | KTYF(S)KPFHPK | 241 | CVVNSNDYKLSF | 255 | CASSPRWSTEAFF | A03:01 |
| TCR218 | TPP2 | 223 | CFSEVSAKF | 228 | CAESSPSGGYNKLIF | 242 | CASSAIRTYEQYF | A24:02 |
| TCR219 | IL8 | 224 | KTYF(S)KPFHPK | 229 | CAVNSGSARQLTF | 243 | CASSNNNEQFF | A03:01 |
| TCR220 | IL8 | 224 | KTYF(S)KPFHPK | 230 | CVVNGENDYKLSF | 244 | CASQRMYDNEQFF | A03:01 |
| TCR221 | IL8 | 225 | YF(S)KPFHPKF | 231 | CAMTYGNNRLAF | 245 | CASSMGQGADEQYF | A24:02 |
| TCR222 | PUM1 | 226 | AMMDYFFQR | 232 | CAVRRGSGAGSYQLTF | 246 | CASGPDTPLYGYTF | A03:01 |
| TCR223 | IL8 | 224 | KTYF(S)KPFHPK | 233 | CAVRDYNQGGKLIF | 247 | CASSEAWGYEQYF | A03:01 |
| TCR224 | IL8 | 224 | KTYF(S)KPFHPK | 234 | CAVNDPNDYKLSF | 248 | CASSHKWSTEAFF | A03:01 |

T Cell Activation

Figure 47:
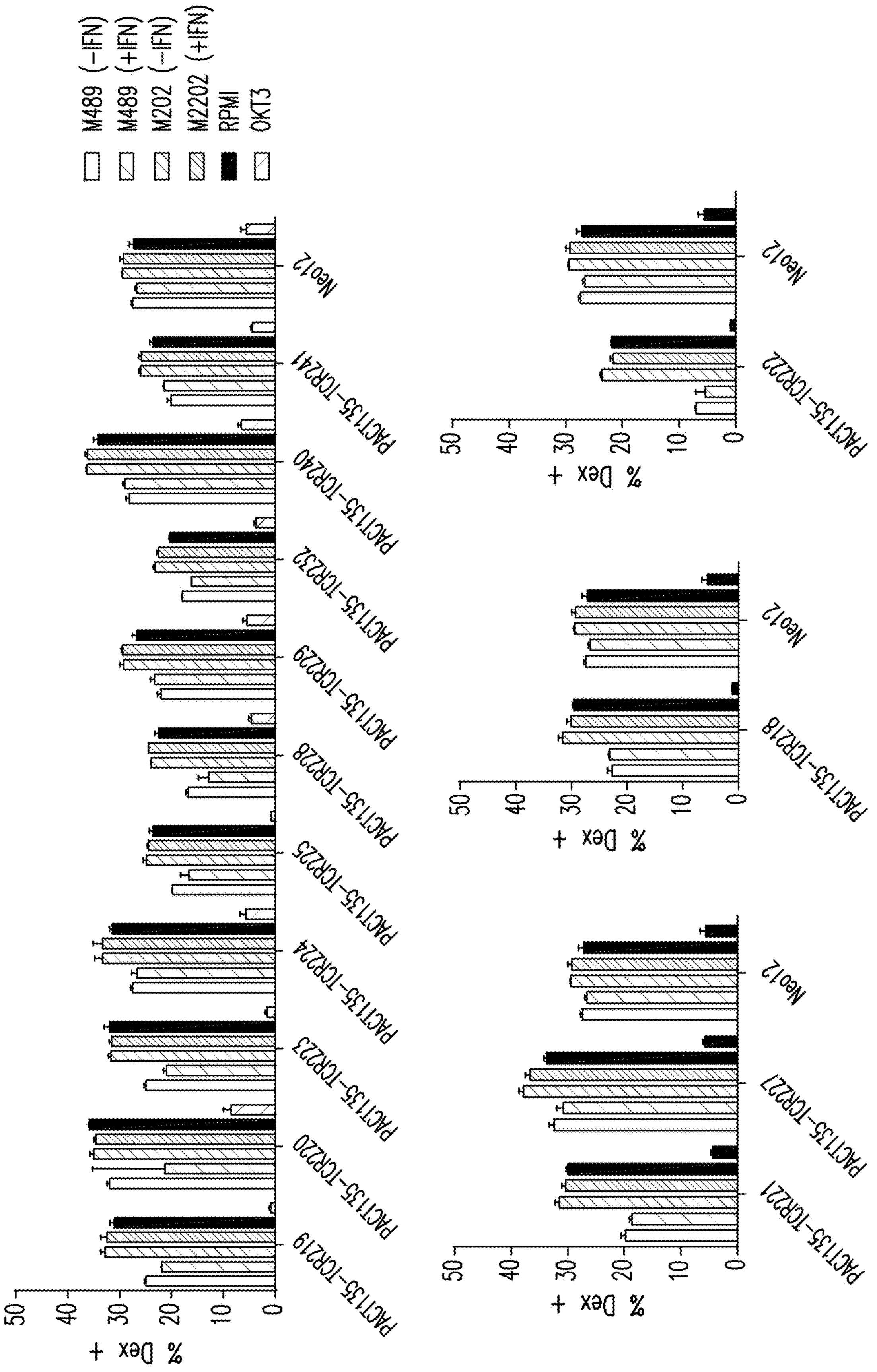
FIG. 47 shows that neoTCRs were internalized upon co-culture of the neoTCR T cells cognate comPACT-dextramers and the melanoma matched cell line M489 with and without IFNγ pre-incubation.

NeoTCRs were internalized upon co-culture of the neoTCR T cells cognate comPACT-dextramers and the melanoma matched cell line M489 with and without IFNγ pre-incubation (FIG. 47). A decrease in the percentage of comPACT-dextramer positive T cells indicates internalization of the neoTCR, which is a surrogate marker for T cell activation. Cells incubated with only RPMI media did not internalize the neoTCR-bound dextramer complexes, while T cells incubated with the anti-CD3 antibody OKT3 internalized the neoTCR-bound dextramer complexes. Neo12 antigen was also used as a negative control for each sample.

The neoTCR T cells derived from patient PACT135 also expressed activation markers 4-1BB (FIG. 48) and OX40 (FIG. 49) after incubation with the M489 cell line with and without IFNγ pre-incubation. No expression of 4-1BB or OX40 was observed in the TCR222 CD4 T cells as the neoTCR did not bind the cognate neoantigen.

Figure 48:
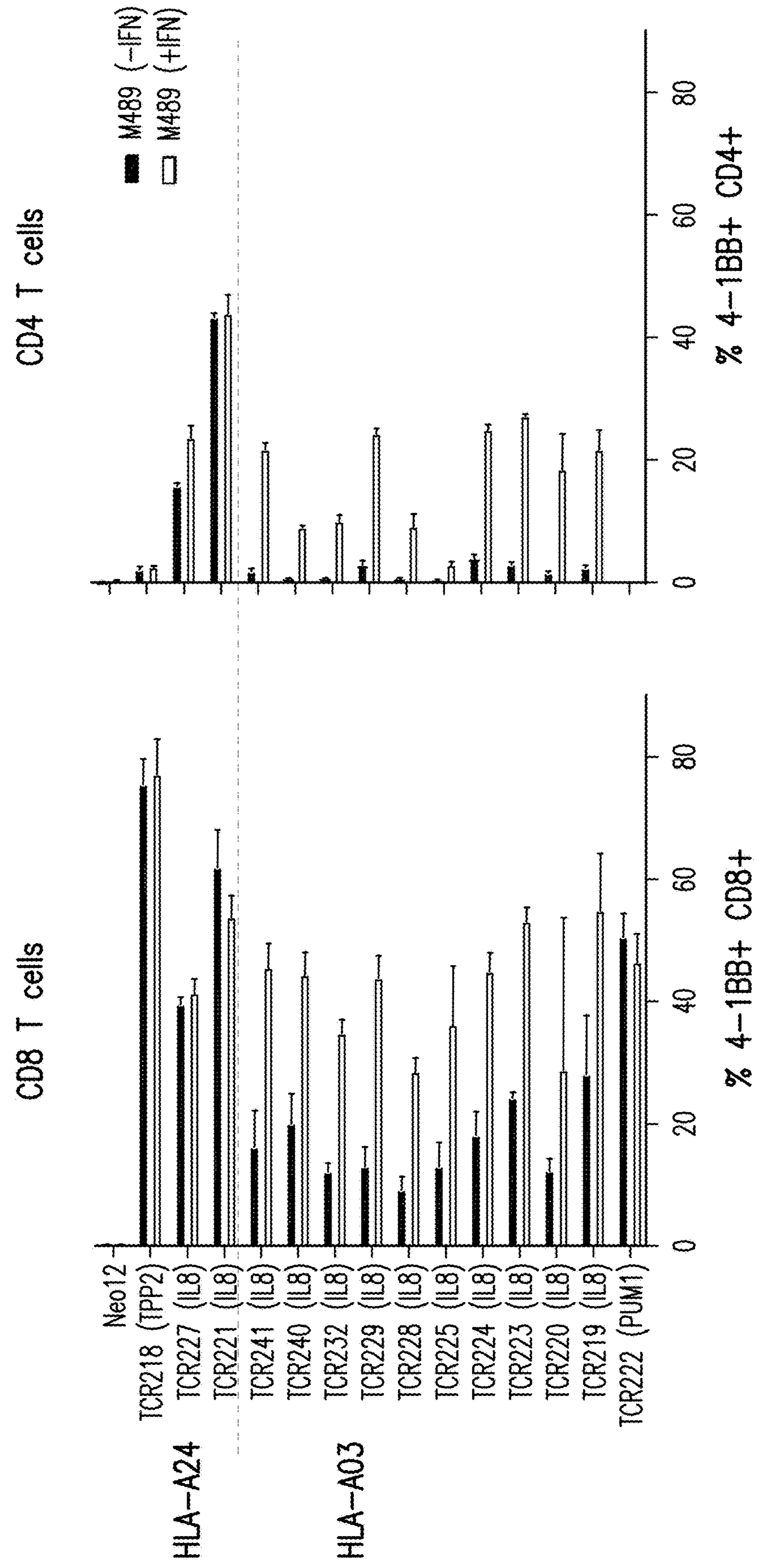
FIG. 48 shows that the neoTCR T cells derived from patient PACT135 expressed activation markers 4-1BB.
Figure 49:
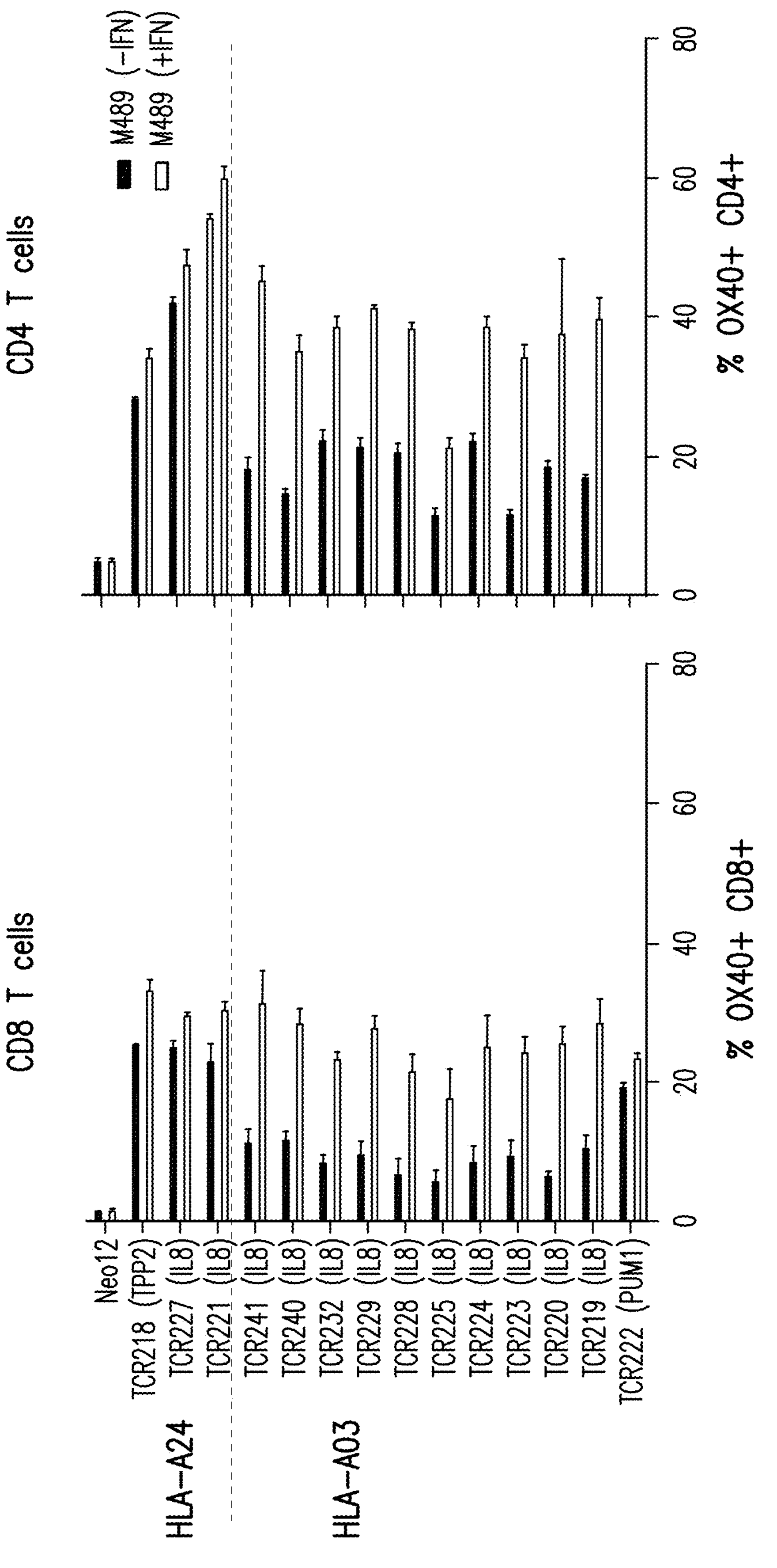
FIG. 49 shows that the neoTCR T cells derived from patient PACT135 expressed activation markers OX40.

4-1BB expression increased in the IL8-HLA-A03 TCRs when the tumor cells were pre-treated with IFNγ to activate the immunoproteasome and enhance HLA expression (FIG. 48). OX40 expression increased in the IL8-HLA-A03 TCRs when the tumor cells were pre-treated with IFNγ to activate the immunoproteasome and enhance HLA expression (FIG. 49).

T Cell Cytotoxicity Assay

Figure 50:
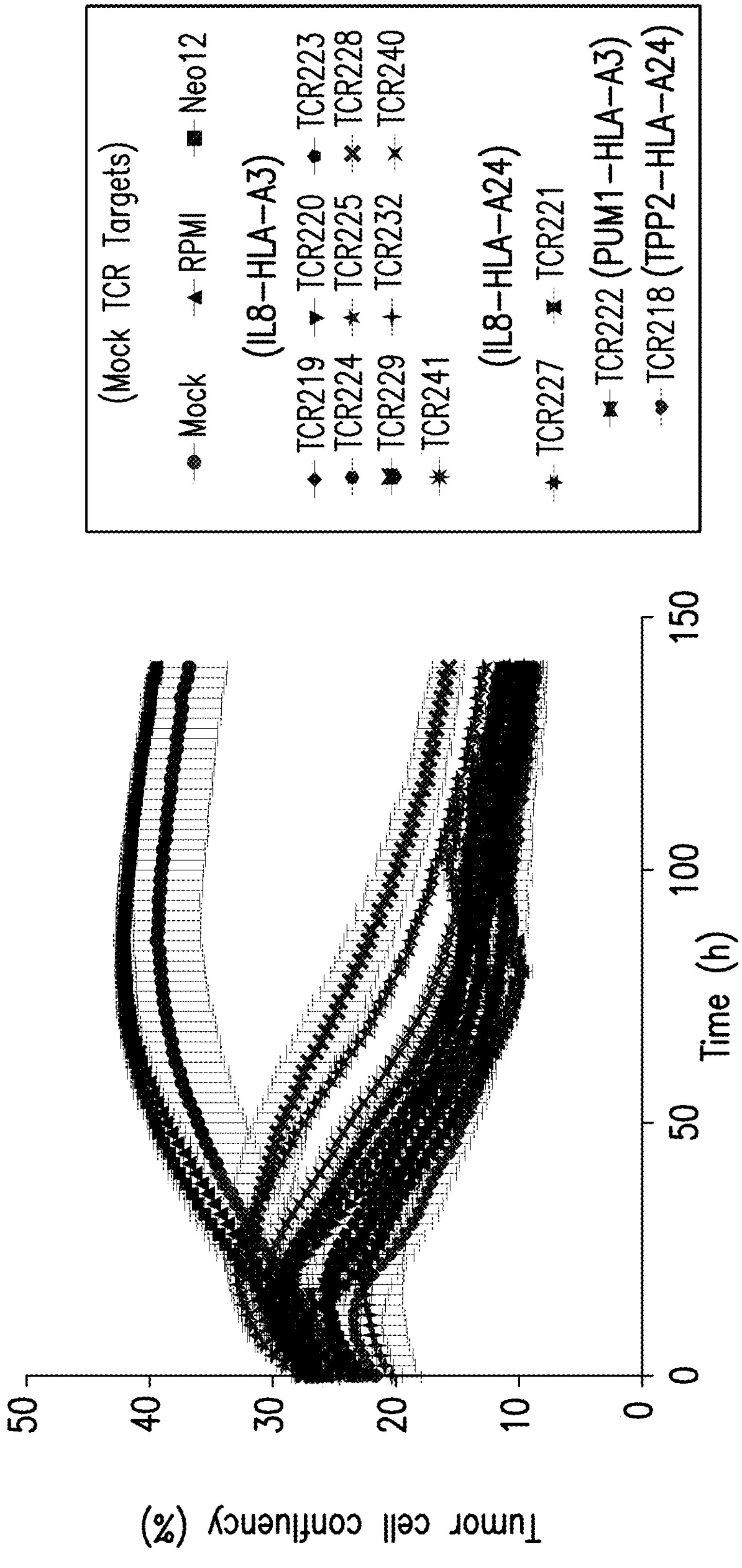
FIG. 50 provides a graph of the percentage of tumor cell confluency after co-culture with all neoTCR T cells identified from PACT135.
Figure 51A:
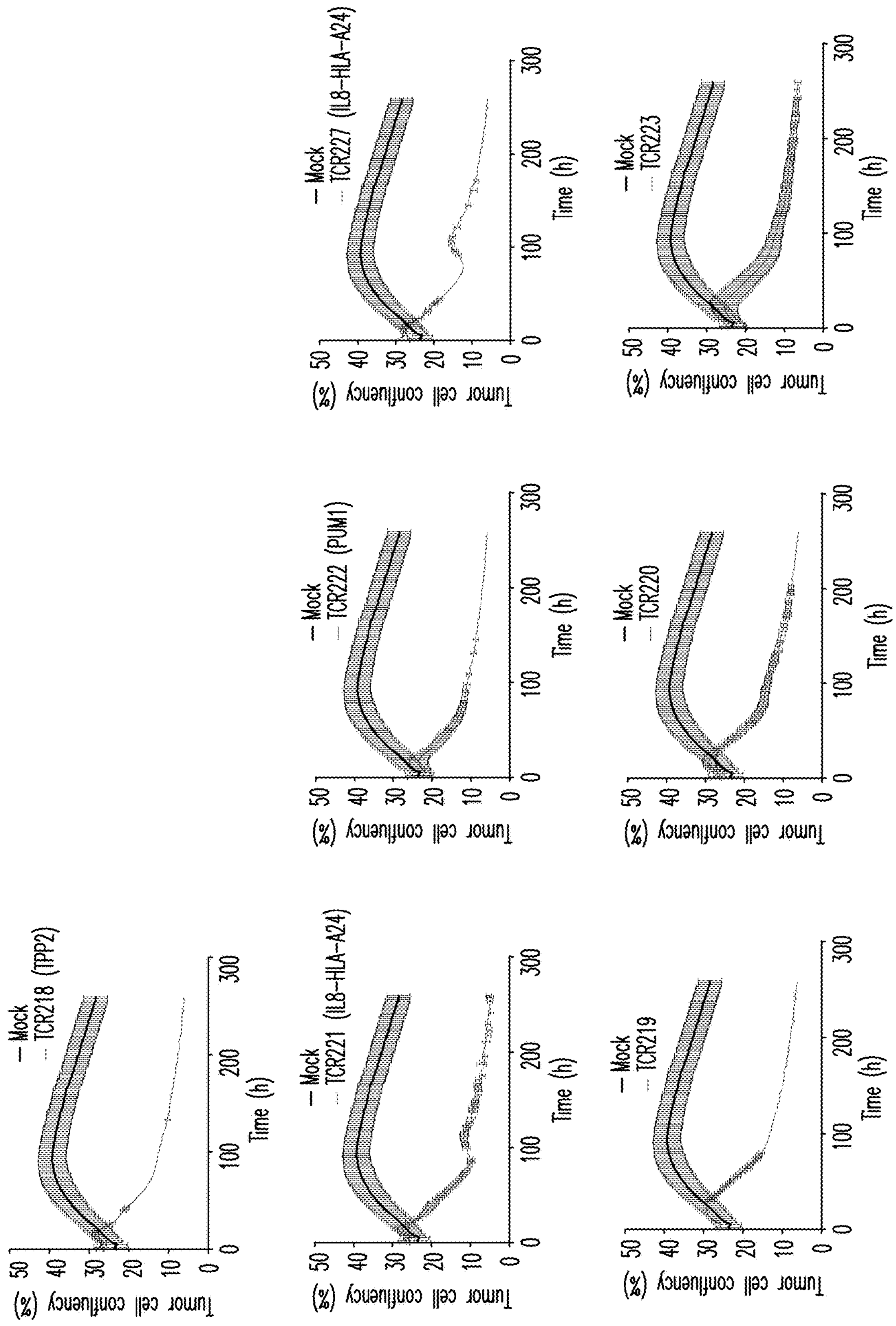
FIG. 51A provides individual graphs of the percentages of tumor cell confluency after co-culture with each neoTCR T cell.
Figure 51B:
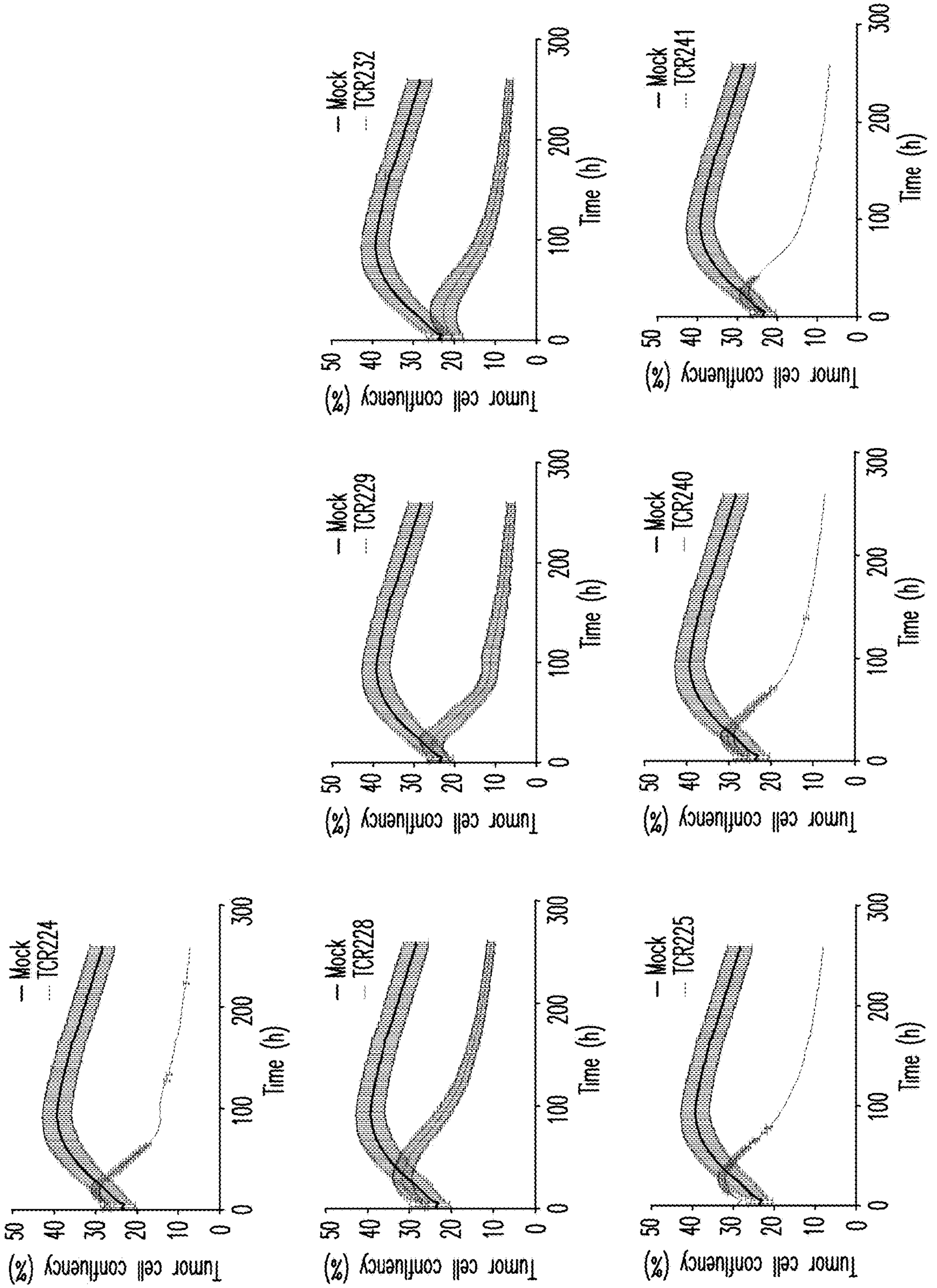
FIG. 51B provides individual graphs of the percentages of tumor cell confluency after co-culture with each neoTCR T cell.

All 14 T cell preparations expressing the identified neoTCRs displayed specific cytotoxicity against the matched autologous melanoma cell line M489, as determined by the cytotoxicity assay. FIG. 50 provides a graph of the percentage of tumor cell confluency after co-culture with all neoTCR T cells identified from PACT135 as compared to the percentage of tumor cell confluence after mock treatment, or incubation with RPMI media or neo12 TCR T cells. FIGS. 51A and 51B provide individual graphs of the percentages of tumor cell confluency after co-culture with each neoTCR T cell.

The neoTCR expressing T cells demonstrated strong killing of the matched tumor cells at both T cell:tumor cell ratios tested (1:1 and 5:1 (data not shown)). No cytotoxic activity was observed against mismatched tumor cell line M202 (data not shown). The control sample had 42% nuclei confluence as compared to less than 20% nuclei confluence in each sample incubated with a 1:1 ratio of neoTCR T cell at 96 hrs post incubation ($p<0.000001$ for each neoTCR T cell sample; FIG. 50 and FIGS. 51A-B). Importantly, while tumor cell number decreased the number of T cells increased indicating that the neoTCR T cells proliferated in response to cognate antigens endogenously expressed by the patient matched tumor cells (data not shown). Two days after co-culture with the cognate tumor cells, the neoTCR T cells became activated, indicated by the formation of clusters. The T cells proliferated and by day 5 they covered the surface of the entire well and no tumor cells were detected.

Even neoTCRs with low frequency in the PBMC or TIL samples, such as neoTCRs expressed only in one T cell, had strong activity against the patient matched tumor cell lines, proving the high accuracy and sensitivity of the imPACT technology.

T Cell Cytokine Secretion

Figure 52:
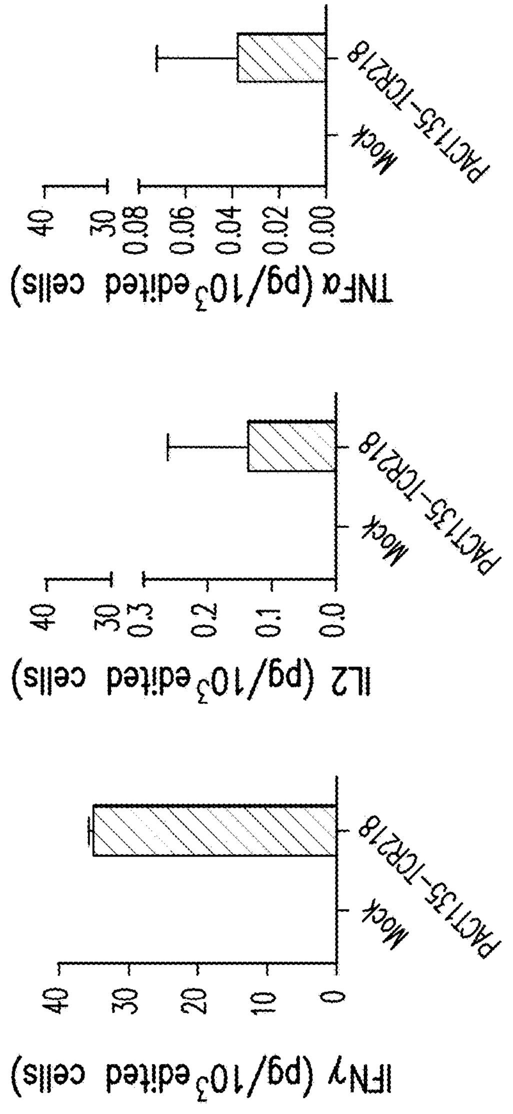
FIG. 52 shows IFNγ, IL2, and TNFα secretion by TCR218 T cells after co-culture with M489 cells.
Figure 53:
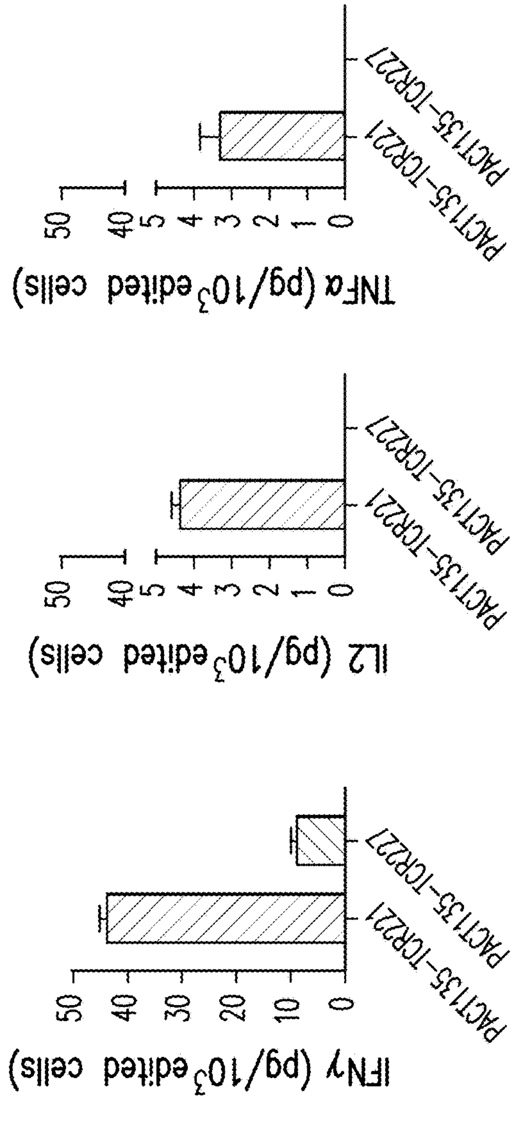
FIG. 53 shows IFNγ, IL2, and TNFα secretion by TCR221 and TCR227 T cells after co-culture with M489 cells.
Figure 54:
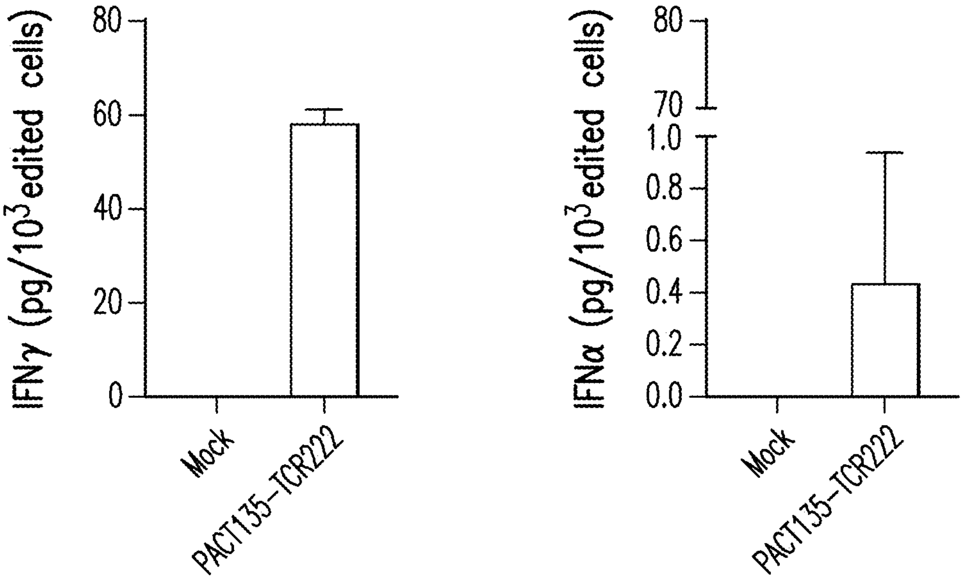
FIG. 54 shows IFNγ and TNFα secretion by TCR222 T cells after co-culture with M489 cells.
Figure 55:
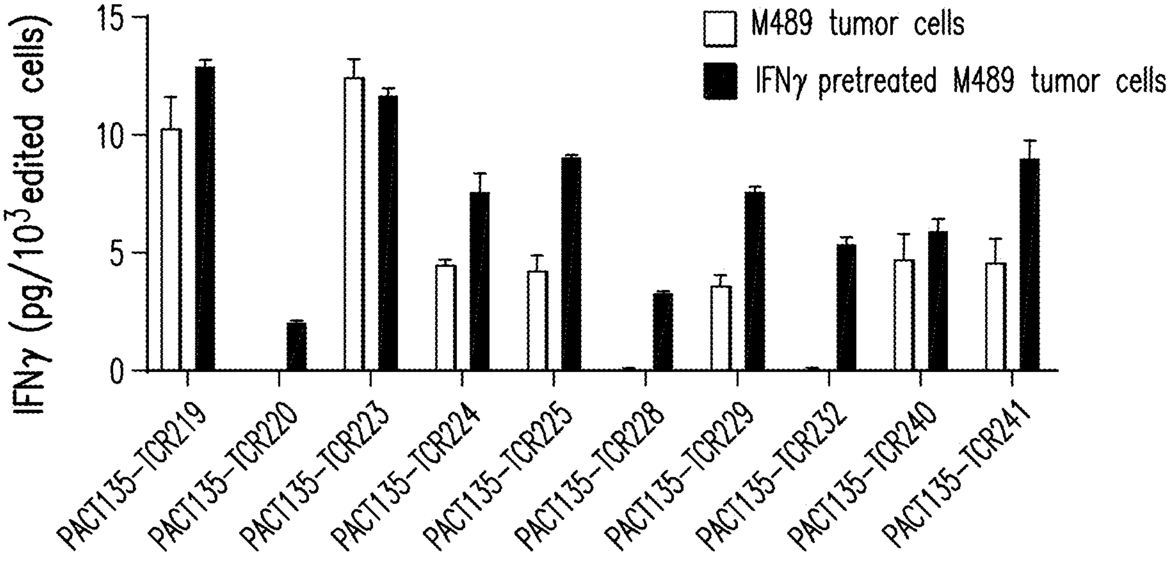
FIG. 55 shows IFNγ secretion by TCR219, TCR220, TCR223, TCR224, TCR225, TCR228, TCR229, TCR232, TCR240, TCR241 T cells after co-culture with M489 cells with or without IFNγ pretreatment.

NeoTCR expressing T cells were assessed for antigen-specific cytokine production NeoTCR T cells secreted IFNγ, IL-2 and TNFα cytokines after co-culture in the presence of the patient matched melanoma cell line M489. No cytokine secretion was measured when the neoTCR T cells were co-cultured with the unmatched melanoma cell line M202. FIG. 52 shows IFNγ, IL2, and TNFα secretion by TCR218 T cells after co-culture in the presence of M489. FIG. 53 shows IFNγ, IL2, and TNFα secretion by TCR221 T cells and IFNγ secretion by TCR227 T cells after co-culture in the presence of M489. FIG. 54 shows IFNγ and TNFα secretion by TCR222 T cells after co-culture in the presence of M489. No IL2 was detected at 48 hours. FIG. 55 shows IFNγ secretion by TCR219, TCR223, TCR224, TCR225, TCR229, TCR240 and TCR241 T cells after co-culture in the presence of M489 alone (black bars) and after the M489 cells were pre-treated with IFNγ for an hour (gray bars). TCR220, TCR228, and TCR232 T cells secreted IFNγ after co-culture with IFNγ-pretreated M489 cells. No IL2 or TNFα was detected at 48 hours.

Example 21: Validation of NeoTCRs Isolated from Colorectal Patient Samples Using the Impact Method Materials and Methods comPACT Library Preparation 144 neoepitopes were predicted for a treatment naïve patient with colorectal cancer. A library of 61 comPACTs (neoepitope-HLA complexes) was produced across HLA-A*03:01, A*02:01 and B*07:03, as described in Examples 10 and 11.

T Cell Isolation

PBMCs collected from a subject (PACT035) were incubated with the comPACT library. Neoantigen-specific T cells were isolated using the imPACT method as described in Examples 10 and 11. Seven neoTCRs clonotypes against the COX6C protein were identified.

NeoTCR Gene Editing

Healthy donor-derived CD4 and CD8 T cells were engineered to express the seven COX6C neoantigen-specific TCRs using a CRISPR-based non-viral method as described in International Patent Application No. WO2019089610, published May 9, 2019, hereby incorporated by reference in its entirety.

COX6C R20Q Stable Expression Cell Lines

PACT precision genome engineering expertise was used to generate stable tumor cell lines expressing the COX6C R20Q neoantigen under control of endogenous regulatory elements. Colon cancer cell line SW620 that expresses high levels of cell surface HLA-A02 was used to express the neoantigen. SW620 cells were nucleofected with gRNA/Cas9 and an HDR template to make COX6C R20Q knock-in cell lines. Edited cells with single sorted and propagated. The COX6C locus was sequenced. Sequencing analysis showed high edited at about 80% of single cells. Four cell lines expressing COX6C R20Q in the endogenous locus were selected: SW620 cells expressing the wild type COX6C gene, SW620 cells heterozygous for the COX6C-R20Q mutation, and two lines of SW620 cells homozygous for the COX6C-R20Q mutation (one shown).

Expression of HLA-A02 in the engineered SW620 cell line was confirmed via flow cytometry using the BB7.2 anti-HLA*A2 antibody. K562 cell lines constitutively expressing HLA-A*02 and HLA-C*02 were used as positive and negative controls, respectively. SW620 cells were nucleofected with a GFP construct to confirm transfection efficiency.

T Cell Activation

Expression of activation marker Nur77 was also determined in the CD4 and CD8 TCR089 neoTCR T cells co-cultured with the SW620 cells homozygous for COX6C-R20Q mutation. As a negative control, TCR089 neoTCR T cells were also co-cultured with wild type SW620 cells, or alone. Cells were stained for Nur77 using an anti-Nur77 mAb (eBiosciences) and expression of Nur77 assessed via flow cytometry.

T Cell Cytotoxicity Assay, Incucyte

NeoTCR T cell-induced killing of the tumor cells over time was also determined via immunofluorescence using the IncuCyte imaging system (Essen BioSciences). T cells expressing each of the seven identified COX6C neoTCR clonotypes were used in this assay. SW620 cells homozygous for COX6C-R20Q mutation or wild type SW620 cells were labeled in red using the NucLight Red Lentivirus (Essen). Labeling the tumor cells in red allows to differentiate them from T cells in co-culture and monitor the tumor cell killing overtime. 40,000 tumor cells/well were seeded in a 96-well plate and left overnight in the incubator. The following day neoTCR T cells were added at a 1:1 T cell:tumor cell ratio. Each neoTCR T cell was added to an individual tumor cell sample. RNPs (T cells electroporated with ribonucleoprotein (RNP) complexes only), neo12 TCR T cells, and media alone were used as negative controls. The co-culture samples were monitored by collecting time-lapse images at 2 hour intervals for 5 days using the IncuCyte imaging system with the 10× objective.

T Cell Cytotoxicity Assay, Flow Cytometry

TCR089 neoTCR T cells were assessed for antigen-specific T cell-mediated killing. 100,000 TCR089 neoTCR T cells were co-cultured with SW620 cells homozygous for COX6C-R20Q mutation (+/+) or wild type SW620 at different T cell:tumor cell ratios.

Following 24 hours of co-culturing T cells and target cells, cells were stained using the Live/Dead Cell staining kit (Live/Dead Near IR viability stain for flow, cat #NC0584313, ThermoFisher) for 20 minutes at 4° C. in the dark. In cells with compromised membranes, the dye reacts with free amines both in the cell interior and on the cell surface, yielding intense fluorescent staining. In viable cells, the dye's reactivity is restricted to the cell-surface amines, resulting in less intense fluorescence. The difference in intensity is typically greater than 50-fold between live and dead cells, allowing for easy discrimination. After incubation cells were washed, fixed with the eBioscience IC Fixation Buffer (ThermoFisher, cat #00-8222-49) and analyzed by flow cytometry.

Cytokine Secretion Assay

TCR089 neoTCR T cells were co-cultured with SW620 cells homozygous for the COX6C-R20Q mutation or SW620 cells heterozygous for the COX6C-R20Q mutation at a 5:1 T cell:tumor cell ratio. As a positive control, TCR089-expressing T cells were co-cultured with SW620 WT were pulsed with 1 μM for 1 hour. As negative control, TCR089-expressing T cells were co-cultured with SW620 wild type cells. After 24 hour the supernatant was collected, and cytokine production was assessed using the cytokine bead assay (CBA, BEAD-BASED IMMUNOASSAY from BD BioSciences). CBA is a flow cytometry multiplexed bead-based immunoassays application that allows quantification of multiple proteins simultaneously by using antibody-coated beads to efficiently capture analytes.

Results

Identification of neoTCRs in PACT035

Figure 56:
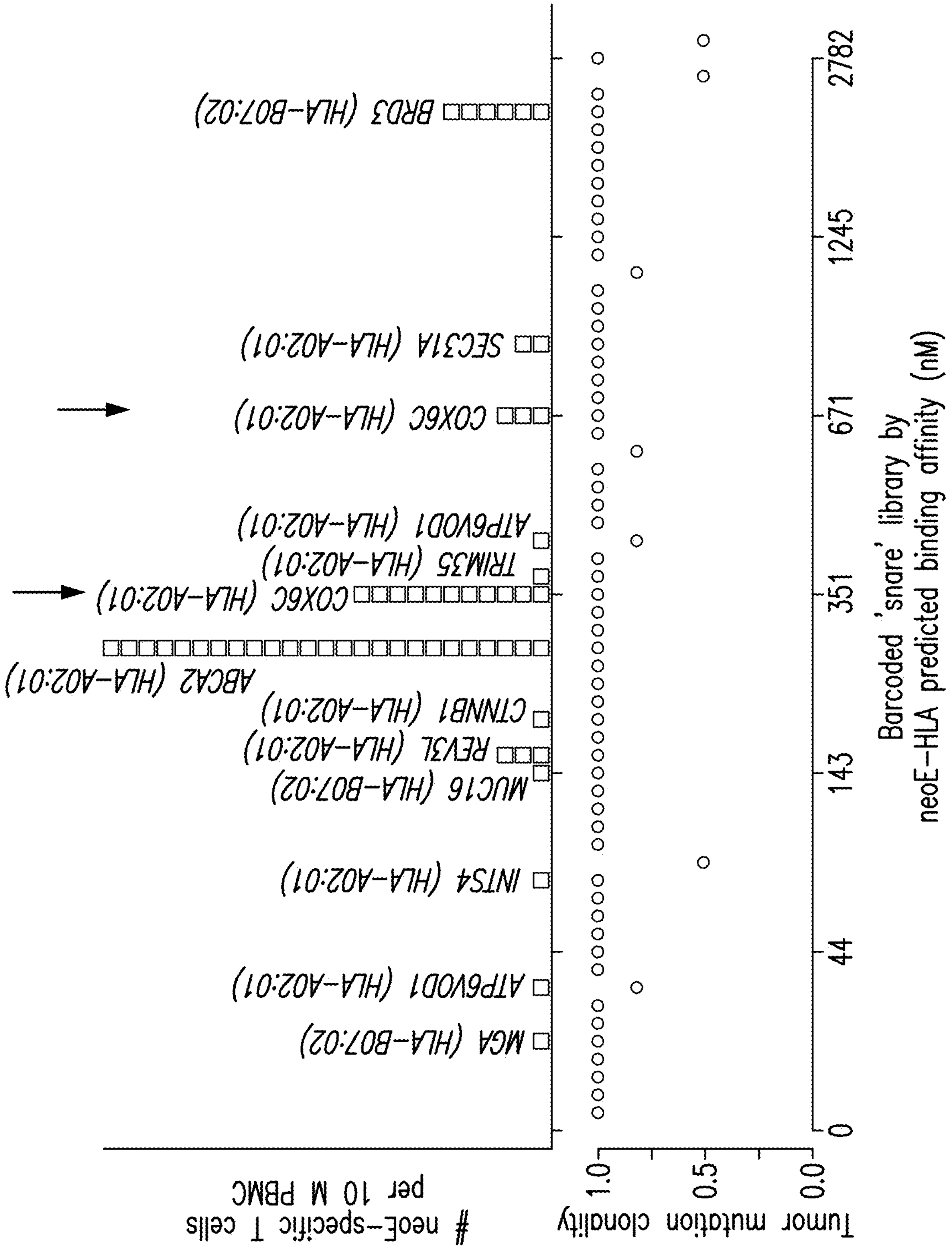
FIG. 56 provides a summary of the number of neoantigen-specific T cells isolated from patient PACT035.

Seven neoTCR clonotypes against the COX6C protein were identified in the patient sample using the imPACT T cell isolation method (FIG. 56, indicated by arrows). Two of seven bound neoantigen-HLA complexes when engineered into CD4 T cells and are thus CD8-independent neoTCRs. COX6C is a subunit of the mitochondrial enzyme Cytochrome C Oxidase, which is expressed in essentially all tissues at a moderate level. The neoantigen target peptide was residues 18-20, with an R20Q mutation. The neoTCRs that bound the R20Q COX6C peptide (residues 18-26) were termed TCR089, TCR091, TCR092, TCR094, TCR097, TCR098, and TCR099. The neoantigen peptide sequences, alpha and beta TCR CDR3 sequences, and HLA alleles isolated from patient PACT035 are shown in Table 9 below.

TABLE 9

| ID # | Gene | SEQ ID NO | Neoantigen peptide | SEQ ID NO | Alpha CDR3 | SEQ ID NO | Beta CDR3 | HLA |
|---|---|---|---|---|---|---|---|---|
| TCR089 | COX6C | 257 | RLQNHMAVA | 258 | CAVGELDTGFQKLVF | 264 | CASSEDSYEQYF | A02:01 |
| TCR091 | COX6C | 257 | RLQNHMAVA | 259 | CAYPSGNQFYF | 265 | CASWGAGLPLNTEAFF | A02:01 |
| TCR092 | COX6C | 257 | RLQNHMAVA | 260 | CAVEDSGYALNF | 266 | CSASRPTDGEQFF | A02:01 |
| TCR094 | COX6C | 257 | RLQNHMAVA | 261 | CALQDSNYQLIW | 267 | CSAIAGLTDTQYF | A02:01 |
| TCR097 | COX6C | 257 | RLQNHMAVA | 262 | CAFGNFNKFYF | 268 | CASSLQVPYNEQFF | A02:01 |
| TCR098 | COX6C | 257 | RLQNHMAVA | 260 | CAVEDSGYALNF | 266 | CSASRPTDGEQFF | A02:01 |
| TCR099 | COX6C | 257 | RLQNHMAVA | 263 | CAEDYDMRF | 269 | CASLKEGEAQNIQYF | A02:01 |

Transfection of SW620 Cell Lines

Figure 57A:
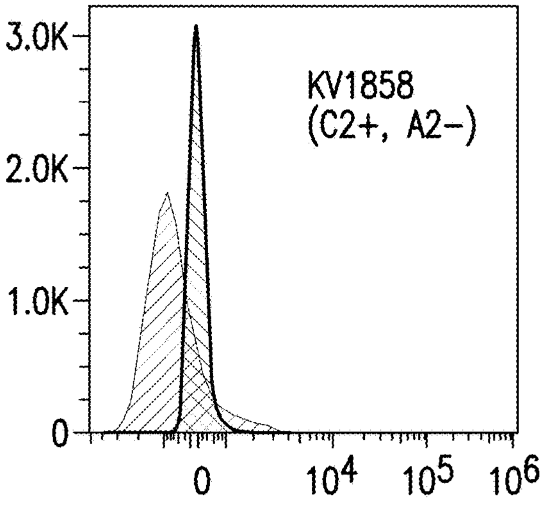
FIG. 57A shows HLA-A2 expression in the KV1858 cell line.
Figure 57B:
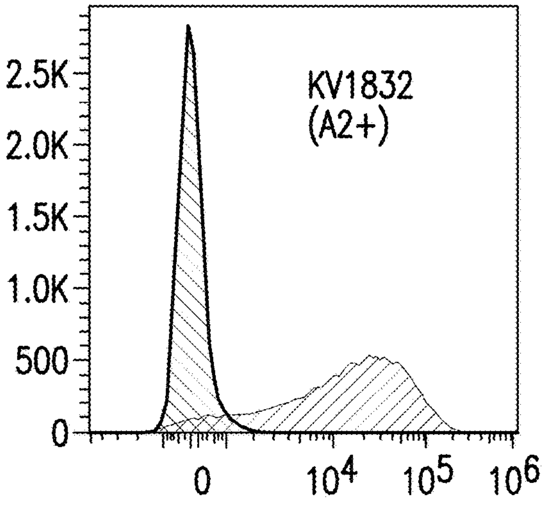
FIG. 57B shows HLA-A2 expression in the KV1832 cell line.
Figure 57C:
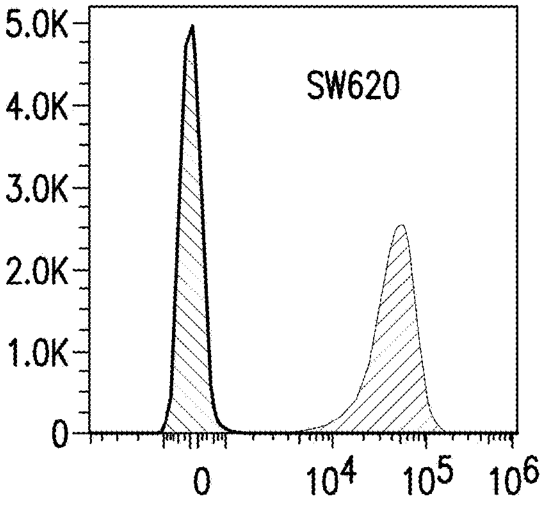
FIG. 57C shows HLA-A2 expression in the SW620 cell line.
Figure 57D:
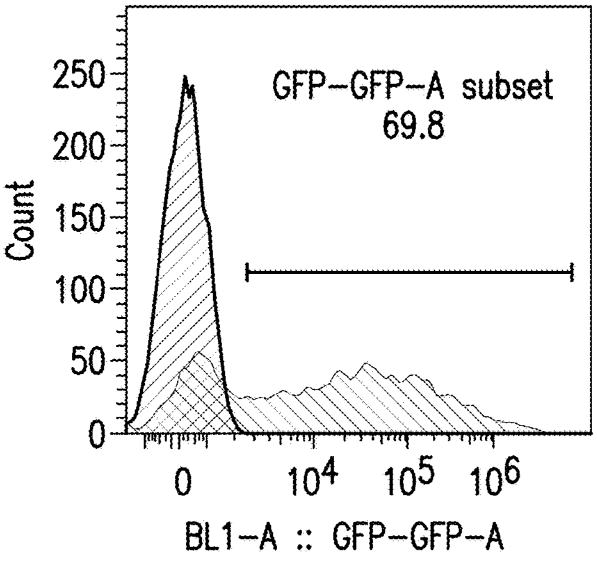
FIG. 57D shows GFP expression in transfected SW620 cells.

FIG. 57A shows no HLA*A2 expression in the KV1858 cell line (expresses HLA*C2, but not HLA*A2). FIG. 57B shows HLA*A2 expression in the KV1832 cell line (expresses HLA*A2). FIG. 57C shows HLA*A2 expression in the SW620 cell line (expresses HLA*A2). FIG. 57D shows GFP quantification in nucleofected SW620 cells. Isotype control antibodies were used as negative controls.

T Cell Activation

Figure 58:
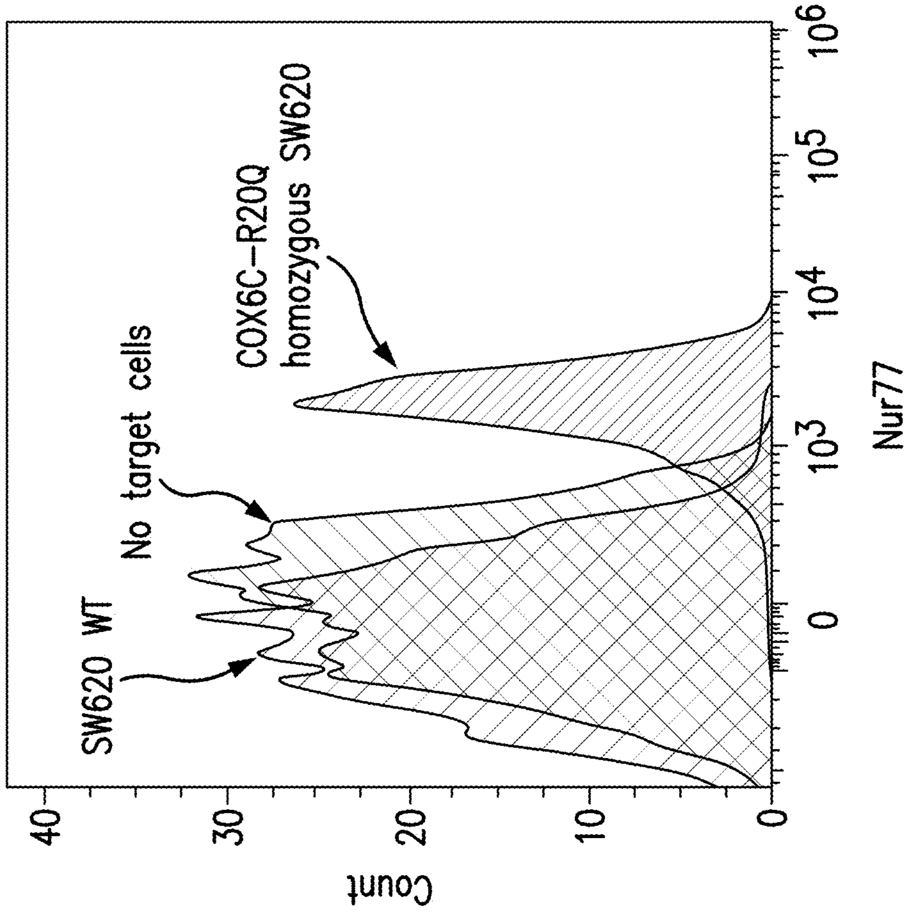
FIG. 58 shows Nur77 expression in TCR089 neoTCR T cells that were co-cultured with SW620 cells homozygous for COX6C-R20Q mutation

Nur77 is an immediate early gene whose expression is rapidly upregulated by TCR signaling. The expression of Nur77 is rapidly upregulated by antigen-TCR signaling. Nur77 expression was detected in TCR089 neoTCR T cells that were co-cultured with SW620 cells homozygous for COX6C-R20Q mutation (FIG. 58). No Nur77 induction was observed when the TCR089 neoTCR T cells were cocultured alone or with SW620 cells expressing the WT COX6C protein.

T Cell Cytotoxicity Assay, IncuCyte

Figure 59B:
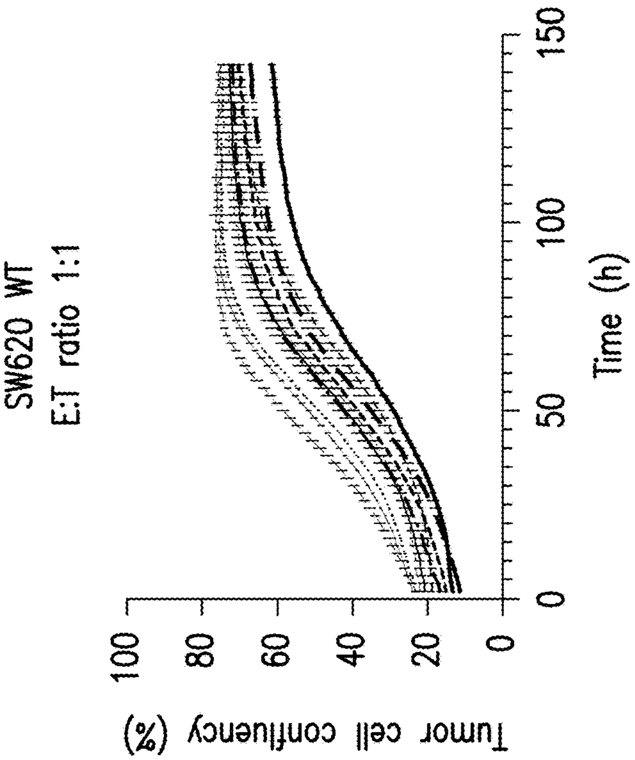
FIG. 59B shows no killing of wildtype SW620 cells.
Figure 59A:
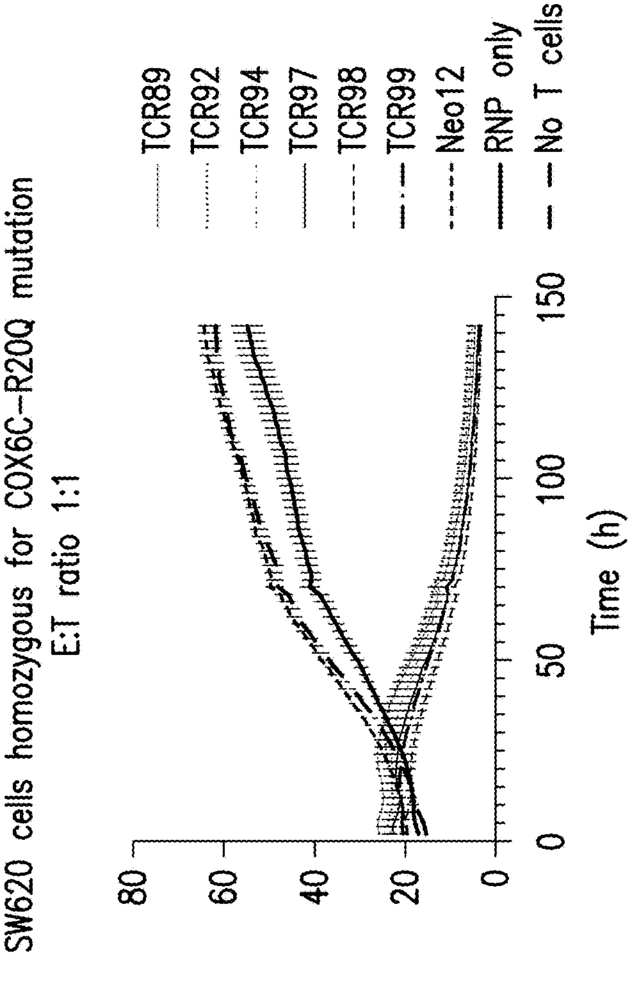
FIG. 59A shows neoTCR-expressing T cells killed SW620 homozygous tumor cells.

Target cell killing was also measured for each COX6C neoTCR T cell. All the neoTCR-expressing T cells demonstrated strong killing of the SW620 homozygous tumor cells (FIG. 59A). No cytotoxic activity was observed against SW620 cells expressing the wild type COX6C protein (FIG. 59B). The amount of T cell-induced killing was dose dependent and increased with increasing T cell:tumor cell ratios.

The IncuCyte images collected during the killing assay using the TCR089 neoTCR T cells also showed that while tumor cell number decreased, the number of T cells increased (data not shown). This indicates that the TCR089 T cells proliferated in response to the cognate antigen endogenously expressed by the SW620 cells homozygous for COX6C-R20Q mutation.

TCR089 T Cell Cytotoxicity Assay, Flow Cytometry

Figure 60:
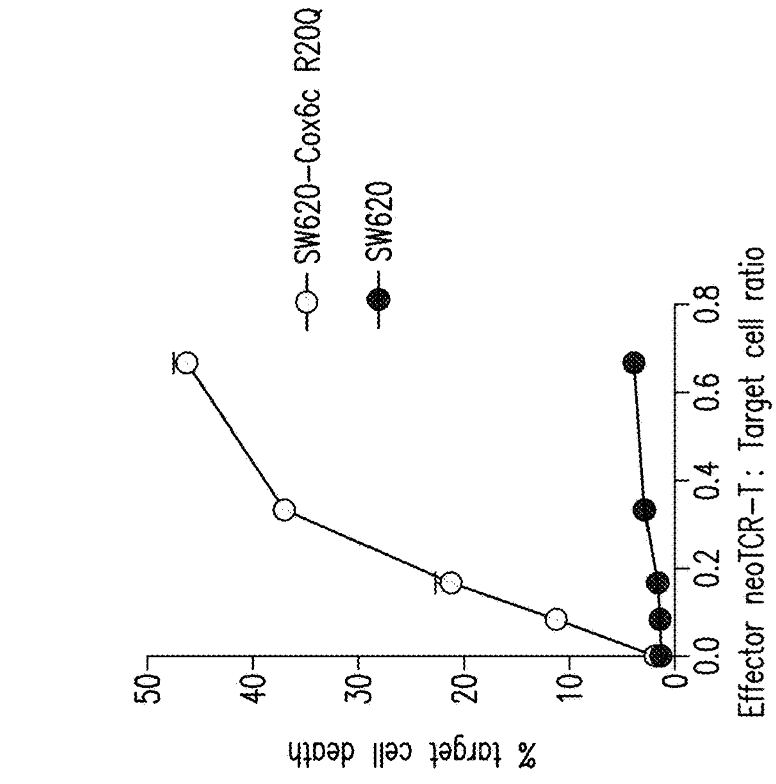
FIG. 60 shows TCR089 killed SW620 cells homozygous for COX6C-R20Q mutation but not wild type SW620 cells

TCR089 killed SW620 cells homozygous for COX6C-R20Q mutation but not wild type SW620 cells. No cytotoxic activity was observed against SW620 cells expressing the wild type COX6C protein (FIG. 60). The amount of T cell-induced killing was dose dependent and increased with increasing TCR089 T cell:tumor cell ratios.

Cytokine Secretion Assay

Figure 61:
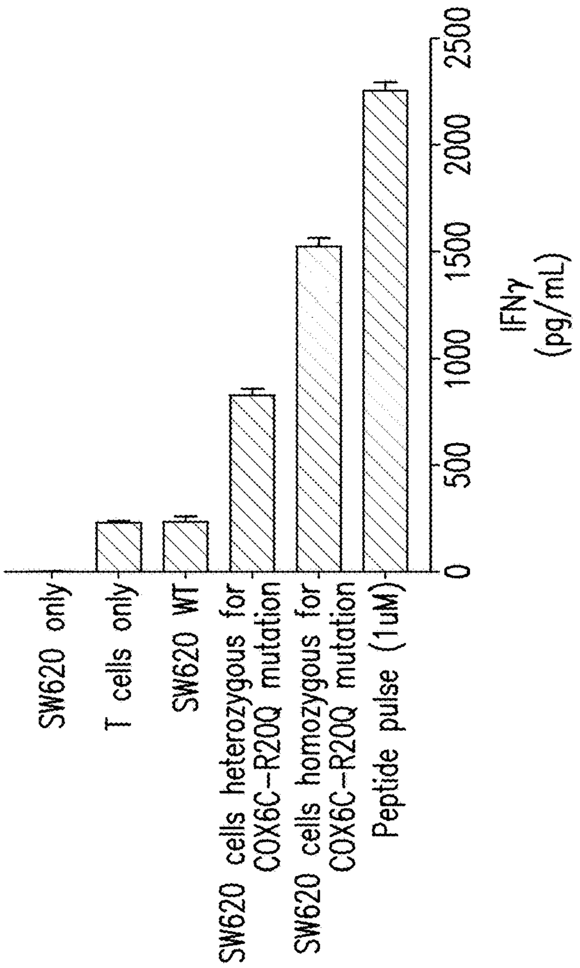
FIG. 61 shows IFNγ secretion in TCR089 T cells after co-culture with the SW620 cells homozygous for COX6C-R20Q mutation.

Strong IFNγ secretion was measured in the TCR089 T cells samples after co-culture with the SW620 cells homozygous for COX6C-R20Q mutation (FIG. 61). Half of the amount of IFNγ was measured when the TCR089 T cells were co-cultured with SW620 cells heterozygous for COX6C-R20Q mutation. Similar IFNγ was detected for TCR089 T cells alone, in absence of tumor cells, or when the T cells were co-cultured with wild type SW620 cells.

Example 22: Method of Treating Cancer Patients with NeoTCR T Cells

Patients with cancer or another proliferative disease may need an interventional therapy to slow or stop the proliferation of cells and to kill existing cells that may or do cause harm to the patient (e.g. cause pain, discomfort, or sickness). Specifically, The neoTCR T cells disclosed herein may be used to treat cancer.

Figure 62:
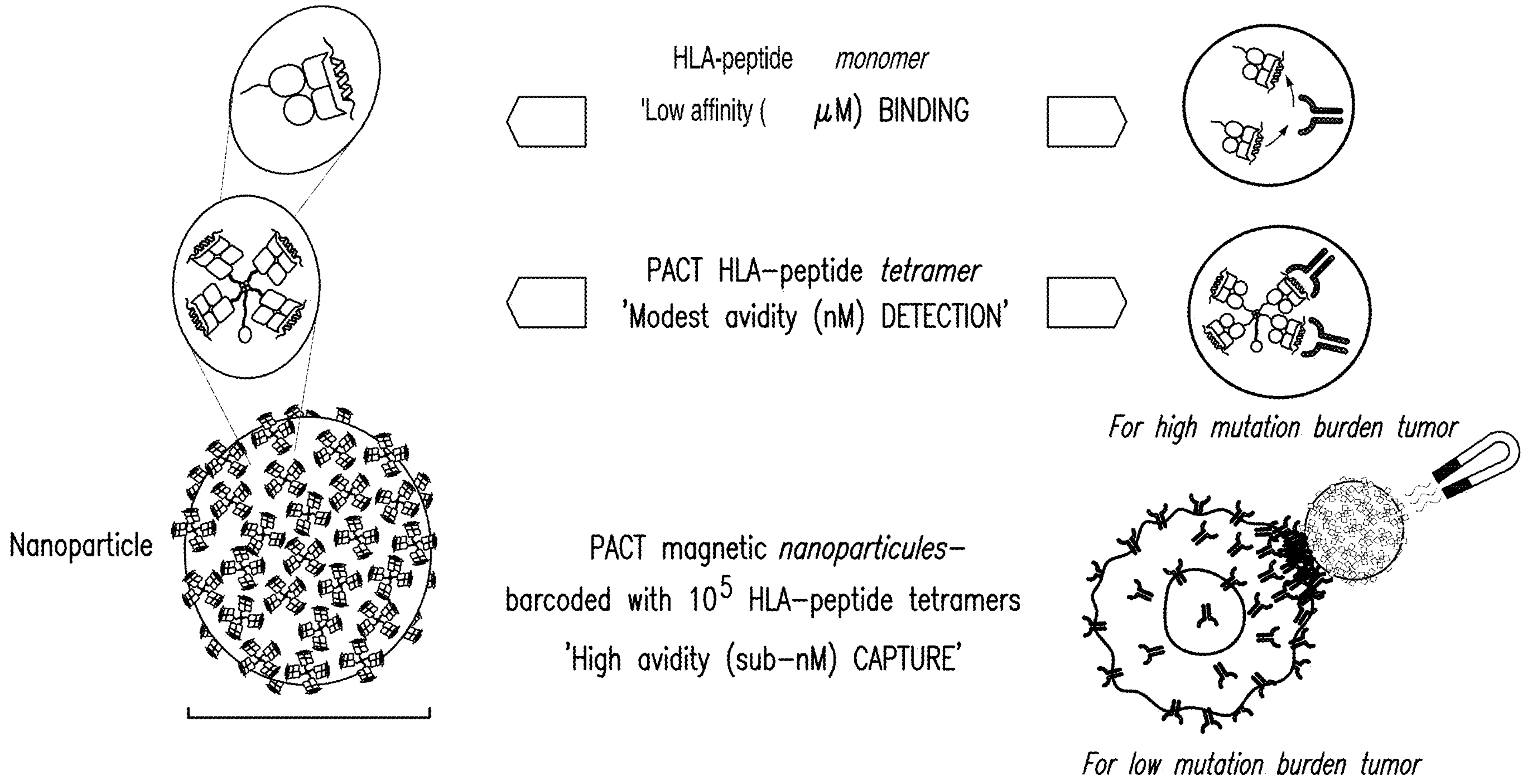
FIG. 62 shows the methodology of the imPACT Isolation Technology: NeoE specific TCRs were isolated from patients treated with a checkpoint inhibitor, sequencing was performed, tumor antigens were identified, algorithms were used to select the neoepitopes to screen using comPACT polypeptides and the imPACT Isolation Technology, and neoepitope-specific T cells were captured.

As shown in FIG. 62, Neo-E specific TCRs were isolated from patients treated with PD-1 therapy. RNA and DNA were collected from the biopsies and tumor cell lines and RNAseq and WES (whole exome sequencing) were performed on the biopsies and cells. DNA was also collected from the PBMCs of the patients for WES to use a control. Once tumor antigens were identified using the RNAseq and WES, algorithms were used to select neoepitope candidates to screen using comPACT polypeptides (with the predicted neoepitopes expressed therein) and the imPACT Isolation Technology. Barcoded comPACT particle libraries were assembled and combined with patient samples. The comPACT particles were able to associate with and capture the neoepitope-specific T cells.

Example 23: Impact Isolation Technology Example

Based on computational prediction of patient-specific neoE, hundreds of capture reagents were made consisting of the patient HLA class I subtypes loaded with the corresponding predicted neoE (Peng et al. AACR 2019); neoE-specific T cells were then isolated and the TCR alpha and beta sequenced. Isolated neoTCRs were studied functionally by generation of primary human T cells expressing the neoTCRs using non-viral precision genome engineering to replace the endogenous TCRs (Jacoby et al., AACR 2019, Sennino et al., AACR 2019).

T cell responses were analyzed in two patients with metastatic melanoma receiving anti-PD-1 therapy. NeoE-specific T cells were isolated from peripheral blood mononuclear cells (PBMC) and tumor infiltrating lymphocytes (TIL) at different time points. Patient PT476 had a durable response; tumor mutational burden (TMB) was 2556; 243 neoE-HLA complexes were produced across 3 HLA types, HLA-A03:01, A24:01 and C12:03. This resulted in isolation of 17 TCRs specific for 5 neoE-HLAs. T cells specific for neoE's were present at baseline in TILs and expanded during treatment in TILs and PBMCs. Patient PT461 had rapid disease progression on anti-PD-1; TMB was 61; 78 neoE-HLA-complexes covering HLA-A02:01, A03:01, B07:02, C05:01 and C07:02 were produced, resulting in isolation of 2 TCRs to 1 neoE-HLA.

To further characterize the T cell responses, T cells were gene edited to express 14 different TCRs isolated from patient PT476, specific for neoEs in the mutated IL8, PUM1 and TPP2 genes. All 14 T cell preparations displayed specific cytotoxicity against a matched autologous melanoma cell line established from a biopsy of patient PT476 (50-75% tumor growth inhibition compared to melanoma cell line growth in co-culture with a mismatched control TCR, 96 hour assay using P:T 1:1, $p<0.000001$ for each comparison), and had no cytotoxic effect against an unmatched control human melanoma cell line. Upon co-culture with the matched autologous melanoma cell line, neoE TCR T cells upregulated 4-1BB and OX-40, secreted IFNγ, IL-2 and TNFα, and induced T cell proliferation and degranulation. No responses were seen when T cells were co-cultured with unmatched targets.

These results show that anti-PD-1 therapy induces focused neoE-specific T cell responses to a restricted number of neoE's, and that non-viral precision genome engineering can successfully redirect T cells to neoE expressing tumors which can be used as an approach for personalized ACT therapy.

Similarly, in addition to anti-PD-1 therapy, other checkpoint therapies and additional combinations could be used; for example, an anti-PD-L1 or an anti-CTLA4 therapy could be used.

Figure 63:
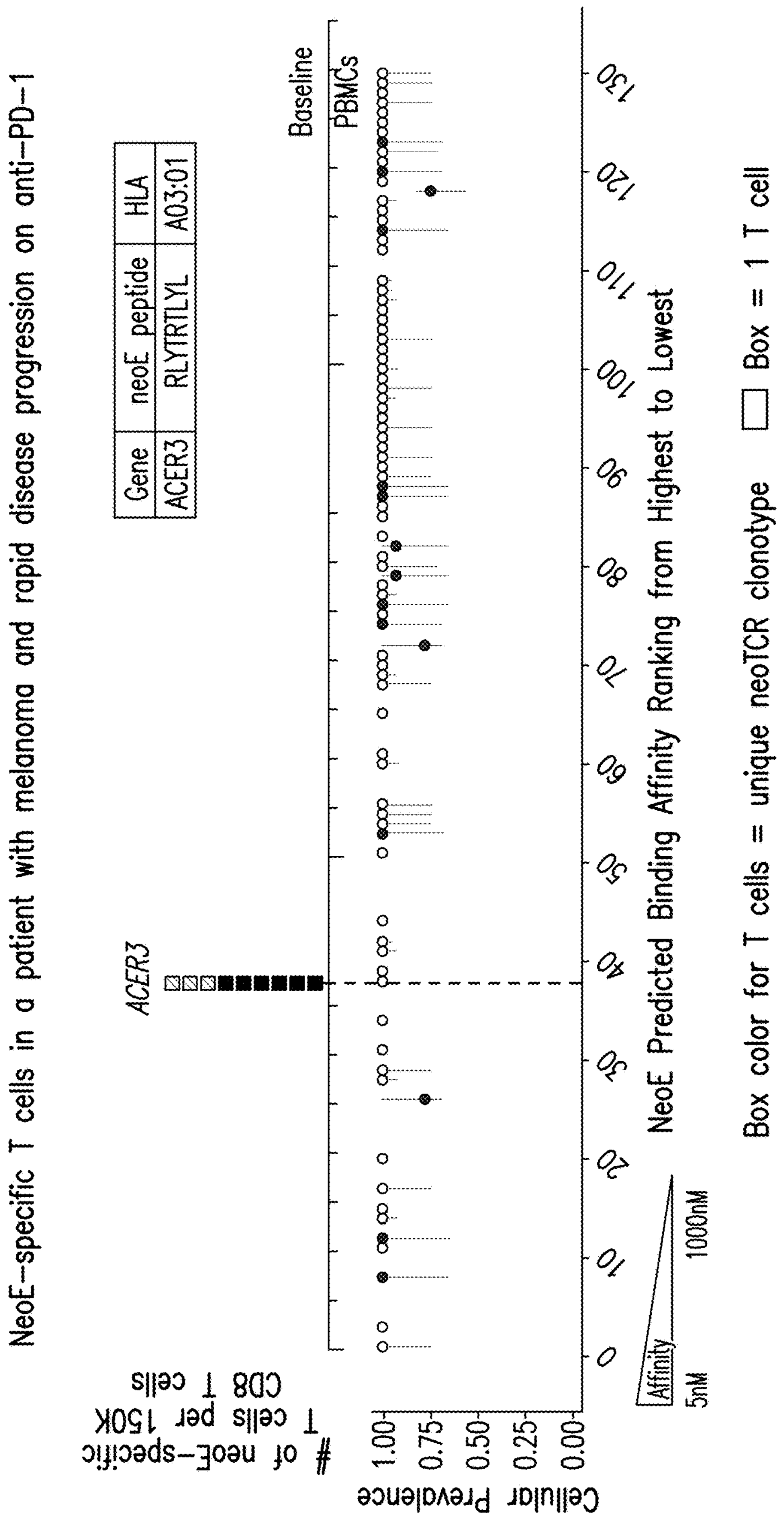
FIG. 63 shows a patient sample from a patient who did not respond to anti-PD-1 treatment with a breakdown of the patient's neoE-HLA complexes and the resulting identified TCRs.

As partially described in Example 20, biopsies and PBMCs were collected at multiple time-points after anti-PD-1 treatment (FIG. 45: PT476 responder, and FIG. 63: PT461 non-responder). TILs and cell lines were established from the patient's biopsies. The imPACT Isolation Technology was used to isolate NeoE-specific T cells and monitor their evolution over time. NeoE derived from non-synonymous mutations were predicted using the Whole Exome Sequencing (WES) and RNAseq from the baseline cell lines and ranked according to the predicted HLA-binding affinity, the truncality of the mutation and the level of expression. HLA-NeoE capture reagents for the top-ranked NeoE were used to isolate the NeoE-specific T cells. FIG. 45 shows PT476: 243 neoE-HLA complexes were produced across 3 HLA types, HLA-A03:01, A24:01 and C12:03 and 17 TCRs specific for 5 neoE-HLAs were isolated. FIG. 63 shows Patient PT461: 78 neoE-HLA-complexes covering HLA-A02:01, A03:01, B07:02, C05:01 and C07:02 were produced, resulting in isolation of 2 TCRs to 1 neoE-HLA.

Example 24: Impact Isolation Technology Methodology Example

As described in Example 22, NeoE-specific T cells can be isolated from patient samples. In this example, the imPACT Isolation Technology resulted in the identification of 14 neoTCR-T candidates which included: 12 IL-8 (HLA-A24:02 and HLA-A03:01) neoTCR-T candidates, 1 PUM1 (HLA-A3:01) neoTCR-T candidate, and 1 TPP2 (HLA-A24:02) neoTCR-T candidate As shown in FIG. 62, the methodology of the imPACT Isolation Technology includes three work streams: Gene Editing, Co-Culture Assay, and Cell Based Assay.

Gene editing: CD8 and CD4 T cells from healthy donor were precision genome engineered to express the neoTCR. Briefly, neoE-specific TCR sequences were cloned into homologous recombination (HR) DNA templates. These HR templates were used with site-specific nucleases to engineer primary human T cells. The single-step (non-viral) precision genome engineering resulted in the seamless replacement of the endogenous TCR with the patient's neoE-specific TCR (of native sequence), whose expression is under endogenous regulation.

Co-Culture assay: NeoTCR-P1 T cells were co-cultured with a melanoma cell line derived from the baseline biopsy of the same patient (M489) or a mismatched melanoma tumor cell line at a final Product to Target (P:T) ratio of 1:1 or 5:1. Target cell killing was evaluated over 6 days using the IncuCyte system. Expression of the proliferation marker Ki67 was assessed by flow cytometry at 48 h. Expression of activation marker was assessed by flow cytometry at 24 h. Cytokine secretion was measured in the cell supernatant at 48 h using the BD Cytokine Bead Array (CBA) Human Th1/Th2 Cytokine Kit II.

Co-Culture assay: Peptide-HLA: recognition/stimulation, target cell killing, proliferation, activation markers, and cytokine secretion assays were performed.

Example 25: Engineered NeoTCR-T Cells Kill Autologous Tumor Cells

Figure 64:
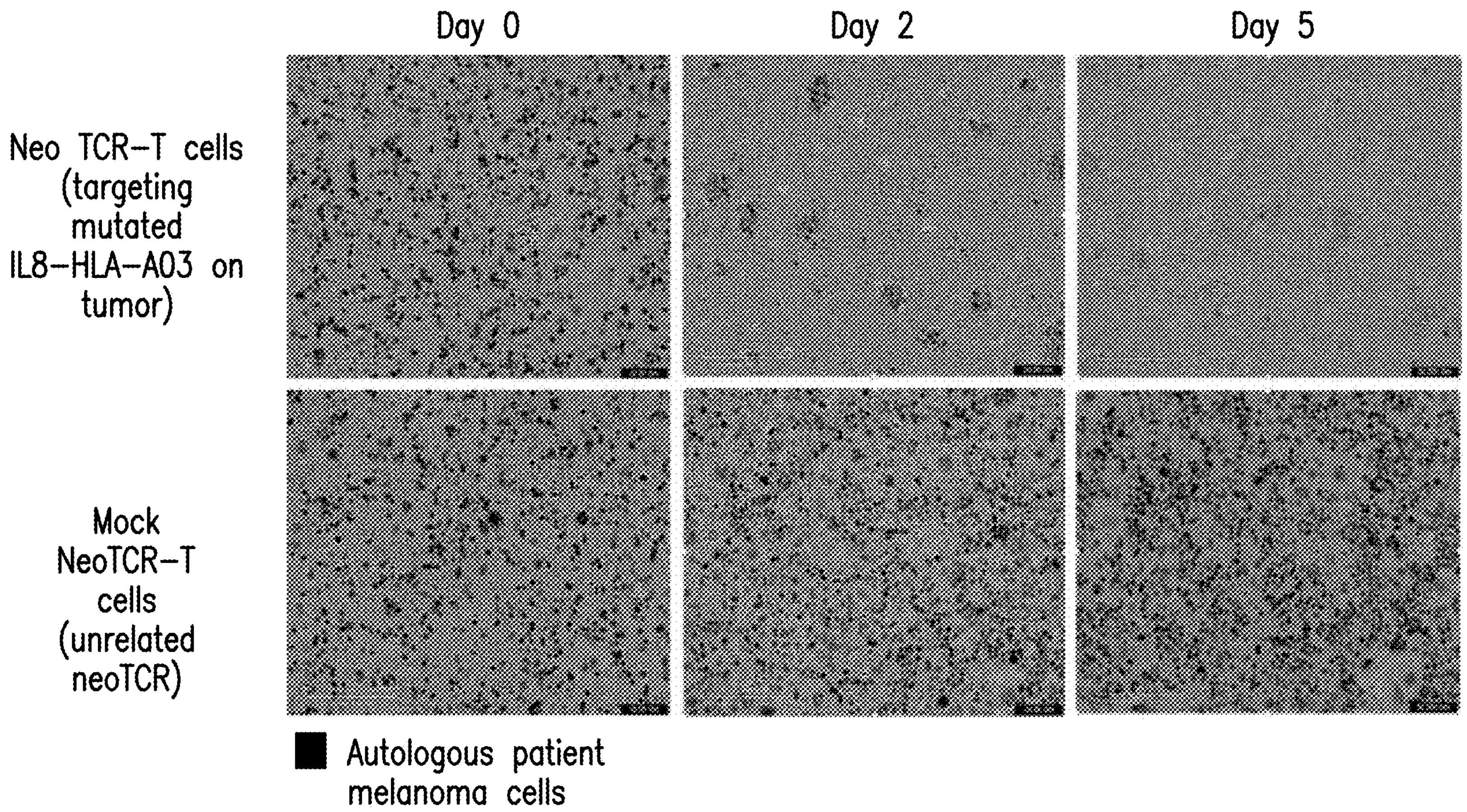
FIG. 64 shows that neoTCR-T cells kill autologous melanoma tumor cells.

As shown in FIG. 64, neoTCR-T cells kill autologous melanoma tumor cells. Using time-lapse microscopy of tumor cell death and T cell proliferation, NeoTCR-T cells were co-cultured with autologous melanoma cell lines expressing a red fluorescent protein (nuclear RFP) in a stable manner. More specifically, NeoTCRs were made to target the IL-8-HLA-A*03:01 neoantigen on the melanoma cell lines and those NeoTCRs were cultured with the IL-8-HLA-A*03:01 neoantigen melanoma cell line (top three images in FIG. 64) and that was compared to the negative control (bottom three images in FIG. 64). Images shown here were collected at time 0 (left panels), 2 days (middle panels) and 5 days (right panels). Accordingly, the NeoTCRs are specific to the tumor neoantigen and are capable of effectively killing autologous tumor cells.

Figure 65A:
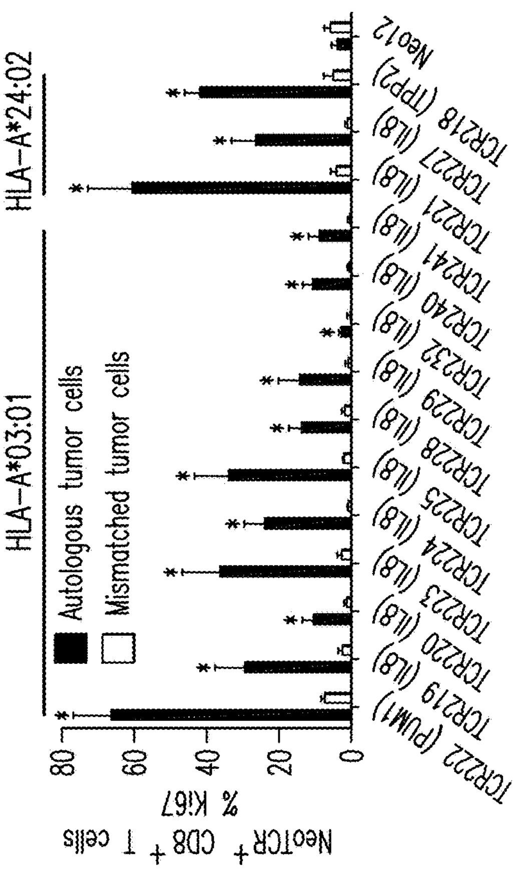
FIG. 65A shows the ability of neoTCR-T cells to kill autologous tumor cells.

The ability of neoTCR-T Cells to kill autologous tumor cells can also be seen in FIG. 65A. NeoTCR-T cells were co-cultured with autologous (black bars) or mismatched melanoma tumor cells (white bars) and after 48 h the percentage of Ki67 (proliferation marker) expressing CD8 neoTCR T cells was assessed by flow cytometry. * $p<0.05$ compared to mismatched melanoma tumor cells (t test with Holm-Sidak method for multiple comparison correction). T cells expressing the NeoTCR neo12 were used as negative control.

Figure 65B:
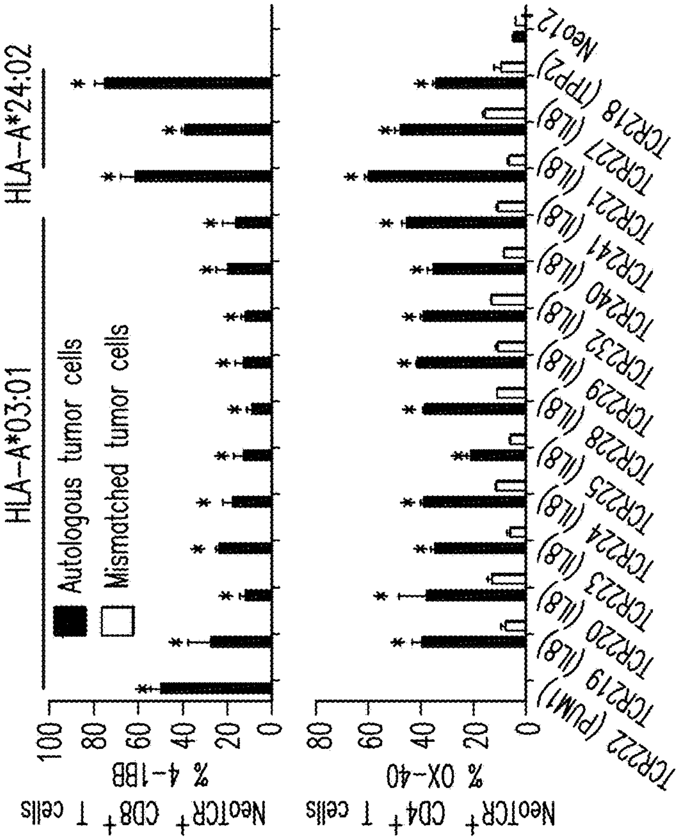
FIG. 65B shows that neoTCR-T cells express activation markers upon co-culture with autologous tumor cells.

Similarly, NeoTCR-T cells were shown to express activation markers upon co-culture with autologous tumor cells. This can be seen in FIG. 65B. NeoTCR-T cells were co-cultured with autologous (black bars) or mismatched tumor cell line (white bars) and after 24 h the percentage of CD8 neoTCR T cells expressing the activation markers 4-1BB (top) or the percentage of CD4 neoTCR T cells expressing the activation marker OX40 (bottom bar graph) was assessed by flow cytometry. * $p<0.05$ compared to mismatched melanoma tumor cells (t test with Holm-Sidak method for multiple comparison correction). T cells expressing the NeoTCR neo12 were used as negative control. To measure OX-40 upregulation in the CD4 neoTCR T cells, melanoma cells were pre-treated with IFNγ for 24 h prior to the co-culture with T cells.

Figure 65C:
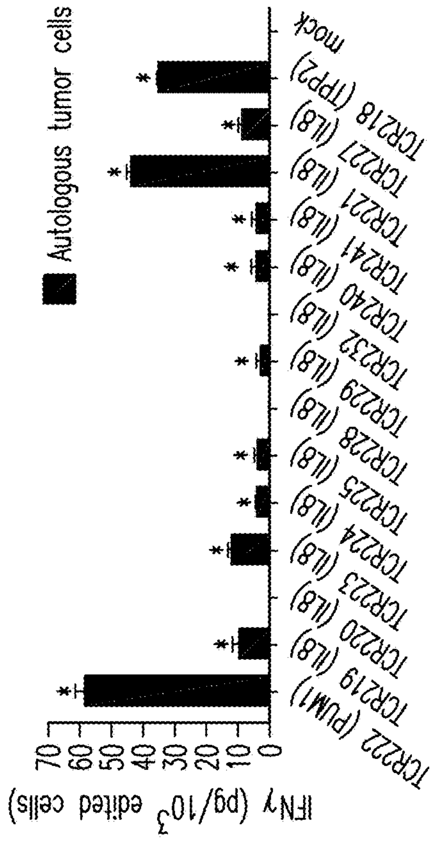
FIG. 65C shows that neoTCR-T cells secrete interferon gamma upon co-culture with autologous tumor cells.

Lastly, it was shown that NeoTCR-T cells secrete interferon-gamma upon co-culture with autologous tumor cells. This can be seen in FIG. 65C. NeoTCR-T cells were co-cultured with autologous melanoma tumor cells and after 48 h IFNγ secretion was assessed by flow cytometry (CBA). mock T cells were used as negative control. * $p<0.05$ (t test with Holm-Sidak method for multiple comparison correction).

This collectively shows that newly generated NeoTCR-T cells expressing the TCRs isolated using the imPACT Isolation technology upregulated markers of activation and proliferation upon co-culture with autologous tumor cells. More importantly, all NeoTCR-T cells specifically kill patient derived autologous melanoma cells

Figure 66B:
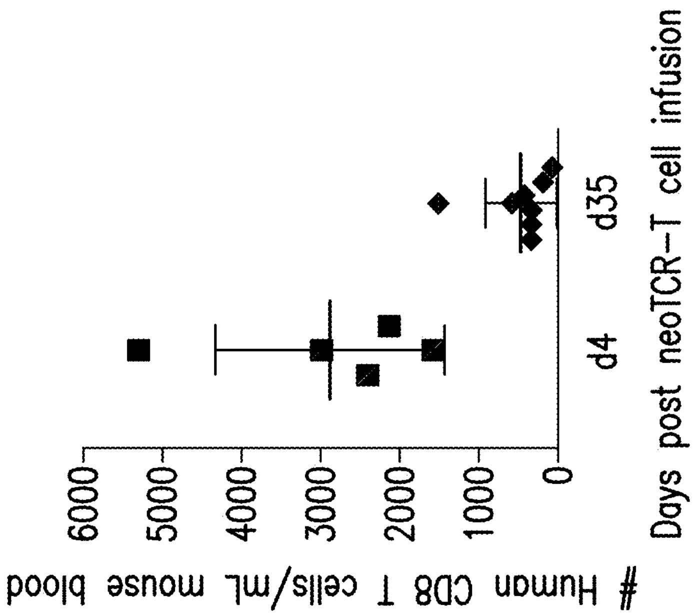
FIG. 66B shows the number of human CD8 T cells/mL present in mouse blood at Day 4 post-neoTCR T cell infusion and at Day 35 post-infusion.
Figure 66A:
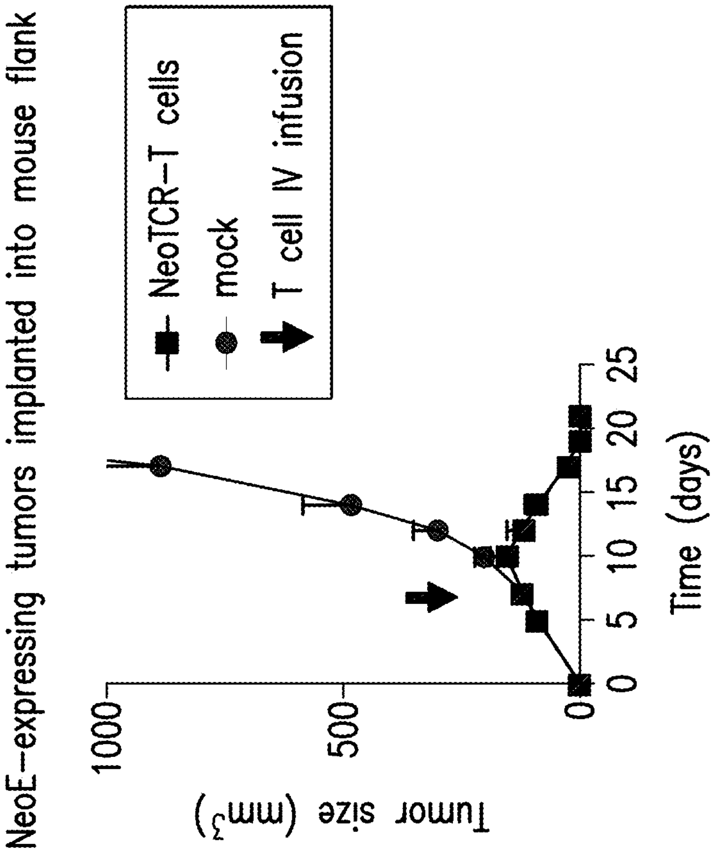
FIG. 66A shows that neoTCR T cell therapy eradicated a tumor that was implanted into a mouse.

Example 26: Dosing with NeoTCR-T Cells Eradicates Tumors in Mice and In Vitro in an Engineered Cell Line Neoantigen-expressing tumors were implanted into the flank of 15 NOD scid gamma (NSG) mice. When the tumors reached 95 $mm^3$ in size the mice were divided in two groups: control group (7 mice), which received PBS and treated group (8 mice), which were dosed with neoTCR T cells ($5*10^6$ total T cells/mouse; gene editing efficiency 50%). As shown in FIG. 66A after infusion of the NeoTCR-T cells (see arrow in figure) the tumor size decreased and by day 19 the tumors were completely eradicated. FIG. 66B shows the number of human CD8 T cells/mL present in mouse blood at Day 4 post neoTCR-T cell infusion and at Day 35 post neoTCR-T cell infusion. Even though NSG mice lack human cytokines NeoTCR-T cells were present in circulation after the tumors eradication, showing that the NeoTCR-T cells not only kill the target cells but also proliferate and persist.

Example 27: Design of NeoTCR-T Cells that are Specific to Truncal Tumor Mutations The subclonal mutation nature of tumor progression in primary tumors and in metastases creates a problem in the field of oncology because oncology drugs that are "personalized" in the sense that they are designed to target a protein, chemical, or cell with a specific mutation (e.g., many small molecule drugs are designed to target point-mutation based tumors). Because tumors often mutate (mutations accumulate during cancer growth and length of disease) in the later stages of primary tumors and in metastasis, a drug that worked well to shrink or slow the progression of the tumor when the tumor was first detected and treated, may lose its efficacy over time.

Disclosed here is the ability to design and make neoTCR-T cells that are specific to the truncal tumor mutations. Using algorithms and bioinformatics approaches, tumor-exclusive truncal mutations that are expressed by all cancer cells in a patient were identified.

Example 28: NeoTCR-T Cells Address all HLA Types in the Global Population

There are 13,000 HLAs in the human population. Each person has a set of 6 HLAs. As a result, less than 1% of any NeoE-HLA tumor target is the same between patients (data generated from the analysis of 60,000 patients (Hartmaier et al. (2017) Genome Medicine) and 20,000 patients (Schumacher & Schrieber (2015) Science). The analysis performed shows that the HLA allele catalog for PBMC interrogation is: >99% with at least 1 HLA allele covered, >90% with between 4 and 6 alleles covered, and >60% of potential trial subjects in the US are predicted to have all 6 alleles covered.

Example 29: NeoTCR Therapy can be Used for Tumors with a Low Mutational Load, a Moderate Mutational Load, and a High Mutational Load Because the imPACT Isolation Technology is extremely sensitive, it is possible to detect neoantigens on tumor will all degrees of mutational loads. For example, NeoTCR-T Cells can be used to treat tumors with a low tumor mutation load such as prostate and breast cancer, tumors with a mid-tumor mutation load such as ovarian and colorectal cancer, and tumors with a high tumor mutation load such as bladder and melanoma cancer.

Accordingly, the imPACT Isolation Technology described herein can be used design, engineer, and make NeoTCRs for low, mid, and high tumor mutation load tumors. In certain aspects, the imPACT Isolation Technology methods can be used to detect neoantigens on low, mid, and high tumor mutation load tumors. In certain aspects, the imPACT Isolation Technology methods has been used be used to detect neoantigens on low, mid, and high tumor mutation load tumors. In certain aspects, the imPACT Isolation Technology methods can be used to make a composition comprising NeoTCRs to treat low, mid, and high tumor mutation load tumors in patients suffering from such tumor. In certain aspects, the imPACT Isolation Technology methods can be used to make a population of NeoTCRs to treat low, mid, and high tumor mutation load tumors in patients suffering from such tumor.

Example 30: Method of Treating Patients with a NeoTCR-T Cell Therapy

The initial step in treating patients with a NeoTCR-T cell therapy is screening the patients. Once screened and biopsies are taken, the patient can enroll and leukapheresis will take place. During the manufacturing time for the NeoTCR T cells (patient specific) as described herein, including the comPACT library creation, the imPACT Isolation Technology screening, and the editing of T cells to express the NeoTCR, patients may optionally enroll in a bridging therapy (e.g., a standard of care therapy including first line, second line, third line, and later line therapies for the specific cancer indication). Such bridging therapy may be prescribed and administered between 0 and 60 days and on average between 21 and 42 days. Following such optional bridging therapy, the patient may be prescribed a conditional chemotherapy. This conditioning chemotherapy may be given 5, 4, and 3 days prior to administration of the NeoTCR T cell therapy. On the administration day, patients will receive an infusion of the NeoTCRs. Thereafter, the tumor(s) will be assessed.

Example 31: Compositions and Method for Treating Non-Cancer Diseases and Disorders Using NeoTCR T Cell Without limitation, diseases other than cancer can be treated with NeoTCR T cell therapy. Specifically, any disease or disorders that cause the afflicted cell population to produce a disease/disorder specific neoantigen can be treated with a NeoTCR T cell therapy. Such cells include cells that are infected by a virus, a fungus, or a bacteria that, as a result of the infection, present infection-specific neoantigens that are detectable by a NeoTCR T cell. Cells associated with inflammatory or autoimmune disease may also present disease-specific neoantigens from which NeoTCR T cells to be made. For example, if a patient is suffering from an allergy or an inflammatory disease, if a NeoTCR can be made against a neoantigen that is specific to the inflammatory cytokine's ligand that is presented on the inflamed cell.

Example 32: Method of Imaging Using a NeoTCR T Cell

Once a the comPACT and imPACT Isolation Technology methods have been employed on a patient tumor sample, the NeoTCR T cells can be used for treating disease, as described herein, and can also be used to image, detect, and/or monitor tumor burden, progression, remission, and eradication. This can be done by labeling the NeoTCR T cells with a detectable label (e.g. any label that can be imaged such as with a dye or with a zirconium label; see, e.g., U.S. Pat. No. 8,771,966 which is hereby incorporated by reference in its entirety).

For example, a NeoTCR T cell can be genetically modified to express a dye or fluorescent protein. Such a labeled NeoTCR T cell can be used to determine the efficacy of the NeoTCR T cell therapy at eradicating the tumor(s); wherein if the labeled NeoTCR T cell can be imaged proliferating and expanding, it can be extrapolated that the NeoTCR T cell therapy is effective because the cells are differentiating into T effector cells upon target antigen encounter.

For example, a NeoTCR T cell can be labeled with an agent such as zirconium89. Such a labeled NeoTCR T cell can be used to determine the presence of any tumor (before, during, or after) NeoTCR T cell therapy based on the interaction or lack thereof between the NeoTCR T cell and the tumor cell (if present).

Without limitation, cells other than tumor cells can also be imaged that present neoantigens that allow for NeoTCR T cells to be made. Such cells include but are not limited to those described in Example 30. For example, if an inflammatory disease was treated by designing and administering a NeoTCR T cell therapy using the methods described herein such that an inflamed cell specific neoepitope (e.g., a neoepitope on the ligand of the inflammation-causing inflammatory cytokine) was found and NeoTCR T cells were designed and made therefrom, the same NeoTCR T cell could be labeled with an imaging agent to later determine if the ligand presenting cells are still present or if the NeoTCR effectively eradicated or sufficiently reduced such cell population to ameliorate the disease state of the patient.

Example 33: Method of Determining Efficacy of a NeoTCR-T Cell Therapy and Methods of Adjusting Dosing of the NeoTCR-T Cell Therapy Upon dosing of a patient with a neoTCR-T cell therapy, the efficacy can be monitored using imaging methods known in the art. For example, a patient can be infused with a neoTCR-T cell therapy as described herein followed by administration of a tumor tracer that can be imaged 1, 2, 3, 4, 5, 6, 7, 8, 9, 10, 11, 12, 13, 14, or 15 days after such tracer administration. In certain embodiments the tracer can be administered the same week as the neoTCR-T cell therapy, the week following the neoTCR-T cell therapy, two weeks following the neoTCR-T cell therapy, three weeks following the neoTCR-T cell therapy, or one or months following the neoTCR-T cell therapy.

In certain embodiments, if the tumor, after neoTCR-T cell therapy, does not progress but does not shrink (as visualized using imaging), additional administrations of the neoTCR-T cell therapy may be given. In certain embodiments, if the tumor, after neoTCR-T cell therapy, does not shrink and optionally increases in size (as visualized using imaging), additional administrations of the neoTCR-T cell therapy may be given.

In certain embodiments, a tracer and imaging are used every 3-6 months following neoTCR-T cell therapy to monitor the status of the disease. In certain embodiments, a tracer and imaging are used every 6-12 months following neoTCR-T cell therapy to monitor the status of the disease.

Example 34: Methods of Treating a Patient Using a NeoTCR T Cell

Neoepitope candidates are synthesized and cloned into the comPACT polynucleotide as described in Examples 1-9. Briefly, a polynucleotide sequence encoding a candidate antigen peptide is inserted into an MEW template described in FIGS. 1-5. Mammalian cells are seeded and transfected with the comPACT polynucleotides comprising the candidate antigen peptide sequence. Transfected cells express and secrete the comPACT polypeptides in the cell media. Conditioned media from the cells is collected and the comPACT polypeptides are purified via size-exclusion chromatography. The purified comPACT polypeptides are then assembled with multimer particles (e.g., tetramers, dextramers, NTAmer) that comprise multiple copies of the comPACT polypeptides, a DNA barcode and a fluorophore (e.g., APC or PE). One of the advantages of this approach is the high-throughput production and screening of multiple neoepitope candidates at the same time. Furthermore, this process can be automated. Two different types of particles, a first with APC and a second with PE as fluorophore are combined to obtain a particle set able to recognize a patient specific antigen peptide.

In order to identify the neoTCR T cells and the sequences of their TCR, freshly isolated or cryopreserved T cells from the patient are stained with the multimer particles, as well as with a set of antibodies for the phenotypical characterization. Viable and barcoded T cells are sorted into single cells and their DNA and RNA are extracted and analyzed by next-generation sequencing. As described in the Examples 11-13, the sequencing data obtained from the comPACT positive T cells are analyzed to identify and validate the predicted antigen peptide, the neoTCR T cells and the validated neoepitope TCR candidates and their sequences.

The identified neoepitope TCR sequences are cloned into a homology-directed recombination (HDR) template for genome editing in T cells. Further details on the sequence and structure of the template can be found in the International Patent Application No. PCT/US2018/058230, the content of which is herein incorporated by reference. T cells from the patient, freshly collected or previously cryopreserved, are engineered for the disruption of the TCR gene and the integration of the HDR template by using non-viral methods. A CRISPR/Cas9 approach comprising gRNA for the endogenous loci of TCR-alpha and TCR-beta gene sequences can be used to disrupt the endogenous TCR loci. The HDR template will recombine with one of the endogenous disrupted TCR gene sequence to introduce the identified neoepitope TCR. The engineered T cells therefore lack expression of the endogenous TCR and express the neoepitope TCR. These neoTCR T cells are then adoptively transferred in the patient and target specifically the tumor cells expressing the neoantigen.

Compared to other adoptive cell transfer methods, this process has significant advantages including, but not limited to: i) it is flexible since it allows a personalized targeting of tumor-exclusive mutations presented in the context of patient-specific HLAs; ii) it provides a clinical tool to attack cancer cells expressing neoantigens not express on the cell surface; iii) it works regardless of the patient ethnicity or the cancer type; and iv) it can be automated for multiple steps and it has a small footprint manufacturing.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

SEQUENCE LISTING

```
Sequence total quantity: 324
SEQ ID NO: 1            moltype = DNA  length = 78
FEATURE                 Location/Qualifiers
source                  1..78
                        mol_type = other DNA
                        organism = Homo sapiens
SEQUENCE: 1
atggcgacgg gttcaagaac ttccctactt cttgcatttg gcctgctttg tttgccgtgg  60
ttacaggagg gctcagca                                                78

SEQ ID NO: 2            moltype = AA  length = 26
FEATURE                 Location/Qualifiers
source                  1..26
                        mol_type = protein
                        organism = Homo sapiens
SEQUENCE: 2
MATGSRTSLL LAFGLLCLPW LQEGSA                                       26

SEQ ID NO: 3            moltype = DNA  length = 23
FEATURE                 Location/Qualifiers
misc_feature            1..23
```

-continued

```
                        note = Description of Unknown: Universal target sequence
source                  1..23
                        mol_type = other DNA
                        organism = synthetic construct
SEQUENCE: 3
cgtggttaca ggagggctca gca                                              23

SEQ ID NO: 4            moltype = DNA  length = 19
FEATURE                 Location/Qualifiers
misc_feature            1..19
                        note = Description of Unknown: Universal target sequence
source                  1..19
                        mol_type = other DNA
                        organism = synthetic construct
SEQUENCE: 4
ggatgcggag gatccggcg                                                   19

SEQ ID NO: 5            moltype = DNA  length = 19
FEATURE                 Location/Qualifiers
misc_feature            1..19
                        note = Description of Unknown: Universal target sequence
source                  1..19
                        mol_type = other DNA
                        organism = synthetic construct
SEQUENCE: 5
ggaagcggag gatccggcg                                                   19

SEQ ID NO: 6            moltype = DNA  length = 21
FEATURE                 Location/Qualifiers
misc_feature            1..21
                        note = Description of Unknown: Universal target sequence
source                  1..21
                        mol_type = other DNA
                        organism = synthetic construct
SEQUENCE: 6
ggaagcggag gatccaccag c                                                21

SEQ ID NO: 7            moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 7
atgtacgggc cagatatacg c                                                21

SEQ ID NO: 8            moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 8
acacccgccg cgcttaatg                                                   19

SEQ ID NO: 9            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 9
GGGGS                                                                  5

SEQ ID NO: 10           moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 10
ggcggcggcg gcagc                                                       15

SEQ ID NO: 11           moltype = AA  length = 5
```

```
FEATURE                Location/Qualifiers
REGION                 1..5
                       note = Description of Artificial Sequence: Synthetic peptide
source                 1..5
                       mol_type = protein
                       organism = synthetic construct
SEQUENCE: 11
GSGGS                                                                  5

SEQ ID NO: 12          moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 12
ggcagcggcg gcagc                                                       15

SEQ ID NO: 13          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 13
GCGGS                                                                  5

SEQ ID NO: 14          moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 14
ggctgcggcg gcagc                                                       15

SEQ ID NO: 15          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 15
GCGGSGGGGS GGGGS                                                       15

SEQ ID NO: 16          moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 16
ggctgcggcg gcagcggcgg cggcggcagc ggcggcggcg gcagc                      45

SEQ ID NO: 17          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 17
GGGGSGGGGS GGGGS                                                       15

SEQ ID NO: 18          moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
```

-continued

```
                         organism = synthetic construct
SEQUENCE: 18
ggcggcggcg gcagcggcgg cggcggcagc ggcggcggcg gcagc                  45

SEQ ID NO: 19            moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 19
GGGGSGGGGS GGGGSGGGGS                                              20

SEQ ID NO: 20            moltype = DNA  length = 60
FEATURE                  Location/Qualifiers
misc_feature             1..60
                         note = Description of Artificial Sequence: Synthetic
                          oligonucleotide
source                   1..60
                         mol_type = other DNA
                         organism = synthetic construct
SEQUENCE: 20
ggcggcggcg gcagcggcgg cggcggcagc ggcggcggcg gcagcggcgg cggcggcagc  60

SEQ ID NO: 21            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 21
GSGGSGGSAG G                                                       11

SEQ ID NO: 22            moltype = DNA  length = 33
FEATURE                  Location/Qualifiers
misc_feature             1..33
                         note = Description of Artificial Sequence: Synthetic
                          oligonucleotide
source                   1..33
                         mol_type = other DNA
                         organism = synthetic construct
SEQUENCE: 22
ggcagcggcg gcagcggcgg cagcgcgggc ggc                               33

SEQ ID NO: 23            moltype = AA  length = 22
FEATURE                  Location/Qualifiers
source                   1..22
                         mol_type = protein
                         organism = Homo sapiens
SEQUENCE: 23
MDMRVPAQLL GLLLLWLSGA RC                                           22

SEQ ID NO: 24            moltype = DNA  length = 66
FEATURE                  Location/Qualifiers
source                   1..66
                         mol_type = other DNA
                         organism = synthetic construct
SEQUENCE: 24
atggatatgc gcgtgccggc gcagctgctg ggcctgctgc tgctgtggct gagcggcgcg  60
cgctgc                                                             66

SEQ ID NO: 25            moltype = AA  length = 20
FEATURE                  Location/Qualifiers
REGION                   1..20
                         note = Description of Unknown: Beta 2 microglobulin sequence
source                   1..20
                         mol_type = protein
                         organism = unidentified
SEQUENCE: 25
MSRSVALAVL ALLSLSGLEA                                              20

SEQ ID NO: 26            moltype = DNA  length = 60
FEATURE                  Location/Qualifiers
misc_feature             1..60
                         note = Description of Unknown: Beta 2 microglobulin sequence
source                   1..60
                         mol_type = other DNA
```

-continued

```
                         organism = synthetic construct
SEQUENCE: 26
atgagccgca gcgtggcgct ggcggtgctg gcgctgctga gcctgagcgg cctggaagcg  60

SEQ ID NO: 27            moltype = AA  length = 20
FEATURE                  Location/Qualifiers
REGION                   1..20
                         note = Description of Unknown: IL2 signal sequence
source                   1..20
                         mol_type = protein
                         organism = unidentified
SEQUENCE: 27
MYRMQLLSCI ALSLALVTNS                                              20

SEQ ID NO: 28            moltype = DNA  length = 60
FEATURE                  Location/Qualifiers
misc_feature             1..60
                         note = Description of Unknown: IL2 signal sequence
source                   1..60
                         mol_type = other DNA
                         organism = synthetic construct
SEQUENCE: 28
atgtatcgca tgcagctgct gagctgcatt gcgctgagcc tggcgctggt gaccaacagc  60

SEQ ID NO: 29            moltype = DNA  length = 45
FEATURE                  Location/Qualifiers
misc_feature             1..45
                         note = Description of Artificial Sequence: Synthetic
                          oligonucleotide
source                   1..45
                         mol_type = other DNA
                         organism = synthetic construct
SEQUENCE: 29
ggcctgaacg acatcttcga ggctcagaaa atcgaatggc acgaa                  45

SEQ ID NO: 30            moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 30
GLNDIFEAQK IEWHE                                                   15

SEQ ID NO: 31            moltype = DNA  length = 23
FEATURE                  Location/Qualifiers
misc_feature             1..23
                         note = Description of Unknown: TEV sequence
source                   1..23
                         mol_type = other DNA
                         organism = synthetic construct
SEQUENCE: 31
gagagaacct gtacttccag ggc                                          23

SEQ ID NO: 32            moltype = AA  length = 7
FEATURE                  Location/Qualifiers
REGION                   1..7
                         note = Description of Unknown: TEV sequence
source                   1..7
                         mol_type = protein
                         organism = unidentified
SEQUENCE: 32
ENLYFQG                                                            7

SEQ ID NO: 33            moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 33
catcatcatc atcatcat                                                18

SEQ ID NO: 34            moltype = AA  length = 6
FEATURE                  Location/Qualifiers
REGION                   1..6
```

```
                        note = Description of Artificial Sequence: Synthetic 6xHis
                         tag
source                  1..6
                        mol_type = protein
                        organism = synthetic construct
SEQUENCE: 34
HHHHHH                                                                   6

SEQ ID NO: 35           moltype = DNA  length = 66
FEATURE                 Location/Qualifiers
misc_feature            1..66
                        note = Description of Artificial Sequence: Synthetic
                         oligonucleotide
source                  1..66
                        mol_type = other DNA
                        organism = synthetic construct
SEQUENCE: 35
catcatcatc atcatcatgg cggcggcagc ggcggcggca gcggcagcca tcatcatcat  60
catcat                                                             66

SEQ ID NO: 36           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 36
HHHHHHGGGS GGGSGSHHHH HH                                           22

SEQ ID NO: 37           moltype = AA  length = 49
FEATURE                 Location/Qualifiers
REGION                  1..49
                        note = Description of Artificial Sequence: Synthetic
                         polypeptide
source                  1..49
                        mol_type = protein
                        organism = synthetic construct
SEQUENCE: 37
GLNDIFEAQK IEWHEGGGEN LYFQGGSHHH HHHGGGSGGG SGSHHHHHH              49

SEQ ID NO: 38           moltype = DNA  length = 576
FEATURE                 Location/Qualifiers
misc_feature            1..576
                        note = Description of Artificial Sequence: Synthetic
                         polynucleotide
source                  1..576
                        mol_type = other DNA
                        organism = synthetic construct
SEQUENCE: 38
tagtaatcaa ttacggggtc attagttcat agcccatata tggagttccg cgttacataa  60
cttacggtaa atggcccgcc tggctgaccg cccaacgacc cccgcccatt gacgtcaata  120
atgacgtatg ttcccatagt aacgccaata gggactttcc attgacgtca atgggtggag  180
tatttacggt aaactgccca cttggcagta catcaagtgt atcatatgcc aagtacgccc  240
cctattgacg tcaatgacgg taaatggccc gcctggcatt atgcccagta catgacctta  300
tgggactttc ctacttggca gtacatctac gtattagtca tcgctattac catggtgatg  360
cggttttggc agtacatcaa tgggcgtgga tagcggtttg actcacgggg atttccaagt  420
ctccacccca ttgacgtcaa tgggagtttg ttttggcacc aaaatcaacg ggactttcca  480
aaatgtcgta acaactccgc cccattgacg caaatgggcg gtaggcgtgt acggtgggag  540
gtctatataa gcagagctgg tttagtgaac cgtcag                            576

SEQ ID NO: 39           moltype = AA  length = 276
FEATURE                 Location/Qualifiers
source                  1..276
                        mol_type = protein
                        organism = Homo sapiens
SEQUENCE: 39
GSHSMRYFFT SVSRPGRGEP RFIAVGYVDD TQFVRFDSDA ASQKMEPRAP WIEQEGPEYW  60
DQETRNMKAH SQTDRANLGT LRGCYNQSED GSHTIQIMYG CDVGPDGRFL RGYRQDAYDG  120
KDYIALNEDL RSWTAADMAA QITKRKWEAV HAAEQRRVYL EGRCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                            276

SEQ ID NO: 40           moltype = AA  length = 276
FEATURE                 Location/Qualifiers
source                  1..276
                        mol_type = protein
                        organism = Homo sapiens
SEQUENCE: 40
```

-continued

```
GSHSMRYFFT SVSRPGRGEP RFIAVGYVDD TQFVRFDSDA ASQRMEPRAP WIEQEGPEYW  60
DGETRKVKAH SQTHRVDLGT LRGCYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWEP                            276

SEQ ID NO: 41          moltype = AA  length = 276
FEATURE                Location/Qualifiers
source                 1..276
                       mol_type = protein
                       organism = Homo sapiens
SEQUENCE: 41
GSHSMRYFFT SVSRPGRGEP RFIAVGYVDD TQFVRFDSDA ASQRMEPRAP WIEQEGPEYW  60
DQETRNVKAQ SQTDRVDLGT LRGCYNQSEA GSHTIQIMYG CDVGSDGRFL RGYRQDAYDG  120
KDYIALNEDL RSWTAADMAA QITKRKWEAA HEAEQLRAYL DGTCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                            276

SEQ ID NO: 42          moltype = AA  length = 276
FEATURE                Location/Qualifiers
source                 1..276
                       mol_type = protein
                       organism = Homo sapiens
SEQUENCE: 42
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEP                            276

SEQ ID NO: 43          moltype = AA  length = 276
FEATURE                Location/Qualifiers
source                 1..276
                       mol_type = protein
                       organism = Homo sapiens
SEQUENCE: 43
GSHSMRYFST SVSRPGSGEP RFIAVGYVDD TQFVRFDSDA ASQRMEPRAP WIEQERPEYW  60
DQETRNVKAH SQTDRENLGT LRGCYNQSEA GSHTIQIMYG CDVGSDGRFL RGYEQHAYDG  120
KDYIALNEDL RSWTAADMAA QITQRKWEAA RRAEQLRAYL EGTCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                            276

SEQ ID NO: 44          moltype = AA  length = 276
FEATURE                Location/Qualifiers
source                 1..276
                       mol_type = protein
                       organism = Homo sapiens
SEQUENCE: 44
GSHSMRYFTT SVSRPGRGEP RFIAVGYVDD TQFVRFDSDA ASQRMEPRAP WIEQERPEYW  60
DQETRNVKAH SQIDRVDLGT LRGCYNQSEA GSHTIQMMYG CDVGSDGRFL RGYQQDAYDG  120
KDYIALNEDL RSWTAADMAA QITQRKWEAA RVAEQLRAYL EGTCVEWLRR YLENGKETLQ  180
RTDPPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                            276

SEQ ID NO: 45          moltype = AA  length = 276
FEATURE                Location/Qualifiers
source                 1..276
                       mol_type = protein
                       organism = Homo sapiens
SEQUENCE: 45
GSHSMRYFFT SVSRPGRGEP RFIAVGYVDD TQFVRFDSDA ASQRMEPRAP WIEQEGPEYW  60
DQETRNVKAH SQTDRESLRI ALRCYNQSEA GSHTIQMMYG CDVGPDGRLL RGYQQDAYDG  120
KDYIALNEDL RSWTAADMAA QITQRKWEAA RVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                            276

SEQ ID NO: 46          moltype = AA  length = 276
FEATURE                Location/Qualifiers
source                 1..276
                       mol_type = protein
                       organism = Homo sapiens
SEQUENCE: 46
GSHSMRYFTT SVSRPGRGEP RFIAVGYVDD TQFVRFDSDA ASQRMEPRAP WIEQEGPEYW  60
DRNTRNVKAH SQIDRVDLGT LRGCYNQSEA GSHTIQMMYG CDVGSDGRFL RGYQQDAYDG  120
KDYIALNEDL RSWTAADMAA QITQRKWEAA RVAEQLRAYL EGTCVEWLRR HLENGKETLQ  180
RTDPPRTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                            276

SEQ ID NO: 47          moltype = AA  length = 276
```

-continued

```
FEATURE                Location/Qualifiers
source                 1..276
                       mol_type = protein
                       organism = Homo sapiens
SEQUENCE: 47
GSHSMRYFYT SVSRPGRGEP RFIAVGYVDD TQFVRFDSDA ASQRMEPRAP WIEQEGPEYW  60
DRNTRNVKAQ SQTDRVDLGT LRGCYNQSEA GSHTIQMMYG CDVGSDGRFL RGYRQDAYDG  120
KDYIALKEDL RSWTAADMAA QTTKHKWEAA HVAEQWRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWVAVVVP SGQEQRYTCH VQHEGLPKPL TLRWEP                            276

SEQ ID NO: 48          moltype = AA  length = 276
FEATURE                Location/Qualifiers
source                 1..276
                       mol_type = protein
                       organism = Homo sapiens
SEQUENCE: 48
GSHSMRYFYT SVSRPGRGEP RFISVGYVDD TQFVRFDSDA ASPREEPRAP WIEQEGPEYW  60
DRNTQIYKAQ AQTDRESLRN LRGCYNQSEA GSHTLQSMYG CDVGPDGRLL RGHDQYAYDG  120
KDYIALNEDL RSWTAADTAA QITQRKWEAA REAEQRRAYL EGECVEWLRR YLENGKDKLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 49          moltype = AA  length = 276
FEATURE                Location/Qualifiers
source                 1..276
                       mol_type = protein
                       organism = Homo sapiens
SEQUENCE: 49
GSHSMRYFYT AVSRPGRGEP RFISVGYVDD TQFVRFDSDA ASPREEPRAP WIEQEGPEYW  60
DRNTQICKTN TQTDRESLRN LRGCYNQSEA GSHTLQWMYG CDVGPDGRLL RGYNQFAYDG  120
KDYIALNEDL SSWTAADTAA QITQRKWEAA REAEQLRAYL EGTCVEWLRR HLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 50          moltype = AA  length = 276
FEATURE                Location/Qualifiers
source                 1..276
                       mol_type = protein
                       organism = Homo sapiens
SEQUENCE: 50
GSHSMRYFHT SVSRPGRGEP RFISVGYVDG TQFVRFDSDA ASPRTEPRAP WIEQEGPEYW  60
DRNTQISKTN TQTYRESLRN LRGCYNQSEA GSHTLQRMYG CDVGPDGRLL RGHDQSAYDG  120
KDYIALNEDL SSWTAADTAA QITQRKWEAA RVAEQLRAYL EGTCVEWLRR HLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 51          moltype = AA  length = 276
FEATURE                Location/Qualifiers
source                 1..276
                       mol_type = protein
                       organism = Homo sapiens
SEQUENCE: 51
GSHSMRYFHT SVSRPGRGEP RFITVGYVDD TLFVRFDSDA ASPREEPRAP WIEQEGPEYW  60
DRETQICKAK AQTDRENLRI ALRCYNQSEA GSHTLQNMYG CDVGPDGRLL RGYHQDAYDG  120
KDYIALNEDL SSWTAADTAA QITQRKWEAA RVAEQLRAYL EGECVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 52          moltype = AA  length = 276
FEATURE                Location/Qualifiers
source                 1..276
                       mol_type = protein
                       organism = Homo sapiens
SEQUENCE: 52
GSHSMRYFYT SVSRPGRGEP RFISVGYVDD TQFVRFDSDA ASPREEPRAP WIEQEGPEYW  60
DRNTQICKTN TQTDRESLRN LRGCYNQSEA GSHTLQRMYG CDVGPDGRLL RGHNQFAYDG  120
KDYIALNEDL SSWTAADTAA QITQRKWEAA RVAEQLRTYL EGTCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 53          moltype = AA  length = 276
FEATURE                Location/Qualifiers
source                 1..276
                       mol_type = protein
                       organism = Homo sapiens
SEQUENCE: 53
GSHSMRYFHT AMSRPGRGEP RFITVGYVDD TLFVRFDSDA TSPRKEPRAP WIEQEGPEYW  60
DRETQISKTN TQTYRESLRN LRGCYNQSEA GSHTLQRMYG CDVGPDGRLL RGHNQYAYDG  120
```

-continued

```
KDYIALNEDL RSWTAADTAA QISQRKLEAA RVAEQLRAYL EGECVEWLRR YLENGKDKLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 54          moltype = AA  length = 276
FEATURE                Location/Qualifiers
source                 1..276
                       mol_type = protein
                       organism = Homo sapiens
SEQUENCE: 54
GSHSMRYFYT AMSRPGRGEP RFITVGYVDD TLFVRFDSDA TSPRKEPRAP WIEQEGPEYW  60
DRETQISKTN TQTYRENLRT ALRCYNQSEA GSHIIQRMYG CDVGPDGRLL RGYDQDAYDG  120
KDYIALNEDL SSWTAADTAA QITQRKWEAA RVAEQDRAYL EGLCVESLRR YLENGKETLQ  180
RADPPKTHVT HHPISDHEVT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 55          moltype = AA  length = 276
FEATURE                Location/Qualifiers
source                 1..276
                       mol_type = protein
                       organism = Homo sapiens
SEQUENCE: 55
GSHSMRYFYT AMSRPGRGEP RFIAVGYVDD TQFVRFDSDA ASPRMAPRAP WIEQEGPEYW  60
DRETQKYKRQ AQTDRVSLRN LRGCYNQSEA GSHTLQRMYG CDVGPDGRLL RGHDQSAYDG  120
KDYIALNEDL SSWTAADTAA QITQRKWEAA REAEQWRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 56          moltype = AA  length = 276
FEATURE                Location/Qualifiers
source                 1..276
                       mol_type = protein
                       organism = Homo sapiens
SEQUENCE: 56
GSHSMRYFHT AMSRPGRGEP RFITVGYVDD TLFVRFDSDA TSPRKEPRAP WIEQEGPEYW  60
DRETQISKTN TQTYRESLRN LRGCYNQSEA GSHTWQRMYG CDLGPDGRLL RGYNQLAYDG  120
KDYIALNEDL SSWTAADTAA QITQRKWEAA REAEQLRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 57          moltype = AA  length = 276
FEATURE                Location/Qualifiers
source                 1..276
                       mol_type = protein
                       organism = Homo sapiens
SEQUENCE: 57
GSHSMRYFYT AMSRPGRGEP RFIAVGYVDD TQFVRFDSDA ASPRMAPRAP WIEQEGPEYW  60
DGETRNMKAS AQTYRENLRI ALRCYNQSEA GSHIIQVMYG CDVGPDGRLL RGHDQSAYDG  120
KDYIALNEDL SSWTAADTAA QITQRKWEAA RVAEQLRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 58          moltype = AA  length = 276
FEATURE                Location/Qualifiers
source                 1..276
                       mol_type = protein
                       organism = Homo sapiens
SEQUENCE: 58
GSHSMRYFYT AMSRPGRGEP RFIAVGYVDD TQFVRFDSDA ASPRTEPRAP WIEQEGPEYW  60
DGETRNMKAS AQTYRENLRI ALRCYNQSEA GSHIIQRMYG CDLGPDGRLL RGHDQSAYDG  120
KDYIALNEDL SSWTAADTAA QITQRKWEAA RVAEQLRAYL EGLCVEWLRR YLENGKETLQ  180
RADPPKTHVT HHPVSDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 59          moltype = AA  length = 276
FEATURE                Location/Qualifiers
source                 1..276
                       mol_type = protein
                       organism = Homo sapiens
SEQUENCE: 59
CSHSMRYFYT AVSRPSRGEP HFIAVGYVDD TQFVRFDSDA ASPRGEPRAP WVEQEGPEYW  60
DRETQKYKRQ AQTDRVNLRK LRGCYNQSEA GSHTLQRMYG CDLGPDGRLL RGYDQSAYDG  120
KDYIALNEDL RSWTAADTAA QITQRKWEAA REAEQWRAYL EGECVEWLRR YLENGKETLQ  180
RAEHPKTHVT HHPVSDHEAT LRCWALGFYP TEITLTWQRD GEDQTQDTEL VETRPAGDGT  240
FQKWAAVVVP SGEEQRYTCH VQHEGLPEPL TLRWEP                            276

SEQ ID NO: 60          moltype = AA  length = 276
FEATURE                Location/Qualifiers
source                 1..276
```

```
                         mol_type = protein
                         organism = Homo sapiens
SEQUENCE: 60
GSHSMRYFYT AVSRPGRGEP HFIAVGYVDD TQFVRFDSDA ASPRGEPRAP WVEQEGPEYW  60
DRETQKYKRQ AQTDRVSLRN LRGCYNQSEA GSHIIQRMYG CDVGPDGRLL RGYDQYAYDG  120
KDYIALNEDL RSWTAADTAA QITQRKWEAA REAEQLRAYL EGLCVEWLRR YLKNGKETLQ  180
RAEHPKTHVT HHPVSDHEAT LRCWALGFYP AEITLTWQWD GEDQTQDTEL VETRPAGDGT  240
FQKWAAVVVP SGEEQRYTCH VQHEGLPEPL TLRWEP                           276

SEQ ID NO: 61            moltype = AA  length = 276
FEATURE                  Location/Qualifiers
source                   1..276
                         mol_type = protein
                         organism = Homo sapiens
SEQUENCE: 61
CSHSMRYFYT AVSRPGRGEP RFIAVGYVDD TQFVQFDSDA ASPRGEPRAP WVEQEGPEYW  60
DRETQKYKRQ AQTDRVNLRK LRGCYNQSEA GSHTLQRMYG CDLGPDGRLL RGYNQFAYDG  120
KDYIALNEDL RSWTAADKAA QITQRKWEAA REAEQRRAYL EGTCVEWLRR YLENGKKTLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWGP                           276

SEQ ID NO: 62            moltype = AA  length = 276
FEATURE                  Location/Qualifiers
source                   1..276
                         mol_type = protein
                         organism = Homo sapiens
SEQUENCE: 62
CSHSMRYFDT AVSRPGRGEP RFISVGYVDD TQFVRFDSDA ASPRGEPRAP WVEQEGPEYW  60
DRETQNYKRQ AQADRVSLRN LRGCYNQSED GSHTLQRMYG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                           276

SEQ ID NO: 63            moltype = AA  length = 276
FEATURE                  Location/Qualifiers
source                   1..276
                         mol_type = protein
                         organism = Homo sapiens
SEQUENCE: 63
GSHSMRYFYT SVSRPGRGEP RFIAVGYVDD TQFVRFDSDA ASQRMEPRAP WIEQEGPEYW  60
DQETRNVKAQ SQTDRVDLGT LRGCYNQSED GSHTIQIMYG CDVGPDGRFL RGYRQDAYDG  120
KDYIALNEDL RSWTAADMAA QITKRKWEAA HAAEQQRAYL EGRCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                           276

SEQ ID NO: 64            moltype = AA  length = 276
FEATURE                  Location/Qualifiers
source                   1..276
                         mol_type = protein
                         organism = Homo sapiens
SEQUENCE: 64
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITQRKWEAA RVAEQLRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEP                           276

SEQ ID NO: 65            moltype = AA  length = 276
FEATURE                  Location/Qualifiers
source                   1..276
                         mol_type = protein
                         organism = Homo sapiens
SEQUENCE: 65
GSHSMRYFST SVSRPGSGEP RFIAVGYVDD TQFVRFDSDA ASQRMEPRAP WIEQERPEYW  60
DQETRNVKAQ SQTDRVDLGT LRGCYNQSEA GSHTIQIMYG CDVGSDGRFL RGYEQHAYDG  120
KDYIALNEDL RSWTAADMAA QITQRKWEAA RWAEQLRAYL EGTCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                           276

SEQ ID NO: 66            moltype = AA  length = 276
FEATURE                  Location/Qualifiers
source                   1..276
                         mol_type = protein
                         organism = Homo sapiens
SEQUENCE: 66
GSHSMRYFTT SVSRPGRGEP RFIAVGYVDD TQFVRFDSDA ASQRMEPRAP WIEQEGPEYW  60
DRNTRNVKAH SQIDRVDLGT LRGCYNQSEA GSHTIQMMYG CDVGSDGRFL RGYQQDAYDG  120
KDYIALNEDL RSWTAADMAA QITQRKWEAA RVAEQLRAYL EGTCVEWLRR YLENGKETLQ  180
RTDPPKTHMT HHAVSDHEAT LRCWALSFYP AEITLTWQRD GEDQTQDTEL VETRPAGDGT  240
```

-continued

```
FQKWASVVVP SGQEQRYTCH VQHEGLPKPL TLRWEP                        276

SEQ ID NO: 67           moltype = AA  length = 276
FEATURE                 Location/Qualifiers
source                  1..276
                        mol_type = protein
                        organism = Homo sapiens
SEQUENCE: 67
GSHSMRYFDT AMSRPGRGEP RFISVGYVDD TQFVRFDSDA ASPREEPRAP WIEQEGPEYW  60
DRNTQIFKTN TQTDRESLRN LRGCYNQSEA GSHTLQSMYG CDVGPDGRLL RGHNQYAYDG  120
KDYIALNEDL RSWTAADTAA QITQRKWEAA RVAEQDRAYL EGTCVEWLRR YLENGKDTLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                        276

SEQ ID NO: 68           moltype = AA  length = 276
FEATURE                 Location/Qualifiers
source                  1..276
                        mol_type = protein
                        organism = Homo sapiens
SEQUENCE: 68
GSHSMRYFYT AMSRPGRGEP RFIAVGYVDD TQFVRFDSDA ASPRMAPRAP WIEQEGPEYW  60
DRETQISKTN TQTYRESLRN LRGCYNQSEA GSHTLQRMYG CDVGPDGRLL RGHDQSAYDG  120
KDYIALNEDL SSWTAADTAA QITQRKWEAA REAEQWRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                        276

SEQ ID NO: 69           moltype = AA  length = 276
FEATURE                 Location/Qualifiers
source                  1..276
                        mol_type = protein
                        organism = Homo sapiens
SEQUENCE: 69
GSHSMRYFYT AMSRPGRGEP RFISVGYVDD TQFVRFDSDA ASPREEPRAP WIEQEGPEYW  60
DRETQISKTN TQTYRESLRN LRGCYNQSEA GSHTLQRMYG CDVGPDGRLL RGHDQSAYDG  120
KDYIALNEDL SSWTAADTAA QITQRKWEAA REAEQLRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                        276

SEQ ID NO: 70           moltype = AA  length = 276
FEATURE                 Location/Qualifiers
source                  1..276
                        mol_type = protein
                        organism = Homo sapiens
SEQUENCE: 70
GSHSMRYFYT AMSRPGRGEP RFIAVGYVDD TQFVRFDSDA ASPRTEPRAP WIEQEGPEYW  60
DRNTQIFKTN TQTYRESLRN LRGCYNQSEA GSHIIQRMYG CDLGPDGRLL RGHDQSAYDG  120
KDYIALNEDL SSWTAADTAA QITQRKWEAA RVAEQLRAYL EGLCVEWLRR YLENGKETLQ  180
RADPPKTHVT HHPVSDHEAT LRCWALGFYP AEITLTWQRD GEDQTQDTEL VETRPAGDRT  240
FQKWAAVVVP SGEEQRYTCH VQHEGLPKPL TLRWEP                        276

SEQ ID NO: 71           moltype = AA  length = 276
FEATURE                 Location/Qualifiers
source                  1..276
                        mol_type = protein
                        organism = Homo sapiens
SEQUENCE: 71
GSHSMRYFHT SVSRPGRGEP RFITVGYVDD TLFVRFDSDA TSPRKEPRAP WIEQEGPEYW  60
DRETQISKTN TQTYRESLRN LRGCYNQSEA GSHTLQSMYG CDVGPDGRLL RGHNQYAYDG  120
KDYIALNEDL RSWTAADTAA QITQRKWEAA RVAEQLRAYL EGECVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                        276

SEQ ID NO: 72           moltype = AA  length = 276
FEATURE                 Location/Qualifiers
source                  1..276
                        mol_type = protein
                        organism = Homo sapiens
SEQUENCE: 72
GSHSMRYFYT SVSRPGRGEP RFISVGYVDD TQFVRFDSDA ASPREEPRAP WIEQEGPEYW  60
DRNTQIYKAQ AQTDRESLRN LRGCYNQSEA GSHTLQSMYG CDVGPDGRLL RGHNQYAYDG  120
KDYIALNEDL RSWTAADTAA QITQRKWEAA RVAEQDRAYL EGTCVEWLRR YLENGKDTLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                        276

SEQ ID NO: 73           moltype = AA  length = 276
FEATURE                 Location/Qualifiers
source                  1..276
                        mol_type = protein
                        organism = Homo sapiens
```

```
SEQUENCE: 73
GSHSMRYFYT AMSRPGRGEP RFITVGYVDD TLFVRFDSDA TSPRKEPRAP WIEQEGPEYW  60
DRETQISKTN TQTYRENLRT ALRCYNQSEA GSHIIQRMYG CDVGPDGRLL RGYDQDAYDG  120
KDYIALNEDL SSWTAADTAA QITQRKWEAA RVAEQLRAYL EGLCVESLRR YLENGKETLQ  180
RADPPKTHVT HHPISDHEVT LRCWALGFYP AEITLTWQRD GEDQTQDTEL VETRPAGDRT  240
FQKWAAVVVP SGEEQRYTCH VQHEGLPKPL TLRWEP                           276

SEQ ID NO: 74          moltype = AA  length = 276
FEATURE                Location/Qualifiers
source                 1..276
                       mol_type = protein
                       organism = Homo sapiens
SEQUENCE: 74
GSHSMRYFYT AMSRPGRGEP RFIAVGYVDD TQFVRFDSDA ASPRTEPRAP WIEQEGPEYW  60
DRNTQIFKTN TQTYRENLRI ALRCYNQSEA GSHTWQTMYG CDVGPDGRLL RGHNQYAYDG  120
KDYIALNEDL SSWTAADTAA QITQRKWEAA REAEQLRAYL EGLCVEWLRR HLENGKETLQ  180
RADPPKTHVT HHPVSDHEAT LRCWALGFYP AEITLTWQRD GEDQTQDTEL VETRPAGDRT  240
FQKWAAVVVP SGEEQRYTCH VQHEGLPKPL TLRWEP                           276

SEQ ID NO: 75          moltype = AA  length = 276
FEATURE                Location/Qualifiers
source                 1..276
                       mol_type = protein
                       organism = Homo sapiens
SEQUENCE: 75
GSHSMRYFYT AMSRPGRGEP RFIAVGYVDD TQFVRFDSDA ASPRTEPRAP WIEQEGPEYW  60
DRNTQIFKTN TQTYRENLRI ALRCYNQSEA GSHIIQRMYG CDLGPDGRLL RGHDQSAYDG  120
KDYIALNEDL SSWTAADTAA QITQRKWEAA RVAEQLRAYL EGLCVEWLRR YLENGKETLQ  180
RADPPKTHVT HHPVSDHEAT LRCWALGFYP AEITLTWQRD GEDQTQDTEL VETRPAGDRT  240
FQKWAAVVVP SGEEQRYTCH VQHEGLPKPL TLRWEP                           276

SEQ ID NO: 76          moltype = AA  length = 276
FEATURE                Location/Qualifiers
source                 1..276
                       mol_type = protein
                       organism = Homo sapiens
SEQUENCE: 76
CSHSMKYFFT SVSRPGRGEP RFISVGYVDD TQFVRFDSDA ASPRGEPRAP WVEQEGPEYW  60
DRETQKYKRQ AQTDRVSLRN LRGCYNQSEA GSHTLQWMCG CDLGPDGRLL RGYDQYAYDG  120
KDYIALNEDL RSWTAADTAA QITQRKWEAA REAEQRRAYL EGTCVEWLRR YLENGKETLQ  180
RAEHPKTHVT HHPVSDHEAT LRCWALGFYP AEITLTWQWD GEDQTQDTEL VETRPAGDGT  240
FQKWAAVMVP SGEEQRYTCH VQHEGLPEPL TLRWEP                           276

SEQ ID NO: 77          moltype = AA  length = 276
FEATURE                Location/Qualifiers
source                 1..276
                       mol_type = protein
                       organism = Homo sapiens
SEQUENCE: 77
GSHSMRYFST SVSWPGRGEP RFIAVGYVDD TQFVRFDSDA ASPRGEPREP WVEQEGPEYW  60
DRETQKYKRQ AQADRVNLRK LRGCYNQSED GSHTLQRMFG CDLGPDGRLL RGYNQFAYDG  120
KDYIALNEDL RSWTAADTAA QITQRKWEAA REAEQRRAYL EGTCVEWLRR YLENGKETLQ  180
RAEHPKTHVT HHPVSDHEAT LRCWALGFYP AEITLTWQWD GEDQTQDTEL VETRPAGDGT  240
FQKWAAVVVP SGEEQRYTCH VQHEGLPEPL TLRWKP                           276

SEQ ID NO: 78          moltype = AA  length = 275
FEATURE                Location/Qualifiers
source                 1..275
                       mol_type = protein
                       organism = Homo sapiens
SEQUENCE: 78
CSHSMRYFDT AVSRPGRGEP RFISVGYVDD TQFVRFDSDA ASPRGEPRAP WVEQEGPEYW  60
DRETQKYKRQ AQADRVNLRK LRGCYNQSED GSHTLQWMYG CDLGPDGRLL RGYDQSAYDG  120
KDYIALNEDL RSWTAADTAA QITQRKWEAA REAEQWRAYL EGTCVEWLRR YLENGKETLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWE                            275

SEQ ID NO: 79          moltype = AA  length = 276
FEATURE                Location/Qualifiers
source                 1..276
                       mol_type = protein
                       organism = Homo sapiens
SEQUENCE: 79
CSHSMRYFDT AVSRPGRGEP RFISVGYVDD TQFVRFDSDA ASPRGEPRAP WVEQEGPEYW  60
DRETQKYKRQ AQADRVSLRN LRGCYNQSED GSHTLQRMSG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                           276
```

-continued

```
SEQ ID NO: 80           moltype = AA  length = 276
FEATURE                 Location/Qualifiers
source                  1..276
                        mol_type = protein
                        organism = Homo sapiens
SEQUENCE: 80
CSHSMRYFYT AVSRPGRGEP RFIAVGYVDD TQFVRFDSDA ASPRGEPRAP WVEQEGPEYW  60
DRETQKYKRQ AQTDRVSLRN LRGCYNQSEA GSHTLQWMYG CDLGPDGRLL RGYDQSAYDG  120
KDYIALNEDL RSWTAADTAA QITQRKWEAA RAAEQQRAYL EGTCVEWLRR YLENGKETLQ  180
RAEHPKTHVT HHLVSDHEAT LRCWALGFYP AEITLTWQRD GEDQTQDTEL VETRPAGDGT  240
FQKWAAVVVP SGEEQRYTCH VQHEGLPEPL TLRWEP                          276

SEQ ID NO: 81           moltype = AA  length = 276
FEATURE                 Location/Qualifiers
source                  1..276
                        mol_type = protein
                        organism = Homo sapiens
SEQUENCE: 81
GSHSMRYFYT SVSRPGRGEP RFIAVGYVDD TQFVRFDSDA ASQRMEPRAP WIEQEGPEYW  60
DRNTRNVKAH SQTDRESLRI ALRCYNQSED GSHTIQRMYG CDVGPDGRFL RGYQQDAYDG  120
KDYIALNEDL RSWTAADMAA QITQRKWETA HEAEQWRAYL EGRCVEWLRR YLENGKETLQ  180
RTDAPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                          276

SEQ ID NO: 82           moltype = AA  length = 276
FEATURE                 Location/Qualifiers
source                  1..276
                        mol_type = protein
                        organism = Homo sapiens
SEQUENCE: 82
GSHSMRYFYT SVSRPGRGEP RFIAVGYVDD TQFVRFDSDA ASQRMEPRAP WIEQEGPEYW  60
DRNTRNVKAH SQTDRANLGT LRGCYNQSED GSHTIQRMYG CDVGPDGRFL RGYQQDAYDG  120
KDYIALNEDL RSWTAADMAA QITQRKWETA HEAEQWRAYL EGRCVEWLRR YLENGKETLQ  180
RTDAPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                          276

SEQ ID NO: 83           moltype = AA  length = 276
FEATURE                 Location/Qualifiers
source                  1..276
                        mol_type = protein
                        organism = Homo sapiens
SEQUENCE: 83
GSHSMRYFTT SVSRPGRGEP RFIAVGYVDD TQFVRFDSDA ASQRMEPRAP WIEQEGPEYW  60
DLQTRNVKAQ SQTDRANLGT LRGCYNQSEA GSHTIQMMYG CDVGSDGRFL RGYRQDAYDG  120
KDYIALNEDL RSWTAADTAA QITQRKWEAA RVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                          276

SEQ ID NO: 84           moltype = AA  length = 276
FEATURE                 Location/Qualifiers
source                  1..276
                        mol_type = protein
                        organism = Homo sapiens
SEQUENCE: 84
GSHSMRYFYT SMSRPGRGEP RFIAVGYVDD TQFVRFDSDA ASQRMEPRAP WIEQEGPEYW  60
DRNTRNVKAQ SQTDRVDLGT LRGCYNQSEA GSHTIQRMYG CDVGPDGRFL RGYHQYAYDG  120
KDYIALKEDL RSWTAADMAA QTTKHKWEAA HVAEQWRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWVAVVVP SGQEQRYTCH VQHEGLPKPL TLRWEP                          276

SEQ ID NO: 85           moltype = AA  length = 276
FEATURE                 Location/Qualifiers
source                  1..276
                        mol_type = protein
                        organism = Homo sapiens
SEQUENCE: 85
GSHSMRYFYT AMSRPGRGEP RFITVGYVDD TQFVRFDSDA TSPRMAPRAP WIEQEGPEYW  60
DRETQISKTN TQTYRENLRT ALRCYNQSEA GSHTWQTMYG CDLGPDGRLL RGHNQLAYDG  120
KDYIALNEDL SSWTAADTAA QITQLKWEAA RVAEQLRAYL EGECVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                          276

SEQ ID NO: 86           moltype = AA  length = 276
FEATURE                 Location/Qualifiers
source                  1..276
                        mol_type = protein
                        organism = Homo sapiens
SEQUENCE: 86
GSHSMRYFYT AMSRPGRGEP RFIAVGYVDD TQFVRFDSDA ASPRMAPRAP WIEQEGPEYW  60
```

```
DRETQISKTN TQTYRESLRN LRGCYNQSEA GSHTLQSMYG CDVGPDGRLL RGHDQSAYDG  120
KDYIALNEDL SSWTAADTAA QITQRKWEAA REAEQWRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 87          moltype = AA  length = 276
FEATURE                Location/Qualifiers
source                 1..276
                       mol_type = protein
                       organism = Homo sapiens
SEQUENCE: 87
GSHSMRYFHT SVSRPGRGEP RFITVGYVDD TLFVRFDSDA ASPREEPRAP WIEQEGPEYW  60
DRETQICKAK AQTDREDLRT LLRCYNQSEA GSHTLQNMYG CDVGPDGRLL RGYHQDAYDG  120
KDYIALNEDL SSWTAADTAA QITQRKWEAA RVAEQLRAYL EGECVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 88          moltype = AA  length = 276
FEATURE                Location/Qualifiers
source                 1..276
                       mol_type = protein
                       organism = Homo sapiens
SEQUENCE: 88
GSHSMRYFYT AMSRPGRGEP RFIAVGYVDD TQFVRFDSDA ASPRTEPRAP WIEQEGPEYW  60
DRNTQIFKTN TQTYRESLRN LRGCYNQSEA GSHIIQRMYG CDLGPDGRLL RGHDQFAYDG  120
KDYIALNEDL SSWTAADTAA QITQRKWEAA RVAEQLRAYL EGLCVEWLRR YLENGKETLQ  180
RADPPKTHVT HHPVSDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 89          moltype = AA  length = 276
FEATURE                Location/Qualifiers
source                 1..276
                       mol_type = protein
                       organism = Homo sapiens
SEQUENCE: 89
GSHSMRYFHT SVSRPGRGEP RFISVGYVDD TQFVRFDSDA ASPRTEPRAP WIEQEGPEYW  60
DRETQISKTN TQTYREDLRT LLRCYNQSEA GSHTIQRMSG CDVGPDGRLL RGYNQFAYDG  120
KDYIALNEDL SSWTAADTAA QITQRKWEAA RVAEQDRAYL EGTCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 90          moltype = AA  length = 276
FEATURE                Location/Qualifiers
source                 1..276
                       mol_type = protein
                       organism = Homo sapiens
SEQUENCE: 90
GSHSMRYFYT SVSRPGRGEP RFISVGYVDD TQFVRFDSDA ASPREEPRAP WIEQEGPEYW  60
DRNTQICKTN TQTYRENLRI ALRCYNQSEA GSHTLQRMYG CDVGPDGRLL RGHNQFAYDG  120
KDYIALNEDL SSWTAADTAA QITQRKWEAA RVAEQLRTYL EGTCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 91          moltype = AA  length = 276
FEATURE                Location/Qualifiers
source                 1..276
                       mol_type = protein
                       organism = Homo sapiens
SEQUENCE: 91
GSHSMRYFHT AMSRPGRGEP RFITVGYVDD TLFVRFDSDA TSPRKEPRAP WIEQEGPEYW  60
DRETQISKTN TQTYRESLRN LRGCYNQSEA GSHTLQSMYG CDVGPDGRLL RGHNQYAYDG  120
KDYIALNEDL RSWTAADTAA QITQRKWEAA RVAEQDRAYL EGTCVEWLRR YLENGKDTLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 92          moltype = AA  length = 276
FEATURE                Location/Qualifiers
source                 1..276
                       mol_type = protein
                       organism = Homo sapiens
SEQUENCE: 92
GSHSMRYFYT AMSRPGRGEP RFITVGYVDD TLFVRFDSDA TSPRKEPRAP WIEQEGPEYW  60
DRETQISKTN TQTYRENLRT ALRCYNQSEA GSHIIQRMYG CDVGPDGRLL RGYDQYAYDG  120
KDYIALNEDL SSWTAADTAA QITQRKWEAA RVAEQDRAYL EGLCVESLRR YLENGKETLQ  180
RADPPKTHVT HHPISDHEVT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 93          moltype = AA  length = 276
FEATURE                Location/Qualifiers
```

-continued

```
source                 1..276
                       mol_type = protein
                       organism = Homo sapiens
SEQUENCE: 93
GSHSMRYFHT AMSRPGRGEP RFITVGYVDD TLFVRFDSDA TSPRKEPRAP WIEQEGPEYW  60
DRETQISKTN TQTYRENLRI ALRCYNQSEA GSHTWQRMYG CDLGPDGRLL RGYNQLAYDG  120
KDYIALNEDL SSWTAADTAA QITQRKWEAA REAEQLRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                          276

SEQ ID NO: 94          moltype = AA  length = 276
FEATURE                Location/Qualifiers
source                 1..276
                       mol_type = protein
                       organism = Homo sapiens
SEQUENCE: 94
GSHSMRYFYT AMSRPGRGEP RFIAVGYVDD TQFVRFDSDA ASPRTEPRAP WIEQEGPEYW  60
DRETQISKTN TQTYRENLRI ALRCYNQSEA GSHTWQTMYG CDVGPDGRLL RGHNQYAYDG  120
KDYIALNEDL SSWTAADTAA QITQRKWEAA REAEQLRAYL EGLCVEWLRR HLENGKETLQ  180
RADPPKTHVT HHPVSDHEAT LRCWALGFYP AEITLTWQRD GEDQTQDTEL VETRPAGDRT  240
FQKWAAVVVP SGEEQRYTCH VQHEGLPKPL TLRWEP                          276

SEQ ID NO: 95          moltype = AA  length = 276
FEATURE                Location/Qualifiers
source                 1..276
                       mol_type = protein
                       organism = Homo sapiens
SEQUENCE: 95
GSHSMRYFYT AMSRPGRGEP RFIAVGYVDD TQFVRFDSDA ASPREEPRAP WIEQEGPEYW  60
DRNTQIYKAQ AQTDRESLRN LRGCYNQSEA GSHTWQTMYG CDLGPDGRLL RGHNQLAYDG  120
KDYIALNEDL SSWTAADTAA QITQRKWEAA REAEQLRAYL EGTCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                          276

SEQ ID NO: 96          moltype = AA  length = 276
FEATURE                Location/Qualifiers
source                 1..276
                       mol_type = protein
                       organism = Homo sapiens
SEQUENCE: 96
GSHSMRYFYT AVSRPGRGEP HFIAVGYVDD TQFVRFDSDA ASPRGEPRAP WVEQEGPEYW  60
DRETQKYKRQ AQTDRVSLRN LRGCYNQSEA RSHIIQRMYG CDVGPDGRLL RGYDQYAYDG  120
KDYIALNEDL RSWTAADTAA QITQRKWEAA REAEQLRAYL EGLCVEWLRR YLKNGKETLQ  180
RAEHPKTHVT HHPVSDHEAT LRCWALGFYP AEITLTWQWD GEDQTQDTEL VETRPAGDGT  240
FQKWAAVVVP SGEEQRYTCH VQHEGLPEPL TLRWEP                          276

SEQ ID NO: 97          moltype = AA  length = 276
FEATURE                Location/Qualifiers
source                 1..276
                       mol_type = protein
                       organism = Homo sapiens
SEQUENCE: 97
CSHSMRYFDT AVSRPGRGEP RFISVGYVDD TQFVRFDSDA ASPRGEPRAP WVEQEGPEYW  60
DRETQKYKRQ AQADRVSLRN LRGCYNQSED GSHTFQRMYG CDLGPDGRLL RGYDQFAYDG  120
KDYIALNEDL RSWTAADTAA QITQRKLEAA RAAEQDRAYL EGTCVEWLRR YLENGKKTLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                          276

SEQ ID NO: 98          moltype = AA  length = 276
FEATURE                Location/Qualifiers
source                 1..276
                       mol_type = protein
                       organism = Homo sapiens
SEQUENCE: 98
CSHSMRYFYT AVSRPGRGEP RFIAVGYVDD TQFVQFDSDA ASPRGEPRAP WVEQEGPEYW  60
DRETQKYKRQ AQTDRVSLRN LRGCYNQSEA GSHTLQRMYG CDLGPDGRLL RGYNQFAYDG  120
KDYIALNEDL RSWTAADTAA QITQRKWEAA RTAEQLRAYL EGTCVEWLRR YLENGKKTLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWGP                          276

SEQ ID NO: 99          moltype = AA  length = 276
FEATURE                Location/Qualifiers
source                 1..276
                       mol_type = protein
                       organism = Homo sapiens
SEQUENCE: 99
CSHSMRYFYT AVSRPGRGEP RFIAVGYVDD TQFVQFDSDA ASPRGEPRAP WVEQEGPEYW  60
DRETQKYKRQ AQTDRVSLRN LRGCYNQSEA GSHTLQRMYG CDLGPDGRLL RGYNQFAYDG  120
KDYIALNEDL RSWTAADKAA QITQRKWEAA REAEQRRAYL EGTCVEWLRR YLENGKKTLQ  180
```

```
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWGP                            276

SEQ ID NO: 100         moltype = AA  length = 276
FEATURE                Location/Qualifiers
source                 1..276
                       mol_type = protein
                       organism = Homo sapiens
SEQUENCE: 100
CSHSMRYFYT AVSRPGRGEP RFIAVGYVDD TQFVRFDSDA ASPRGEPRAP WVEQEGPEYW  60
DRETQKYKRQ AQADRVSLRN LRGCYNQSEA GSHTLQRMYG CDLGPDGRLL RGYDQSAYDG  120
KDYIALNEDL RSWTAADTAA QITQRKWEAA REAEQWRAYL EGTCVEWLRR YLENGKETLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWEP                            276

SEQ ID NO: 101         moltype = AA  length = 276
FEATURE                Location/Qualifiers
source                 1..276
                       mol_type = protein
                       organism = Homo sapiens
SEQUENCE: 101
CSHSMRYFYT AVSRPGRGEP RFIAVGYVDD TQFVRFDSDA ASPRGEPRAP WVEQEGPEYW  60
DRETQKYKRQ AQADRVSLRN LRGCYNQSEA GSHTLQWMYG CDLGPDGRLL RGYDQSAYDG  120
KDYIALNEDL RSWTAADTAA QITQRKWEAA REAEQWRAYL EGTCVEWLRR YLENGKETLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWEP                            276

SEQ ID NO: 102         moltype = AA  length = 276
FEATURE                Location/Qualifiers
source                 1..276
                       mol_type = protein
                       organism = Homo sapiens
SEQUENCE: 102
CSHSMRYFST SVSRPGRGEP RFIAVGYVDD TQFVRFDSDA ASPRGEPRAP WVEQEGPEYW  60
DRETQKYKRQ AQTDRVSLRN LRGCYNQSEA GSHTLQWMFG CDLGPDGRLL RGYDQSAYDG  120
KDYIALNEDL RSWTAADTAA QITQRKWEAA REAEQRRAYL EGTCVEWLRR YLENGKETLQ  180
RAEHPKTHVT HHPVSDHEAT LRCWALGFYP AEITLTWQWD GEDQTQDTEL VETRPAGDGT  240
FQKWAAVVVP SGEEQRYTCH VQHEGLPEPL TLRWEP                            276

SEQ ID NO: 103         moltype = AA  length = 276
FEATURE                Location/Qualifiers
source                 1..276
                       mol_type = protein
                       organism = Homo sapiens
SEQUENCE: 103
CSHSMRYFYT AVSRPGRGEP HFIAVGYVDD TQFVRFDSDA ASPRGEPRAP WVEQEGPEYW  60
DRETQNYKRQ AQTDRVNLRK LRGCYNQSEA GSHIIQRMYG CDLGPDGRLL RGHDQLAYDG  120
KDYIALNEDL RSWTAADTAA QITQRKWEAA REAEQLRAYL EGTCVEWLRR YLENGKETLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWEP                            276

SEQ ID NO: 104         moltype = AA  length = 276
FEATURE                Location/Qualifiers
source                 1..276
                       mol_type = protein
                       organism = Homo sapiens
SEQUENCE: 104
GSHSMRYFYT AVSRPGRGEP RFIAVGYVDD TQFVRFDSDA ASPRGEPRAP WVEQEGPEYW  60
DRETQKYKRQ AQADRVNLRK LRGCYNQSEA GSHTIQRMYG CDLGPDGRLL RGYNQFAYDG  120
KDYIALNEDL RSWTAADTAA QISQRKLEAA REAEQLRAYL EGECVEWLRG YLENGKETLQ  180
RAERPKTHVT HHPVSDHEAT LRCWALGFYP AEITLTWQRD GEDQTQDTEL VETRPAGDGT  240
FQKWAAVVVP SGQEQRYTCH VQHEGLQEPC TLRWKP                            276

SEQ ID NO: 105         moltype = AA  length = 99
FEATURE                Location/Qualifiers
REGION                 1..99
                       note = Description of Unknown: Beta 2 microglobulin sequence
source                 1..99
                       mol_type = protein
                       organism = unidentified
SEQUENCE: 105
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDM                         99

SEQ ID NO: 106         moltype = DNA  length = 297
FEATURE                Location/Qualifiers
misc_feature           1..297
                       note = Description of Unknown: Beta 2 microglobulin sequence
source                 1..297
```

```
                         mol_type = other DNA
                         organism = synthetic construct
SEQUENCE: 106
atccagcgta ctccaaagat tcaggtttac tcacgtcatc cagcagagaa tggaaagtca  60
aatttcctga attgctatgt gtctgggttt catccatccg acattgaagt tgacttactg  120
aagaatggag agagaattga aaaagtggag cattcagact tgtctttcag caaggactgg  180
tctttctatc tcttgtacta cactgaattc acccccactg aaaaagatga gtatgcctgc  240
cgtgtgaacc atgtgacttt gtcacagccc aagatagtta agtgggatcg agacatg     297

SEQ ID NO: 107           moltype = AA  length = 99
FEATURE                  Location/Qualifiers
REGION                   1..99
                         note = Description of Artificial Sequence: Synthetic
                          polypeptide
source                   1..99
                         mol_type = protein
                         organism = synthetic construct
SEQUENCE: 107
IQRTPKIQVY SRHPAENGKS NFLNCYVSGF HPSDIEVDLL KNGERIEKVE HSDLSFSKDW  60
SFYLLYYTEF TPTEKDEYAC RVNHVTLCQP KIVKWDRDM                         99

SEQ ID NO: 108           moltype = DNA  length = 297
FEATURE                  Location/Qualifiers
misc_feature             1..297
                         note = Description of Artificial Sequence: Synthetic
                          polynucleotide
source                   1..297
                         mol_type = other DNA
                         organism = synthetic construct
SEQUENCE: 108
atccagcgta ctccaaagat tcaggtttac tcacgtcatc cagcagagaa tggaaagtca  60
aatttcctga attgctatgt gtctgggttt catccatccg acattgaagt tgacttactg  120
aagaatggag agagaattga aaaagtggag cattcagact tgtctttcag caaggactgg  180
tctttctatc tcttgtacta cactgaattc acccccactg aaaaagatga gtatgcctgc  240
cgtgtgaacc atgtgacttt gtgccagccc aagatagtta agtgggatcg agacatg     297

SEQ ID NO: 109           moltype = DNA  length = 828
FEATURE                  Location/Qualifiers
source                   1..828
                         mol_type = other DNA
                         organism = synthetic construct
SEQUENCE: 109
ggctcccact ccatgaggta tttcttcaca tccgtgtccc ggcccggccg cggggagccc  60
cgcttcatcg ccgtgggcta cgtggacgac acgcagttcg tgcggttcga cagcgacgcc  120
gcgagccaga agatggagcc gcgggcgccg tggatagagc aggaggggcc ggagtattgg  180
gaccaggaga cacggaatat gaaggcccac tcacagactg accgagcgaa cctggggacc  240
ctgcgcggct gctacaacca gagcgaggac ggttctcaca ccatccagat aatgtatggc  300
tgcgacgtgg ggccggacgg gcgcttcctc cgcgggtacc ggcaggacgc ctacgacggc  360
aaggattaca tcgccctgaa cgaggacctg cgctcttgga ccgcggcgga catggcagct  420
cagatcacca agcgcaagtg ggaggcggtc catgcggcgg agcagcggag agtctacctg  480
gagggccggt gcgtggacgg gctccgcaga tacctggaga acgggaagga gacgctgcag  540
cgcacggacc cccccaagac acatatgacc caccacccca tctctgacca tgaggccacc  600
ctgaggtgct gggccctggg cttctaccct gcggagatca cactgacctg gcagcgggat  660
ggggaggacc agacccagga cacggagctc gtggagacca ggcctgcagg ggatggaacc  720
ttccagaagt gggcggctgt ggtggtgcct tctggagagg agcagagata cacctgccat  780
gtgcagcatg agggtctgcc caagcccctc accctgagat gggagctg               828

SEQ ID NO: 110           moltype = DNA  length = 828
FEATURE                  Location/Qualifiers
source                   1..828
                         mol_type = other DNA
                         organism = synthetic construct
SEQUENCE: 110
ggctctcact ccatgaggta tttcttcaca tccgtgtccc ggcccggccg cggggagccc  60
cgcttcatcg cagtgggcta cgtggacgac acgcagttcg tgcggttcga cagcgacgcc  120
gcgagccaga ggatggagcc gcgggcgccg tggatagagc aggagggtcc cgagtattgg  180
gacggggaga cacggaaagt gaaggcccac tcacagactc accgagtgga cctggggacc  240
ctgcgcggct gctacaacca gagcgaggcc ggttctcaca ccgtccagag gatgtatggc  300
tgcgacgtgg ggtcggactg gcgcttcctc cgcgggtacc accagtacgc ctacgacggc  360
aaggattaca tcgccctgaa agaggacctg cgctcttgga ccgcggcgga catggcagct  420
cagaccacca agcacaagtg ggaggcggcc catgtggcgg agcagttgag agcctacctg  480
gagggcacgt gcgtggagtg gctccgcaga tacctggaga acgggaagga gacgctgcag  540
cgcacggacg cccccaaaac gcatatgact caccacgctg tctctgacca tgaagccacc  600
ctgaggtgct gggccctgag cttctaccct gcggagatca cactgacctg gcagcgggat  660
ggggaggacc agacccagga cacggagctc gtggagacca ggcctgcagg ggatggaacc  720
ttccagaagt gggcggctgt ggtggtgcct tctggacagg agcagagata cacctgccat  780
gtgcagcatg agggtttgcc caagcccctc accctgagat gggagccg               828

SEQ ID NO: 111           moltype = DNA  length = 828
```

```
FEATURE                Location/Qualifiers
source                 1..828
                       mol_type = other DNA
                       organism = synthetic construct
SEQUENCE: 111
ggctcccact ccatgaggta tttcttcaca tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccaggaga cacggaatgt gaaggcccag tcacagactg accgagtgga cctggggacc  240
ctgcgcggct gctacaacca gagcgaggcc ggttctcaca ccatccagat aatgtatggc  300
tgcgacgtgg ggtcggacgg gcgcttcctc cgcgggtacc ggcaggacgc ctacgacggc  360
aaggattaca tcgccctgaa cgaggacctg cgctcttgga ccgcggcgga catggcggct  420
cagatcacca agcgcaagtg ggaggcggcc catgaggcgg agcagttgag agcctacctg  480
gatggcacgt gcgtggagtg gctccgcaga tacctggaga acgggaagga gacgctgcag  540
cgcacggacc cccccaagac acatatgacc caccacccca tctctgacca tgaggccacc  600
ctgaggtgct gggccctggg cttctaccct gcggagatca cactgacctg gcagcgggat  660
ggggaggacc agacccagga cacggagctc gtggagacca ggcctgcagg ggatggaacc  720
ttccagaagt gggcggctgt ggtggtgcct tctggagagg agcagagata cacctgccat  780
gtgcagcatg agggtctgcc caagcccctc accctgagat gggagctg                828

SEQ ID NO: 112         moltype = DNA  length = 828
FEATURE                Location/Qualifiers
source                 1..828
                       mol_type = other DNA
                       organism = synthetic construct
SEQUENCE: 112
ggctcccact ccatgaggta tttctccaca tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gacgaggaga cagggaaagt gaaggcccac tcacagactg accgagagaa cctgcggatc  240
gcgctccgct gctacaacca gagcgaggcc ggttctcaca ccctccagat gatgtttggc  300
tgcgacgtgg ggtcggacgg gcgcttcctc cgcgggtacc accagtacgc ctacgacggc  360
aaggattaca tcgccctgaa agaggacctg cgctcttgga ccgcggcgga catggcggct  420
cagatcacca agcgcaagtg ggaggcggcc catgtggcgg agcagcagag agcctacctg  480
gagggcacgt gcgtggacgg gctccgcaga tacctggaga acgggaagga gacgctgcag  540
cgcacggacc cccccaagac acatatgacc caccacccca tctctgacca tgaggccact  600
ctgagatgct gggccctggg cttctaccct gcggagatca cactgacctg gcagcgggat  660
ggggaggacc agacccagga cacggagctt gtggagacca ggcctgcagg ggatggaacc  720
ttccagaagt gggcagctgt ggtggtacct tctggagagg agcagagata cacctgccat  780
gtgcagcatg agggtctgcc caagcccctc accctgagat gggagcca                828

SEQ ID NO: 113         moltype = DNA  length = 828
FEATURE                Location/Qualifiers
source                 1..828
                       mol_type = other DNA
                       organism = synthetic construct
SEQUENCE: 113
ggctcccact ccatgaggta tttctccaca tccgtgtccc ggcccggcag tggagagccc  60
cgcttcatcg cagtgggcta cgtggacgac acgcagttcg tgcggttcga cagcgacgcc  120
gcgagccaga ggatggagcc gcgggcgccg tggatagagc aggagaggcc tgagtattgg  180
gaccaggaga cacggaatgt gaaggcccac tcacagactg accgagagaa cctggggacc  240
ctgcgcggct gctacaacca gagcgaggcc ggttctcaca ccatccagat aatgtatggc  300
tgcgacgtgg ggtcggacgg gcgcttcctc cgcgggtatg aacagcacgc ctacgacggc  360
aaggattaca tcgccctgaa cgaggacctg cgctcttgga ccgcggcgga catggcggct  420
cagatcaccc agcgcaagtg ggaggcggcc cgtcgggcgg agcagttgag agcctacctg  480
gagggcacgt gcgtggagtg gctccgcaga tacctggaga acgggaagga gacgctgcag  540
cgcacggacc cccccaagac acatatgacc caccacccca tctctgacca tgaggccacc  600
ctgaggtgct gggccctggg cttctaccct gcggagatca cactgacctg gcagcgggat  660
ggggaggacc agacccagga cacggagctc gtggagacca ggcctgcagg ggatggaacc  720
ttccagaagt gggcggctgt ggtggtgcct tctggagagg agcagagata cacctgccat  780
gtgcagcatg agggtctgcc caagcccctc accctgagat gggagctg                828

SEQ ID NO: 114         moltype = DNA  length = 828
FEATURE                Location/Qualifiers
source                 1..828
                       mol_type = other DNA
                       organism = synthetic construct
SEQUENCE: 114
ggctcccact ccatgaggta tttcaccaca tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggagaggcc tgagtattgg  180
gaccaggaga cacggaatgt gaaggcccac tcacagattg accgagtgga cctggggacc  240
ctgcgcggct gctacaacca gagcgaggcc ggttctcaca ccatccagat gatgtatggc  300
tgcgacgtgg ggtcggacgg gcgcttcctc cgcgggtacc agcaggacgc ctacgacggc  360
aaggattaca tcgccttgaa cgaggacctg cgctcttgga ccgcggcgga catggcggct  420
cagatcaccc agcgcaagtg ggaggcggcc cgtgtggcgg agcagttgag agcctacctg  480
gagggcacgt gcgtggagtg gctccgcaga tacctggaga acgggaagga gacgctgcag  540
cgcacggacc cccccaagac gcatatgact caccacgctg tctctgacca tgaggccacc  600
ctgaggtgct gggccctgag cttctaccct gcggagatca cactgacctg gcagcgggat  660
```

-continued

```
ggggaggacc agacccagga cacggagctc gtggagacca ggcctgcagg ggatggaacc  720
ttccagaagt gggcgtctgt ggtggtgcct tctggacagg agcagagata cacctgccat  780
gtgcagcatg agggtctccc caagcccctc accctgagat gggagccg               828

SEQ ID NO: 115         moltype = DNA  length = 828
FEATURE                Location/Qualifiers
source                 1..828
                       mol_type = other DNA
                       organism = synthetic construct
SEQUENCE: 115
ggctcccact ccatgaggta tttcttcaca tccgtgtccc ggcccggccg cggggagccc  60
cgcttcatcg ccgtgggcta cgtggacgac acgcagttcg tgcggtttga cagcgacgcc  120
gcgagccaga ggatggagcc gcgggcgccg tggatagagc aggaggggcc ggagtattgg  180
gaccaggaga cacggaatgt gaaggcccac tcacagactg accgagagag cctgcggatc  240
gcgctccgct gctacaacca gagcgaggcc ggttctcaca ccatccagat gatgtatggc  300
tgcgacgtgg ggccggacgg gcgcctcctc cgcgggtacc agcaggacgc ctacgacggc  360
aaggattaca tcgccttgaa cgaggacctg cgctcttgga ccgcggcgga catggcggct  420
cagatcaccc agcgcaagtg ggaggcggcc cgtgtggcgg agcagttgag agcctacctg  480
gagggcacgt gcgtggagtg gctccgcaga tacctggaga acgggaagga gacgctgcag  540
cgcacggacg cccccaagac gcatatgact caccacgctg tctctgacca tgaggccacc  600
ctgaggtgct gggccctgag cttctaccct gcggagatca cactgacctg gcagcgggat  660
ggggaggacc agacccagga cacggagctt gtggagacca ggcctgcagg ggatggaacc  720
ttccagaagt gggcgtctgt ggtggtgcct tctggacagg agcagagata cacctgccat  780
gtgcagcatg agggtctgcc caagcccctc accctgagat gggagccg               828

SEQ ID NO: 116         moltype = DNA  length = 828
FEATURE                Location/Qualifiers
source                 1..828
                       mol_type = other DNA
                       organism = synthetic construct
SEQUENCE: 116
ggctcccact ccatgaggta tttcaccaca tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccggaaca cacggaatgt gaaggcccac tcacagattg accgagtgga cctggggacc  240
ctgcgcggct gctacaacca gagcgaggcc ggttctcaca ccatccagat gatgtatggc  300
tgcgacgtgg ggtcggacgg gcgcttcctc cgcgggtacc agcaggacgc ctacgacggc  360
aaggattaca tcgccttgaa cgaggacctg cgctcttgga ccgcggcgga catggcggct  420
cagatcaccc agcgcaagtg ggaggcggcc cgtgtggcgg agcagttgag agcctacctg  480
gagggcacgt gcgtggagtg gctccgcaga cacctggaga acgggaagga gacgctgcag  540
cgcacggacc cccccaggac gcatatgact caccacgctg tctctgacca tgaggccacc  600
ctgaggtgct gggccctgag cttctaccct gcggagatca cactgacctg gcagcgggat  660
ggggaggacc agacccagga cacggagctc gtggagacca ggcctgcagg ggatggaacc  720
ttccagaagt gggcgtctgt ggtggtgcct tctggacagg agcagagata cacctgccat  780
gtgcagcatg agggtctccc caagcccctc accctgagat gggagccg               828

SEQ ID NO: 117         moltype = DNA  length = 828
FEATURE                Location/Qualifiers
source                 1..828
                       mol_type = other DNA
                       organism = synthetic construct
SEQUENCE: 117
ggctcccact ccatgaggta tttctacacc tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccggaaca cacggaatgt gaaggcccag tcacagactg accgagtgga cctggggacc  240
ctgcgcggct gctacaacca gagcgaggcc ggttctcaca ccatccagat gatgtatggc  300
tgcgacgtgg ggtcggacgg gcgcttcctc cgcgggtacc ggcaggacgc ctacgacggc  360
aaggattaca tcgccctgaa agaggacctg cgctcttgga ccgcggcgga catggcagct  420
cagaccacca agcacaagtg ggaggcggcc catgtggcgg agcagtggag agcctacctg  480
gagggcacgt gcgtggagtg gctccgcaga tacctggaga acgggaagga gacgctgcag  540
cgcacggacg cccccaaaac gcatatgact caccacgctg tctctgacca tgaagccacc  600
ctgaggtgct gggccctgag cttctaccct gcggagatca cactgacctg gcagcgggat  660
ggggaggacc agacccagga cacggagctc gtggagacca ggcctgcagg ggatggaacc  720
ttccagaagt gggtggctgt ggtggtgcct tctggacagg agcagagata cacctgccat  780
gtgcagcatg agggtttgcc caagcccctc accctgagat gggagccg               828

SEQ ID NO: 118         moltype = DNA  length = 828
FEATURE                Location/Qualifiers
source                 1..828
                       mol_type = other DNA
                       organism = synthetic construct
SEQUENCE: 118
ggctcccact ccatgaggta tttctacacc tccgtgtccc ggcccggccg cggggagccc  60
cgcttcatct cagtgggcta cgtggacgac acccagttcg tgaggttcga cagcgacgcc  120
gcgagtccga gagaggagcc gcgggcgccg tggatagagc aggaggggcc ggagtattgg  180
gaccggaaca cacagatcta caaggcccag gcacagactg accgagagag cctgcggaac  240
ctgcgcggct gctacaacca gagcgaggcc gggtctcaca ccctccagag catgtacggc  300
tgcgacgtgg ggccggacgg gcgcctcctc cgcgggcatg accagtacgc ctacgacggc  360
```

```
aggattaca tcgccctgaa cgaggacctg cgctcctgga ccgccgcgga cacggcggct  420
cagatcaccc agcgcaagtg ggaggcggcc cgtgaggcgg agcagcggag agcctacctg  480
gagggcgagt gcgtggagtg gctccgcaga tacctggaga acgggaagga caagctggag  540
cgcgctgacc ccccaaagac acacgtgacc caccacccca tctctgacca tgaggccacc  600
ctgaggtgct gggccctggg tttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 119         moltype = DNA  length = 828
FEATURE                Location/Qualifiers
source                 1..828
                       mol_type = other DNA
                       organism = synthetic construct
SEQUENCE: 119
ggctcccact ccatgaggta tttctacacc gccgtgtccc ggcccggccg cggggagccc  60
cgcttcatct cagtgggcta cgtggacgac acgcagttcg tgaggttcga cagcgacgcc  120
gcgagtccga gagaggagcc gcgggcgccg tggatagagc aggaggggcc ggaatattgg  180
gaccggaaca cacagatctg caagaccaac acacagactg accgagagag cctgcggaac  240
ctgcgcggct gctacaacca gagcgaggcc gggtctcaca ccctccagtg gatgtatggc  300
tgcgacgtgg ggccggacgg gcgcctcctc cgcgggtata accagttcgc ctacgacggc  360
aaggattaca tcgccctgaa cgaggacctg agctcctgga ccgcggcgga caccgcggct  420
cagatcaccc agcgcaagtg ggaggcggcc cgtgaggcgg agcagctgag agcctacctg  480
gagggcacgt gcgtggagtg gctccgcaga cacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agacagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 120         moltype = DNA  length = 828
FEATURE                Location/Qualifiers
source                 1..828
                       mol_type = other DNA
                       organism = synthetic construct
SEQUENCE: 120
ggctcccact ccatgaggta tttccacacc tccgtgtccc ggcccggccg cggggagccc  60
cgcttcatct cagtgggcta cgtggacggc acccagttcg tgaggttcga cagcgacgcc  120
gcgagtccga ggacggagcc ccgggcgccg tggatagagc aagaggggcc ggagtattgg  180
gaccggaaca cacagatctc caagaccaac acacagactt accgagagag cctgcggaac  240
ctgcgcggct gctacaacca gagcgaggcc gggtctcaca ccctccagag gatgtacggc  300
tgcgacgtgg ggccggacgg gcgcctcctc cgcgggcatg accagtccgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag agcctacctg  480
gagggcacgt gcgtggagtg gctccgcaga cacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 121         moltype = DNA  length = 828
FEATURE                Location/Qualifiers
source                 1..828
                       mol_type = other DNA
                       organism = synthetic construct
SEQUENCE: 121
ggctcccact ccatgaggta tttccacacc tccgtgtccc ggcccggccg cggggagccc  60
cgcttcatca ccgtgggcta cgtggacgac acgctgttcg tgaggttcga cagcgacgcc  120
gcgagtccga gagaggagcc gcgggcgccg tggatagagc aggaggggcc ggagtattgg  180
gaccgggaga cacagatctg caaggccaag gcacagactg accgagagaa cctgcggatc  240
gcgctccgct gctacaacca gagcgaggcc gggtctcaca ccctccagaa tatgtatggc  300
tgcgacgtgg ggccggacgg gcgcctcctc cgcgggtacc accaggacgc ctacgacggc  360
aaggattaca tcgccctgaa cgaggacctg agctcctgga ccgccgcgga cacggcggct  420
cagatcaccc agcgcaagtg ggaggcggcc cgtgtggcgg agcagctgag agcctacctg  480
gagggcgagt gcgtggagtg gctccgcaga tacctggaga acgggaagga gacgctgcag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 122         moltype = DNA  length = 828
FEATURE                Location/Qualifiers
source                 1..828
                       mol_type = other DNA
                       organism = synthetic construct
SEQUENCE: 122
ggctcccact ccatgaggta tttctacacc tccgtgtccc ggcccggccg cggggagccc  60
```

```
cgcttcatct cagtgggcta cgtggacgac acgcagttcg tgaggttcga cagcgacgcc  120
gcgagtccga gagaggagcc gcgggcgccg tggatagagc aggaggggcc ggaatattgg  180
gaccggaaca cacagatctg caagaccaac acacagactg accgagagag cctgcggaac  240
ctgcgcggct gctacaacca gagcgaggcc gggtctcaca ccctccagag gatgtacggc  300
tgcgacgtgg ggccggacgg gcgcctcctc cgcgggcata accagttcgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag aacctacctg  480
gagggcacgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agacagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 123         moltype = DNA  length = 828
FEATURE                Location/Qualifiers
source                 1..828
                       mol_type = other DNA
                       organism = synthetic construct
SEQUENCE: 123
ggctcccact ccatgaggta tttccacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca ccctccagag gatgtacggc  300
tgcgacgtgg ggccggacgg gcgcctcctc cgcgggcata accagtacgc ctacgacggc  360
aaggattaca tcgccctgaa cgaggacctg cgctcctgga ccgccgcgga cacggcggct  420
cagatctccc agcgcaagtt ggaggcggcc cgtgtggcgg agcagctgag agcctacctg  480
gagggcgagt gcgtggagtg gctccgcaga tacctggaga acgggaagga caagctggag  540
cgcgctgacc ccccaaagac acacgtgacc caccacccca tctctgacca tgaggccacc  600
ctgaggtgct gggccctggg tttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 124         moltype = DNA  length = 828
FEATURE                Location/Qualifiers
source                 1..828
                       mol_type = other DNA
                       organism = synthetic construct
SEQUENCE: 124
ggctcccact ccatgaggta tttctacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagaa cctgcgcacc  240
gcgctccgct gctacaacca gagcgaggcc gggtctcaca tcatccagag gatgtacggc  300
tgcgacgtgg ggccggacgg gcgcctcctc cgcgggtatg accaggacgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcaggacag agcctacctg  480
gagggcctgt gcgtggagtc gctccgcaga tacctggaga acgggaagga gacgctgcag  540
cgcgcggacc ccccaaagac acatgtgacc caccacccca tctctgacca tgaggtcacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 125         moltype = DNA  length = 828
FEATURE                Location/Qualifiers
source                 1..828
                       mol_type = other DNA
                       organism = synthetic construct
SEQUENCE: 125
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggatggcgcc ccgggcgcca tggatagagc aggaggggcc ggagtattgg  180
gaccgggaga cacagaagta caagcgccag gcacagactg accgagtgag cctgcggaac  240
ctgcgcggct gctacaacca gagcgaggcc gggtctcaca ccctccagag gatgtacggc  300
tgcgacgtgg ggccggacgg gcgcctcctc cgcgggcatg accagtccgc ctacgacggc  360
aaggattaca tcgccctgaa cgaggacctg agctcctgga ccgcggcgga cacggcggct  420
cagatcaccc agcgcaagtg ggaggcggcc cgtgaggcgg agcagtggag agcctacctg  480
gagggcctgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 126         moltype = DNA  length = 828
FEATURE                Location/Qualifiers
```

```
source                  1..828
                        mol_type = other DNA
                        organism = synthetic construct
SEQUENCE: 126
ggctcccact ccatgaggta tttccacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca cttggcagag gatgtatggc  300
tgcgacctgg ggcccgacgg gcgcctcctc cgcgggtata accagttagc ctacgacggc  360
aaggattaca tcgccctgaa cgaggacctg agctcctgga ccgcggcgga caccgcggct  420
cagatcaccc agcgcaagtg ggaggcggcc cgtgaggcgg agcagctgag agcctacctg  480
gagggcctgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 127          moltype = DNA  length = 828
FEATURE                 Location/Qualifiers
source                  1..828
                        mol_type = other DNA
                        organism = synthetic construct
SEQUENCE: 127
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggatggcgcc ccgggcgcca tggatagagc aggaggggcc ggagtattgg  180
gacggggaga cacggaacat gaaggcctcc gcgcagactt accgagagaa cctgcggatc  240
gcgctccgct gctacaacca gagcgaggcc gggtctcaca tcatccaggt gatgtatggc  300
tgcgacgtgg ggccggacgg gcgcctcctc cgcgggcatg accagtccgc ctacgacggc  360
aaggattaca tcgccctgaa cgaggacctg agctcctgga ccgcggcgga cacggcggct  420
cagatcaccc agcgcaagtg ggaggcggcc cgtgtggcgg agcagctgag agcctacctg  480
gagggcctgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc aaagcccctc accctgagat gggagcca              828

SEQ ID NO: 128          moltype = DNA  length = 828
FEATURE                 Location/Qualifiers
source                  1..828
                        mol_type = other DNA
                        organism = synthetic construct
SEQUENCE: 128
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggacggagcc ccgggcgcca tggatagagc aggaggggcc ggagtattgg  180
gacggggaga cacggaacat gaaggcctcc gcgcagactt accgagagaa cctgcggatc  240
gcgctccgct gctacaacca gagcgaggcc gggtctcaca tcatccagag gatgtatggc  300
tgcgacctgg ggcccgacgg gcgcctcctc cgcgggcatg accagtccgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag agcctacctg  480
gagggcctgt gcgtggagtg gctccgcaga tacctggaga acgggaagga gacgctgcag  540
cgcgcggacc ccccaaagac acacgtgacc caccaccccg tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 129          moltype = DNA  length = 828
FEATURE                 Location/Qualifiers
source                  1..828
                        mol_type = other DNA
                        organism = synthetic construct
SEQUENCE: 129
tgctcccact ccatgaggta tttctacacc gctgtgtccc ggcccagccg cggagagccc  60
cacttcatcg cagtgggcta cgtggacgac acgcagttcg tgcggttcga cagcgacgcc  120
gcgagtccaa gaggggagcc gcgggcgccg tgggtggagc aggaggggcc ggagtattgg  180
gaccgggaga cacagaagta caagcgccag gcacagactg accgagtgaa cctgcggaaa  240
ctacgcggct gctacaacca gagcgaggcc gggtctcaca ccctccagag gatgtacggc  300
tgcgacctgg ggcccgacgg gcgcctcctc cgcgggtatg accagtccgc ctacgacggc  360
aaggattaca tcgccctgaa cgaggacctg cgctcctgga ccgccgcgga cacagcggct  420
cagatcaccc agcgcaagtg ggaggcggcc cgtgaggcgg agcagtggag agcctacctg  480
gagggcgagt gcgtggagtg gctccgcaga tacctggaga acgggaagga gacgctgcag  540
cgcgcggaac acccaaagac acacgtgacc caccatcccg tctctgacca tgaggccacc  600
ctgaggtgct gggccctggg cttctaccct acggagatca cactgacctg gcagcgggat  660
ggcgaggacc aaactcagga caccgagctt gtggagacca ggccagcagg agatggaacc  720
```

```
ttccagaagt gggcagctgt ggtggtgcct tctggagaag agcagagata cacgtgccat  780
gtgcagcacg aggggctgcc ggagcccctc accctgagat gggagcca               828

SEQ ID NO: 130          moltype = DNA  length = 828
FEATURE                 Location/Qualifiers
source                  1..828
                        mol_type = other DNA
                        organism = synthetic construct
SEQUENCE: 130
ggctcccact ccatgaggta tttctacacc gctgtgtccc ggcccggccg cggggagccc  60
cacttcatcg cagtgggcta cgtggacgac acgcagttcg tgcggttcga cagcgacgcc  120
gcgagtccga gaggggagcc gcgggcgccg tgggtggagc aggaggggcc ggagtattgg  180
gaccgggaga cacagaagta caagcgccag gcacagactg accgagtgag cctgcggaac  240
ctgcgcggct gctacaacca gagcgaggcc gggtctcaca tcatccagag gatgtatggc  300
tgcgacgtgg ggcccgacgg gcgcctcctc cgcgggtatg accagtacgc ctacgacggc  360
aaggattaca tcgccctgaa cgaggatctg cgctcctgga ccgccgcgga cacggcggct  420
cagatcaccc agcgcaagtg ggaggcggcc cgtgaggcgg agcagctgag agcctacctg  480
gagggcctgt gcgtggagtg gctccgcaga tacctgaaga atgggaagga gacgctgcag  540
cgcgcggaac acccaaagac acacgtgacc caccatcccg tctctgacca tgaggccacc  600
ctgaggtgct gggccctggg cttctaccct gcggagatca cactgacctg gcagtgggat  660
ggggaggacc aaactcagga cactgagctt gtggagacca ggccagcagg agatggaacc  720
ttccagaagt gggcagctgt ggtggtgcct tctggagaag agcagagata cacgtgccat  780
gtgcagcacg aggggctgcc ggagcccctc accctgagat gggagccg               828

SEQ ID NO: 131          moltype = DNA  length = 828
FEATURE                 Location/Qualifiers
source                  1..828
                        mol_type = other DNA
                        organism = synthetic construct
SEQUENCE: 131
tgctcccact ccatgaggta tttctacacc gccgtgtccc ggcccggccg cggagagccc  60
cgcttcatcg cagtgggcta cgtggacgac acgcagttcg tgcagttcga cagcgacgcc  120
gcgagtccaa gaggggagcc gcgggcgccg tgggtggagc aggaggggcc ggagtattgg  180
gaccgggaga cacagaagta caagcgccag gcacagactg accgagtgaa cctgcggaaa  240
ctgcgcggct gctacaacca gagcgaggcc gggtctcaca ccctccagag gatgtatggc  300
tgcgacctgg ggcccgacgg gcgcctcctc cgcgggtata accagttcgc ctacgacggc  360
aaggattaca tcgccctgaa tgaggacctg cgctcctgga ccgccgcgga caaggcggct  420
cagatcaccc agcgcaagtg ggaggcggcc cgtgaggcgg agcagcggag agcctacctg  480
gagggcacgt gcgtggagtg gctccgcaga tacctggaga acgggaagaa gacgctgcag  540
cgcgcggaac acccaaagac acacgtgacc caccatcccg tctctgacca tgaggccacc  600
ctgaggtgct gggccctggg cttctaccct gcggagatca cactgacctg gcagcgggat  660
ggcgaggacc aaactcagga caccgagctt gtggagacca ggccagcagg agatggaacc  720
ttccagaagt gggcagctgt ggtggtgcct tctggagaag agcagagata cacgtgccat  780
gtgcagcacg aggggctgcc agagcccctc accctgagat gggggcca               828

SEQ ID NO: 132          moltype = DNA  length = 828
FEATURE                 Location/Qualifiers
source                  1..828
                        mol_type = other DNA
                        organism = synthetic construct
SEQUENCE: 132
tgctcccact ccatgaggta tttcgacacc gccgtgtccc ggcccggccg cggagagccc  60
cgcttcatct cagtgggcta cgtggacgac acgcagttcg tgcggttcga cagcgacgcc  120
gcgagtccga gaggggagcc gcgggcgccg tgggtggagc aggaggggcc ggagtattgg  180
gaccgggaga cacagaacta caagcgccag gcacaggctg accgagtgag cctgcggaac  240
ctgcgcggct gctacaacca gagcgaggac gggtctcaca ccctccagag gatgtatggc  300
tgcgacctgg ggcccgacgg gcgcctcctc cgcgggtatg accagtccgc ctacgacggc  360
aaggattaca tcgccctgaa cgaggacctg cgctcctgga ccgccgcgga caccgcggct  420
cagatcaccc agcgcaagtt ggaggcggcc cgtgcggcgg agcagctgag agcctacctg  480
gagggcacgt gcgtggagtg gctccgcaga tacctggaga acgggaagga gacgctgcag  540
cgcgcagaac ccccaaagac acacgtgacc caccaccccc tctctgacca tgaggccacc  600
ctgaggtgct gggccctggg cttctaccct gcggagatca cactgacctg gcagcgggat  660
ggggaggacc agacccagga caccgagctt gtggagacca ggccagcagg agatggaacc  720
ttccagaagt gggcagctgt ggtggtgcct tctggacaag agcagagata cacgtgccat  780
atgcagcacg aggggctgca agagcccctc accctgagct gggagcca               828

SEQ ID NO: 133          moltype = DNA  length = 828
FEATURE                 Location/Qualifiers
source                  1..828
                        mol_type = other DNA
                        organism = synthetic construct
SEQUENCE: 133
ggctcccact ccatgaggta tttctacacc tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccaggaga cacggaatgt gaaggcccag tcacagactg accgagtgga cctggggacc  240
ctgcgcggct gctacaacca gagcgaggac ggttctcaca ccatccagat aatgtatggc  300
tgcgacgtgg ggccggacgg gcgcttcctc cgcgggtacc ggcaggacgc ctacgacggc  360
aaggattaca tcgccctgaa cgaggacctg cgctcttgga ccgcggcgga catggcagct  420
```

-continued

```
cagatcacca agcgcaagtg ggaggcggcc catgcggcgg agcagcagag agcctacctg  480
gagggccggt gcgtggagtg gctccgcaga tacctggaga acgggaagga gacgctgcag  540
cgcacggacc cccccaagac acatatgacc caccaccccca tctctgacca tgaggccacc  600
ctgaggtgct gggccctggg cttctaccct gcggagatca cactgacctg gcagcgggat  660
ggggaggacc agacccagga cacggagctc gtggagacca ggcctgcagg ggatggaacc  720
ttccagaagt gggcggctgt ggtggtgcct tctggagagg agcagagata cacctgccat  780
gtgcagcatg agggtctgcc caagcccctc accctgagat gggagctg              828

SEQ ID NO: 134         moltype = DNA  length = 828
FEATURE                Location/Qualifiers
source                 1..828
                       mol_type = other DNA
                       organism = synthetic construct
SEQUENCE: 134
ggctcccact ccatgaggta tttctccaca tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gacgaggaga cagggaaagt gaaggcccac tcacagactg accgagagaa cctgcggatc  240
gcgctccgct gctacaacca gagcgaggcc ggttctcaca ccctccagat gatgtttggc  300
tgcgacgtgg ggtcggacgg gcgcttcctc cgcgggtacc accagtacgc ctacgacggc  360
aaggattaca tcgccctgaa agaggacctg cgctcttgga ccgcggcgga catggcggct  420
cagatcaccc agcgcaagtg ggaggcggcc cgtgtggcgg agcagttgag agcctacctg  480
gagggcacgt gcgtggacgg gctccgcaga tacctggaga acgggaagga gacgctgcag  540
cgcacggacc cccccaagac acatatgacc caccaccccca tctctgacca tgaggccact  600
ctgagatgct gggccctggg cttctaccct gcggagatca cactgacctg gcagcgggat  660
ggggaggacc agacccagga cacggagctt gtggagacca ggcctgcagg ggatggaacc  720
ttccagaagt gggcagctgt ggtggtacct tctggagagg agcagagata cacctgccat  780
gtgcagcatg agggtctgcc caagcccctc accctgagat gggagcca              828

SEQ ID NO: 135         moltype = DNA  length = 828
FEATURE                Location/Qualifiers
source                 1..828
                       mol_type = other DNA
                       organism = synthetic construct
SEQUENCE: 135
ggctcccact ccatgaggta tttctccaca tccgtgtccc ggcccggcag tggagagccc  60
cgcttcatcg cagtgggcta cgtggacgac acgcagttcg tgcggttcga cagcgacgcc  120
gcgagccaga ggatggagcc gcgggcgccg tggatagagc aggagaggcc tgagtattgg  180
gaccaggaga cacggaatgt gaaggcccag tcacagactg accgagtgga cctggggacc  240
ctgcgcggct gctacaacca gagcgaggcc ggttctcaca ccatccagat aatgtatggc  300
tgcgacgtgg ggtcggacgg gcgcttcctc cgcgggtatg aacagcacgc ctacgacggc  360
aaggattaca tcgccctgaa cgaggacctg cgctcttgga ccgcggcgga catggcggct  420
cagatcaccc agcgcaagtg ggaggcggcc cgttgggcgg agcagttgag agcctacctg  480
gagggcacgt gcgtggagtg gctccgcaga tacctggaga acgggaagga gacgctgcag  540
cgcacggacc cccccaagac acatatgacc caccaccccca tctctgacca tgaggccacc  600
ctgaggtgct gggccctggg cttctaccct gcggagatca cactgacctg gcagcgggat  660
ggggaggacc agacccagga cacggagctc gtggagacca ggcctgcagg ggatggaacc  720
ttccagaagt gggcggctgt ggtggtgcct tctggagagg agcagagata cacctgccat  780
gtgcagcatg agggtctgcc caagcccctc accctgagat gggagctg              828

SEQ ID NO: 136         moltype = DNA  length = 828
FEATURE                Location/Qualifiers
source                 1..828
                       mol_type = other DNA
                       organism = synthetic construct
SEQUENCE: 136
ggctcccact ccatgaggta tttcaccaca tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccggaaca cacggaatgt gaaggcccac tcacagattg accgagtgga cctggggacc  240
ctgcgcggct gctacaacca gagcgaggcc ggttctcaca ccatccagat gatgtatggc  300
tgcgacgtgg ggtcggacgg gcgcttcctc cgcgggtacc agcaggacgc ctacgacggc  360
aaggattaca tcgccttgaa cgaggacctg cgctcttgga ccgcggcgga catggcggct  420
cagatcaccc agcgcaagtg ggaggcggcc cgtgtggcgg agcagttgag agcctacctg  480
gagggcacgt gcgtggagtg gctccgcaga tacctggaga acgggaagga gacgctgcag  540
cgcacggacc cccccaagac gcatatgact caccacgctg tctctgacca tgaggccacc  600
ctgaggtgct gggccctgag cttctaccct gcggagatca cactgacctg gcagcgggat  660
ggggaggacc agacccagga cacggagctc gtggagacca ggcctgcagg ggatggaacc  720
ttccagaagt gggcgtctgt ggtggtgcct tctggacagg agcagagata cacctgccat  780
gtgcagcatg agggtctccc caagcccctc accctgagat gggagccg              828

SEQ ID NO: 137         moltype = DNA  length = 828
FEATURE                Location/Qualifiers
source                 1..828
                       mol_type = other DNA
                       organism = synthetic construct
SEQUENCE: 137
ggctcccact ccatgaggta tttcgacacc gccatgtccc ggcccggccg cggggagccc  60
cgcttcatct cagtgggcta cgtggacgac acgcagttcg tgaggttcga cagcgacgcc  120
```

```
gcgagtccga gagaggagcc gcgggcgccg tggatagagc aggaggggcc ggagtattgg  180
gaccggaaca cacagatctt caagaccaac acacagactg accgagagag cctgcggaac  240
ctgcgcggct gctacaacca gagcgaggcc gggtctcaca ccctccagag catgtacggc  300
tgcgacgtgg ggccggacgg gcgcctcctc cgcgggcata accagtacgc ctacgacggc  360
aaggattaca tcgccctgaa cgaggacctg cgctcctgga ccgcggcgga caccgcggct  420
cagatcaccc agcgcaagtg ggaggcggcc cgtgtggcgg agcaggacag agcctacctg  480
gagggcacgt gcgtggagtg gctccgcaga tacctggaga acgggaagga cacgctggag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828
```

```
SEQ ID NO: 138         moltype = DNA  length = 828
FEATURE                Location/Qualifiers
source                 1..828
                       mol_type = other DNA
                       organism = synthetic construct
SEQUENCE: 138
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggatggcgcc ccgggcgcca tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca ccctccagag gatgtacggc  300
tgcgacgtgg ggccggacgg gcgcctcctc cgcgggcatg accagtccgc ctacgacggc  360
aaggattaca tcgccctgaa cgaggacctg agctcctgga ccgcggcgga cacggcggct  420
cagatcaccc agcgcaagtg ggaggcggcc cgtgaggcgg agcagtggag agcctacctg  480
gagggcctgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828
```

```
SEQ ID NO: 139         moltype = DNA  length = 828
FEATURE                Location/Qualifiers
source                 1..828
                       mol_type = other DNA
                       organism = synthetic construct
SEQUENCE: 139
ggctcccact ccatgaggta tttctacacc gccatgtccc ggcccggccg cggggagccc  60
cgcttcatct cagtgggcta cgtggacgac acgcagttcg tgaggttcga cagcgacgcc  120
gcgagtccga gagaggagcc gcgggcgccg tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca ccctccagag gatgtacggc  300
tgcgacgtgg ggccggacgg gcgcctcctc cgcgggcatg accagtccgc ctacgacggc  360
aaggattaca tcgccctgaa cgaggacctg agctcctgga ccgcggcgga cacggcggct  420
cagatcaccc agcgcaagtg ggaggcggcc cgtgaggcgg agcagctgag agcctacctg  480
gagggcctgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828
```

```
SEQ ID NO: 140         moltype = DNA  length = 828
FEATURE                Location/Qualifiers
source                 1..828
                       mol_type = other DNA
                       organism = synthetic construct
SEQUENCE: 140
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggacggagcc ccgggcgcca tggatagagc aggaggggcc ggagtattgg  180
gaccggaaca cacagatctt caagaccaac acacagactt accgagagag cctgcggaac  240
ctgcgcggct gctacaacca gagcgaggcc gggtctcaca tcatccagag gatgtatggc  300
tgcgacctgg ggcccgacgg gcgcctcctc cgcgggcatg accagtccgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag agcctacctg  480
gagggcctgt gcgtggagtg gctccgcaga tacctggaga acgggaagga gacgctgcag  540
cgcgcggacc ccccaaagac acacgtgacc caccaccccg tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828
```

```
SEQ ID NO: 141         moltype = DNA  length = 828
FEATURE                Location/Qualifiers
source                 1..828
```

```
                         mol_type = other DNA
                         organism = synthetic construct
SEQUENCE: 141
ggctcccact ccatgaggta tttccacacc tccgtgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca ccctccagag catgtacggc  300
tgcgacgtgg ggccggacgg gcgcctcctc cgcgggcata accagtacgc ctacgacggc  360
aaggattaca tcgccctgaa cgaggacctg cgctcctgga ccgccgcgga cacggcggct  420
cagatcaccc agcgcaagtg ggaggcggcc cgtgtggcgg agcagctgag agcctacctg  480
gagggcgagt gcgtggagtg gctccgcaga tacctggaga acgggaagga gacgctgcag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 142           moltype = DNA  length = 828
FEATURE                  Location/Qualifiers
source                   1..828
                         mol_type = other DNA
                         organism = synthetic construct
SEQUENCE: 142
ggctcccact ccatgaggta tttctacacc tccgtgtccc ggcccggccg cggggagccc  60
cgcttcatct cagtgggcta cgtggacgac acccagttcg tgaggttcga cagcgacgcc  120
gcgagtccga gagaggagcc gcgggcgccg tggatagagc aggaggggcc ggagtattgg  180
gaccggaaca cacagatcta caaggcccag gcacagactg accgagagag cctgcggaac  240
ctgcgcggct gctacaacca gagcgaggcc gggtctcaca ccctccagag catgtacggc  300
tgcgacgtgg ggccggacgg gcgcctcctc cgcgggcata accagtacgc ctacgacggc  360
aaggattaca tcgccctgaa cgaggacctg cgctcctgga ccgcggcgga caccgcggct  420
cagatcaccc agcgcaagtg ggaggcggcc cgtgtggcgg agcaggacag agcctacctg  480
gagggcacgt gcgtggagtg gctccgcaga tacctggaga acgggaagga cacgctggag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 143           moltype = DNA  length = 828
FEATURE                  Location/Qualifiers
source                   1..828
                         mol_type = other DNA
                         organism = synthetic construct
SEQUENCE: 143
ggctcccact ccatgaggta tttctacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagaa cctgcgcacc  240
gcgctccgct gctacaacca gagcgaggcc gggtctcaca tcatccagag gatgtacggc  300
tgcgacgtgg ggccggacgg gcgcctcctc cgcgggtatg accaggacgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag agcctacctg  480
gagggcctgt gcgtggagtc gctccgcaga tacctggaga acgggaagga gacgctgcag  540
cgcgcggacc ccccaaagac acatgtgacc caccacccca tctctgacca tgaggtcacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 144           moltype = DNA  length = 828
FEATURE                  Location/Qualifiers
source                   1..828
                         mol_type = other DNA
                         organism = synthetic construct
SEQUENCE: 144
ggctcccact ccatgaggta tttctacacc gccatgtccc ggcccggccg cggggagccc  60
cgcttcattg cagtgggcta cgtggacgac acccagttcg tgaggttcga cagcgacgcc  120
gcgagtccga ggacggagcc ccgggcgcca tggatagagc aggaggggcc ggagtattgg  180
gaccggaaca cacagatctt caagaccaac acacagactt accgagagaa cctgcggatc  240
gcgctccgct gctacaacca gagcgaggcc gggtctcaca cttggcagac gatgtatggc  300
tgcgacgtgg ggccggacgg gcgcctcctc cgcgggcata accagtacgc ctacgacggc  360
aaagattaca tcgccctgaa cgaggacctg agctcctgga ccgcggcgga caccgcggct  420
cagatcaccc agcgcaagtg ggaggcggcc cgtgaggcgg agcagctgag agcctacctg  480
gagggcctgt gcgtggagtg gctccgcaga cacctggaga acgggaagga gacgctgcag  540
cgcgcggacc ccccaaagac acacgtgacc caccaccccg tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
```

```
gtacagcatg aggggctgcc gaagcccctc accctgagat gggagcca              828

SEQ ID NO: 145          moltype = DNA  length = 828
FEATURE                 Location/Qualifiers
source                  1..828
                        mol_type = other DNA
                        organism = synthetic construct
SEQUENCE: 145
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggacggagcc ccgggcgcca tggatagagc aggaggggcc ggagtattgg  180
gaccggaaca cacagatctt caagaccaac acacagactt accgagagaa cctgcggatc  240
gcgctccgct gctacaacca gagcgaggcc gggtctcaca tcatccagag gatgtatggc  300
tgcgacctgg ggcccgacgg gcgcctcctc cgcgggcatg accagtccgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag agcctacctg  480
gagggcctgt gcgtggagtg gctccgcaga tacctggaga acgggaagga gacgctgcag  540
cgcgcggacc ccccaaagac acacgtgacc caccaccccg tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 146          moltype = DNA  length = 828
FEATURE                 Location/Qualifiers
source                  1..828
                        mol_type = other DNA
                        organism = synthetic construct
SEQUENCE: 146
tgctcccact ccatgaagta tttcttcaca tccgtgtccc ggcctggccg cggagagccc  60
cgcttcatct cagtgggcta cgtggacgac acgcagttcg tgcggttcga cagcgacgcc  120
gcgagtccga gaggggagcc gcgggcgccg tgggtggagc aggaggggcc ggagtattgg  180
gaccgggaga cacagaagta caagcgccag gcacagactg accgagtgag cctgcggaac  240
ctgcgcggct gctacaacca gagcgaggcc gggtctcaca ccctccagtg gatgtgtggc  300
tgcgacctgg ggcccgacgg gcgcctcctc cgcgggtatg accagtacgc ctacgacggc  360
aaggattaca tcgccctgaa cgaggacctg cgctcctgga ccgccgcgga caccgcggct  420
cagatcaccc agcgcaagtg ggaggcggcc cgtgaggcgg agcagcggag agcctacctg  480
gagggcacgt gcgtggagtg gctccgcaga tacctggaga acgggaagga gacgctgcag  540
cgcgcggaac acccaaagac acacgtgacc caccatcccg tctctgacca tgaggccacc  600
ctgaggtgct gggccctggg cttctaccct gcggagatca cactgacctg gcagtgggat  660
ggggaggacc aaactcagga caccgagctt gtggagacca ggccagcagg agatggaacc  720
ttccagaagt gggcagctgt gatggtgcct tctggagaag agcagagata cacgtgccat  780
gtgcagcacg aggggctgcc ggagcccctc accctgagat gggagccg              828

SEQ ID NO: 147          moltype = DNA  length = 828
FEATURE                 Location/Qualifiers
source                  1..828
                        mol_type = other DNA
                        organism = synthetic construct
SEQUENCE: 147
ggctcccact ccatgaggta tttctccaca tccgtgtcct ggcccggccg cggggagccc  60
cgcttcatcg cagtgggcta cgtggacgac acgcagttcg tgcggttcga cagcgacgcc  120
gcgagtccaa gaggggagcc gcgggagccg tgggtggagc aggaggggcc ggagtattgg  180
gaccgggaga cacagaagta caagcgccag gcacaggctg accgagtgaa cctgcggaaa  240
ctgcgcggct gctacaacca gagcgaggac gggtctcaca ccctccagag gatgtttggc  300
tgcgacctgg ggccggacgg gcgcctcctc cgcgggtata accagttcgc ctacgacggc  360
aaggattaca tcgccctgaa cgaggatctg cgctcctgga ccgccgcgga cacggcggct  420
cagatcaccc agcgcaagtg ggaggcggcc cgtgaggcgg agcagcggag agcctacctg  480
gagggcacgt gcgtggagtg gctccgcaga tacctggaga acgggaagga gacgctgcag  540
cgcgcggaac acccaaagac acacgtgacc caccatcccg tctctgacca tgaggccacc  600
ctgaggtgct gggccctggg cttctaccct gcggagatca cactgacctg gcagtgggat  660
ggggaggacc aaactcagga caccgagctt gtggagacca ggccagcagg agatggaacc  720
ttccagaagt gggcagctgt ggtggtgcct tctggagaag agcagagata cacgtgccat  780
gttcagcacg aggggctgcc ggagcccctc accctgagat ggaagccg              828

SEQ ID NO: 148          moltype = DNA  length = 828
FEATURE                 Location/Qualifiers
source                  1..828
                        mol_type = other DNA
                        organism = synthetic construct
SEQUENCE: 148
tgctcccact ccatgaggta tttcgacacc gccgtgtccc ggcccggccg cggagagccc  60
cgcttcatct cagtgggcta cgtggacgac acgcagttcg tgcggttcga cagcgacgcc  120
gcgagtccga gaggggagcc ccgggcgccg tgggtggagc aggaggggcc ggagtattgg  180
gaccgggaga cacagaagta caagcgccag gcacaggctg accgagtgaa cctgcggaaa  240
ctgcgcggct gctacaacca gagcgaggac gggtctcaca ccctccagtg gatgtatggc  300
tgcgacctgg ggcccgacgg gcgcctcctc cgcgggtatg accagtccgc ctacgacggc  360
aaggattaca tcgccctgaa cgaggacctg cgctcctgga ccgccgcgga cacggcggct  420
cagatcaccc agcgcaagtg ggaggcggcc cgtgaggcgg agcagtggag agcctacctg  480
```

```
gagggcacgt gcgtggagtg gctccgcaga tacctggaga acgggaagga gacgctgcag  540
cgcgcggaac acccaaagac acacgtgacc caccatcccg tctctgacca tgaggccacc  600
ctgaggtgct gggccctggg cttctaccct gcggagatca cactgacctg gcagcgggat  660
ggcgaggacc aaactcagga caccgagctt gtggagacca ggccagcagg agatggaacc  720
ttccagaagt gggcagctgt ggtggtgcct tctggagaag agcagagata cacgtgccat  780
gtgcagcacg aggggctgcc agagcccctc accctgagat gggagcca              828

SEQ ID NO: 149         moltype = DNA  length = 828
FEATURE                Location/Qualifiers
source                 1..828
                       mol_type = other DNA
                       organism = synthetic construct
SEQUENCE: 149
tgctcccact ccatgaggta tttcgacacc gccgtgtccc ggcccggccg cggagagccc  60
cgcttcatct cagtgggcta cgtggacgac acgcagttcg tgcggttcga cagcgacgcc  120
gcgagtccga gaggggagcc gcgggcgccg tgggtggagc aggaggggcc ggagtattgg  180
gaccgggaga cacagaagta caagcgccag gcacaggctg accgagtgag cctgcggaac  240
ctgcgcggct gctacaacca gagcgaggac gggtctcaca ccctccagag gatgtctggc  300
tgcgacctgg ggcccgacgg gcgcctcctc cgcgggtatg accagtccgc ctacgacggc  360
aaggattaca tcgccctgaa cgaggacctg cgctcctgga ccgccgcgga caccgcggct  420
cagatcaccc agcgcaagtt ggaggcggcc cgtgcggcgg agcagctgag agcctacctg  480
gagggcacgt gcgtggagtg gctccgcaga tacctggaga acgggaagga gacgctgcag  540
cgcgcagaac ccccaaagac acacgtgacc caccaccccc tctctgacca tgaggccacc  600
ctgaggtgct gggccctggg cttctaccct gcggagatca cactgacctg gcagcgggat  660
ggggaggacc agacccagga caccgagctt gtggagacca ggccagcagg agatggaacc  720
ttccagaagt gggcagctgt ggtggtgcct tctggacaag agcagagata cacgtgccat  780
atgcagcacg aggggctgca agagcccctc accctgagct gggagcca              828

SEQ ID NO: 150         moltype = DNA  length = 828
FEATURE                Location/Qualifiers
source                 1..828
                       mol_type = other DNA
                       organism = synthetic construct
SEQUENCE: 150
tgctcccact ccatgaggta tttctacacc gccgtgtccc ggcccggccg cggagagccc  60
cgcttcatcg cagtgggcta cgtggacgac acgcagttcg tgcggttcga cagcgacgcc  120
gcgagtccaa gaggggagcc gcgggcgccg tgggtggagc aggaggggcc ggagtattgg  180
gaccgggaga cacagaagta caagcgccag gcacagactg accgagtgag cctgcggaac  240
ctgcgcggct gctacaacca gagcgaggcc gggtctcaca ccctccagtg gatgtatggc  300
tgcgacctgg ggcccgacgg gcgcctcctc cgcgggtatg accagtccgc ctacgacggc  360
aaggattaca tcgccctgaa cgaggacctg cgctcctgga ccgccgcgga cacggcggct  420
cagatcaccc agcgcaagtg ggaggcggcc cgtgcggcgg agcagcagag agcctacctg  480
gagggcacgt gcgtggagtg gctccgcaga tacctggaga acgggaagga gacgctgcag  540
cgcgcggaac acccaaagac acacgtgacc caccatctcg tctctgacca tgaggccacc  600
ctgaggtgct gggccctggg cttctaccct gcggagatca cactgacctg gcagcgggat  660
ggcgaggacc aaactcagga caccgagctt gtggagacca ggccagcagg agatggaacc  720
ttccagaagt gggcagctgt ggtggtgcct tctggagaag agcagagata cacgtgccat  780
gtgcagcacg aggggctgcc ggagcccctc accctgagat gggagcca              828

SEQ ID NO: 151         moltype = DNA  length = 828
FEATURE                Location/Qualifiers
source                 1..828
                       mol_type = other DNA
                       organism = synthetic construct
SEQUENCE: 151
ggctcccact ccatgaggta tttctacacc tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccggaaca cacggaatgt gaaggcccac tcacagactg accgagagag cctgcggatc  240
gcgctccgct gctacaacca gagcgaggac ggttctcaca ccatccagag gatgtatggc  300
tgcgacgtgg ggccggacgg gcgcttcctc cgcgggtacc agcaggacgc ttacgacggc  360
aaggattaca tcgccctgaa cgaggacctg cgctcttgga ccgcggcgga catggcggct  420
cagatcaccc agcgcaagtg ggagacggcc catgaggcgg agcagtggag agcctacctg  480
gagggccggt gcgtggagtg gctccgcaga tacctggaga acgggaagga gacgctgcag  540
cgcacggacg cccccaagac gcatatgact caccacgctg tctctgacca tgaggccacc  600
ctgaggtgct gggccctgag cttctaccct gcggagatca cactgacctg gcagcgggat  660
ggggaggacc agacccagga cacggagctc gtggagacca ggcctgcagg ggatgggacc  720
ttccagaagt gggcgtctgt ggtggtgcct tctggacagg agcagagata cacctgccat  780
gtgcagcatg agggtctgcc caagcccctc accctgagat gggagccg              828

SEQ ID NO: 152         moltype = DNA  length = 828
FEATURE                Location/Qualifiers
source                 1..828
                       mol_type = other DNA
                       organism = synthetic construct
SEQUENCE: 152
ggctcccact ccatgaggta tttctacacc tccgtgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
```

```
gaccggaaca cacggaatgt gaaggcccac tcacagactg accgagcgaa cctggggacc  240
ctgcgcggct gctacaacca gagcgaggac ggttctcaca ccatccagag gatgtatggc  300
tgcgacgtgg ggccggacgg gcgcttcctc cgcgggtacc agcaggacgc ttacgacggc  360
aaggattaca tcgccctgaa cgaggacctg cgctcttgga ccgcggcgga catggcggct  420
cagatcaccc agcgcaagtg ggagacggcc catgaggcgg agcagtggag agcctacctg  480
gagggccggt gcgtggagtg gctccgcaga tacctggaga acgggaagga gacgctgcag  540
cgcacggacg cccccaagac gcatatgact caccacgctg tctctgacca tgaggccacc  600
ctgaggtgct gggccctgag cttctaccct gcggagatca cactgacctg gcagcgggat  660
ggggaggacc agacccagga cacggagctc gtggagacca ggcctgcagg ggatgggacc  720
ttccagaagt gggcgtctgt ggtggtgcct tctggacagg agcagagata cacctgccat  780
gtgcagcatg agggtctgcc caagcccctc accctgagat gggagccg               828
```

```
SEQ ID NO: 153         moltype = DNA  length = 828
FEATURE                Location/Qualifiers
source                 1..828
                       mol_type = other DNA
                       organism = synthetic construct
SEQUENCE: 153
ggctcccact ccatgaggta tttcaccaca tccgtgtccc ggcccggccg cggggagccc  60
cgcttcatcg ccgtgggcta cgtggacgac acgcagttcg tgcggtttga cagcgacgcc  120
gcgagccaga ggatggagcc gcgggcaccg tggatagagc aggaggggcc ggagtattgg  180
gacctgcaga cacggaatgt gaaggcccag tcacagactg accgagcgaa cctggggacc  240
ctgcgcggct gctacaacca gagcgaggcc ggttctcaca ccatccagat gatgtatggc  300
tgcgacgtgg ggtcggacgg gcgcttcctc cgcgggtacc ggcaggacgc ctacgacggc  360
aaggattaca tcgccttgaa cgaggacctg cgctcttgga ccgcggcgga catggcggct  420
cagatcaccc agcgcaagtg ggaggcggcc cgtgtggcgg agcagttgag agcctacctg  480
gagggcacgt gcgtggagtg gctccgcaga tacctggaga acgggaagga gacgctgcag  540
cgcacggacg cccccaagac gcatatgact caccacgctg tctctgacca tgaggccacc  600
ctgaggtgct gggccctgag cttctaccct gcggagatca cactgacctg gcagcgggat  660
ggggaggacc agacccagga cacggagctt gtggagacca ggcctgcagg ggatggaacc  720
ttccagaagt gggcgtctgt ggtggtgcct tctggacagg agcagagata cacctgccat  780
gtgcagcatg agggtctgcc caagcccctc accctgagat gggagccg               828
```

```
SEQ ID NO: 154         moltype = DNA  length = 828
FEATURE                Location/Qualifiers
source                 1..828
                       mol_type = other DNA
                       organism = synthetic construct
SEQUENCE: 154
ggctcccact ccatgaggta tttctacacc tccatgtccc ggcccggccg cggggagccc  60
cgcttcatcg ccgtgggcta cgtggacgac acgcagttcg tgcggttcga cagcgacgcc  120
gcgagccaga ggatggagcc gcgggcgccg tggatagagc aggaggggcc ggagtattgg  180
gaccggaaca cacggaatgt gaaggcccag tcacagactg accgagtgga cctggggacc  240
ctgcgcggct gctacaacca gagcgaggcc ggttctcaca ccatccagag gatgtatggc  300
tgcgacgtgg ggccggacgg gcgcttcctc cgcgggtacc accagtacgc ctacgacggc  360
aaggattaca tcgccctgaa agaggacctg cgctcttgga ccgcggcgga catggcagct  420
cagaccacca agcacaagtg ggaggcggcc catgtggcgg agcagtggag agcctacctg  480
gagggcacgt gcgtggagtg gctccgcaga tacctggaga acgggaagga gacgctgcag  540
cgcacggacg cccccaaaac gcatatgact caccacgctg tctctgacca tgaagccacc  600
ctgaggtgct gggccctgag cttctaccct gcggagatca cactgacctg gcagcgggat  660
ggggaggacc agacccagga cacggagctc gtggagacca ggcctgcagg ggatggaacc  720
ttccagaagt gggtggctgt ggtggtgcct tctggacagg agcagagata cacctgccat  780
gtgcagcatg agggtttgcc caagcccctc accctgagat gggagccg               828
```

```
SEQ ID NO: 155         moltype = DNA  length = 828
FEATURE                Location/Qualifiers
source                 1..828
                       mol_type = other DNA
                       organism = synthetic construct
SEQUENCE: 155
ggctcccact ccatgaggta tttctacacc gccatgtccc ggcccggccg cggggagccc  60
cgcttcatca ccgtgggcta cgtggacgac acccagttcg tgaggttcga cagcgacgcc  120
acgagtccga ggatggcgcc ccgggcgcca tggatagagc aggaggggcc ggagtattgg  180
gaccgggaga cacagatctc caagaccaac acacagactt accgagagaa cctgcgcacc  240
gcgctccgct gctacaacca gagcgaggcc gggtctcaca cttggcagac gatgtatggc  300
tgcgacctgg ggccggacgg gcgcctcctc cgcgggcata accagttagc ctacgacggc  360
aaggattaca tcgccctgaa cgaggacctg agctcctgga ccgcggcgga caccgcggct  420
cagatcaccc agctcaagtg ggaggcggcc cgtgtggcgg agcagctgag agcctacctg  480
gagggcgagt gcgtggagtg gctccgcaga tacctggaga acgggaagga gacgctgcag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca               828
```

```
SEQ ID NO: 156         moltype = DNA  length = 828
FEATURE                Location/Qualifiers
source                 1..828
                       mol_type = other DNA
```

```
                        organism = synthetic construct
SEQUENCE: 156
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggatggcgcc ccgggcgcca tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca ccctccagag catgtacggc  300
tgcgacgtgg ggccggacgg gcgcctcctc cgcgggcatg accagtccgc ctacgacggc  360
aaggattaca tcgccctgaa cgaggacctg agctcctgga ccgcggcgga cacggcggct  420
cagatcaccc agcgcaagtg ggaggcggcc cgtgaggcgg agcagtggag agcctacctg  480
gagggcctgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 157          moltype = DNA  length = 828
FEATURE                 Location/Qualifiers
source                  1..828
                        mol_type = other DNA
                        organism = synthetic construct
SEQUENCE: 157
ggctcccact ccatgaggta tttccacacc tccgtgtccc ggcccggccg cggggagccc  60
cgcttcatca ccgtgggcta cgtggacgac acgctgttcg tgaggttcga cagcgacgcc  120
gcgagtccga gagaggagcc gcgggcgccg tggatagagc aggaggggcc ggagtattgg  180
gaccgggaga cacagatctg caaggccaag gcacagactg accgagagga cctgcggacc  240
ctgctccgct gctacaacca gagcgaggcc gggtctcaca ccctccagaa tatgtatggc  300
tgcgacgtgg ggccggacgg gcgcctcctc cgcgggtacc accaggacgc ctacgacggc  360
aaggattaca tcgccctgaa cgaggacctg agctcctgga ccgccgcgga cacggcggct  420
cagatcaccc agcgcaagtg ggaggcggcc cgtgtggcgg agcagctgag agcctacctg  480
gagggcgagt gcgtggagtg gctccgcaga tacctggaga acgggaagga gacgctgcag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg              828

SEQ ID NO: 158          moltype = DNA  length = 828
FEATURE                 Location/Qualifiers
source                  1..828
                        mol_type = other DNA
                        organism = synthetic construct
SEQUENCE: 158
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggacggagcc ccgggcgcca tggatagagc aggaggggcc ggagtattgg  180
gaccggaaca cacagatctt caagaccaac acacagactt accgagagag cctgcggaac  240
ctgcgcggct gctacaacca gagcgaggcc gggtctcaca tcatccagag gatgtatggc  300
tgcgacctgg ggcccgacgg gcgcctcctc cgcgggcatg accagttcgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag agcctacctg  480
gagggcctgt gcgtggagtg gctccgcaga tacctggaga acgggaagga gacgctgcag  540
cgcgcggacc ccccaaagac acacgtgacc caccaccccg tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 159          moltype = DNA  length = 828
FEATURE                 Location/Qualifiers
source                  1..828
                        mol_type = other DNA
                        organism = synthetic construct
SEQUENCE: 159
ggctcccact ccatgaggta tttccacacc tccgtgtccc ggcccggccg cggggagccc  60
cgcttcatct cagtgggcta cgtggacgac acccagttcg tgaggttcga cagcgacgcc  120
gcgagtccga ggacggagcc ccgggcgccg tggatagagc aggaggggcc ggagtattgg  180
gaccgggaga cacagatctc caagaccaac acacagactt accgagagga cctgcggacc  240
ctgctccgct gctacaacca gagcgaggcc gggtctcaca ccatccagag gatgtctggc  300
tgcgacgtgg ggccggacgg gcgcctcctc cgcgggtata accagttcgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcaggacag agcctacctg  480
gagggcacgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828
```

```
SEQ ID NO: 160         moltype = DNA  length = 828
FEATURE                Location/Qualifiers
source                 1..828
                       mol_type = other DNA
                       organism = synthetic construct
SEQUENCE: 160
ggctcccact ccatgaggta tttctacacc tccgtgtccc ggcccggccg cggggagccc  60
cgcttcatct cagtgggcta cgtggacgac acgcagttcg tgaggttcga cagcgacgcc  120
gcgagtccga gagaggagcc gcgggcgccg tggatagagc aggaggggcc ggaatattgg  180
gaccggaaca cacagatctg caagaccaac acacagactt accgagagaa cctgcggatc  240
gcgctccgct gctacaacca gagcgaggcc gggtctcaca ccctccagag gatgtacggc  300
tgcgacgtgg ggccggacgg gcgcctcctc cgcgggcata accagttcgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcagctgag aacctacctg  480
gagggcacgt gcgtggagtg gctccgcaga tacctggaga acgggaagga gacgctgcag  540
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agacagaacc  720
ttccagaagt gggcagctgt ggtggtgcct tctggagaag agcagagata cacatgccat  780
gtacagcatg aggggctgcc gaagcccctc accctgagat gggagcca               828

SEQ ID NO: 161         moltype = DNA  length = 828
FEATURE                Location/Qualifiers
source                 1..828
                       mol_type = other DNA
                       organism = synthetic construct
SEQUENCE: 161
ggctcccact ccatgaggta tttccacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagag cctgcggaac  240
ctgcgcggct gctacaacca gagcgaggcc gggtctcaca ccctccagag catgtacggc  300
tgcgacgtgg ggccggacgg gcgcctcctc cgcgggcata accagtacgc ctacgacggc  360
aaggattaca tcgccctgaa cgaggacctg cgctcctgga ccgcggcgga caccgcggct  420
cagatcaccc agcgcaagtg ggaggcggcc cgtgtggcgg agcaggacag agcctacctg  480
gagggcacgt gcgtggagtg gctccgcaga tacctggaga acgggaagga cacgctggag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg               828

SEQ ID NO: 162         moltype = DNA  length = 828
FEATURE                Location/Qualifiers
source                 1..828
                       mol_type = other DNA
                       organism = synthetic construct
SEQUENCE: 162
ggctcccact ccatgaggta tttctacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagaa cctgcgcacc  240
gcgctccgct gctacaacca gagcgaggcc gggtctcaca tcatccagag gatgtacggc  300
tgcgacgtgg ggccggacgg gcgcctcctc cgcgggtatg accagtacgc ctacgacggc  360
aaggattaca tcgccctgaa cgaggacctg agctcctgga ccgcggcgga caccgcggct  420
cagatcaccc agcgcaagtg ggaggcggcc cgtgtggcgg agcaggacag agcctacctg  480
gagggcctgt gcgtggagtc gctccgcaga tacctggaga acgggaagga gacgctgcag  540
cgcgcggacc ccccaaagac acatgtgacc caccacccca tctctgacca tgaggtcacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagccg               828

SEQ ID NO: 163         moltype = DNA  length = 828
FEATURE                Location/Qualifiers
source                 1..828
                       mol_type = other DNA
                       organism = synthetic construct
SEQUENCE: 163
ggctcccact ccatgaggta tttccacacc gccatgtccc ggcccggccg cggggagccc  60
cgcttcatca ccgtgggcta cgtggacgac acgctgttcg tgaggttcga cagcgacgcc  120
acgagtccga ggaaggagcc gcgggcgcca tggatagagc aggaggggcc ggagtattgg  180
gaccgggaga cacagatctc caagaccaac acacagactt accgagagaa cctgcggatc  240
gcgctccgct gctacaacca gagcgaggcc gggtctcaca cttggcagag gatgtatggc  300
tgcgacctgg ggcccgacgg gcgcctcctc cgcgggtata accagttagc ctacgacggc  360
aaggattaca tcgccctgaa cgaggacctg agctcctgga ccgcggcgga caccgcggct  420
cagatcaccc agcgcaagtg ggaggcggcc cgtgaggcgg agcagctgag agcctacctg  480
gagggcctgt gcgtggagtg gctccgcaga tacctggaga acgggaagga gacgctgcag  540
```

```
cgcgcggacc ccccaaagac acatgtgacc caccacccca tctctgacca tgaggccacc  600
ctgaggtgct gggccctggg cttctaccct gcggagatca cactgacctg gcagcgggat  660
ggcgaggacc aaactcagga caccgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 164         moltype = DNA  length = 828
FEATURE                Location/Qualifiers
source                 1..828
                       mol_type = other DNA
                       organism = synthetic construct
SEQUENCE: 164
ggctcccact ccatgaggta tttctacacc gccatgtccc ggcccggccg cggggagccc  60
cgcttcatcg cagtgggcta cgtggacgac acccagttcg tgaggttcga cagcgacgcc  120
gcgagtccga ggacggagcc ccgggcgcca tggatagagc aggaggggcc ggagtattgg  180
gaccgggaga cacagatctc caagaccaac acacagactt accgagagaa cctgcggatc  240
gcgctccgct gctacaacca gagcgaggcc gggtctcaca cttggcagac gatgtatggc  300
tgcgacgtgg ggccggacgg gcgcctcctc cgcgggcata accagtacgc ctacgacggc  360
aaagattaca tcgccctgaa cgaggacctg agctcctgga ccgcggcgga caccgcggct  420
cagatcaccc agcgcaagtg ggaggcggcc cgtgaggcgg agcagctgag agcctacctg  480
gagggcctgt gcgtggagtg gctccgcaga cacctggaga acgggaagga gacgctgcag  540
cgcgcggacc ccccaaagac acacgtgacc caccaccccg tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 165         moltype = DNA  length = 828
FEATURE                Location/Qualifiers
source                 1..828
                       mol_type = other DNA
                       organism = synthetic construct
SEQUENCE: 165
ggctcccact ccatgaggta tttctacacc gccatgtccc ggcccggccg cggggagccc  60
cgcttcatcg cagtgggcta cgtggacgac acgcagttcg tgaggttcga cagcgacgcc  120
gcgagtccga gagaggagcc gcgggcgccg tggatagagc aggaggggcc ggagtattgg  180
gaccggaaca cacagatcta caaggcccag gcacagactg accgagagag cctgcggaac  240
ctgcgcggct gctacaacca gagcgaggcc gggtctcaca cttggcagac gatgtatggc  300
tgcgacctgg ggccggacgg gcgcctcctc cgcgggcata accagttagc ctacgacggc  360
aaggattaca tcgccctgaa cgaggacctg agctcctgga ccgcggcgga caccgcggct  420
cagatcaccc agcgcaagtg ggaggcggcc cgtgaggcgg agcagctgag agcctacctg  480
gagggcacgt gcgtggagtg gctccgcaga tacctggaga acgggaagga gacgctgcag  540
cgcgcggacc ccccaaagac acacgtgacc caccacccca tctctgacca tgaggccacc  600
ctgaggtgct gggccctggg cttctaccct gcggagatca cactgacctg gcagcgggat  660
ggcgaggacc aaactcagga cactgagctt gtggagacca gaccagcagg agatagaacc  720
ttccagaagt gggcagctgt ggtggtgcct tctggagaag agcagagata cacatgccat  780
gtacagcatg aggggctgcc gaagcccctc accctgagat gggagcca              828

SEQ ID NO: 166         moltype = DNA  length = 828
FEATURE                Location/Qualifiers
source                 1..828
                       mol_type = other DNA
                       organism = synthetic construct
SEQUENCE: 166
ggctcccact ccatgaggta tttctacacc gctgtgtccc ggcccggccg cggggagccc  60
cacttcatcg cagtgggcta cgtggacgac acgcagttcg tgcggttcga cagcgacgcc  120
gcgagtccga gaggggagcc gcgggcgccg tgggtggagc aggaggggcc ggagtattgg  180
gaccgggaga cacagaagta caagcgccag gcacagactg accgagtgag cctgcggaac  240
ctgcgcggct gctacaacca gagcgaggcc aggtctcaca tcatccagag gatgtatggc  300
tgcgacgtgg ggcccgacgg gcgcctcctc cgcgggtatg accagtacgc ctacgacggc  360
aaggattaca tcgccctgaa cgaggatctg cgctcctgga ccgccgcgga cacggcggct  420
cagatcaccc agcgcaagtg ggaggcggcc cgtgaggcgg agcagctgag agcctacctg  480
gagggcctgt gcgtggagtg gctccgcaga tacctgaaga atgggaagga gacgctgcag  540
cgcgcggaac acccaaagac acacgtgacc caccatcccg tctctgacca tgaggccacc  600
ctgaggtgct gggccctggg cttctaccct gcggagatca cactgacctg gcagtgggat  660
ggggaggacc aaactcagga cactgagctt gtggagacca ggccagcagg agatggaacc  720
ttccagaagt gggcagctgt ggtggtgcct tctggagaag agcagagata cacgtgccat  780
gtgcagcacg aggggctgcc ggagcccctc accctgagat gggagccg              828

SEQ ID NO: 167         moltype = DNA  length = 828
FEATURE                Location/Qualifiers
source                 1..828
                       mol_type = other DNA
                       organism = synthetic construct
SEQUENCE: 167
tgctcccact ccatgaggta tttcgacacc gccgtgtccc ggcccggccg cggagagccc  60
cgcttcatct cagtgggcta cgtggacgac acgcagttcg tgcggttcga cagcgacgcc  120
gcgagtccga gaggggagcc ccgggcgccg tgggtggagc aggaggggcc ggagtattgg  180
gaccgggaga cacagaagta caagcgccag gcacaggctg accgagtgag cctgcggaac  240
```

```
ctgcgcggct gctacaacca gagcgaggac gggtctcaca ccttccagag gatgtatggc  300
tgcgacctgg ggcccgacgg gcgcctcctc cgcgggtatg accagttcgc ctacgacggc  360
aaggattaca tcgccctgaa cgaggacctg cgctcctgga ccgccgcgga caccgcggct  420
cagatcaccc agcgcaagtt ggaggcggcc cgtgcggcgg agcaggacag agcctacctg  480
gagggcacgt gcgtggagtg gctccgcaga tacctggaga acgggaagaa gacgctgcag  540
cgcgcggaac ccccaaagac acacgtgacc caccaccccc tctctgacca tgaggccacc  600
ctgaggtgct gggccctggg cttctaccct gcggagatca cactgacctg gcagcgggat  660
ggggaggacc agacccagga caccgagctt gtggagacca ggccagcagg agatggaacc  720
ttccagaagt gggcagctgt ggtggtgcct tctggacaag agcagagata cacgtgccat  780
atgcagcacg aggggctgca agagcccctc accctgagct gggagcca             828

SEQ ID NO: 168         moltype = DNA  length = 828
FEATURE                Location/Qualifiers
source                 1..828
                       mol_type = other DNA
                       organism = synthetic construct
SEQUENCE: 168
tgctcccact ccatgaggta tttctacacc gccgtgtccc ggcccggccg cggagagccc  60
cgcttcatcg cagtgggcta cgtggacgac acgcagttcg tgcagttcga cagcgacgcc  120
gcgagtccaa gaggggagcc gcgggcgccg tgggtggagc aggaggggcc ggagtattgg  180
gaccgggaga cacagaagta caagcgccag gcacagactg accgagtgag cctgcggaac  240
ctgcgcggct gctacaacca gagcgaggcc gggtctcaca ccctccagag gatgtatggc  300
tgcgacctgg ggcccgacgg gcgcctcctc cgcgggtata accagttcgc ctacgacggc  360
aaggattaca tcgccctgaa tgaggacctg cgctcctgga ccgccgcgga cacggcggct  420
cagatcaccc agcgcaagtg ggaggcggcc cgtacggcgg agcagctgag agcctacctg  480
gagggcacgt gcgtggagtg gctccgcaga tacctggaga acgggaagaa gacgctgcag  540
cgcgcggaac acccaaagac acacgtgacc caccatcccg tctctgacca tgaggccacc  600
ctgaggtgct gggccctggg cttctaccct gcggagatca cactgacctg gcagcgggat  660
ggcgaggacc aaactcagga caccgagctt gtggagacca ggccagcagg agatggaacc  720
ttccagaagt gggcagctgt ggtggtgcct tctggagaag agcagagata cacgtgccat  780
gtgcagcacg aggggctgcc agagcccctc accctgagat gggggcca             828

SEQ ID NO: 169         moltype = DNA  length = 828
FEATURE                Location/Qualifiers
source                 1..828
                       mol_type = other DNA
                       organism = synthetic construct
SEQUENCE: 169
tgctcccact ccatgaggta tttctacacc gccgtgtccc ggcccggccg cggagagccc  60
cgcttcatcg cagtgggcta cgtggacgac acgcagttcg tgcagttcga cagcgacgcc  120
gcgagtccaa gaggggagcc gcgggcgccg tgggtggagc aggaggggcc ggagtattgg  180
gaccgggaga cacagaagta caagcgccag gcacagactg accgagtgag cctgcggaac  240
ctgcgcggct gctacaacca gagcgaggcc gggtctcaca ccctccagag gatgtatggc  300
tgcgacctgg ggcccgacgg gcgcctcctc cgcgggtata accagttcgc ctacgacggc  360
aaggattaca tcgccctgaa tgaggacctg cgctcctgga ccgccgcgga caaggcggct  420
cagatcaccc agcgcaagtg ggaggcggcc cgtgaggcgg agcagcggag agcctacctg  480
gagggcacgt gcgtggagtg gctccgcaga tacctggaga acgggaagaa gacgctgcag  540
cgcgcggaac acccaaagac acacgtgacc caccatcccg tctctgacca tgaggccacc  600
ctgaggtgct gggccctggg cttctaccct gcggagatca cactgacctg gcagcgggat  660
ggcgaggacc aaactcagga caccgagctt gtggagacca ggccagcagg agatggaacc  720
ttccagaagt gggcagctgt ggtggtgcct tctggagaag agcagagata cacgtgccat  780
gtgcagcacg aggggctgcc agagcccctc accctgagat gggggcca             828

SEQ ID NO: 170         moltype = DNA  length = 828
FEATURE                Location/Qualifiers
source                 1..828
                       mol_type = other DNA
                       organism = synthetic construct
SEQUENCE: 170
tgctcccact ccatgaggta tttctacacc gccgtgtccc ggcccggccg cggagagccc  60
cgcttcatcg cagtgggcta cgtggacgac acgcagttcg tgcggttcga cagcgacgcc  120
gcgagtccaa gaggggagcc gcgggcgccg tgggtggagc aggaggggcc ggagtattgg  180
gaccgggaga cacagaagta caagcgccag gcacaggctg accgagtgag cctgcggaac  240
ctgcgcggct gctacaacca gagcgaggcc gggtctcaca ccctccagag gatgtacggc  300
tgcgacctgg ggcccgacgg gcgcctcctc cgcgggtatg accagtccgc ctacgacggc  360
aaggattaca tcgccctgaa cgaggacctg cgctcctgga ccgctgcgga cacggcggct  420
cagatcaccc agcgcaagtg ggaggcggcc cgtgaggcgg agcagtggag agcctacctg  480
gagggcacgt gcgtggagtg gctccgcaga tacctggaga acgggaagga gacgctgcag  540
cgcgcggaac acccaaagac acacgtgacc caccatcccg tctctgacca tgaggccacc  600
ctgaggtgct gggccctggg cttctaccct gcggagatca cactgacctg gcagcgggat  660
ggcgaggacc aaactcagga caccgagctt gtggagacca ggccagcagg agatggaacc  720
ttccagaagt gggcagctgt ggtggtgcct tctggagaag agcagagata cacgtgccat  780
gtgcagcacg aggggctgcc ggagcccctc accctgagat gggagcca             828

SEQ ID NO: 171         moltype = DNA  length = 828
FEATURE                Location/Qualifiers
source                 1..828
                       mol_type = other DNA
                       organism = synthetic construct
```

-continued

SEQUENCE: 171
tgctcccact ccatgaggta tttctacacc gccgtgtccc ggcccggccg cggagagccc 60
cgcttcatcg cagtgggcta cgtggacgac acgcagttcg tgcggttcga cagcgacgcc 120
gcgagtccaa gaggggagcc gcgggcgccg tgggtggagc aggaggggcc ggagtattgg 180
gaccgggaga cacagaagta caagcgccag gcacaggctg accgagtgag cctgcggaac 240
ctgcgcggct gctacaacca gagcgaggcc gggtctcaca ccctccagtg gatgtatggc 300
tgcgacctgg ggcccgacgg gcgcctcctc cgcgggtatg accagtccgc ctacgacggc 360
aaggattaca tcgccctgaa cgaggacctg cgctcctgga ctgccgcgga cacggcggct 420
cagatcaccc agcgcaagtg ggaggcggcc cgtgaggcgg agcagtggag agcctacctg 480
gagggcacgt gcgtggagtg gctccgcaga tacctggaga acgggaagga gacgctgcag 540
cgcgcggaac acccaaagac acacgtgacc caccatcccg tctctgacca tgaggccacc 600
ctgaggtgct gggccctggg cttctaccct gcggagatca cactgacctg gcagcgggat 660
ggcgaggacc aaactcagga caccgagctt gtggagacca ggccagcagg agatggaacc 720
ttccagaagt gggcagctgt ggtggtgcct tctggagaag agcagagata cacgtgccat 780
gtgcagcacg aggggctgcc agagcccctc accctgagat gggagccca 828

SEQ ID NO: 172 moltype = DNA length = 828
FEATURE Location/Qualifiers
source 1..828
mol_type = other DNA
organism = synthetic construct
SEQUENCE: 172
tgctcccact ccatgaggta tttctccaca tccgtgtccc ggcccggccg cggggagccc 60
cgcttcatcg cagtgggcta cgtggacgac acgcagttcg tgcggttcga cagcgacgcc 120
gcgagtccga gaggggagcc gcgggcgccg tgggtggagc aggaggggcc ggagtattgg 180
gaccgggaga cacagaagta caagcgccag gcacagactg accgagtgag cctgcggaac 240
ctgcgcggct gctacaacca gagcgaggcc gggtctcaca ccctccagtg gatgtttggc 300
tgcgacctgg ggcccgacgg gcgcctcctc cgcgggtatg accagtccgc ctacgacggc 360
aaggattaca tcgccctgaa cgaggatctg cgctcctgga ccgccgcgga cacggcggct 420
cagatcaccc agcgcaagtg ggaggcggcc cgtgaggcgg agcagcggag agcctacctg 480
gagggcacgt gcgtggagtg gctccgcaga tacctggaga acgggaagga gacgctgcag 540
cgcgcggaac acccaaagac acacgtgacc caccatcccg tctctgacca tgaggccacc 600
ctgaggtgct gggccctggg cttctaccct gcggagatca cactgacctg gcagtgggat 660
ggggaggacc aaactcagga caccgagctt gtggagacca ggccagcagg agatggaacc 720
ttccagaagt gggcagctgt ggtggtgcct tctggagaag agcagagata cacgtgccat 780
gtgcagcacg aggggctgcc ggagcccctc accctgagat gggagccg 828

SEQ ID NO: 173 moltype = DNA length = 828
FEATURE Location/Qualifiers
source 1..828
mol_type = other DNA
organism = synthetic construct
SEQUENCE: 173
tgctcccact ccatgaggta tttctacacc gctgtgtccc ggcccggccg cggagagccc 60
cacttcatcg cagtgggcta cgtggacgac acgcagttcg tgcggttcga cagcgacgcc 120
gcgagtccaa gaggggagcc gcgggcgccg tgggtggagc aggaggggcc ggagtattgg 180
gaccgggaga cacagaacta caagcgccag gcacagactg accgagtgaa cctgcggaaa 240
ctgcgcggct gctacaacca gagcgaggcc gggtctcaca tcatccagag gatgtatggc 300
tgcgacctgg ggcccgacgg gcgcctcctc cgcgggcatg accagttagc ctacgacggc 360
aaggattaca tcgccctgaa cgaggacctg cgctcctgga ccgccgcgga cacggcggct 420
cagatcaccc agcgcaagtg ggaggcggcc cgtgaggcgg agcagctgag agcctacctg 480
gagggcacgt gcgtggagtg gctccgcaga tacctggaga acgggaagga gacgctgcag 540
cgcgcggaac acccaaagac acacgtgacc caccatcccg tctctgacca tgaggccacc 600
ctgaggtgct gggccctggg cttctaccct gcggagatca cactgacctg gcagcgggat 660
ggcgaggacc aaactcagga caccgagctt gtggagacca ggccagcagg agatggaacc 720
ttccagaagt gggcagctgt ggtggtgcct tctggagaag agcagagata cacgtgccat 780
gtgcagcacg aggggctgcc ggagcccctc accctgagat gggagcca 828

SEQ ID NO: 174 moltype = DNA length = 828
FEATURE Location/Qualifiers
source 1..828
mol_type = other DNA
organism = synthetic construct
SEQUENCE: 174
ggctcccact ccatgaggta tttctacacc gccgtgtccc ggcccggccg cggagagccc 60
cgcttcatcg cagtgggcta cgtggacgac acgcagttcg tgcggttcga cagcgacgcc 120
gcgagtccga gaggggagcc gcgggcgccg tgggtggagc aggaggggcc ggagtattgg 180
gaccgggaga cacagaagta caagcgccag gcacaggctg accgagtgaa cctgcggaaa 240
ctgcgcggct gctacaacca gagcgaggcc ggttctcaca ccatccagag gatgtatggc 300
tgcgacctgg ggcccgacgg gcgcctcctc cgcgggtata accagttcgc ctacgacggc 360
aaggattaca tcgccctgaa cgaggacctg cgctcctgga ccgcggcgga cacggcggct 420
cagatctccc agcgcaagtt ggaggcggcc cgtgaggcgg agcagctgag agcctacctg 480
gagggcgagt gcgtggagtg gctccgcgga tacctggaga acgggaagga gacgctgcag 540
cgcgcggaac gcccaaagac acacgtgacc caccatcccg tctctgacca tgaggccacc 600
ctgaggtgct gggccctggg cttctaccct gcggagatca cactgacctg gcagcgggat 660
ggggaggacc aaactcagga caccgagctt gtggagacca ggccagcagg agatggaacc 720
ttccagaagt gggcagctgt ggtggtgcct tctggacaag aacagagata cacgtgccat 780
gtgcagcacg aggggctgca ggagccctgc accctgagat ggaagccg 828

-continued

```
SEQ ID NO: 175          moltype = DNA  length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 175
ggcagcggcg gcagcggggg ctccgccggc ggaggcctga acgacatctt cgaagcccag  60
aagatcgagt ggcacgaggg cgggggagag aacctgtact tccagggcgg cagccaccac  120
catcaccacc atggcggcgg aagcggcggc gggtccggca gccaccatca ccatcaccat  180

SEQ ID NO: 176          moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 176
GSGGSGGSAG GGLNDIFEAQ KIEWHEGGGE NLYFQGGSHH HHHHGGGSGG GSGSHHHHHH  60

SEQ ID NO: 177          moltype = DNA  length = 78
FEATURE                 Location/Qualifiers
misc_feature            1..78
                        note = Description of Unknown: Signal sequence universal
                         target sequence
source                  1..78
                        mol_type = other DNA
                        organism = synthetic construct
SEQUENCE: 177
atggcgacgg gttcaagaac ttccctactt cttgcatttg gcctgctttg tttgccgtgg  60
ttacaggagg gctcagca                                                78

SEQ ID NO: 178          moltype = AA  length = 26
FEATURE                 Location/Qualifiers
REGION                  1..26
                        note = Description of Unknown: Signal sequence universal
                         target sequence
source                  1..26
                        mol_type = protein
                        organism = synthetic construct
SEQUENCE: 178
MATGSRTSLL LAFGLLCLPW LQEGSA                                       26

SEQ ID NO: 179          moltype = DNA  length = 225
FEATURE                 Location/Qualifiers
source                  1..225
                        mol_type = other DNA
                        organism = synthetic construct
SEQUENCE: 179
tgtgccttct agttgccagc catctgttgt ttgcccctcc cccgtgcctt ccttgaccct  60
ggaaggtgcc actcccactg tcctttccta ataaaatgag gaaattgcat cgcattgtct  120
gagtaggtgt cattctattc tggggggtgg ggtggggcag gacagcaagg gggaggattg  180
ggaagacaat agcaggcatg ctggggatgc ggtgggctct atggc                  225

SEQ ID NO: 180          moltype = DNA  length = 131
FEATURE                 Location/Qualifiers
source                  1..131
                        mol_type = other DNA
                        organism = synthetic construct
SEQUENCE: 180
acttgtttat tgcagcttat aatggttaca aataaagcaa tagcatcaca aatttcacaa  60
ataaagcatt tttttcactg cattctagtt gtggtttgtc caaactcatc aatgtatctt  120
atcatgtctg t                                                       131

SEQ ID NO: 181          moltype = DNA  length = 479
FEATURE                 Location/Qualifiers
source                  1..479
                        mol_type = other DNA
                        organism = synthetic construct
SEQUENCE: 181
acgggtggca tccctgtgac ccctccccag tgcctctcct ggccctggaa gttgccactc  60
cagtgcccac cagccttgtc ctaataaaat taagttgcat cattttgtct gactaggtgt  120
ccttctataa tattatgggg tggagggggg tggtatggag caaggggcaa gttgggaaga  180
caacctgtag ggcctgcggg gtctattggg aaccaagctg gagtgcagtg gcacaatctt  240
ggctcactgc aatctccgcc tcctgggttc aagcgattct cctgcctcag cctcccgagt  300
```

-continued

```
tgttgggatt ccaggcatgc atgaccaggc tcagctaatt tttgtttttt tggtagagac  360
ggggtttcac catattggcc aggctggtct ccaactccta atctcaggtg atctacccac  420
cttggcctcc caaattgctg ggattacagg cgtgaaccac tgctcccttc cctgtcctt   479

SEQ ID NO: 182         moltype = DNA  length = 527
FEATURE                Location/Qualifiers
misc_feature           1..527
                       note = Description of Unknown: rbGlob polyA sequence
source                 1..527
                       mol_type = other DNA
                       organism = synthetic construct
SEQUENCE: 182
ttcactcctc aggtgcaggc tgcctatcag aaggtggtgg ctggtgtggc caatgccctg  60
gctcacaaat accactgaga tctttttccc tctgccaaaa attatgggga catcatgaag  120
ccccttgagc atctgacttc tggctaataa aggaaattta ttttcattgc aatagtgtgt  180
tggaattttt tgtgtctctc actcggaagg acatatggga gggcaaatca tttaaaacat  240
cagaatgagt atttggttta gagtttggca acatatgccc atatgctggc tgccatgaac  300
aaaggttggc tataaagagg tcatcagtat atgaaacagc cccctgctgt ccattcctta  360
ttccatagaa aagccttgac ttgaggttag attttttta tattttgttt tgtgttattt  420
ttttctttaa catccctaaa attttcctta catgttttac tagccagatt tttcctcctc  480
tcctgactac tcccagtcat agctgtccct cttctcttat ggagatc               527

SEQ ID NO: 183         moltype = AA  length = 6
FEATURE                Location/Qualifiers
REGION                 1..6
                       note = Description of Unknown: Thrombin cleavage site
                        sequence
source                 1..6
                       mol_type = protein
                       organism = synthetic construct
SEQUENCE: 183
LVPRGS                                                             6

SEQ ID NO: 184         moltype = DNA  length = 18
FEATURE                Location/Qualifiers
misc_feature           1..18
                       note = Description of Unknown: Thrombin cleavage site
                        sequence
source                 1..18
                       mol_type = other DNA
                       organism = synthetic construct
SEQUENCE: 184
ctggtgccgc gcggcagc                                                18

SEQ ID NO: 185         moltype = AA  length = 4
FEATURE                Location/Qualifiers
REGION                 1..4
                       note = Description of Unknown: Factor Xa site sequence
source                 1..4
                       mol_type = protein
                       organism = synthetic construct
SEQUENCE: 185
IEGR                                                               4

SEQ ID NO: 186         moltype = DNA  length = 12
FEATURE                Location/Qualifiers
misc_feature           1..12
                       note = Description of Unknown: Factor Xa site sequence
source                 1..12
                       mol_type = other DNA
                       organism = synthetic construct
SEQUENCE: 186
attgaaggcc gc                                                      12

SEQ ID NO: 187         moltype = AA  length = 8
FEATURE                Location/Qualifiers
REGION                 1..8
                       note = Description of Unknown: Rhinovirus 3C site sequence
source                 1..8
                       mol_type = protein
                       organism = synthetic construct
SEQUENCE: 187
LEVLFQGP                                                           8

SEQ ID NO: 188         moltype = DNA  length = 24
FEATURE                Location/Qualifiers
misc_feature           1..24
                       note = Description of Unknown: Rhinovirus 3C site sequence
source                 1..24
```

-continued

```
                        mol_type = other DNA
                        organism = synthetic construct
SEQUENCE: 188
ctggaagtgc tgtttcaggg cccg                                             24

SEQ ID NO: 189          moltype = AA  length = 5
FEATURE                 Location/Qualifiers
REGION                  1..5
                        note = Description of Unknown: Enterokinase site sequence
source                  1..5
                        mol_type = protein
                        organism = synthetic construct
SEQUENCE: 189
DDDDK                                                                  5

SEQ ID NO: 190          moltype = DNA  length = 15
FEATURE                 Location/Qualifiers
misc_feature            1..15
                        note = Description of Unknown: Enterokinase site sequence
source                  1..15
                        mol_type = other DNA
                        organism = synthetic construct
SEQUENCE: 190
gatgatgatg ataaa                                                       15

SEQ ID NO: 191          moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 191
gattacaagg atgacgacga taag                                             24

SEQ ID NO: 192          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 192
DYKDDDDK                                                               8

SEQ ID NO: 193          moltype = DNA  length = 27
FEATURE                 Location/Qualifiers
misc_feature            1..27
                        note = Description of Artificial Sequence: Synthetic
                         oligonucleotide
source                  1..27
                        mol_type = other DNA
                        organism = synthetic construct
SEQUENCE: 193
tacccatacg atgttccaga ttacgct                                          27

SEQ ID NO: 194          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 194
YPYDVPDYA                                                              9

SEQ ID NO: 195          moltype = DNA  length = 30
FEATURE                 Location/Qualifiers
misc_feature            1..30
                        note = Description of Artificial Sequence: Synthetic
                         oligonucleotide
source                  1..30
                        mol_type = other DNA
                        organism = synthetic construct
SEQUENCE: 195
gaacaaaaac ttatttctga agaagatctg                                       30

SEQ ID NO: 196          moltype = AA  length = 10
```

-continued

```
FEATURE               Location/Qualifiers
REGION                1..10
                      note = Description of Artificial Sequence: Synthetic peptide
source                1..10
                      mol_type = protein
                      organism = synthetic construct
SEQUENCE: 196
EQKLISEEDL                                                             10

SEQ ID NO: 197        moltype = DNA  length = 549
FEATURE               Location/Qualifiers
misc_feature          1..549
                      note = Description of Artificial Sequence: Synthetic
                       polynucleotide
source                1..549
                      mol_type = other DNA
                      organism = synthetic construct
SEQUENCE: 197
cgcaagatcg tcgttgcagc catcgccgtt tccctgacca cggtctcgat tacggccagc  60
gcttcggcag accccctccaa ggactcgaag gcccaggtct cggccgccga ggccggcatc  120
accggcacct ggtacaacca gctcggctcg accttcatcg tgaccgcggg cgccgacggc  180
gccctgaccg gaacctacga gtcggccgtc ggcaacgccg agagccgcta cgtcctgacc  240
ggtcgttacg acagcgcccc ggccaccgac ggcagcggca ccgccctcgg ttggacggtg  300
gcctggaaga ataactaccg caacgcccac tccgcgacca cgtggagcgg ccagtacgtc  360
ggcggcgccg aggcgaggat caacacccag tggctgctga cctccggcac caccgaggcc  420
aacgcctgga agtccacgct ggtcggccac gacaccttca ccaaggtgaa gccgtccgcc  480
gcctccatcg acgcggcgaa gaaggccggc gtcaacaacg gcaacccgct cgacgccgtt  540
cagcagtag                                                          549

SEQ ID NO: 198        moltype = AA  length = 182
FEATURE               Location/Qualifiers
REGION                1..182
                      note = Description of Artificial Sequence: Synthetic
                       polypeptide
source                1..182
                      mol_type = protein
                      organism = synthetic construct
SEQUENCE: 198
RKIVVAAIAV SLTTVSITAS ASADPSKDSK AQVSAAEAGI TGTWYNQLGS TFIVTAGADG  60
ALTGTYESAV GNAESRYVLT GRYDSAPATD GSGTALGWTV AWKNNYRNAH SATTWSGQYV  120
GGAEARINTQ WLLTSGTTEA NAWKSTLVGH DTFTKVKPSA ASIDAAKKAG VNNGNPLDAV  180
QQ                                                                 182

SEQ ID NO: 199        moltype = AA  length = 9
FEATURE               Location/Qualifiers
REGION                1..9
                      note = Description of Unknown: Neo12 epitope sequence
source                1..9
                      mol_type = protein
                      organism = unidentified
SEQUENCE: 199
YLYHRVDVI                                                          9

SEQ ID NO: 200        moltype = AA  length = 10
FEATURE               Location/Qualifiers
REGION                1..10
                      note = Description of Unknown: MART1 epitope sequence
source                1..10
                      mol_type = protein
                      organism = unidentified
SEQUENCE: 200
ELAGIGILTV                                                         10

SEQ ID NO: 201        moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 201
GGGS                                                               4

SEQ ID NO: 202        moltype = DNA  length = 77
FEATURE               Location/Qualifiers
misc_feature          1..77
                      note = Description of Artificial Sequence: Synthetic
                       oligonucleotide
variation             30..35
```

```
                        note = n = a, c, t, g, unknown or other
variation               44..49
                        note = n = a, c, t, g, unknown or other
source                  1..77
                        mol_type = other DNA
                        organism = synthetic construct
SEQUENCE: 202
ctcgccacgt cggctatcct gatcggatgn nnnnntcaat ccgnnnnnnc tggacgtgag  60
caagctacag cgacctc                                                 77

SEQ ID NO: 203          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 203
EYIPGTTFL                                                          9

SEQ ID NO: 204          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 204
IYNIIVTTL                                                          9

SEQ ID NO: 205          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 205
KTSVALHLI                                                          9

SEQ ID NO: 206          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 206
HLSLELLGVD                                                         10

SEQ ID NO: 207          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 207
DEYIPGTTF                                                          9

SEQ ID NO: 208          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 208
RCSPEQLKKA W                                                       11

SEQ ID NO: 209          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 209
CAVRDVSARL MF                                                      12
```

```
SEQ ID NO: 210          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 210
CARNTGNQFY F                                                      11

SEQ ID NO: 211          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 211
CAVLMDSNYQ LIW                                                    13

SEQ ID NO: 212          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 212
CAVRDVNARL MF                                                     12

SEQ ID NO: 213          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 213
CAVMLYTDKL IF                                                     12

SEQ ID NO: 214          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 214
CAFNDYKLSF                                                        10

SEQ ID NO: 215          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 215
CAVFFGNVLH C                                                      11

SEQ ID NO: 216          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 216
CASSPVAGNN RKLIW                                                  15

SEQ ID NO: 217          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 217
```

```
CILVNNNDMR F                                                 11

SEQ ID NO: 218          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 218
CAVLRDSNYQ LIW                                               13

SEQ ID NO: 219          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 219
CALVYDKIIF                                                   10

SEQ ID NO: 220          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 220
CAFPYGSNRL AF                                                12

SEQ ID NO: 221          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 221
CAHNYGQNFV F                                                 11

SEQ ID NO: 222          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 222
CAGPHAGGTS YGKLTF                                            16

SEQ ID NO: 223          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 223
CFSEVSAKF                                                    9

SEQ ID NO: 224          moltype = AA  length = 10
FEATURE                 Location/Qualifiers
REGION                  1..10
                        note = Description of Artificial Sequence: Synthetic peptide
VARIANT                 4
                        note = Phe or Ser
source                  1..10
                        mol_type = protein
                        organism = synthetic construct
SEQUENCE: 224
KTYXKPFHPK                                                   10

SEQ ID NO: 225          moltype = AA  length = 9
FEATURE                 Location/Qualifiers
REGION                  1..9
                        note = Description of Artificial Sequence: Synthetic peptide
VARIANT                 2
```

```
                        note = Phe or Ser
source                  1..9
                        mol_type = protein
                        organism = synthetic construct
SEQUENCE: 225
YXKPFHPKF                                                     9

SEQ ID NO: 226          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 226
AMMDYFFQR                                                     9

SEQ ID NO: 227          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 227
YFKPFHPKF                                                     9

SEQ ID NO: 228          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 228
CAESSPSGGY NKLIF                                              15

SEQ ID NO: 229          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 229
CAVNSGSARQ LTF                                                13

SEQ ID NO: 230          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 230
CVVNGENDYK LSF                                                13

SEQ ID NO: 231          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 231
CAMTYGNNRL AF                                                 12

SEQ ID NO: 232          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 232
CAVRRGSGAG SYQLTF                                             16

SEQ ID NO: 233          moltype = AA  length = 14
FEATURE                 Location/Qualifiers
```

-continued

```
REGION                 1..14
                       note = Description of Artificial Sequence: Synthetic peptide
source                 1..14
                       mol_type = protein
                       organism = synthetic construct
SEQUENCE: 233
CAVRDYNQGG KLIF                                                     14

SEQ ID NO: 234         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 234
CAVNDPNDYK LSF                                                      13

SEQ ID NO: 235         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 235
CAGYQGGSEK LVF                                                      13

SEQ ID NO: 236         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 236
CAVGSNAGGT SYGKLTF                                                  17

SEQ ID NO: 237         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 237
CVVNVPNDYK LSF                                                      13

SEQ ID NO: 238         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 238
CVVNPSGGSY IPTF                                                     14

SEQ ID NO: 239         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 239
CVVNLSNDYK LSF                                                      13

SEQ ID NO: 240         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 240
CAVSGDDYKL SF                                                       12

SEQ ID NO: 241         moltype = AA  length = 12
```

-continued

```
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 241
CVVNSNDYKL SF                                                        12

SEQ ID NO: 242          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 242
CASSAIRTYE QYF                                                       13

SEQ ID NO: 243          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 243
CASSNNNEQF F                                                         11

SEQ ID NO: 244          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 244
CASQRMYDNE QFF                                                       13

SEQ ID NO: 245          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 245
CASSMGQGAD EQYF                                                      14

SEQ ID NO: 246          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 246
CASGPDTPLY GYTF                                                      14

SEQ ID NO: 247          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 247
CASSEAWGYE QYF                                                       13

SEQ ID NO: 248          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 248
CASSHKWSTE AFF                                                       13
```

-continued

```
SEQ ID NO: 249          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 249
CASSQNNEQY F                                                              11

SEQ ID NO: 250          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 250
CASSSDRAPP LHF                                                            13

SEQ ID NO: 251          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 251
CASSLAYRVE QYF                                                            13

SEQ ID NO: 252          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 252
CASSYEGGLA AFTGELFF                                                       18

SEQ ID NO: 253          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 253
CASSSSWNTE AFF                                                            13

SEQ ID NO: 254          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 254
CASSSSTVVE QYF                                                            13

SEQ ID NO: 255          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 255
CASSPRWSTE AFF                                                            13

SEQ ID NO: 256          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 256
KTYFKPFHPK                                                                10
```

```
SEQ ID NO: 257          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 257
RLQNHMAVA                                                          9

SEQ ID NO: 258          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 258
CAVGELDTGF QKLVF                                                   15

SEQ ID NO: 259          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 259
CAYPSGNQFY F                                                       11

SEQ ID NO: 260          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 260
CAVEDSGYAL NF                                                      12

SEQ ID NO: 261          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 261
CALQDSNYQL IW                                                      12

SEQ ID NO: 262          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 262
CAFGNFNKFY F                                                       11

SEQ ID NO: 263          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 263
CAEDYDMRF                                                          9

SEQ ID NO: 264          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 264
```

-continued

```
CASSEDSYEQ YF                                                12

SEQ ID NO: 265          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 265
CASWGAGLPL NTEAFF                                            16

SEQ ID NO: 266          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 266
CSASRPTDGE QFF                                               13

SEQ ID NO: 267          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 267
CSAIAGLTDT QYF                                               13

SEQ ID NO: 268          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 268
CASSLQVPYN EQFF                                              14

SEQ ID NO: 269          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 269
CASLKEGEAQ NIQYF                                             15

SEQ ID NO: 270          moltype = DNA  length = 60
FEATURE                 Location/Qualifiers
misc_feature            1..60
                        note = Description of Artificial Sequence: Synthetic
                         oligonucleotide
source                  1..60
                        mol_type = other DNA
                        organism = synthetic construct
SEQUENCE: 270
ggagggctca gcatgactcg agataaaatg tgaataatga ggatgcggag gatccggcgg  60

SEQ ID NO: 271          moltype = DNA  length = 43
FEATURE                 Location/Qualifiers
misc_feature            1..43
                        note = Description of Artificial Sequence: Synthetic
                         oligonucleotide
source                  1..43
                        mol_type = other DNA
                        organism = synthetic construct
SEQUENCE: 271
tcagcatacc tgtaccaccg ggtggacgtg atcggatgcg gag              43

SEQ ID NO: 272          moltype = DNA  length = 10
FEATURE                 Location/Qualifiers
misc_feature            1..10
                        note = Description of Artificial Sequence: Synthetic
                         oligonucleotide
```

```
source                  1..10
                        mol_type = other DNA
                        organism = synthetic construct
SEQUENCE: 272
gatccggcgg                                                        10

SEQ ID NO: 273          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 273
tgagccctcc                                                        10

SEQ ID NO: 274          moltype = DNA  length = 44
FEATURE                 Location/Qualifiers
misc_feature            1..44
                        note = Description of Artificial Sequence: Synthetic
                         oligonucleotide
source                  1..44
                        mol_type = other DNA
                        organism = synthetic construct
SEQUENCE: 274
gatcctccgc atccgatcac gtccacccgg tggtacaggt atgc                  44

SEQ ID NO: 275          moltype = DNA  length = 56
FEATURE                 Location/Qualifiers
misc_feature            1..56
                        note = Description of Artificial Sequence: Synthetic
                         oligonucleotide
variation               1..3
                        note = n = a, c, t, g, unknown or other
source                  1..56
                        mol_type = other DNA
                        organism = synthetic construct
SEQUENCE: 275
nnngctcagc atacctgtac caccgggtgg acgtgatcgg aagcggagga tccggc      56

SEQ ID NO: 276          moltype = DNA  length = 22
FEATURE                 Location/Qualifiers
misc_feature            1..22
                        note = Description of Artificial Sequence: Synthetic
                         oligonucleotide
variation               1..4
                        note = n = a, c, t, g, unknown or other
source                  1..22
                        mol_type = other DNA
                        organism = synthetic construct
SEQUENCE: 276
nnnngccggt acctccgctt cc                                          22

SEQ ID NO: 277          moltype = DNA  length = 200
FEATURE                 Location/Qualifiers
misc_feature            1..200
                        note = Description of Artificial Sequence: Synthetic
                         polynucleotide
source                  1..200
                        mol_type = other DNA
                        organism = synthetic construct
SEQUENCE: 277
gtttaaactt aagcttgcgg ccgccatggc gacgggttca agaacttccc tacttcttgc  60
atttggcctg ctttgtttgc cgtggttaca ggagggctca gcatacctgt accaccgggt  120
ggacgtgatc ggatgcggag gatccggcgg aggcgggagc ggaggcggag ggtctatcca  180
gcgtactcca aagattcagg                                             200

SEQ ID NO: 278          moltype = DNA  length = 43
FEATURE                 Location/Qualifiers
misc_feature            1..43
                        note = Description of Artificial Sequence: Synthetic primer
source                  1..43
                        mol_type = other DNA
                        organism = synthetic construct
SEQUENCE: 278
tcagcatacc tgtaccaccg ggtggacgtg atcggatgcg gag                   43

SEQ ID NO: 279          moltype = DNA  length = 44
```

-continued

```
FEATURE                Location/Qualifiers
misc_feature           1..44
                       note = Description of Artificial Sequence: Synthetic primer
source                 1..44
                       mol_type = other DNA
                       organism = synthetic construct
SEQUENCE: 279
gatcctccgc atccgatcac gtccacccgg tggtacaggt atgc                   44

SEQ ID NO: 280         moltype = AA  length = 42
FEATURE                Location/Qualifiers
REGION                 1..42
                       note = Description of Artificial Sequence: Synthetic
                        polypeptide
source                 1..42
                       mol_type = protein
                       organism = synthetic construct
SEQUENCE: 280
GSGGSGGSAG GGLNDIFEAQ KIEWHEGGGE NLYFQGHHHH HH                     42

SEQ ID NO: 281         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 281
GGGLNDIFEA QKIEWH                                                  16

SEQ ID NO: 282         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 282
CAVRDLYSSA SKIIF                                                   15

SEQ ID NO: 283         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 283
CASSYKGPEA FF                                                      12

SEQ ID NO: 284         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 284
ITFHDMESV                                                          9

SEQ ID NO: 285         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 285
CASSSSGNTI YF                                                      12

SEQ ID NO: 286         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 286
CASSLKSRDS TNYGYTF                                                 17
```

```
SEQ ID NO: 287          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 287
CASSLDSGVS YEQYF                                                  15

SEQ ID NO: 288          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 288
CASSLKLRGT GDYEQYF                                                17

SEQ ID NO: 289          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 289
CSVTPWGSGS YNEQFF                                                 16

SEQ ID NO: 290          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 290
CASSLKDRDS SNQPQHF                                                17

SEQ ID NO: 291          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 291
CASSSGLADT QYF                                                    13

SEQ ID NO: 292          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 292
CASRFLQGST EAFF                                                   14

SEQ ID NO: 293          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 293
CAVPQTSGAG SYQLTF                                                 16

SEQ ID NO: 294          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 294
```

-continued

```
CAVRTNYGGS QGNLIF                                                    16

SEQ ID NO: 295          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 295
CAVRLTGGGN KLTF                                                      14

SEQ ID NO: 296          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 296
CALANQAGTA LIF                                                       13

SEQ ID NO: 297          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 297
CAYRNFGNEK LTF                                                       13

SEQ ID NO: 298          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 298
CAVRGRDSNY QLIW                                                      14

SEQ ID NO: 299          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 299
CAVNSNYQLI W                                                         11

SEQ ID NO: 300          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 300
CAVWPNNNDM RF                                                        12

SEQ ID NO: 301          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 301
DEYIPGTTFL                                                           10

SEQ ID NO: 302          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
```

SEQUENCE: 302
HLSLELLGV 9

SEQ ID NO: 303 moltype = AA length = 17
FEATURE Location/Qualifiers
REGION 1..17
note = Description of Artificial Sequence: Synthetic peptide
source 1..17
mol_type = protein
organism = synthetic construct
SEQUENCE: 303
CASSWGLAAT KTYEQYF 17

SEQ ID NO: 304 moltype = AA length = 15
FEATURE Location/Qualifiers
REGION 1..15
note = Description of Artificial Sequence: Synthetic peptide
source 1..15
mol_type = protein
organism = synthetic construct
SEQUENCE: 304
CASSSGTSGG NIQYF 15

SEQ ID NO: 305 moltype = AA length = 13
FEATURE Location/Qualifiers
REGION 1..13
note = Description of Artificial Sequence: Synthetic peptide
source 1..13
mol_type = protein
organism = synthetic construct
SEQUENCE: 305
CASSFGLSGE QYF 13

SEQ ID NO: 306 moltype = AA length = 9
FEATURE Location/Qualifiers
REGION 1..9
note = Description of Artificial Sequence: Synthetic peptide
source 1..9
mol_type = protein
organism = synthetic construct
SEQUENCE: 306
LQEQVALKY 9

SEQ ID NO: 307 moltype = AA length = 9
FEATURE Location/Qualifiers
REGION 1..9
note = Description of Artificial Sequence: Synthetic peptide
source 1..9
mol_type = protein
organism = synthetic construct
SEQUENCE: 307
LTRPFNFVY 9

SEQ ID NO: 308 moltype = AA length = 13
FEATURE Location/Qualifiers
REGION 1..13
note = Description of Artificial Sequence: Synthetic peptide
source 1..13
mol_type = protein
organism = synthetic construct
SEQUENCE: 308
CAPRGDAGNM LTF 13

SEQ ID NO: 309 moltype = AA length = 12
FEATURE Location/Qualifiers
REGION 1..12
note = Description of Artificial Sequence: Synthetic peptide
source 1..12
mol_type = protein
organism = synthetic construct
SEQUENCE: 309
CLVGDNNNDM RF 12

SEQ ID NO: 310 moltype = AA length = 15
FEATURE Location/Qualifiers
REGION 1..15
note = Description of Artificial Sequence: Synthetic peptide
source 1..15
mol_type = protein

```
                        organism = synthetic construct
SEQUENCE: 310
CAVRDSMEYG NKLVF                                                             15

SEQ ID NO: 311          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 311
CAVRDSDNYG QNFVF                                                             15

SEQ ID NO: 312          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 312
CASLGAGGTS YGKLTF                                                            16

SEQ ID NO: 313          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 313
CASSLSDGPQ PQHF                                                              14

SEQ ID NO: 314          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 314
CASSLEAGST YEQYF                                                             15

SEQ ID NO: 315          moltype = AA  length = 9
FEATURE                 Location/Qualifiers
REGION                  1..9
                        note = Description of Artificial Sequence: Synthetic peptide
VARIANT                 3
                        note = Tyr or Asp
source                  1..9
                        mol_type = protein
                        organism = synthetic construct
SEQUENCE: 315
TLXHQLQPL                                                                    9

SEQ ID NO: 316          moltype = AA  length = 10
FEATURE                 Location/Qualifiers
REGION                  1..10
                        note = Description of Artificial Sequence: Synthetic peptide
VARIANT                 8
                        note = Ser or Arg
source                  1..10
                        mol_type = protein
                        organism = synthetic construct
SEQUENCE: 316
LLFGDLLXVA                                                                   10

SEQ ID NO: 317          moltype = AA  length = 9
FEATURE                 Location/Qualifiers
REGION                  1..9
                        note = Description of Artificial Sequence: Synthetic peptide
VARIANT                 5
                        note = His or Arg
source                  1..9
                        mol_type = protein
                        organism = synthetic construct
SEQUENCE: 317
SVKLXNRVV                                                                    9
```

```
SEQ ID NO: 318          moltype = AA  length = 10
FEATURE                 Location/Qualifiers
REGION                  1..10
                        note = Description of Artificial Sequence: Synthetic peptide
VARIANT                 8
                        note = Leu or Ser
source                  1..10
                        mol_type = protein
                        organism = synthetic construct
SEQUENCE: 318
ETIKNPRXTV                                                                10

SEQ ID NO: 319          moltype = AA  length = 9
FEATURE                 Location/Qualifiers
REGION                  1..9
                        note = Description of Artificial Sequence: Synthetic peptide
VARIANT                 9
                        note = Leu or Pro
source                  1..9
                        mol_type = protein
                        organism = synthetic construct
SEQUENCE: 319
KQSFILRVX                                                                 9

SEQ ID NO: 320          moltype = AA  length = 9
FEATURE                 Location/Qualifiers
REGION                  1..9
                        note = Description of Artificial Sequence: Synthetic peptide
VARIANT                 6
                        note = Ser or Cys
source                  1..9
                        mol_type = protein
                        organism = synthetic construct
SEQUENCE: 320
STDSPXSTL                                                                 9

SEQ ID NO: 321          moltype = AA  length = 9
FEATURE                 Location/Qualifiers
REGION                  1..9
                        note = Description of Artificial Sequence: Synthetic peptide
VARIANT                 8
                        note = Met or Val
source                  1..9
                        mol_type = protein
                        organism = synthetic construct
SEQUENCE: 321
ARSVSSIXR                                                                 9

SEQ ID NO: 322          moltype = AA  length = 9
FEATURE                 Location/Qualifiers
REGION                  1..9
                        note = Description of Artificial Sequence: Synthetic peptide
VARIANT                 2
                        note = Ala or Asp
source                  1..9
                        mol_type = protein
                        organism = synthetic construct
SEQUENCE: 322
RXIDKIYVR                                                                 9

SEQ ID NO: 323          moltype = AA  length = 10
FEATURE                 Location/Qualifiers
REGION                  1..10
                        note = Description of Artificial Sequence: Synthetic peptide
VARIANT                 7
                        note = Ile or Leu
source                  1..10
                        mol_type = protein
                        organism = synthetic construct
SEQUENCE: 323
LATAAAXTYG                                                                10

SEQ ID NO: 324          moltype = AA  length = 9
FEATURE                 Location/Qualifiers
REGION                  1..9
```

-continued

```
                        note = Description of Artificial Sequence: Synthetic peptide
source                  1..9
                        mol_type = protein
                        organism = synthetic construct
SEQUENCE: 324
RLYTRTLYL                                                         9
```

The invention claimed is:

1. A method of treating cancer in a subject, comprising:

(a) contacting a sample with a plurality of particle sets, (i) wherein each particle of each set consists of three polypeptides comprising an antigen peptide, a barcode, and at least one identifying label;

(ii) wherein the sample comprises T cells; and (iii) wherein contacting comprises providing conditions suitable for the T cells to bind to antigen peptides;

(b) isolating a T cell from the sample;

(c) identifying the barcodes of the particles bound to the isolated T cell;

(d) determining a ratio of a most represented barcode and a second most represented barcode identified in (c);

(e) determining the antigen specificity of the T cell based on the ratio of the most represented barcode and the second most represented barcode;

(f) identifying a TCR gene sequence of the T cell;

(g) preparing a polynucleotide comprising homology arms and at least one identified TCR gene sequence, wherein the identified TCR gene sequence is position between the homology arms;

(h) recombining the polynucleotide into an endogenous locus of the T cell;

(i) culturing the modified T cell of (h) to produce a population of T cells; and (j) administering a therapeutically effective amount of the modified T cells to the subject, to thereby treat cancer.

2. The method of claim 1, wherein the ratio is determined by identifying a copy number of the most represented barcode and a copy number of the second most represented barcode and dividing the copy number of the most represented barcode by the copy number of the second most represented barcode.

3. The method of claim 1, wherein the isolated T cell is identified as an antigen-specific T cell if the ratio of the first barcode is above a threshold.

4. The method of claim 3, wherein the threshold is at least or greater than 2, 3, 4, 5, 6, 7, 8, 9, 10, 2-5, 3-6, 4-7, 5-8, 5-10, 7-10, or greater than 10.

5. The method of claim 1, wherein each particle set comprises two or more barcodes, wherein each barcode is associated with the identity of the antigen peptide.

6. The method of claim 1, wherein the identifying the barcodes comprises a PCR assay, an RT-PCR assay, a sequencing assay, or a hybridization assay.

7. The method of claim 1, wherein the identifying the barcodes comprises determining the sequence of each barcode.

8. The method of claim 1, wherein the identifying the barcodes comprises determining the sequence and copy number of each barcode.

9. The method of claim 1, wherein the identifying label is a fluorophore.

10. The method of claim 1, wherein the fluorophore is allophycocyanin (APC) or phycoerythrin (PE).

11. The method of claim 1, wherein the antigen peptide is selected from the group consisting of a tumor antigen, a neoantigen, a tumor neoantigen, a viral antigen, a bacterial antigen, a phospho-antigen, and a microbial antigen.

12. The method of claim 1, wherein each polypeptide further comprises a β2M sequence, and an HLA sequence.

13. The method of claim 12, wherein the polypeptide comprises, in an amino to carboxyl terminus orientation, the antigen peptide, the B2M peptide, and the HLA peptide.

14. The method of claim 12, wherein the HLA is selected from the group consisting of HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, or HLA-C*17:01.

15. The method of claim 1, wherein the particles are selected from the group consisting of magnetic beads, agarose beads, styrene polymer particles, and dextran polymer particles.

16. The method of claim 1, wherein the particles are streptavidin coated.

* * * * *